(12) United States Patent
Choi

(10) Patent No.: US 12,380,977 B2
(45) Date of Patent: Aug. 5, 2025

(54) CORRELATING HEALTH CONDITIONS WITH BEHAVIORS FOR TREATMENT PROGRAMS IN NEUROHUMORAL BEHAVIORAL THERAPY

(71) Applicant: S-Alpha Therapeutics, Inc., Seoul (KR)

(72) Inventor: Seung Eun Choi, Seoul (KR)

(73) Assignee: S-Alpha Therapeutics, Inc., Seoul (KR)

( * ) Notice: Subject to any disclaimer, the term of this patent is extended or adjusted under 35 U.S.C. 154(b) by 499 days.

(21) Appl. No.: 17/736,145

(22) Filed: May 4, 2022

(65) Prior Publication Data

US 2022/0384002 A1    Dec. 1, 2022

Related U.S. Application Data

(63) Continuation-in-part of application No. PCT/KR2021/015832, filed on Nov. 3, 2021.

(60) Provisional application No. 63/337,465, filed on May 2, 2022, provisional application No. 63/133,927, filed on Jan. 5, 2021, provisional application No. 63/108,994, filed on Nov. 3, 2020.

(51) Int. Cl.
*G16H 20/00* (2018.01)
*G16H 10/60* (2018.01)

(52) U.S. Cl.
CPC ............. *G16H 20/00* (2018.01); *G16H 10/60* (2018.01)

(58) Field of Classification Search
None
See application file for complete search history.

(56) References Cited

U.S. PATENT DOCUMENTS

| | | | |
|---|---|---|---|
| 2017/0329933 A1* | 11/2017 | Brust | G06F 16/24575 |
| 2018/0042985 A1* | 2/2018 | Young | A61P 25/00 |
| 2020/0273578 A1* | 8/2020 | Kutzko | H04L 9/0637 |
| 2022/0005066 A1* | 1/2022 | Muradia | G06Q 30/0241 |

OTHER PUBLICATIONS

Smoking Cessation: A Report from the Surgeon General. Jan. 23, 2020. Available from: https://www.hhs.gov/surgeongeneral/reports-and-publications/tobacco/2020-cessation-sgr-factsheet-key-findings/index.html (Year: 2020).*

Qu, Yuan et al. "Correlation of Myopia with Physical Exercise and Sleep Habits among Suburban Adolescents." Feb. 14, 2020. Available at: https://pubmed.ncbi.nlm.nih.gov/32774900. Last accessed Mar. 22, 2025. (Year: 2020)*

* cited by examiner

Primary Examiner — Katherine Kolosowski-Gager
(74) Attorney, Agent, or Firm — Morgan, Lewis & Bockius LLP

(57) ABSTRACT

A method for generating treatment regimen for one or more health conditions includes retrieving a stored healthcare treatment model that has been trained to identify, for each of a plurality of health conditions, one or more respective treatment programs. Each of the treatment programs includes a respective treatment user interface to modify a respective behavior associated with one or more neurohumoral factors that are associated with the respective health condition. In response to receiving input that specifies a first health condition of the one or more health conditions, the method uses the healthcare treatment model to select one or more treatment programs corresponding to the first health condition and provides the treatment user interfaces for the one or more treatment programs.

20 Claims, 88 Drawing Sheets

| NHF | Behavior | Up/down binary code | article number |
|---|---|---|---|
| cortisol | relaxing music | ↓ | 5 |
| oxytocin | slow music (149 touches, 56 crotchets/min) | ↑ | 4 |
| cortisol | | ↓ | 4 |
| oxytocin | fast music (417 touches, 233 crotchets/min) | ↓ | 4 |
| cortisol | | ↑ | 4 |
| norepinephrine | sleep deprivation | ↑ | 11 |
| cortisol | stress | ↑ | 5 |
| dopamine | positive affection | ↑ | 1 |
| cortisol | meditation | ↓ | 3 |
| cortisol | slow exercise (deep breathing exercise) | ↓ | 2 |
| betacatenin | appropriate exercise | ↑ | 6 |
| serotonin | | ↑ | 7 |
| norepinephrine | Fast exercise (High intensity exercise) | ↑ | 11 |
| cortisol | | ↑ | 8 |
| IGF1 | | ↑ | 8 |
| BDNF | | ↑ | 8 |
| beta catenin | HRT (hormone replacement therapy) | ↑ | 10 |
| estrogen | | ↑ | 9 |
| serotonin | | ↑ | 9 |

┌─────────────────────────────────────────────────────────────────────┐
│ 710 A method for building models for selecting healthcare treatment programs is performed at a computing device having one or more processors and memory storing one or more programs configured for execution by the one or more processors. │
└─────────────────────────────────────────────────────────────────────┘

┌─────────────────────────────────────────────────────────────────────┐
│ 720 For health condition of a plurality of health conditions: │
│ ┌─────────────────────────────────────────────────────────────────┐ │
│ │ 722 Provide a respective first plurality of scientific documents. Each scientific document of the first plurality of scientific documents specifies a correlation between the respective health condition and one or more respective neurohumoral factors (NHFs). │ │
│ └─────────────────────────────────────────────────────────────────┘ │
│ ┌─────────────────────────────────────────────────────────────────┐ │
│ │ 724 Using the correlations specified in the first plurality of scientific documents, calculate a respective correlation coefficient between the respective health condition and each of the NHFs correlated with the respective health condition.. │ │
│ │ ┌─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐ │ │
│ │ │ 726 A respective correlation coefficient between the respective health condition and a respective NHF is determined, at least in part, based on: frequency of the respective NHF appearing in the respective first plurality of scientific documents, and/or quality of the respective scientific documents in the first plurality of scientific documents. │ │ │
│ │ └─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘ │ │
│ └─────────────────────────────────────────────────────────────────┘ │
└─────────────────────────────────────────────────────────────────────┘

810 A method for generating treatment plans for one or more health conditions is performed at a computing device having one or more processors and memory storing one or more programs configured for execution by the one or more processors.

820 Retrieve a stored healthcare treatment model that has been trained to identify, for each of a plurality of health conditions, one or more respective treatment programs. Each of the treatment programs includes a respective treatment user interface to modify respective behavior associated with one or more NHFs that are associated with the respective health condition.

830 In response to receiving input that specifies a first health condition of the one or more health conditions: use the healthcare treatment model to select one or more treatment programs corresponding to the first health condition, and provide the treatment user interfaces for the one or more treatment programs.

840 In response to receiving input that specifies a second health condition of the one or more health conditions: use the healthcare treatment model to select one or more treatment programs corresponding to the second health condition, and provide the treatment user interfaces for the one or more treatment programs corresponding to the second health condition. The second health condition is different from the first health condition. The one or more treatment programs corresponding to the second health condition differ from the one or more treatment programs corresponding to the first health condition.

Figure 8B

| disease | neurohumoral effect | behavior | conditional behavior | sensing input |
|---|---|---|---|---|
| bowel recovery after resection and anastomosis of bowel surgery in pediatrics (short bowel syndrome, imperforated anus, Congenital Megacolon) | increasing Ghr/IGF1 | Growth hormone exercise | voluntary skeletal muscle exercise/more than 1 hour/day, outdoor exercise sits | diary/log in/log out |
| | antiinflammation | vagal nerve stimulation | massage/feeding/visceral muscle exercise | heart rate/log in/log out/diary |
| antiviral immunity | increasing NK cell population | NK cell exercise | moderate/aerobic/regular | heart rate/log in/log out |
| | increasing healthy and young T cell population | T cell exercise | aerobic/3 times per week | heart rate/log in/log out |
| | secretion of antibody | B cell exercise | vagal nerve exercise | heart rate/log in/log out |
| autism spectrum disorder | increasing ACTH | social exercise | exercise for improving social communication | data/log in/log out |
| Growth | increasing growth hormone | intensive exercise | soccer, football, basketball | heart rate |
| | increasing insulin like growth factor 1 | moderate exercise | T fitness per week/jinx, speedy walking/slow running/treadmill | heart rate |
| | lowering steroid/cortisol | relax | resting/meditation/walking | log in/log out |
| | balancing b/w androgen/estrogen* lowering proinflammatory cytokines (TNF-a, IL-1b, IL-6) | | planning of diet schedule | diary |
| | lowering TGFbeta signaling | relax/vagal nerve stimulation | resting/meditation/walking /vagal nerve exercise | heart rate/log in/log out |
| | increasing thyroid hormone | no stress | resting/no isolation | diary/heart rate/log in/log out |
| | no physical compression | balanced nutritional intake | planning of diet schedule | diary |
| | no ionizing radiation | stretching/avoid exercise which can beat the joint system | stretching exercise/avoid some exercise | log in/log out/diary |
| | | avoid radiation | avoid radiation | radiation |

Figure 19B

| | disease | neurohumoral effect | behavior | conditional behavior | sensing input |
|---|---|---|---|---|---|
| | obesity | adiponectin | moderate exercise | 1-3 times/week | heart rate/log in/log out |
| | | anti-inflammation | vagal nerve stimulation | vagal nerve exercises | heart rate |
| | | lowering neuropeptides* | no skip meal | more than 3 times eating a day | diary |
| | | no hunger feeling | distraction | imaginary posture/ audiovisual experiences | log in/log out/gazing tracking/mouse tone around face |
| | | increasing of αMSH | | | |
| | | increasing of α-MSH (α-melanocyte stimulating hormone)* | goal achievement | fun/ appropriate task/ positive scoring | data |
| | | | positive affection | focusing on task in appropriate time x | data |
| | | regulating orexin | sustainable tension | day/homework/presentation in | heart rate |
| | | lowering MCH | | | |
| | | avoid too much amounts of leptin | normal life style | balancing b/w day and night more than 3 times eating a day | light intensity sensing |
| | | balance of leptin/agouti-related proteins(AgRP) | no skip meal | more than 3 times eating a day | diary |
| | | lowering ghrelin | no skip meal | more than 3 times eating a day | diary |
| | | no empty gastric intestine | no skip meal | more than 3 times eating a day | diary |
| | | lowering contracting emptying stomach | | | |
| | | high reward mechanisms that regulate hedonic aspects of food intake (suppressant) | fun/entertainment | fun/ appropriate task/positive scoring | data |
| | | healthy diet/lifestyle management1 | balanced nutritional intake | planning of diet schedule | data |
| | | increasing exercise/lifestyle management2 | individualized exercise | calibration of individual exercise | data |
| sarcopenia | | increasing IGF1 | moderate exercise | 3-5 times per week/hike, aggressively walking/slow running/treadmill | heart rate |
| | | | balanced nutritional intake | planning of diet schedule | diary |

Figure 19C

| disease | neurohumoral effect | behavior | conditional behavior | sensing input |
|---|---|---|---|---|
| spinal stenosis | lowering TNF-alpha (inflammation) | VN exercise | VN exercise | heart rate/log in/log out |
| | lowering IL-6 | VN exercise | VN exercise | heart rate/log in/log out |
| | lowering of locally produced IGF 2 | no mechanical stress | no mechanical pressure | diary |
| disc herniation | lowering TNF-alpha (inflammation) | no skeletal muscle exercise | Pilates | height data/log in/log out |
| | lowering IL-6 | VN exercise | stretching | height data/log in/log out |
| | | VN exercise | VN exercise | heart rate/log in/log out |
| | lowering of locally produced IGF 1 | no mechanical stress | no mechanical pressure | diary |
| dry eyes | lacrimal gland/lid hygiene | no skeletal muscle exercise | Pilates | height data/log in/log out |
| | | blinking | stretching | height data/log in/log out |
| | | washing with warm water around eye/eyelid | blinking | gaze sensing/sensing facial tone |
| | lowering proinflammatory factors | | washing with warm water around eye/eyelid | log in/log out/diary |
| | adiponectin | | cold massage around face/eye | facial muscle tone |
| | increasing dopamine | appropriate physical exercise | appropriate physical exercise | heart rate/log in/log out |
| | | fun | fun | data |
| | | positive affection achievement | positive affection training, task can get achievement | data |
| Parkinson's disease | IGF 1 | tolerable tension/horror | tolerable tension/horror | data |
| | | bright environment | day exercise/outdoor exercise | heart rate/light intensity |

S-Alpha Therapeutics, Inc.　　　　　　　　　　　　　　　　　　　　　　　　　　　　SAT Admin

Dashboard

Healthcare Model

Health Conditions

NHFs

Behaviors

Treatment Programs

Doctors

Patients

Log

Healthcare Model > Health Conditions

[Search health condition]　　　　　　　　　　　　　　[+ Add New Health condition]

| ID | | | |
|---|---|---|---|
| 001 | Myopia | Dopamine and 3 more | |
| 002 | Cancer cachexia | Adiponectin and 4 more | |
| 003 | Social communication disorder | Cortisol and 2 more | |
| 004 | Mild cognitive impairment | Adiponectin and 4 more | |
| 005 | Health condition 005 | NHF 003 and 2 more | |
| 006 | Health condition 006 | NHF 003 and 2 more | |
| 007 | Health condition 007 | NHF 003 and 2 more | |
| 008 | Health condition 008 | NHF 003 and 2 more | |
| 009 | Health condition 009 | NHF 003 and 2 more | |
| 010 | Health condition 010 | NHF 003 and 2 more | |
| 011 | Health condition 011 | NHF 003 and 2 more | |
| 012 | Health condition 012 | NHF 006 and 2 more | |
| 013 | Health condition 013 | NHF 006 and 2 more | |
| 014 | Health condition 014 | NHF 006 and 2 more | |
| 015 | Health condition 015 | NHF 006 and 2 more | |
| 016 | Health condition 016 | NHF 006 and 2 more | |

< 1 2 3 4 5 >

S-Alpha Therapeutics, Inc.      SAT Admin

Healthcare Model > NHFs

2209

Dashboard
Healthcare Model
Health Conditions
NHFs
Behaviors
Treatment Programs
Doctors
Patients
Log

| ID | Description | | |
|---|---|---|---|
| 001 | Cortisol | | Bright Environment and 3 more |
| 002 | Adrenaline | | Meditation and 4 more |
| 003 | NHF 003 | | Meditation and 2 more |
| 004 | NHF 004 | | Behavior 008 and 4 more |
| 005 | NHF 005 | | Behavior 003 and 2 more |
| 006 | NHF 006 | | Behavior 003 and 2 more |
| 007 | NHF 007 | | Behavior 003 and 2 more |
| 008 | NHF 008 | | Behavior 003 and 2 more |
| 009 | NHF 009 | | Behavior 003 and 2 more |
| 010 | NHF 010 | | Behavior 006 and 2 more |
| 011 | NHF 011 | | Behavior 006 and 2 more |
| 012 | NHF 012 | | Behavior 006 and 2 more |
| 013 | NHF 013 | | Behavior 006 and 2 more |
| 014 | NHF 014 | | Behavior 006 and 2 more |
| 015 | NHF 015 | | Behavior 006 and 2 more |
| 016 | NHF 016 | | Behavior 006 and 2 more |

Sheet shows a screenshot (2214) of the S-Alpha Therapeutics, Inc. admin interface with navigation items: Dashboard, Healthcare Model, Health Conditions, NHFs, Behaviors, Treatment Programs, Doctors, Patients, Log. Header shows "SAT Admin" and breadcrumb "Healthcare Model > Behaviors".

| ID | Behavior | Day Exercise |
|---|---|---|
| 001 | Break Environment | Task can get achievement and 1 more |
| 002 | Achievement | Comfortable music set |
| 003 | Comfortable music | TP 008 and 4 more |
| 004 | High tempo Music | Deep breathing and 2 more |
| 005 | Meditation | TP 003 and 2 more |
| 006 | Behavior 006 | TP 003 and 2 more |
| 007 | Behavior 007 | TP 003 and 2 more |
| 008 | Behavior 008 | TP 003 and 2 more |
| 009 | Behavior 009 | TP 003 and 2 more |
| 010 | Behavior 010 | TP 006 and 2 more |
| 011 | Behavior 011 | TP 006 and 2 more |
| 013 | Behavior 013 | TP 006 and 2 more |
| 014 | Behavior 014 | TP 006 and 2 more |
| 015 | Behavior 015 | TP 006 and 2 more |
| 016 | Behavior 016 | TP 006 and 2 more |

< 1 2 3 4 5 >

+ Add New Behavior

Figure 22Z

S-Alpha Therapeutics, Inc.                                                                                    SAT Doctor Dashboard Healthcare Model          Patients > 000013. SAT > PC01232

Patients                  SAT #000013

Log                       Date of Birth    3/15/1955      [Edit]
                          #P001232
                          Health condition  Myopia
                          Period            4/11/2020 ~ 7/8/2020
                          Treatment Program
                          Eye movement / Duration : 30 minutes a Day (+- 5 minutes) / Frequency : 5 Times a Week (+- 1 times)

| Day   | Status             |          |          |        |
|-------|--------------------|----------|----------|--------|
| Day 1 | Fully attended     | 08:45:23 | 14:03:44 |        |
| Day 2 | Fully attended     | 09:45:13 | 17:13:24 | Show   |
| Day 3 | Fully attended     | 10:44:23 | 15:06:12 | Show   |
| Day 4 | Rest               | -        | -        | -      |
| Day 5 | Rest               | -        | -        | -      |
| Day 6 | Fully attended     | 12:45:43 | 17:11:44 | Show   |
| Day 7 | Partially attended | 09:41:23 | 14:03:23 | Show   |
| Day 8 | Fully attended     | 11:25:54 | 16:11:44 | Show   |
| Day 9 | Fully attended     | 16:45:14 | 14:03:33 | Show   |

CORRELATING HEALTH CONDITIONS WITH BEHAVIORS FOR TREATMENT PROGRAMS IN NEUROHUMORAL BEHAVIORAL THERAPY

RELATED APPLICATIONS

This application is a continuation-in-part of PCT Application No. PCT/KR2021/015832, filed Nov. 3, 2021, entitled "Correlating Health Conditions with Behaviors for Treatment Programs in Neurohumoral Behavioral Therapy," which claims priority to U.S. Provisional Application Ser. No. 63/133,927, filed Jan. 5, 2021, entitled "Correlating Health Conditions with Behaviors for Treatment Programs in Neurohumoral Behavioral Therapy," and U.S. Provisional Application Ser. No. 63/108,994, filed Nov. 3, 2020, entitled "Correlating Health Conditions with Behaviors for Treatment Programs in Neurohumoral Behavioral Therapy," each of which is incorporated by reference herein in its entirety.

This application also claims priority to U.S. Provisional Application Ser. No. 63/337,465, filed May 2, 2022, entitled "Correlating Health Conditions with Behaviors for Treatment Programs in Neurohumoral Behavioral Therapy," which is incorporated by reference herein in its entirety.

This application is related to:
- U.S. patent application Ser. No. 16/747,980, filed Jan. 21, 2020, entitled "Digital Apparatus and Application for Treating Myopia," which is incorporated by reference in its entirety;
- U.S. patent application Ser. No. 16/883,369, filed May 26, 2020, entitled "Digital Apparatus and Application for Treating Myopia," which is incorporated by reference in its entirety;
- U.S. Provisional Application Ser. No. 63/029,997, filed May 26, 2020, entitled "Digital Apparatus and Application for Cancer Cachexia Therapy and Methods of Use Thereof," which is incorporated by reference in its entirety;
- U.S. Provisional Application Ser. No. 63/061,092, filed Aug. 4, 2020, entitled "Digital Apparatus and Application for Treating Social Communication Disorder," which is incorporated by reference in its entirety;
- U.S. Provisional Application Ser. No. 63/017,413, filed Apr. 29, 2020, entitled "Antiviral Digital Device," which is incorporated by reference in its entirety;
- U.S. Provisional Application Ser. No. 63/051,358, filed Jul. 13, 2020, entitled "Antiviral Digital Device," which is incorporated by reference in its entirety;
- U.S. patent application Ser. No. 16/860,641, filed Apr. 28, 2020, entitled "Amnestic MCI/mild Dementia," which is incorporated by reference in its entirety;
- U.S. Provisional Application Ser. No. 63/037,203, filed Jun. 10, 2020, entitled "Method and Apparatus for Enhancing Performance," which is incorporated by reference in its entirety; and
- U.S. Provisional Application Ser. No. 63/075,414, filed Sep. 8, 2020, entitled "Rehabilitation after Pediatric GI Operation," which is incorporated by reference in its entirety.

TECHNICAL FIELD

The disclosed implementations relate generally to providing treatment programs for neurohumoral behavioral therapy and more specifically to systems and methods for correlating health conditions, neurohumoral factors and behaviors, and providing treatment programs to patients.

BACKGROUND

Many health conditions (e.g., diseases or disorders) are related to neurohumoral factors, many of which are linked to specific behaviors and activities. In some cases, neurohumoral behavioral therapy can be used to help treat such health conditions.

SUMMARY

Many scientific and medical studies measure correlations between various health conditions and neurohumoral factors (NHFs). NHFs include, for example, growth factors, hormones, neuro-transmitters, and nutrients, any of which can be related to or contribute to underlying causes of one or more health conditions. Similarly, many scientific and medical studies measure how different behaviors or activities can affect different NHFs.

Neurohumoral behavioral therapy (NHBT) is a treatment method that includes prescribing a patient with different activities that target specific behaviors that are known to be correlated to (e.g., that affect, regulate, suppress, or activate) NHFs. In some health conditions, NHFs may contribute to or be an underlying cause of a patient's health problems. Thus, knowledge of which NHFs are related to or affect which health condition is an important part of prescribing treatment programs as part of NHBT.

Due to the complexity and interconnectedness of the human body's many systems, mapping the association between health conditions, NHFs, and specific behaviors is not a straightforward task. In order to take advantage of the large number of research findings in the scientific and medical fields, a neural network can be employed to determine correlations (e.g., associations) between various health conditions and specific NHFs, and correlations (e.g., associations) between specific NHFs and specific behaviors, thereby identifying behaviors that can be used to treat or aid treatment of the various health conditions. Additionally, the neural network can be employed to determine correlations (e.g., associations) between various health conditions and specific treatment programs, where the treatment programs include activities that target specific behaviors.

Accordingly, there is a need for tools that can accurately link different treatment programs that prescribe activities targeting specific behaviors with specific health conditions. There is also a need for tools that employ such relationships and associations to allow systems to provide treatment options to a patient and track a patient's progress and/or adherence to the treatment program(s).

The methods and systems disclosed herein are related to a digital behavior-based treatment system and application. In particular, they relate to the development of digital behavior-based treatments that are regularly reported to the doctor, converting the doctor's behavioral and cognitive prescriptions into digital behavioral and cognitive instructions (BCI) with the usage of the application, collecting patient's performance results for specific behavioral and cognitive tasks, and analyzing data on behavior and cognitive adherence (BCA) for the patient's task, in implementing the behavior and cognitive prescription (behavior & cognition prescription, hereinafter BCP).

In addition, the methods and systems disclosed herein are related to a digital behavior-based treatment system and application. Patient personalized digital behavior & cognition instruction (PBCI) is derived from individual long-term follow-up task-performance data, and the PBCI is related to the development of patient-tailored digital behavior-based treatments that collect patient personalized digital behavior & cognition adherence (PBCA).

The methods and systems disclosed herein are related to a digital behavior-based treatment system and application, including the development of evidence-based digital therapeutics that objectively verify the clinical effectiveness and improvement of doctors' behavioral and cognitive prescriptions.

Chronic diseases or neurological diseases often appear as a result of long-term interactions of several complex factors rather than a single cause. In this context, diseases such as heart disease, stroke, obesity, and type II diabetes are sometimes referred to as lifestyle diseases, which are deeply related to deterioration of body function accompanying aging and body changes (e.g., growth, aging, menopause, etc.). For the treatment of such chronic diseases or neurological disorders, or for correcting the decline in physical ability, doctors prescribe behavioral and lifestyle improvements to improve behavior and cognitive ability, in addition to traditional drug and rehabilitation treatment. However, due to individual differences in adherence to prescriptions and difficulty in obtaining long-term tracking data, clinical validation of non-pharmaceutical behavioral and cognitive prescriptions is usually insufficient.

In particular, neurological diseases have a long-term progression and contain many diseases that are difficult to treat and/or cure, and have a great adverse effect on the social life the patient and his or her family members. Even after the outbreak of the disease, care and treatment for the entire life cycle is required, which raises the challenge of health care policy such as social care requests and the accompanying social medical cost increase. Until now, the development of drugs to treat nervous system diseases has been continuously attempted, but there are many diseases that fail to develop drugs. For example, the failure of a large-scale phase 3 clinical trial by a multinational pharmaceutical company for Alzheimer's disease, which accounts for about three-quarters of dementia patients-Eli Lilly's solanezumab and Pfizer Pfizer)'s bapineuzumab-shows the difficulties of developing new drugs for related diseases. Even if treatment is attempted with a drug that has already been developed, the effect of the drug in the entire life cycle of a patient only slows the progression of the neurological disorder or relieves symptoms.

In order to overcome these limitations, as an active mediator of behavioral and cognitive prescription, experts such as clinical dietitians, exercise prescribers, and physical therapists can guide patients' behavioral and cognitive prescriptions, but it is difficult for many patients to use the program provided by the mediator due to various problems such as the skill level of the mediators, labor costs, turnover, and the economics of insurance coverage.

In addition, in the case of conventional treatments, the relationship between prescription and patient compliance is relatively simple (drug prescription-dosing guidance). However, among chronic diseases that induce neurological disorders or chronic nervous system disturbances, the treatment of diseases such as obesity, high blood pressure, dementia, type 2 diabetes, and addiction, which are currently causing social problems, faces a situation where treatment with existing drugs has reached its limit and attempts to develop innovative drug therapies continue to fail.

The methods and systems disclosed herein aim to solve the above problems and challenges by presenting digital behavioral and cognitive tasks for the doctor's behavior and cognitive prescription. By monitoring the patient's performance of the corresponding prescribed task, the invention regularly analyzes the behavioral and cognitive task-performance data of the patient and reports the results to the doctor. The disclosed methods aim to improve or treat a corresponding disease of a patient using a digital behavior-based treatment system and application.

In addition, the disclosed methods and systems aim to objectively verify the clinical effectiveness of a non-pharmaceutical behavioral prescription by constructing individual long-term follow-up patient task-performance data using a patient-tailored digital behavior-based treatment system.

In addition, the disclosed methods and systems aim to provide a digital system and application for encrypted patient-doctoral interactive task-performance feedback, patient medical information collection and storage, and related data encryption and management using digital applications without the involvement of a third party.

In accordance with some implementations, a method for building models for selecting healthcare treatment programs executes at an electronic device with one or more processors, and memory. For example, the electronic device can be a smart phone, a tablet, a notebook computer, a desktop computer, an individual server computer, or a server system (e.g., running in the cloud). The electronic device may be connected to server system, may host a server, or may be an interface for accessing information in the server system. For each health condition of a plurality of health conditions, the device provides a respective first plurality of scientific documents, each of which specifies a correlation between the respective health condition and one or more respective neurohumoral factors. The device uses the correlations specified in the respective first plurality of scientific documents to calculate a respective correlation coefficient between the respective health condition and each of the neurohumoral factors correlated with the respective health condition. For each neurohumoral factor correlated with one or more of the plurality of health conditions, the device provides a respective second plurality of scientific documents, each of which specifies a correlation between the respective neurohumoral factor and one or more respective treatment behaviors. The device uses the correlations specified in the respective second plurality of scientific documents to calculate a respective correlation coefficient between the respective neurohumoral factor and each of the treatment behaviors correlated with the respective neurohumoral factor. The device then forms a model that correlates health conditions to treatment programs based on (i) the correlation coefficients between health conditions and neurohumoral factors, (ii) the correlation coefficients between neurohumoral factors and treatment behaviors, and (iii) correspondence between treatment behaviors and treatment programs. The device then stores the model in a database for subsequent use in providing treatment programs for treating patients with any of the plurality of health conditions.

In some implementations, forming the model that correlates health conditions to treatment programs includes generating a weight matrix between respective neurohumoral factors and respective treatment behaviors. Each row of the weight matrix corresponds to a distinct neurohumoral factor and each column of the weight matrix corresponds to a distinct treatment behavior.

In some implementations, a respective correlation coefficient between a respective health condition and a respective neurohumoral factor is determined, at least in part, based on: frequency of the respective neurohumoral factor appearing in the respective first plurality of scientific documents and/or quality of the scientific documents in the respective first plurality.

In some implementations, a respective correlation coefficient between a respective neurohumoral factor and a respective treatment behavior is determined, at least in part on at least one of: frequency of the respective treatment behavior appearing in the respective second plurality of scientific documents and quality of the scientific documents in the respective second plurality.

In some implementations, each scientific document is (i) a medical and/or scientific publication in a peer reviewed journal, (ii) a published abstract at a medical and/or scientific conference, (iii) a published medical book, or (iv) a presentation at a medical and/or scientific conference.

In some implementations, the plurality of health conditions includes one or more health conditions other than: myopia, cancer cachexia, social communication disorder, mild cognitive impairment, and ophthalmologic rehabilitation.

In some implementations, the one or more treatment programs include at least one treatment regimen other than: improving antiviral immunology and strengthening a pelvic floor muscle.

In accordance with some implementations, a method of generating treatment regimen for one or more health conditions executes at an electronic device with one or more processors, and memory. For example, the electronic device can be a smart phone, a tablet, a notebook computer, a desktop computer, a server computer, a system of server computers, or a wearable device such as a smart watch. The device retrieves a stored healthcare treatment model that has been trained to identify one or more respective treatment programs for each of a plurality of health condition. Each of the treatment programs includes a respective treatment user interface to modify respective behavior associated with one or more neurohumoral factors that are associated with the respective health condition. The device receives health information regarding a patient, including receiving a health condition associated with the patient. In response to receiving the health information, the device uses the healthcare treatment model to select one or more treatment programs corresponding to the health condition. The device then receives a user request to initiate presentation of a first treatment program of the selected one or more treatment programs, and in response to receiving the user request, the device presents a first treatment interface, that corresponds to the first treatment program, to the patient. While presenting the first treatment interface to the patient, the device activates one or more first sensors to record sensor information, including tracking a first activity of the patient. After presenting the first treatment interface to the patient, the device stores first sensor information received from the one or more first sensors in a patient profile, and updates the first treatment interface according to the first sensor information.

In some implementations, in response to receiving input that specifies a second health condition of the one or more health conditions, the device uses the healthcare treatment model to select one or more treatment programs corresponding to the second health condition, and provides treatment user interfaces for the one or more treatment programs corresponding to the second health condition. The second health condition is different from the first health condition, and the one or more treatment programs corresponding to the second health condition differ from the one or more treatment programs corresponding to the first health condition.

In some implementations, the method generates a treatment regimen for the first health condition, and the treatment regimen includes the one or more treatment programs corresponding to the first health condition.

In some implementations, in response to an indication that the healthcare treatment model has been updated, the device retrieves the updated healthcare treatment model and updates the treatment regimen for the first health condition according to the updated healthcare treatment model. The updated treatment regimen (i) includes one or more treatment programs not previously in the treatment regimen and/or (ii) omits one or more treatment programs previously in the treatment regimen.

In some implementations, the device receives information measuring adherence to the one or more treatment programs.

In some implementations, one or more of the treatment interfaces are configured to monitor one or more specific patient activities using sensors of an electronic device on which the treatment interfaces are presented, and the device selects a first specific patient activity to monitor according to a first treatment interface of the provided treatment interfaces.

In some implementations, in response to an indication that the healthcare treatment model has been updated, the device retrieves the updated healthcare treatment model and updates at least one treatment program in accordance with the updated healthcare treatment model.

In some implementations, the plurality of health conditions includes one or more health conditions other than: myopia, cancer cachexia, social communication disorder, mild cognitive impairment, and ophthalmologic rehabilitation.

In some implementations, the one or more treatment programs include at least one treatment regimen other than: improving antiviral immunology and strengthening a pelvic floor muscle.

In accordance with some implementations, a method of treating health conditions executes at an electronic device (e.g., a client device or a user device) with a display, one or more processors, and memory. For example, the electronic device can be a smart phone, a tablet, a notebook computer, a desktop computer, a server computer, a system of server computers, or a wearable device such as a smart watch. The device retrieves a stored healthcare treatment model that has been trained to identify, for each of a plurality of health conditions, one or more respective treatment programs. The treatment programs includes a respective treatment user interface to modify respective behavior associated with one or more neurohumoral factors that are associated with the respective health condition. In response to receiving input that specifies a first health condition of the one or more health conditions, the device uses the healthcare treatment model to select one or more treatment programs corresponding to the first health condition, and provides treatment user interfaces for the one or more treatment programs.

In some implementations, the method of treating health conditions disclosed herein further comprises administering an effective amount of a pharmaceutical composition for the health conditions before, during, or after the user receives the treatment program.

In some implementations, the first health condition is a diagnosis by a healthcare provider. For example, health conditions such as hypertension, diabetes, an asthma are diagnosed by a healthcare provider (e.g., a family doctor, a physician, a primary care doctor, a specialist). In some implementations, the first health condition is self-reported by the patient, such as social anxiety, nervousness, or mild insomnia.

In some implementations, the device receives one or more instructions from a healthcare provider, and the one or more treatment programs are selected in accordance with the one or more received instructions. For example, the healthcare provider may provide instructions to include a new treatment program for meditation for treating a patient's health condition. In another example, the healthcare provider may provide instructions to remove a previously provided (e.g., previously or currently assigned) treatment program for high-impact exercise for treating a patient's health condition. In yet another example, the healthcare provider may provide instructions to modify a previously provided (e.g., previously or currently assigned) treatment program for treating a patient's health condition, such as increasing the duration of a moderate exercise treatment from 30 minutes to 45 minutes and/or decreasing a frequency of a moderate exercise treatment from 5 times a week to 4 times a week.

In some implementations, the device receives one or more user inputs regarding the health information of the patient. For example, the user may input weight, height, blood pressure, glucose levels of a patient as it changes over time (e.g., over the course of receiving treatment).

In some implementations, presenting the first treatment interface includes presenting an audio and/or a visual request for the patient to perform an action (e.g., close your eyes and try to relax as you listen to this calming music, track the ball with your left eye), presenting audio content and/or visual content corresponding to the request, and activating the one or more first sensors to track the requested action (e.g., playing calming music, displaying the ball).

In some implementations, the device transmits first sensor information to a healthcare provider.

In some implementations, after transmitting the first sensor information, the device receives one or more instructions from the healthcare provider, and the first treatment interface is updated in accordance with the one or more instructions.

In some implementations, the updated treatment interface includes audio content and/or visual content that differs (e.g., differs in content, duration) from audio content and/or visual content of the first treatment interface.

In some implementations, the device receives a user request to initiate presentation of a second treatment program of the selected one or more treatment programs, and in response to receiving the user request, presents a second treatment interface, that correspond to the second treatment program, to the patient. While presenting the second treatment interface to the patient, the device activates one or more second sensors to record sensor information, including tracking a second activity of the patient. After presenting the second treatment interface to the patient, the device stores second sensor information received from the one or more second sensors in a patient profile, and updates the second treatment interface according to the second sensor information.

In some implementations, the second treatment program is different from the first treatment program (e.g., different behavior, content, activity, such as meditation versus slow exercise), the second treatment interface is different from the first treatment interface, and the one or more second sensors differ from the one or more first sensors.

In some implementations, the second activity is different from the first activity, and the one or more second sensors perform a different function than the one or more first sensors.

In some implementations, the device determines a stop time of the first treatment program that corresponds to a time when the device ceases to present the first treatment interface to the patient. In response to receiving the user request to initiate presentation of the second treatment program, the device determines a lapsed time between the stop time of the first treatment program and a current time and compares the lapsed time to a predetermined time period. In accordance with the lapsed time exceeding the predetermined time period, the device initiates presentation of the second treatment interface to the patient.

In some implementations, the user and the patient are a same person.

In some implementations, the user is a different person from the patient. For example, the user may be a guardian of the patient who is a child.

In some implementations, the first health condition is a condition other than: myopia, cancer cachexia, social communication disorder, mild cognitive impairment, and ophthalmologic rehabilitation.

In some implementations, the one or more treatment programs are provided for treatment regimens other than: improving antiviral immunology and strengthening a pelvic floor muscle.

Typically, an electronic device includes one or more processors, memory, a display, and one or more programs stored in the memory. The programs are configured for execution by the one or more processors and are configured to perform any of the methods described herein.

In some implementations, a non-transitory computer readable storage medium stores one or more programs configured for execution by a computing device having one or more processors, memory, and a display. The one or more programs are configured to perform any of the methods described herein.

In some implementations, a digital behavior-based treatment system includes a digital behavior and cognitive task generation unit, which converts a second user's behavior prescription prescribed to a first user into a digital behavior and cognitive task. The system includes a sensing data collection unit that collects results of performing the digital behavior and cognitive tasks from the first user, a result analysis unit that calculates the behavior and cognitive compliance of the first user with respect to the digital behavior and cognitive task based on the execution result, and a database for storing data on the digital behavior and cognitive tasks of the first user and the behavior and cognitive compliance.

In accordance with some implementations, an application allows the computing device to perform an operation including providing a digital behavior and cognitive task to a first user, collecting sensing data according to the performance of the digital behavior and cognitive task from the first user, and calculating the behavioral and cognitive compliance of the first user with respect to the digital behavior and cognitive task based on the sensing data.

The digital behavior-based treatment system and application disclosed herein make it is possible to observe the patient's performance and compliance with the doctor's behavior and cognitive prescription in real time, and data for clinical validation of physician behavioral and cognitive prescriptions can be obtained through quantification since long-term tracking and storage in a database are possible.

Thus methods and systems are disclosed that train a healthcare model to correlate health conditions with treatment programs, utilize the healthcare model to generate treatment programs for specific health conditions, and provide the generated treatment programs to patients.

Both the foregoing general description and the following detailed description are exemplary and explanatory, and are intended to provide further explanation of the invention as claimed.

BRIEF DESCRIPTION OF THE DRAWINGS

For a better understanding of these systems, methods, and graphical user interfaces, as well as additional systems, methods, and graphical user interfaces that correlate patients with treating clinicians, refer to the Description of Implementations below, in conjunction with the following drawings, in which like reference numerals refer to corresponding parts throughout the figures.

FIG. 5B provides an example of a neurobehavioral factor-behavior binary decoding table according to some implementations.

FIGS. 7A and 7B provide a flow diagram of a method for building healthcare models for selecting healthcare treatment programs according to some implementations.

FIGS. 8A-8D provide a flow diagram of a method for generating treatment programs using a trained healthcare model according to some implementations.

FIGS. 19A-19D show a table of different diseases and their corresponding neurohumoral effects, behaviors, behavioral treatment options, and treatment sensing inputs according to some implementations.

FIGS. 23A-23H illustrate examples of a web application provided to a doctor for interacting with the digital behavior-based treatment system according to some implementations.

Reference will now be made to implementations, examples of which are illustrated in the accompanying drawings. In the following description, numerous specific details are set forth in order to provide a thorough understanding of the present invention. However, it will be apparent to one of ordinary skill in the art that the present invention may be practiced without requiring these specific details.

DESCRIPTION OF IMPLEMENTATIONS

Figure 1A:
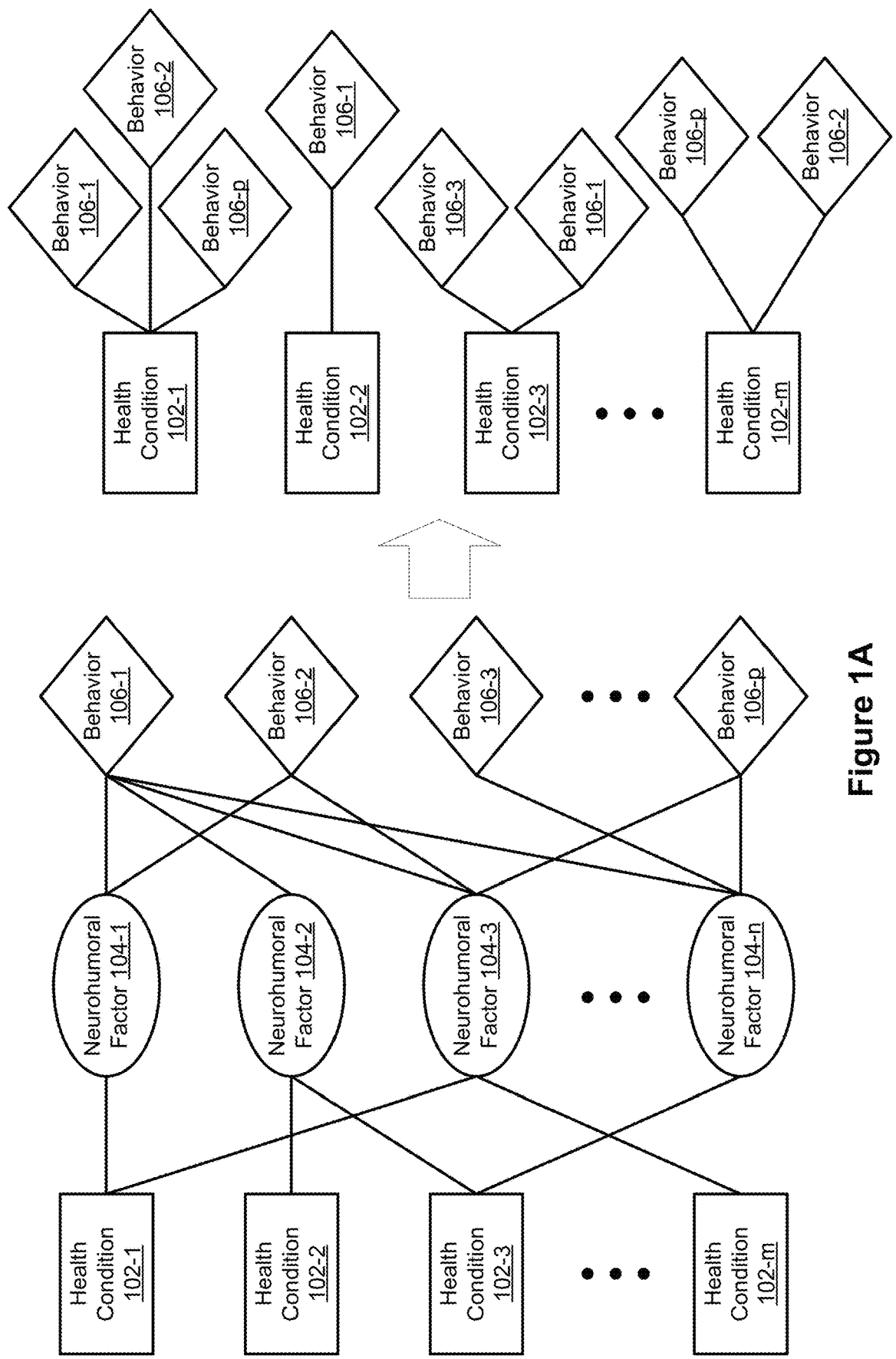
FIG. 1A illustrates training a healthcare model for determining relationships between health conditions and behaviors in accordance with some implementations.

FIG. 1A illustrates training a healthcare model to provide behaviors 106 that are associated with specific health conditions 102 (e.g., diseases, illnesses, disorders, health issues, health problems, ailments). For example, for a given health condition 102, there are numerous medical and scientific findings (such as research articles, peer-reviewed journal articles, conference proceedings) that describe neurohumoral factors 104 (NHFs) that are correlate with the health condition. For example, creatinine, metanephrine, and norepinephrine (all of which are NHFs) are known to be correlated with hypertension (e.g., high blood pressure). Additionally, for each NHF 104, there are also numerous medical and scientific findings regarding the effect specific behaviors 106 or activities can have on the NHF 104. For example, mental arithmetic stress is linked with increase in epinephrin, and dynamic exercise is linked to increases in epinephrin and norepinephrine.

A healthcare model is trained to determine (e.g., identify, learn) correlations between specific health conditions 102 and specific behaviors 106 via NHFs 104. For example, scientific and medical information may indicate correlations between a first health condition 102-1 and two NHFs 104-1 and 104-2. In turn, NHF 104-1 is known to be affected by behaviors 106-1 and 106-2, and NHF 104-2 has been found (e.g., by the scientific and/or medical community) to be affected by behaviors 106-1, 106-2, and 106-p. Thus, based on the information gathered from the medical and scientific community, a healthcare model can be trained to identify behaviors that would affect or regulate NHFs that are associated with specific diseases.

Additionally, while each of the health conditions 102-1 are correlated with different NHFs 104 and each of the NHFs are correlated with different behaviors 106, there is overlap in which behaviors 106 are correlated with which health conditions 102. For example, while health condition 102-1 and 102-2 are not correlated to the same NHFs 104, both health conditions 102-1 and 102-2 are correlated to behavior 106-1.

In some implementations, the healthcare model can be trained to provide treatment programs that are associated with specific health conditions 102 where each treatment program is associated to a specific behavior.

The examples provided above offer a high-level outline of how associations are ingested by the healthcare model during training. However, the there is a large amount of information from the medical and scientific community, each of which may be parts of a same study, may provide contradicting findings, may provide duplicate findings, and/or may vary in publication quality (e.g., journal quality). Additionally, due to the interconnectedness of the human body, a health condition may be affected (even to a small degree) by almost any action or behavior. Thus, the healthcare model is trained not only to learn the correlations between health conditions 102 and behaviors 106 (or treatment programs), but also to discern (e.g., identify, determine) and prioritize behaviors 106 that have the biggest effect or outcome for a specific health condition 102. Details regarding how the healthcare model is trained is provided with respect to FIGS. 4A and 4B.

Figure 1B:
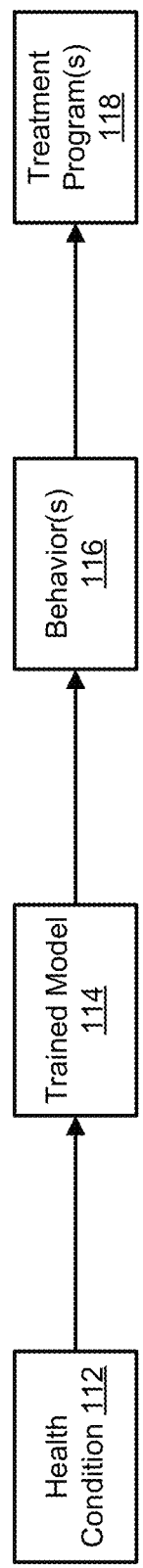
FIG. 1B illustrates using a trained healthcare model to generate treatment regimens for health conditions in accordance with some implementations.

FIG. 1B illustrates using a trained healthcare model 114 to provide treatment program(s) 118 to a patient for treating the patient's health condition 112. For example, a patient who suffers from or experiences a health condition 112 may seek out neurohumoral behavior therapy (NHBT) as a form of treatment for the health condition 112. When the health condition 112 is one of the health conditions 102 that are associated with the process of training the healthcare model 114, the trained healthcare model 114 can be used to determine what treatment program(s) 118 are suitable for this patient. The trained healthcare model 114 can identify behavior(s) 116 that are associated with the patient's health condition 112 and one or more treatment program(s) 118 that each target at least one of the behaviors 116 identified by the trained healthcare model 114 are selected for treating the patient's health condition 112.

In some implementations, the patient may have more than one health condition. In such cases, the trained healthcare model 114 may be able to identify behavior(s) 116 that can affect health conditions and inform selection of treatment program(s) 118 that do not result in contradictory activities or do not include activities that may negatively affect the patient's other health conditions.

In some implementations, a treatment program 118 includes an activity that targets a specific behavior. For example, a first treatment program 118-1 may include fast exercise (such as a circuit training or running). In another example, a second treatment program 118-2 may include a session for listening to calming music.

Figure 1C:
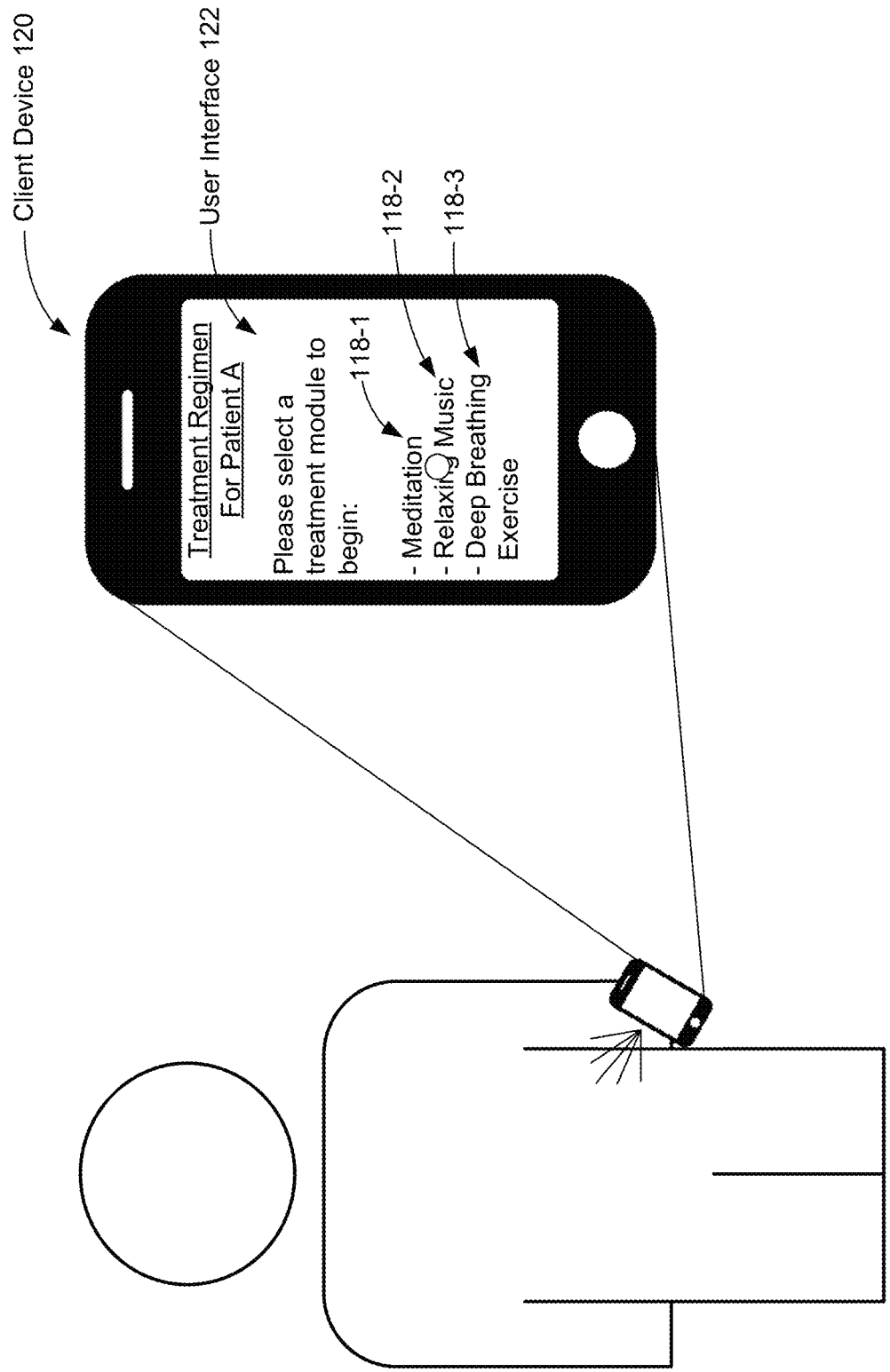
FIG. 1C illustrates providing treatment programs to patients with health conditions in accordance with some implementations.

FIG. 1C illustrates an example of providing one or more treatment programs 118 to a patients in accordance with some implementations. The one or more treatments programs 118 can be provided to a patient via a client device 120 (e.g., a user device, a personal device), such as a computing device, a personal computer, a tablet, a smart phone, or even a wearable smart device such as smart goggles or a smart watch. In the example shown in FIG. 1C, the client device 120 displays a user interface 122 that provides treatment programs 118 for treating a patient's health condition 112. Each of the treatment programs 118 are selected using the trained healthcare model 114, and each of the treatment programs 118 has a user interface associated with the respective treatment program 118. In this example, three treatment programs 118-1, 118-2, and 118-3 are provided for treating a health condition associated with Patient A. In response to receiving a user selection for the Relaxing Music treatment program 118-2, the client device 120 plays relaxing music that is intended to put the listener in a relaxed state. In some implementations, in response to receiving a user selection of the Relaxing Music treatment program 118-2, the client device 120 may display another user interface associated with the selected treatment program 118-2, such as a user interface for selecting song from a preselected list or a user interface showing a lapsed time of the treatment program 118-2.

In some implementations, while the patient is engaging with the selected treatment program 118, the treatment program 118 may cause one or more sensors on the client device 120 to be activated. For example, while Patient A is listening to relaxing music as part of the Relaxing Music treatment program 118-2, the client device 120 may activate a heart rate sensor on a wearable device (such as a smart watch or a smart band), that is part of or in communication with the client device 120, to record Patient A's heart rate. In another example, while Patient A is listening to relaxing music as part of the Relaxing Music treatment program 118-2, the client device 120 may activate a microphone on the client device 120 to track Patient A's breathing.

In some implementations, a treatment program 118 includes provision of audio content and/or video content to the patient. For example, the Relaxing Music treatment program 118-2 plays relaxing music for the patient. In another example, a treatment program for exercise may include audio instructions, such as "next, do ten push-ups," as well as a visual demonstration of a push-up. In yet another example, a treatment program for improving reaction time may provide an activity in a game-like format, where the user has to tap icons as they appear on the screen of the client device 120.

In some implementations, the patient and the user are the same person. For example, Patient A may also be a user of the client device 120 and is be able to input user information or make user selections on client device 120. In some implementations, the patient and the user are different people. For example, the patient may be a child, a minor, a technologically-challenged person, or a person who does not possess the necessary functions (e.g., loss of limb, physically or intellectually disabled person) required to provide user input or make user selections on the client device 120. For example, Patient A may be a child or an elderly person, and the user may be a caretaker or guardian of Patient A.

In some implementations, the one or more treatment programs are provided (e.g., administered or prescribed) to a patient via an digital behavior-based treatment system, details of which are included below with respect to FIG. 1D.

Figure 1D:
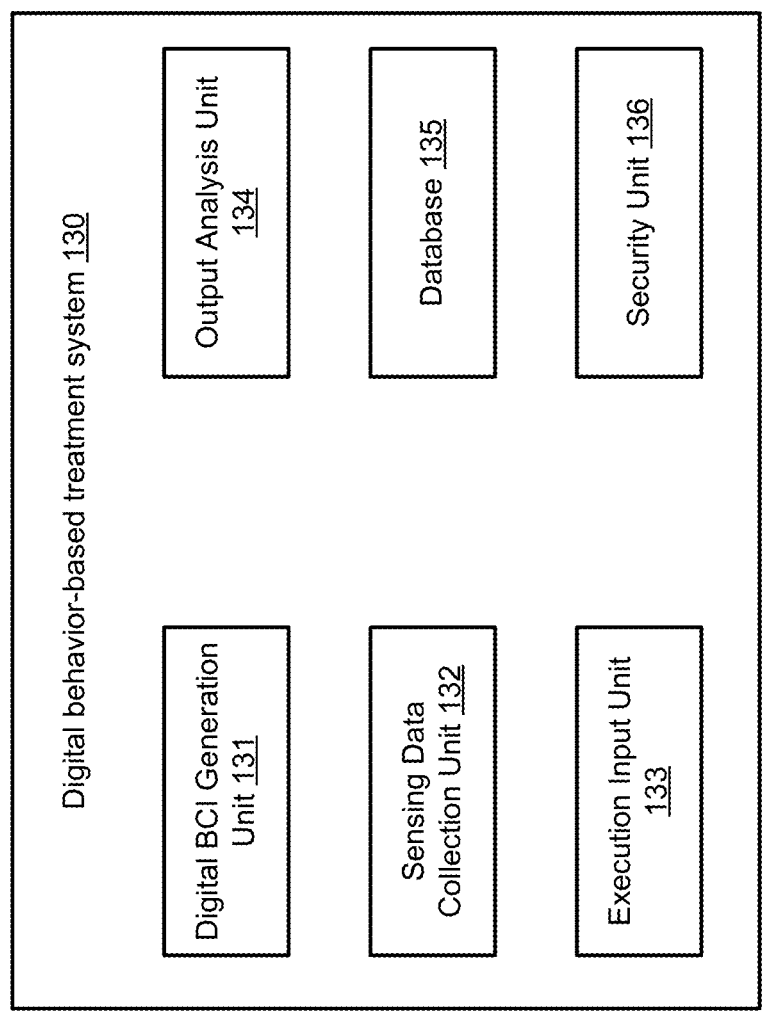
FIG. 1D is a block diagram illustrating a configuration module of a digital behavior-based treatment system in accordance with some implementations.

FIG. 1D is a block diagram illustrating a configuration module of a digital behavior-based treatment system 130 in accordance with some implementations. In some implementations, a digital behavior-based treatment system 130 includes a digital behavior and cognitive task generation unit 131, a sensing data collection unit 132, an execution input unit 133, a result collection 134, a database 135, and a security unit 136.

The digital behavior and cognitive task generation unit 131 may provide a digital behavior and cognitive task to a first user (e.g., a patient). In this case, the digital behavior and cognitive task generation unit 131 may convert the behavior and cognitive prescription provided by the doctor into a detailed digital behavior and cognitive task. In some implementations, the digital behavioral and cognitive task is a behavioral command provided to the patient in the form of a clear task for the purpose of disease treatment, and requires the patient's active, specific, and data-enabled behavior. For example, a digital behavioral and cognitive task may include presentation of a specific task of a behavioral and cognitive prescription from a second user (e.g., a doctor, physician) to a patient, and the indication form may consist of visual, auditory, tactile, motion, or a combination thereof.

In some implementations, the digital behavior and cognitive task generation unit 131 receives personal information from a patient and generates a personalized digital behavior and cognitive task based on the patient's information. For example, patient information may include patient medical information, digital environment, and information on patient participation, as described below.

In addition, the digital behavior and cognitive task generation unit 131 may provide a patient-tailored digital behavior and cognitive task through artificial intelligence and big data analysis on data on the patient's digital behavior and behavior compliance of the cognitive task. The degree of compliance with the digital behavior and cognitive tasks refers to the degree to which the patient performs the digital behavior and cognitive tasks provided based on the doctor's prescription.

In some implementations, the sensing data collection unit 132 collects sensing data according to a patient's digital behavior and performance of a cognitive task. In some implementations, the sensing data collection unit 132 is an output unit of various sensor devices. For example, the sensing data collection unit 132 measures the amount of activity, heart rate, and electrocardiogram with the use of a wearable device; collects image data through video recording; and/or or collects information about the results of behavioral and cognitive tasks with the use of various other sensors. In some implementations, the sensing data collection unit 132 collects information regarding the patient's performance results. In addition, the configuration of the sensing data collection unit 132 may vary in combination according to a disease and a treatment method. In addition, the configuration of the sensing data collection unit 132 may vary in combination according to a disease and a treatment method.

The performance input unit 030 may receive an input regarding a result of performing a digital action and a cognitive task from a patient. That is, in the digital behavior-based treatment system 130 according to some implementations of the present invention, the sensing data on the behavior of the patient and the performance of the cognitive task may be received through the sensing data collection unit 020, but, separately, the patient may directly record data on task performance through the performance input unit 030.

In some implementations, the result analysis unit 134 calculates a degree of compliance to a patient's behavior for a digital behavior and cognitive task based on the sensing data collected from the sensing data collection unit 132. In some implementations, the result analysis unit 134 calculates a degree of compliance to a patient's behavior for a digital behavior and a cognitive task based on the task performance result information directly input from the patient through the performance input unit 133.

In some implementations, the result analysis unit 134 repeatedly performs a process of calculating the degree of behavior compliance with respect to the patient's digital behavior and cognitive task a plurality of times. In this case, the result analysis unit 134 calculates the patient's digital behavior and cognitive task and behavior compliance for the current round by using the data on the patient's digital behavior and cognitive task and behavior compliance provided in the previous round. In some implementations, the result analysis unit 134 implements an optimization of a patient-specific behavior and cognitive prescription suitable for a patient through a feedback loop, as described below.

In some implementations, the result analysis unit 134 collects the calculated behavioral compliance level of the patient at a preset period and reports it externally (e.g., to an external system, an external database, an external application). Therefore, the doctor can continuously monitor the progress of digital behavior and cognitive tasks through the application to be described below, even if the patient does not directly visit the hospital.

In some implementations, the database 135 stores data on a patient's digital behavior and cognitive tasks and behavioral compliance. Therefore, if necessary, the patient and the doctor can utilize information such as digital behavior and cognitive tasks stored in the database 134, a history of task performance, and behavior compliance, through an application. In addition, the database 135 may store the above-described patient medical information, digital environment, information on patient participation, and the like.

In some implementations, the security unit 136 encrypts and manages data on the patient's digital behavior and cognitive tasks and behavior compliance. In order to protect personal information, it is essential to transmit encrypted information between a doctor and a patient who has consented to digital treatment and to operate a security server. Accordingly, in some implementations, the security unit 136 encrypts and protects related information such as digital treatment and result data for the patient's disease.

As described above, by utilizing the digital behavior-based treatment system 130, it is possible to observe in real time whether the patient has adhered to (e.g., complied with, performed tasks in accordance with) the doctor's behavior and cognitive prescription, and the degree of compliance thereof, and long-term tracking of task-performance and storage in a database. Additionally, the data for clinical validation of the doctor's behavioral and cognitive prescriptions can be obtained through quantification of the data.

In addition, in the digital behavior-based treatment system, performance data on the patient's behavior and cognitive prescription can be used as important primary data for a doctor's clinical decision at a later visit. Furthermore, the accumulated behavioral and cognitive task-performance data can be combined with big data analysis and artificial intelligence analysis to be used for the development and improvement of patient-specific behavioral and cognitive prescriptions.

Figure 2A:
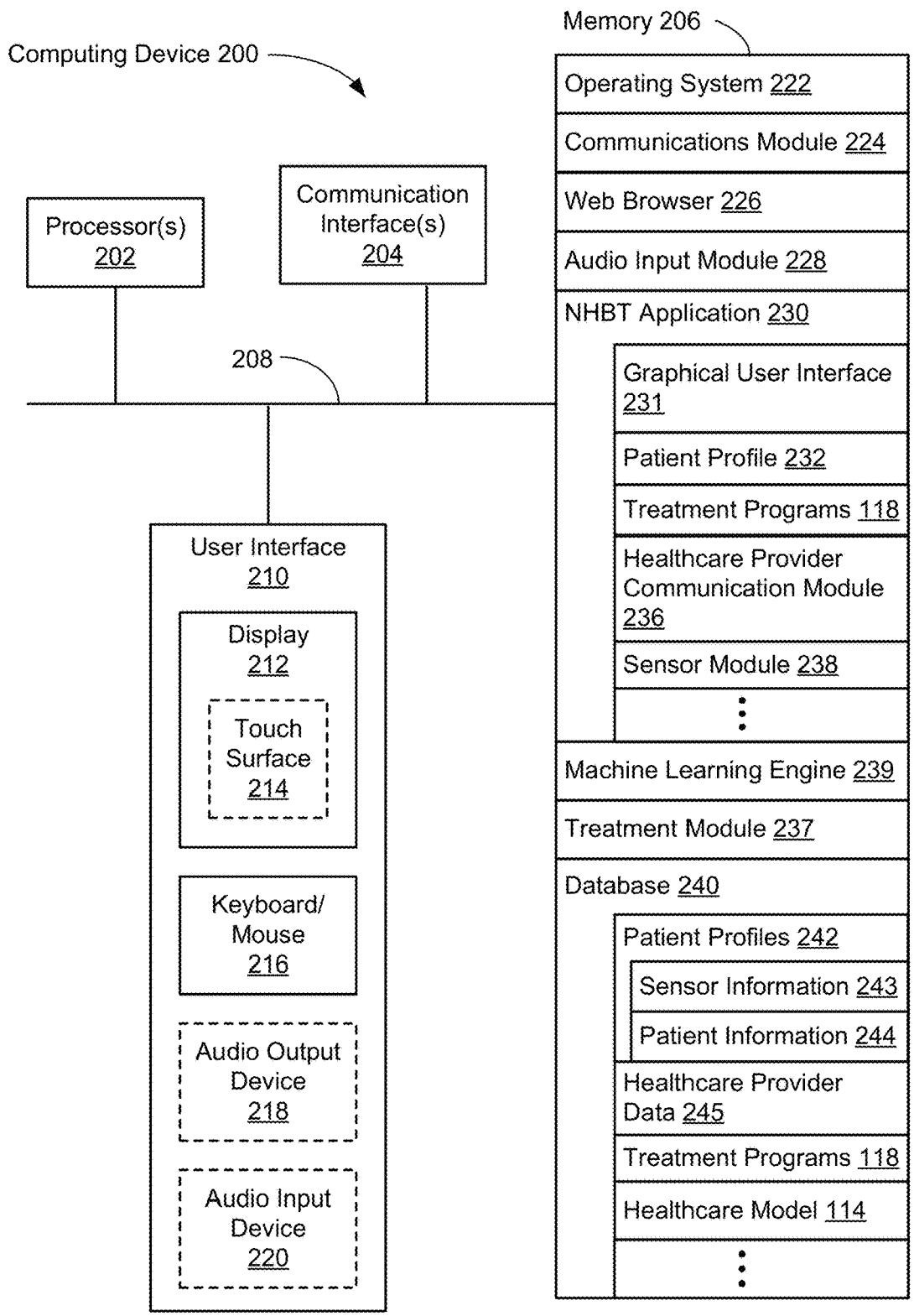
FIG. 2A is a block diagram illustrating a computing device according to some implementations.

FIG. 2A is a block diagram illustrating a computing device 200, corresponding to a computing system, which can train and/or execute healthcare model 114 in accordance with some implementations. Various examples of the computing device 200 include a desktop computer, a laptop computer, a tablet computer, a server computer, a server system, a wearable device such as a smart watch, and other computing devices that have a processor capable of training healthcare model(s) 114, running machine learning algorithm 239 for training healthcare model(s) 114, and/or running trained healthcare model(s) 114. The computing device 200 may be a data server that hosts one or more databases (e.g., database of images or videos), models, or modules, or may provide various executable applications or modules. The computing device 200 typically includes one or more processing units (processors or cores) 202, one or more network or other communications interfaces 204, memory 206, and one or more communication buses 208 for interconnecting these components. The communication buses 208 optionally include circuitry (sometimes called a chipset) that interconnects and controls communications between system components. The computing device 200 typically includes a user interface 210. The user interface 210 typically includes a display device 212 (e.g., a screen or monitor). In some implementations, the computing device 200 includes input devices such as a keyboard, mouse, and/or other input buttons 216. Alternatively or in addition, in some implementations, the display device 212 includes a touch-sensitive surface 214, in which case the display device 212 is a touch-sensitive display. In some implementations, the touch-sensitive surface 214 is configured to detect various swipe gestures (e.g., continuous gestures in vertical and/or horizontal directions) and/or other gestures (e.g., single/double tap). In computing devices that have a touch-sensitive display 214, a physical keyboard is optional (e.g., a soft keyboard may be displayed when keyboard entry is needed). The user interface 210 also includes an audio output device 218, such as speakers or an audio output connection connected to speakers, earphones, or headphones. Furthermore, some computing devices 200 use a microphone 220 and voice recognition software to supplement or replace the keyboard. An audio input device 220 (e.g., a microphone) captures audio (e.g., speech from a user).

The memory 206 includes high-speed random-access memory, such as DRAM, SRAM, DDR RAM, or other random-access solid-state memory devices; and may include non-volatile memory, such as one or more magnetic disk storage devices, optical disk storage devices, flash memory devices, or other non-volatile solid-state storage devices. In some implementations, the memory 206 includes one or more storage devices remotely located from the processors 202. The memory 206, or alternatively the non-volatile memory devices within the memory 206, includes a non-transitory computer-readable storage medium. In some implementations, the memory 206 or the computer-readable storage medium of the memory 206 stores the following programs, modules, and data structures, or a subset or superset thereof.

- an operating system 222, which includes procedures for handling various basic system services and for performing hardware dependent tasks;
- a communications module 224, which is used for connecting the computing device 200 to other computers and devices via the one or more communication network interfaces 204 (wired or wireless), such as the Internet, other wide area networks, local area networks, metropolitan area networks, and so on;
- a web browser 226 (or other application capable of displaying web pages), which enables a user to communicate over a network with remote computers or devices;
- an audio input module 228 (e.g., a microphone module) for processing audio captured by the audio input device 220. The captured audio may be sent to a remote server and/or processed by an application executing on the computing device 200 (e.g., health care application 230);
- a NHBT application 230, which includes a graphical user interface 231 that allows a user to navigate the NHBT application 230, such as accessing a patient profile 232, viewing patient information for the patient profile 232, and selecting treatment programs 118. In some implementations, the NHBT application 230 may utilize a healthcare provider communication module 235 to send patient information, such as adherence information or sensor information to a healthcare provider. The NHBT application 230 may also utilize the healthcare provider communication module 235 to receive instructions from a healthcare provider to update or modify one or more treatment programs 118. In some implementations, the NHBT application 230 may include a sensor module 238 that stores information regarding sensor configurations for tracking user activity or user adherence to the treatment programs 118;
- a machine learning engine 239 configured to train a healthcare model 114 to correlate health conditions with treatment programs 118 and/or to train healthcare model 114 to correlate health conditions with behaviors 106;
- treatment module 237 configured to generate treatment programs 118 and/or modify treatment programs 118 to generate customized treatment programs that are customized for a specific patient based on the patient's patient profile 242; and
- a database 240, which stores information, such as patient profiles 242, healthcare provider data 245, treatment programs 118, and healthcare model 114. Patient profile 232 may include sensor information 243, such as user adherence information and/or use progress information, and patient information 244, such as age, gender, weight height, diagnosis, and health care provider.

In some implementations, the memory 206 stores metrics and/or scores determined by the healthcare model 114, such a calculated weights or correspondence coefficients between health conditions 102 and NHFs 104 and/or calculated weights or correspondence coefficients between NHFs 104 and behaviors 106. In addition, the memory 206 may store thresholds and other criteria, which are compared against the metrics and/or scores determined by the healthcare model 114. For example, for a given health condition 102, the healthcare model 114 may identify (e.g., output) the top three or top five behaviors 106 that are determined have the highest correspondence or correlation with the health condition.

Each of the above identified executable modules, applications, or sets of procedures may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 206 stores a subset of the modules and data structures identified above. Furthermore, the memory 206 may store additional modules or data structures not described above.

Although FIG. 2A shows a computing device 200, FIG. 2A is intended more as a functional description of the various features that may be present rather than as a structural schematic of the implementations described herein. In practice, and as recognized by those of ordinary skill in the art, items shown separately could be combined and some items could be separated.

Figure 2B:
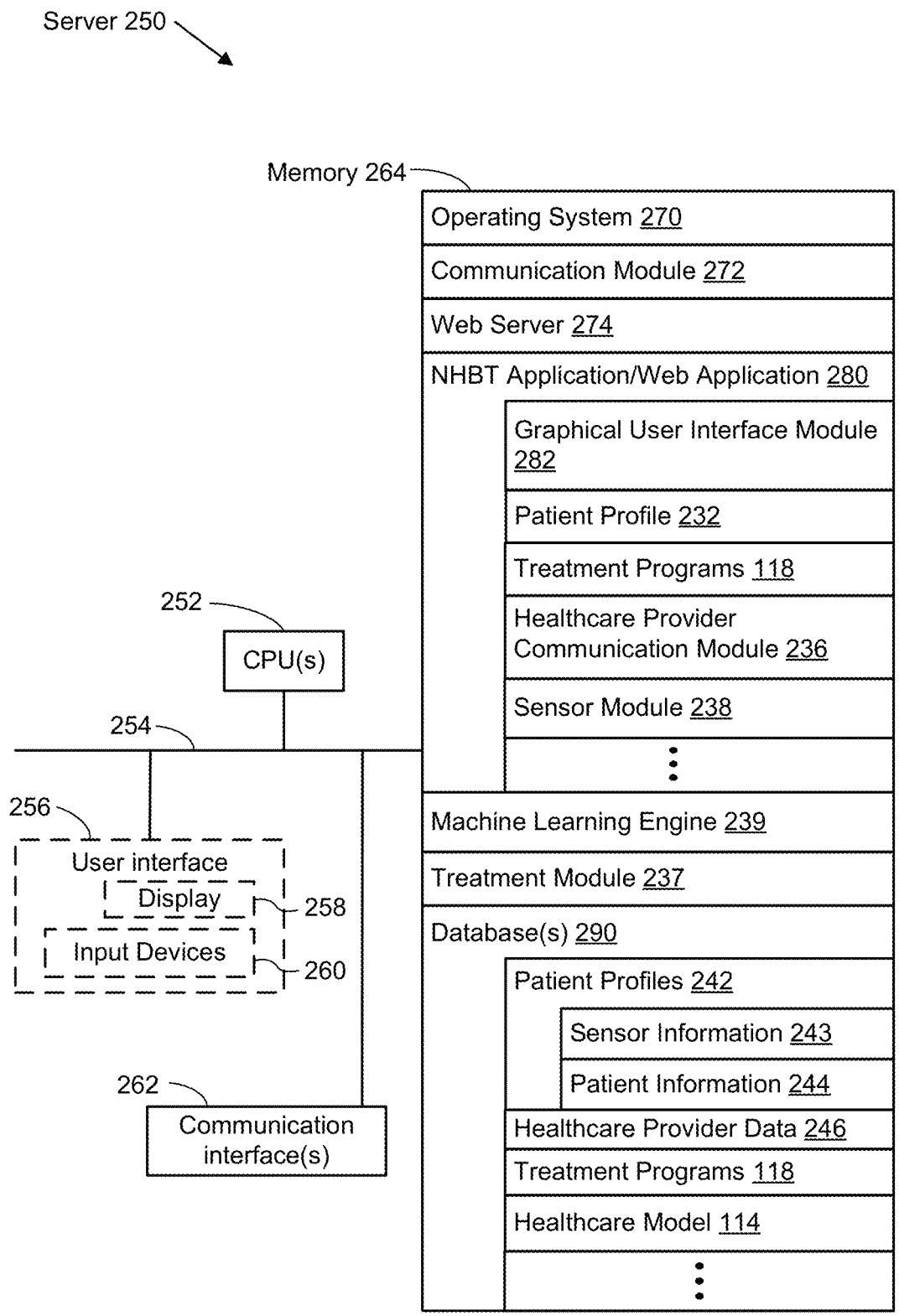
FIG. 2B is a block diagram illustrating a server according to some implementations.

FIG. 2B is a block diagram of a server 250 in accordance with some implementations. A server 250 may host one or more databases 240 or may provide various executable applications or modules. A server 250 typically includes one or more processing units/cores (CPUs) 252, one or more network interfaces 262, memory 264, and one or more communication buses 254 for interconnecting these components. In some implementations, the server 250 includes a user interface 256, which includes a display 258 and one or more input devices 260, such as a keyboard and a mouse. In some implementations, the communication buses 254 include circuitry (sometimes called a chipset) that interconnects and controls communications between system components.

In some implementations, the memory 264 includes high-speed random-access memory, such as DRAM, SRAM, DDR RAM, or other random-access solid-state memory devices, and may include non-volatile memory, such as one or more magnetic disk storage devices, optical disk storage devices, flash memory devices, or other non-volatile solid-state storage devices. In some implementations, the memory 264 includes one or more storage devices remotely located from the CPU(s) 252. The memory 264, or alternatively the non-volatile memory devices within the memory 264, comprises a non-transitory computer readable storage medium.

In some implementations, the memory 264, or the computer readable storage medium of the memory 264, stores the following programs, modules, and data structures, or a subset thereof:
- an operating system 270, which includes procedures for handling various basic system services and for performing hardware dependent tasks;
- a network communication module 272, which is used for connecting the server 250 to other computers via the one or more communication network interfaces (wired or wireless) and one or more communication networks, such as the Internet, other wide area networks, local area networks, metropolitan area networks, and so on;
- a web server 274 (such as an HTTP server), which receives web requests from users and responds by providing responsive web pages or other resources;
- a NHBT application or a NHBT web application 280, which may be downloaded and executed by a web browser 226 on a user's computing device 200. In general, an NHBT web application 280 has the same functionality as a desktop NHBT application 230, but provides the flexibility of access from any device at any location with network connectivity, and does not require installation and maintenance. In some implementations, the NHBT web application 280 includes various software modules to perform certain tasks. In some implementations, the NHBT web application 280 includes a graphical user interface module 282, which provides the user interface for all aspects of the NHBT web application 280;
- in some implementations, the NHBT web application 280 includes patient profiles 232, treatment programs 118, healthcare provider communication module 236, and sensor module 238, as described above for a computing device 200;
- a machine learning engine 239, as described above for a computing device 200;
- a treatment module 237, as described above for a computing device 200; and
- one or more databases 290, which store data used or created by the NHBT web application 280 or NHBT application 230. The databases 290 may store patient profiles 242 (e.g., patient data, including sensor information 243 and patient information 244), healthcare provider data 246, treatment programs 118, and healthcare model 114, as described above.

Each of the above identified executable modules, applications, or sets of procedures may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 264 stores a subset of the modules and data structures identified above. In some implementations, the memory 264 stores additional modules or data structures not described above.

Although FIG. 2B shows a server 250, FIG. 2B is intended more as a functional description of the various features that may be present rather than as a structural schematic of the implementations described herein. In practice, and as recognized by those of ordinary skill in the art, items shown separately could be combined and some items could be separated. In addition, some of the programs, functions, procedures, or data shown above with respect to a server 250 may be stored or executed on a computing device 200. In some implementations, the functionality and/or data may be allocated between a computing device 200 and one or more servers 250. Furthermore, one of skill in the art recognizes that FIG. 2B need not represent a single physical device. In some implementations, the server functionality is allocated across multiple physical devices that comprise a server system. As used herein, references to a "server" include various groups, collections, or arrays of servers that provide the described functionality, and the physical servers need not be physically collocated (e.g., the individual physical devices could be spread throughout the United States or throughout the world).

Figure 3:
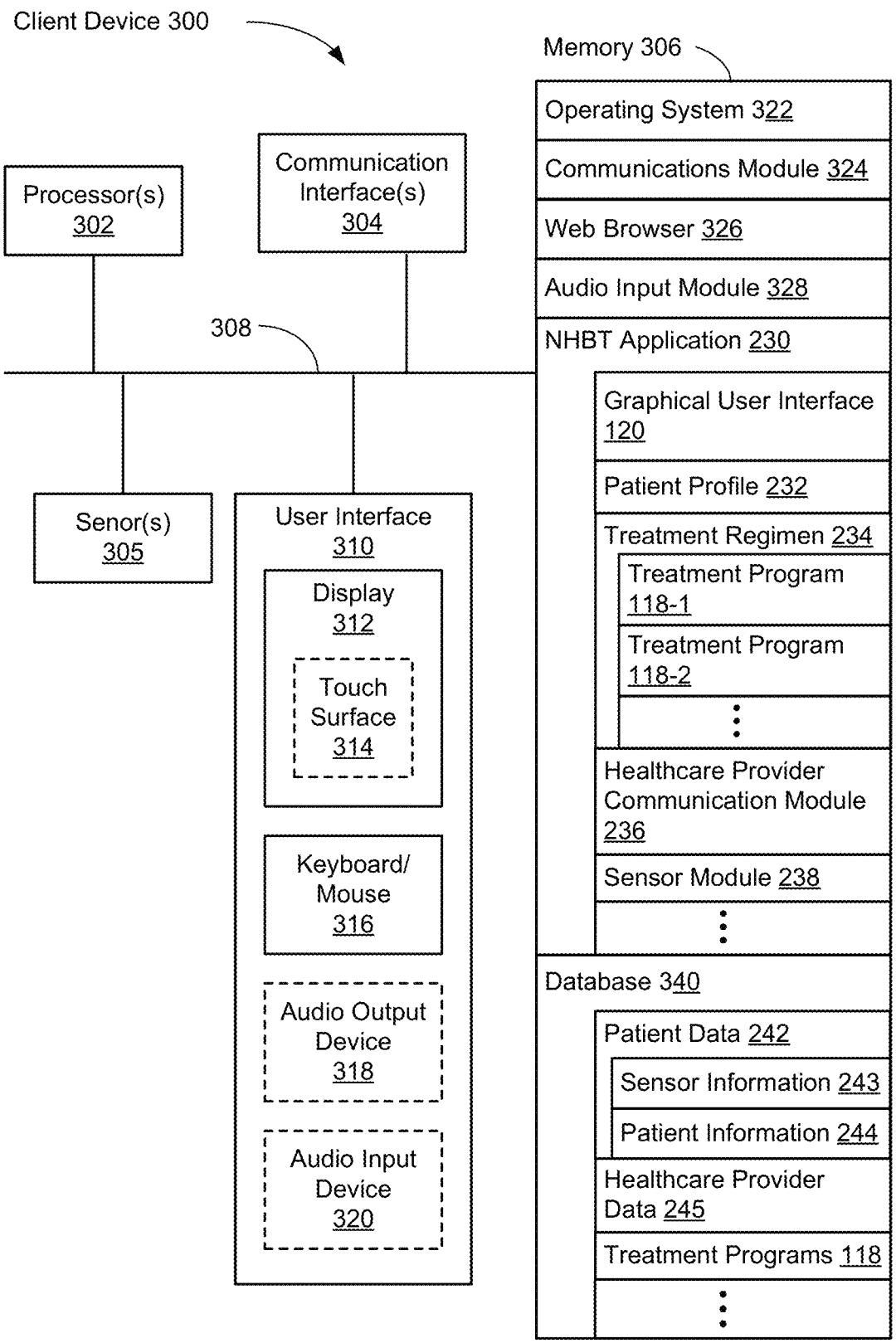
FIG. 3 is a block diagram illustrating a client device according to some implementations.

FIG. 3 is a block diagram illustrating a client device 300 (e.g., a user device corresponding to client device 120 shown in FIG. 1C), corresponding to a computing system, which can execute NHBT application 230 or NHBT web application 280 in accordance with some implementations. Various examples of the client device 300 include a desktop computer, a laptop computer, a tablet computer, a server computer, a server system, a wearable device such as a smart watch, and other computing devices that have a processor capable of running NHBT application 230 or NHBT web application 280. The client device 300 typically includes one or more processing units (processors or cores) 302, one or more network or other communications interfaces 304, memory 306, and one or more communication buses 308 for interconnecting these components. The communication buses 308 optionally include circuitry (sometimes called a chipset) that interconnects and controls communications between system components. The client device 300 typically includes a user interface 310. The user interface 310 typically includes a display device 312 (e.g., a screen or monitor). In some implementations, the client device 300 includes input devices such as a keyboard, mouse, and/or other input buttons 316. Alternatively or in addition, in some implementations, the display device 312 includes a touch-sensitive surface 314, in which case the display device 312 is a touch-sensitive display. In some implementations, the touch-sensitive surface 314 is configured to detect various swipe gestures (e.g., continuous gestures in vertical and/or horizontal directions) and/or other gestures (e.g., single/double tap). In computing devices that have a touch-sensitive display 314, a physical keyboard is optional (e.g., a soft keyboard may be displayed when keyboard entry is needed). The user interface 310 also includes an audio output device 318, such as speakers or an audio output connection connected to speakers, earphones, or headphones. Furthermore, some client device 300 use a microphone 320 and voice recognition software to supplement or replace the keyboard. An audio input device 320 (e.g., a microphone) captures audio (e.g., speech from a user). In some implementations, the client device 300 includes or is in communication with one or more sensors 305 that are configurable to track or monitor specific activities or motions. For example, a sensor of the one or more sensors 305 may be a microphone configured to track a user's breathing or monitor for sounds during a user's relaxation treatment. In another example, a sensor of the one or more sensors 305 may include a gyro meter or accelerometer configured to track or monitor movement of the device (such as movement of a user's arm when the device is a smart watch or fitness band). In yet another example, a sensor of the one or more sensors 305 may include a camera that is configured to track a user's eye movement during and eye movement treatment. Different treatment programs 118 may employ different sensors, and in some cases, two different treatment programs 118 may employ a same sensor but utilize the sensor in different ways and/or to track different activities.

The memory 306 includes high-speed random-access memory, such as DRAM, SRAM, DDR RAM, or other random-access solid-state memory devices; and may include non-volatile memory, such as one or more magnetic disk storage devices, optical disk storage devices, flash memory devices, or other non-volatile solid-state storage devices. In some implementations, the memory 306 includes one or more storage devices remotely located from the processors 302. The memory 306, or alternatively the non-volatile memory devices within the memory 306, includes a non-transitory computer-readable storage medium. In some implementations, the memory 306 or the computer-readable storage medium of the memory 306 stores the following programs, modules, and data structures, or a subset or superset thereof:

an operating system 322, which includes procedures for handling various basic system services and for performing hardware dependent tasks;
a communications module 324, which is used for connecting the client device 300 to other computers and devices via the one or more communication network interfaces 304 (wired or wireless), such as the Internet, other wide area networks, local area networks, metropolitan area networks, and so on;
a web browser 326 (or other application capable of displaying web pages), which enables a user to communicate over a network with remote computers or devices;
an audio input module 328 (e.g., a microphone module) for processing audio captured by the audio input device 320. The captured audio may be sent to a remote server and/or processed by an application executing on the client device 300 (e.g., health care application 230);
an NHBT application 230, which includes a graphical user interface 231 that allows a user to navigate the NHBT application 230, such as accessing a patient profile 232, providing patient information for the patient profile 232, and selecting treatment programs 118 from a generated treatment regimen 234. In some implementations, the NHBT application 230 may utilize a healthcare provider communication module 235 to send patient information, such as adherence information or sensor information to a healthcare provider. The NHBT application 230 may also utilize the healthcare provider communication module 235 to receive instructions from a healthcare provider to update or modify one or more treatment programs 118 of a patient's treatment regimen 234. In some implementations, the NHBT application 230 may include a sensor module 238 that stores information regarding sensor configurations for tracking user activity or user adherence to the treatment programs 118. The NHBT application 230 may perform any of these functions locally on the client device 300, or may perform any of these functions via communications with the computing device 200 and/or server 250 described above with respect to FIGS. 2A and 2B. For example, the client device 300 may not directly send sensor information directly to a healthcare provider, but may communicate with computer system 200 and/or server 250 in order to transmit the sensor information to the healthcare provider. In another example, a user may input information into the graphical user interface 231 of the client device 300, such as a health condition for which the user wishes to see treatment program 118 options. All available treatment programs 118 may be stored on the computing device 200 and/or the server 250, the computing device 200 and/or the server 250 may use the healthcare model 114 to identify appropriate treatment programs 118, and the computing device 200 and/or the server 250 may transmit only the identified treatment programs 118 for presentation and execution at the client device 300; and
a database 240, which stores information, such as patient profiles 242, healthcare provider data 245, and treatment programs 118. Patient profile 232 may include sensor information 243, such as user adherence information and/or use progress information, and patient information 244, such as age, gender, weight height, diagnosis, and health care provider.

Each of the above identified executable modules, applications, or sets of procedures may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 306 stores a subset of the modules and data structures identified above. Furthermore, the memory 306 may store additional modules or data structures not described above.

Although FIG. 3 shows a client device 300, FIG. 3 is intended more as a functional description of the various features that may be present rather than as a structural schematic of the implementations described herein. In practice, and as recognized by those of ordinary skill in the art, items shown separately could be combined and some items could be separated.

Figure 4A:
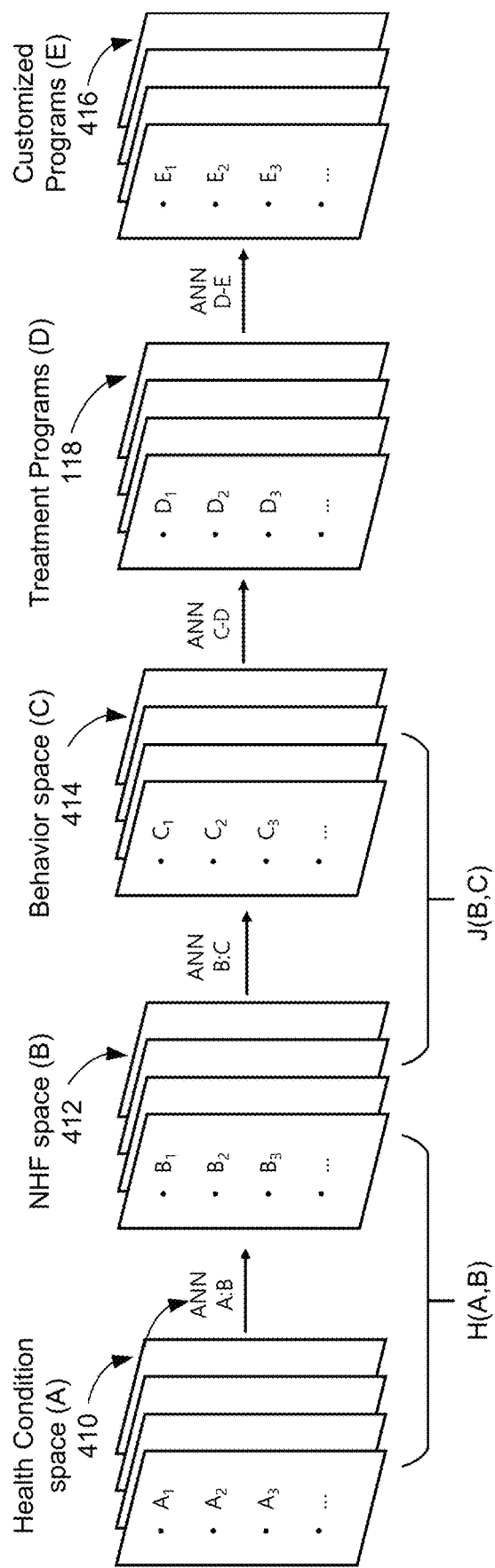
FIGS. 4A-4B illustrate training a healthcare model according to some implementations.
Figure 4B:
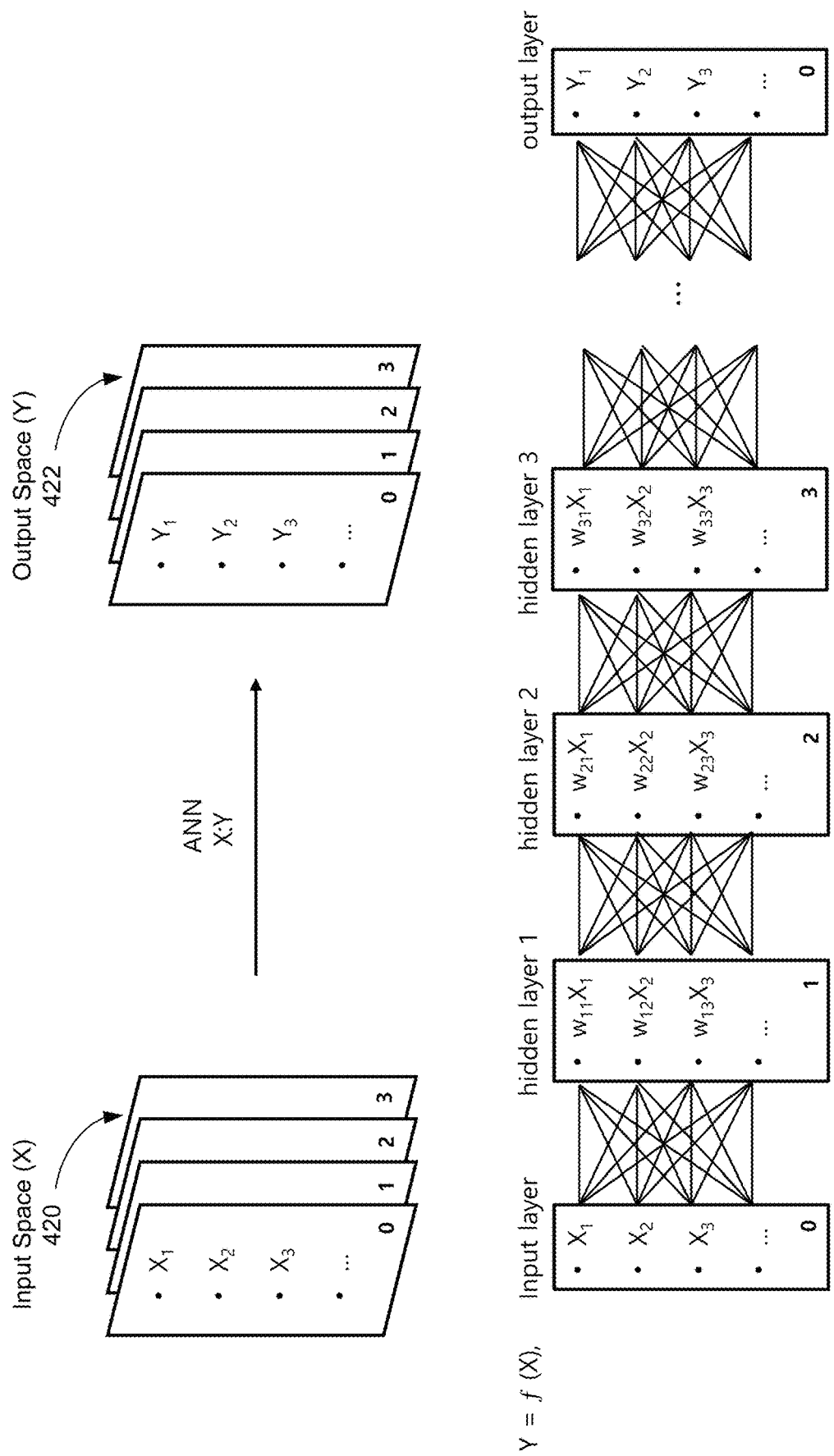

FIGS. 4A-4B illustrate training a healthcare model 114 to determine relationships between health conditions 102 and treatment programs 118 according to some implementations. FIG. 4A illustrates a health condition space 410, an NHF space 412, and a behavior space 414 (e.g., treatment behavior space), treatment programs 118, and customized treatment programs 416.

The health condition space 410 includes a plurality of distinct health conditions 102, each of which is represented in FIG. 4A by the variable A such that $A_1$ corresponds to a first health condition, $A_2$ corresponds to a second health condition, $A_3$ corresponds to a third health condition, and so on and so forth. Thus, each health condition 102 in the plurality of health conditions is different from another health condition in the plurality of health conditions (e.g., $A_1$ corresponds to a first health condition and $A_2$ corresponds to a second health condition that is different from the first health condition, such as $A_1$ represents myopia and $A_2$ represents anxiety).

The NHF space 412 includes a plurality of distinct NHFs 104, each of which is represented in FIG. 4A by the variable B such that $B_1$ corresponds to a first NHF, $B_2$ corresponds to a second NHF, $B_3$ corresponds to a third NHF, and so on and so forth. Thus, each NHF 104 in the plurality of NHFs is different from another NHF in the plurality of health conditions (e.g., $B_1$ corresponds to a first NHF and $B_2$ corresponds to a second NHF that is different from the first NHF, such as $B_1$ represents cortisone and $B_2$ represents dopamine).

The behavior space 414 includes a plurality of distinct behaviors 106, each of which is represented in FIG. 4A by the variable C such that $C_1$ corresponds to a first behavior, $C_2$ corresponds to a second behavior, $C_3$ corresponds to a third behavior, and so on and so forth. Thus, each behavior 106 in the plurality of behaviors is different from another behavior in the plurality of behaviors (e.g., $C_1$ corresponds to a first behavior and $C_2$ corresponds to a second behavior that is different from the first behavior, such as $C_1$ represents breathing and $C_2$ represents fast exercise).

A plurality of treatment programs 118 are each represented in FIG. 4A by the variable D such that $D_1$ corresponds to a first treatment program, $D_2$ corresponds to a second treatment program, $D_3$ corresponds to a third treatment program, and so on and so forth. Thus, each treatment program 118 in the plurality of treatment program is different from another treatment program in the plurality of treatment programs (e.g., $D_1$ corresponds to a first treatment program and $D_2$ corresponds to a second treatment program that is different from the first treatment program, such as $D_1$ represents a slow exercise treatment program such as yoga and $D_2$ represents a meditation treatment program such as mindfulness).

A plurality of customized treatment programs 416 are each represented in FIG. 4A by the variable E such that $E_1$ corresponds to a first customized treatment program, $E_2$ corresponds to a second customized treatment program, $E_3$ corresponds to a third customized treatment program, and so on and so forth. Thus, each customized treatment program 416 corresponds to a treatment program 118. A customized treatment program 416 is based on a corresponding treatment program 118 that has been modified in one or more ways to a specific user (e.g., $E_1$ corresponds to $D_1$). For example, a treatment program 118 for fast exercise may include five exercises completed for 6 minutes each, for a total of 30 minutes. A customized treatment program 416 for a first patient may include the same five exercises from treatment program 118, but may require that the first patient perform each exercise for only 2 minutes. This modification to the treatment program 118 to generate the customized treatment program 416 may be implemented based on instructions received from a healthcare provider of the first patient, or may be automatically implemented based on information about the patient (e.g., from the patient's profile), such as the patient's age, weight, height, or other health conditions that the patient may be suffering from.

For a respective health condition 102 (e.g., health condition $A_1$) in the health condition space 410, a machine learning engine 239 for training healthcare model 114 receives a plurality of NHFs that are each specified to be correlated to the respective health condition 102. The correlation between the NHFs 104 and the respective health condition 102 are specified by medical and/or scientific findings through the publication of a first plurality of scientific documents, P, such as a medical and/or scientific publication in a peer reviewed journal, a published abstract at a medical and/or scientific conference, a published medical book, or a presentation at a medical and/or scientific conference. For example, for the respective health condition 102 (e.g., health condition $A_1$), a first scientific document $P_1$ (e.g., a conference proceeding), may identify an NHF $B_1$ as being correlated with the respective health condition $A_1$, and a second scientific document $P_2$ (e.g., an article in a medical journal), may identify a two NHFs, $B_2$ and $B_3$, as being correlated with the respective health condition. In this example, the machine learning engine 239 receives the information from the first and second scientific documents as $P_1(B_1)$ and $P_2(B_2, B_3)$, respectively. This process is executed for every health condition 102 that the healthcare model 114 will be trained to correlate (e.g., associate) with a behavior 106 (or to correlate with a treatment program 118). In some implementations, the information from the first plurality of scientific documents is automatically extracted from each scientific document of the first plurality of scientific documents. In some implementations, the information from the first plurality of scientific documents is manually extracted from each scientific document of the first plurality of scientific documents and manually entered into the machine learning engine 239 for the purpose of training healthcare model 114.

The machine learning engine 239 calculates a respective correlation coefficient H(A,B) between each respective health condition (A) and each NHF (B) correlated with the respective health condition. For example, a correlation coefficient between health condition $A_1$ and NHF $B_1$ is represented as $H(A_1,B_1)$ in FIG. 4A. A calculated correlation coefficient between a respective health condition and a respective NHF correlated with the respective health condition is determined based on a frequency of the respective NHF appearing in the first plurality of scientific documents, and/or a quality of the scientific document(s) in the first plurality of scientific documents that identify the correlation between the respective NHF and the respective health condition. For example, for a first health condition $A_1$, the first plurality of scientific documents may collectively identify 15 different NHFs, $B_1$ through $B_{15}$, as being correlated to the first health condition $A_1$. Additionally, each of the NHFs may present with different frequencies. For example, NHF $B_1$ may have been specified by 10 papers as being correlated with health condition $A_1$, NHF $B_2$ may have been specified by 24 papers as being correlated with health condition $A_1$, and NHF $B_3$ may have been specified by 1 paper as being correlated with health condition $A_1$. Additionally, the scientific documents in the first plurality of scientific documents may vary in quality. For example, scientific document $P_1$ may be an article with a high number of citations that is published in a highly reputable medical journal with a high impact factor. In contrast, scientific document $P_2$ may be an article with a low number of citations that is published in a mediocre journal with an average impact factor. In yet another example, scientific document $P_3$ may be a conference proceeding with a low number of citations that is published in association with a well-regarded (e.g., well-known, well-attended) scientific conference. In some implementations, each of these scientific documents, $P_1$ through $P_3$, are assigned an associated weight based on one or more metrics of quality, such as a number of citations, an impact factor of the journal in which the article is published, etc. Thus, a respective correspondence coefficient between a respective health condition and a respective NHF correlated with the respective health condition may be determined using any of the information (e.g., any combination) of the metrics (with regards to frequency and quality) described above.

For a respective NHF 104 (e.g., NHF $B_1$) in the NHF space 412 (as determined by the addition of NHFs 104 into the NHF space 412 based on specification, by the first plurality of scientific documents, of the NHF being correlated to at least one health condition 102 of the plurality of health conditions in the health condition space 410), the machine learning engine 239 receives a plurality of behaviors 106 that are each specified to be correlated to the respective NHF 104. The correlation between the behaviors and the respective NHF 104 are specified by medical and/or scientific findings through the publication of a second plurality of scientific documents, Q, such as a medical and/or scientific publication in a peer reviewed journal, a published abstract at a medical and/or scientific conference, a published medical book, or a presentation at a medical and/or scientific conference. For example, for the respective NHF 104 (e.g., NHF $B_1$), a third scientific document $Q_1$ (e.g., a scientific article), may identify an behavior $C_1$ as being correlated with the respective NHF $B_1$, and a fourth scientific document $Q_2$ (e.g., a medical textbook), may identify two behaviors, $C_1$ and $C_2$, as being correlated with the respective NHF. Following this example, the machine learning engine 239 receives the information from the first and second scientific documents as $Q_1(C_1)$ and $Q_2(C_1, C_2)$, respectively. This process is executed for every NHF 104 that is included in the NHF space 412. In some implementations, the information from the second plurality of scientific documents is automatically extracted from each scientific document of the second plurality of scientific documents. In some implementations, the information from the second plurality of scientific documents is manually extracted from each scientific document of the second plurality of scientific documents and manually entered into the machine learning engine 239 for the purpose of training healthcare model 114.

The machine learning engine 239 calculates a respective correlation coefficient J(B,C) between each respective NHF (B) and each behavior (C) correlated with the NHF. For example, a correlation coefficient between NHF $B_1$ and behavior $C_1$ is represented as $J(B_1, C_1)$ in FIG. 4A. A calculated correlation coefficient between a respective NHF and a respective behavior correlated with the respective NHF is determined based on a frequency of the respective behavior appearing in the second plurality of scientific documents, and/or a quality of the scientific document(s) in the second plurality of scientific documents that identify the correlation between the respective behavior and the respective NHF. The frequency of a behavior in the second plurality of scientific documents is determined (e.g., measured, calculated) in the same way as described above with respect to a frequency of an NHF in the first plurality of scientific documents. Details and examples of how frequency is determined, as well as how quality of a scientific document is determined, are provided above and not repeated here for brevity. A respective correspondence coefficient between a respective NHF and a respective behavior correlated with the respective NHF may be determined using any of the information (e.g., any combination) of the metrics (with regards to frequency and quality) described above.

Using (i) the respective correspondence coefficient, H(A, B), between a respective health condition and a respective NHF correlated with the respective health condition, and (ii) the respective correspondence coefficient, J(B, C), between a respective NHF and a respective behavior correlated with the respective NHF, the machine learning engine 239 forms healthcare model 114 that correlates health conditions 102 to behaviors 106.

In some implementations, for a respective health condition 102 (e.g., health condition $A_1$), the machine learning engine 239 generates a weight matrix between respective NHFs 104 and respective behaviors 106. The weight matrix is generated based on the respective correspondence coefficient, J(B, C), between a respective NHF and a respective behavior correlated with the respective NHF for all NHFs that are specified (e.g., by the first plurality of scientific documents) as being correlated to the respective health condition. For example, each row of the weight matrix corresponds to a distinct NHF 104 (e.g., NHF $B_1$, $B_2$, $B_3$, ...) and each column of the weight matrix corresponds to a distinct behavior 106 (e.g., behavior $C_1$, $C_2$, $C_3$, ...). In some implementations, the weight matrix for the respective health condition is used (e.g., also used) by machine learning engine 239 to train healthcare model 114 to correlate health conditions 102 to behaviors 106.

In addition to training healthcare model 114 to correlate health conditions 102 to behaviors 106, the healthcare model 114 can also be trained to correlate health conditions 102 to treatment programs 118. Each treatment program 118 of the plurality of treatment programs 118 is configured (e.g., designed) to target (e.g., modify, encourage, practice) a specific behavior 106 of the plurality of behaviors in the behavior space 414. Thus, each treatment program 118 corresponds to (e.g., is associated) with one or more behaviors 106 in the behavior space 414. While a treatment program 118 of the plurality of treatment programs is associated with a behavior 106, a treatment program 118 may be correlated to more than one NHF, such as when a specific behavior is correlated (e.g., has correspondence with, is associated with) more than one NHF.

Thus, the machine learning engine 239 can form a healthcare model 114 that is trained to correlate health conditions 102 to behaviors 106 using: (i) the using the respective correspondence coefficient, H(A, B), between a respective health condition and a respective NHF correlated with the respective health condition, (ii) the respective correspondence coefficient, J(B, C), between a respective NHF and a respective behavior correlated with the respective NHF, and (iii) correspondence between behaviors 106 and treatment programs 118.

In some implementations, the healthcare model 114 can also be trained to correlate health conditions 102 to customized treatment programs 416 based on patient information provided in a corresponding patient profile (e.g., in the patient's patient profile).

FIG. 4B illustrates an example of a neural network with a plurality of hidden layers. This neural network diagram can be applied to the concepts described above with respect to FIG. 4A. For example, for a healthcare model 114 that is trained to correlate health conditions 102 to behaviors 106, an input space 420 would include health conditions 102, represented in FIG. 4B by the variable X, and an output space 422, represented in FIG. 4B by the variable, Y would include behaviors 106. In another example, for a healthcare model 114 that is trained to correlate health conditions 102 to treatment programs 118, an input space (X) would include health conditions 102 and an output space (Y) would include treatment programs 118. There can be any number of hidden layers between the input layer and output layers of the neural network (e.g., the healthcare model 114). In general, the larger the number of hidden layers a neural network has, the more flexible and complex the neural network (e.g., trained model) can be. For example, a neural network that includes three layers can only connect an input element $X_1$ to an output element $Y_1$ if a connection or link can be formed between the input element $X_1$ and the output element $Y_1$ within four steps. In contrast, a neural network that includes six layers can connect input element $X_1$ to output element $Y_1$ if a connection or link can be formed between the input element $X_1$ and the output element Y1 within seven steps, thereby increasing the possibility that a link may be formed between input element $X_1$ and output element $Y_1$ compared to the neural network having three hidden layers.

Figure 5A:
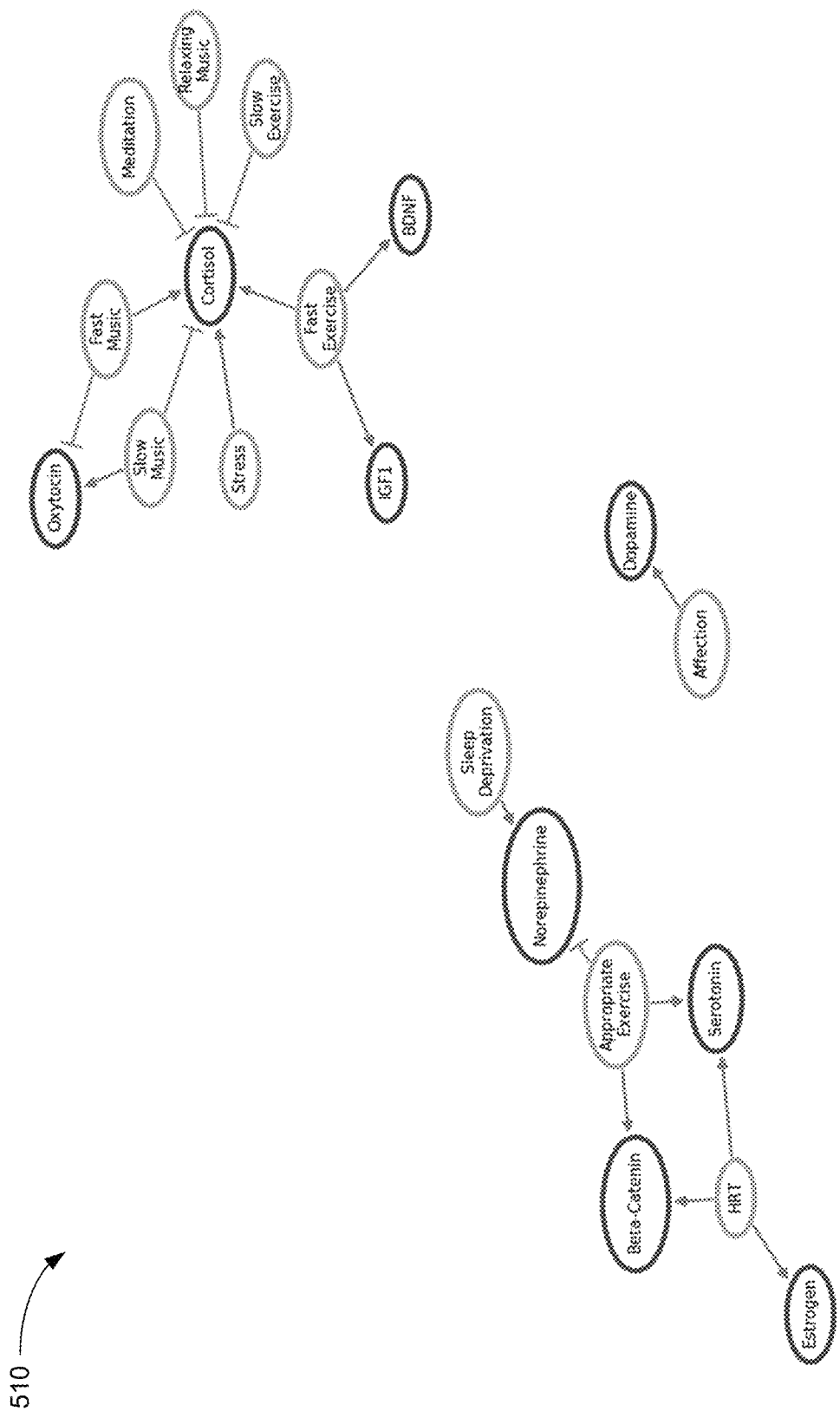
FIG. 5A provides an example of neurobehavioral factor-behavior binary network analysis according to some implementations.

FIG. 5A provides an example of neurobehavioral factor-behavior binary network 510 according to some implementations. Arrows starting at a behavior and pointing to an NHF indicates that the respective behavior activates (e.g., stimulates, increases a level of) the respective NHF. In contrast, lines starting at a behavior 106 and stopping at an NHF 104 with a short line indicates that the respective behavior suppresses (e.g., decreases a level of) the respective NHF. This method of presenting information allows a viewer or user to quickly see which behaviors affect a particular NHF and the effect of the behavior on the NHF.

In this example, the network shows that cortisol, an NHF, can be activated by a plurality of behaviors 106, such as fast exercise, stress, and fast music. Additionally, cortisol can also be suppressed by a plurality of behaviors 106, such as slow music, meditation, relaxing music, and slow exercise.

FIG. 5B provides an example of a neurobehavioral factor-behavior binary decoding table 520 according to some implementations. FIG. 5A and FIG. 5B include complementary information and FIG. 5B is simply another method of presenting information that allows a viewer or user of the table to quickly see the effect that a particular behavior has on one or more NHFs. In this example, an up/down binary code is used to indicate activation or suppression of an NHF by specific behaviors. In this example, fast music activates cortisol and suppresses oxytocin.

Figure 6A:
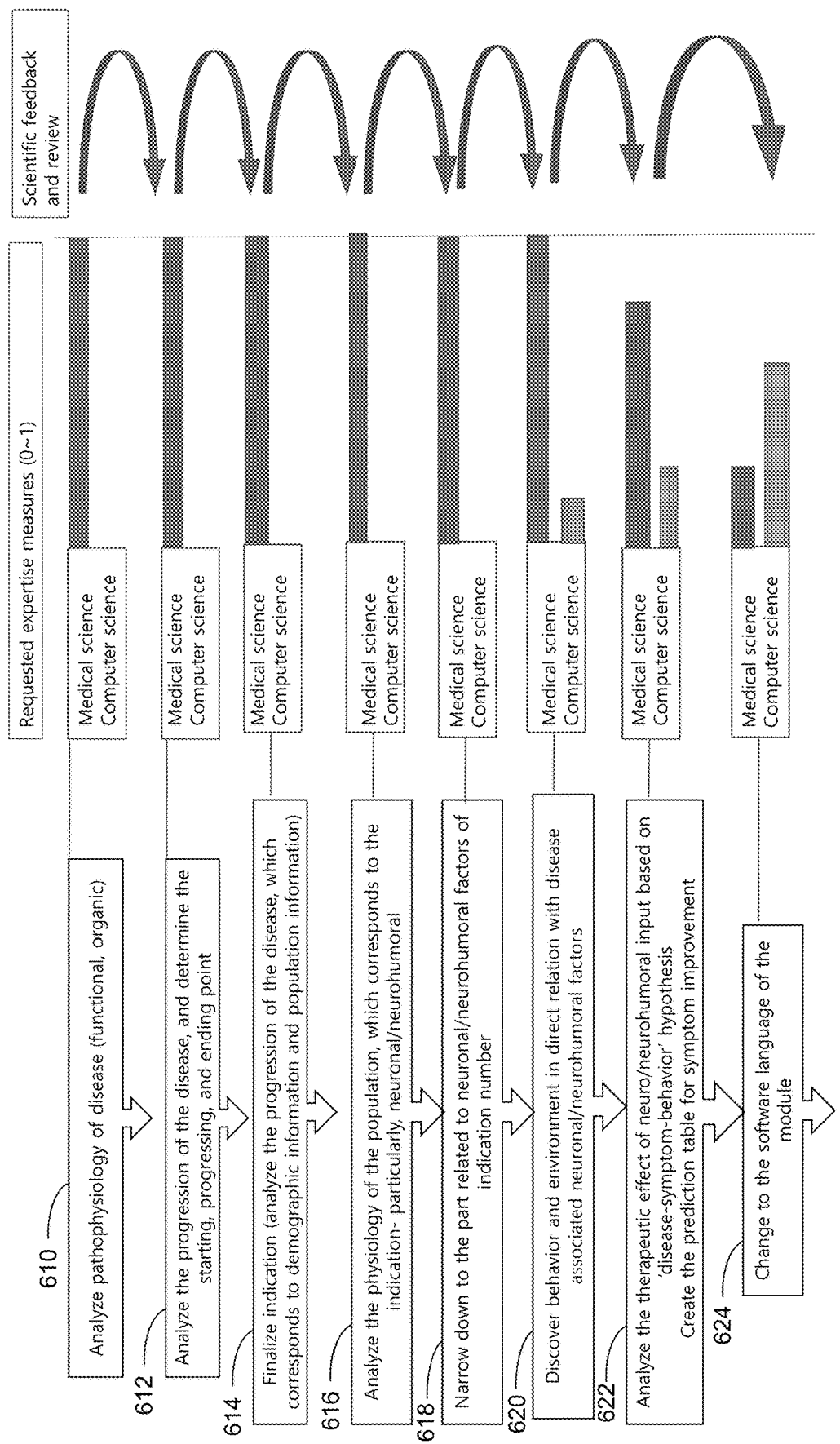
FIG. 6A provides an example of generating a treatment regimen for a health condition according to some implementations.

FIG. 6A provides an example of generating a treatment regimen for a health condition according to some implementations. For a given health condition, research is conducted to analyze (610) a pathology of the health condition (e.g., pathology of the disease), and to analyze (612) the progression of the health condition, such as identifying markers that indicate the emergence (e.g., development) of the health condition, the progression of the health condition, as well as the end of the health condition (e.g., successfully treated). Additional research is also conducted linking (614) the health condition to the demographic and population information, and analyzing (616) the physiology of the population, thereby discerning (e.g., discovering) correlation between the health condition and NHFs. These steps (610-616) are often conducted by scientific and/or medical researchers who publicize their findings or results by publishing medical or scientific articles as well as giving presentations at conferences, or including the findings in new medical textbooks and literature. Using the published scientific findings, a healthcare model (such as healthcare model 114) can be trained (e.g., by a machine learning engine 239) to identify (618) important NHFs that are identified as being correlated with the health condition, discover (620) (e.g., identify) behavioral and environmental factors that are correlated to (e.g., have an association with, a direct relation to, an effect on) the identified NHFs and thereby, the health condition under analysis. The healthcare model is also trained using analysis (622) of the therapeutic effect of behaviors on NHFs and on the health condition based on the correlation between the health condition, the NHF(s), and the behaviors as specified in the published medical and scientific literature. Using this analysis, the generated healthcare model can provide outputs (e.g., predictions) for recommended behaviors 106 or treatment programs 118 for improving symptoms of the health condition. The information output from the healthcare mode can be used to generate or update (624) (e.g., modify, change) treatment programs 118 that are provided to treat patients suffering from the health condition.

Figure 6B:
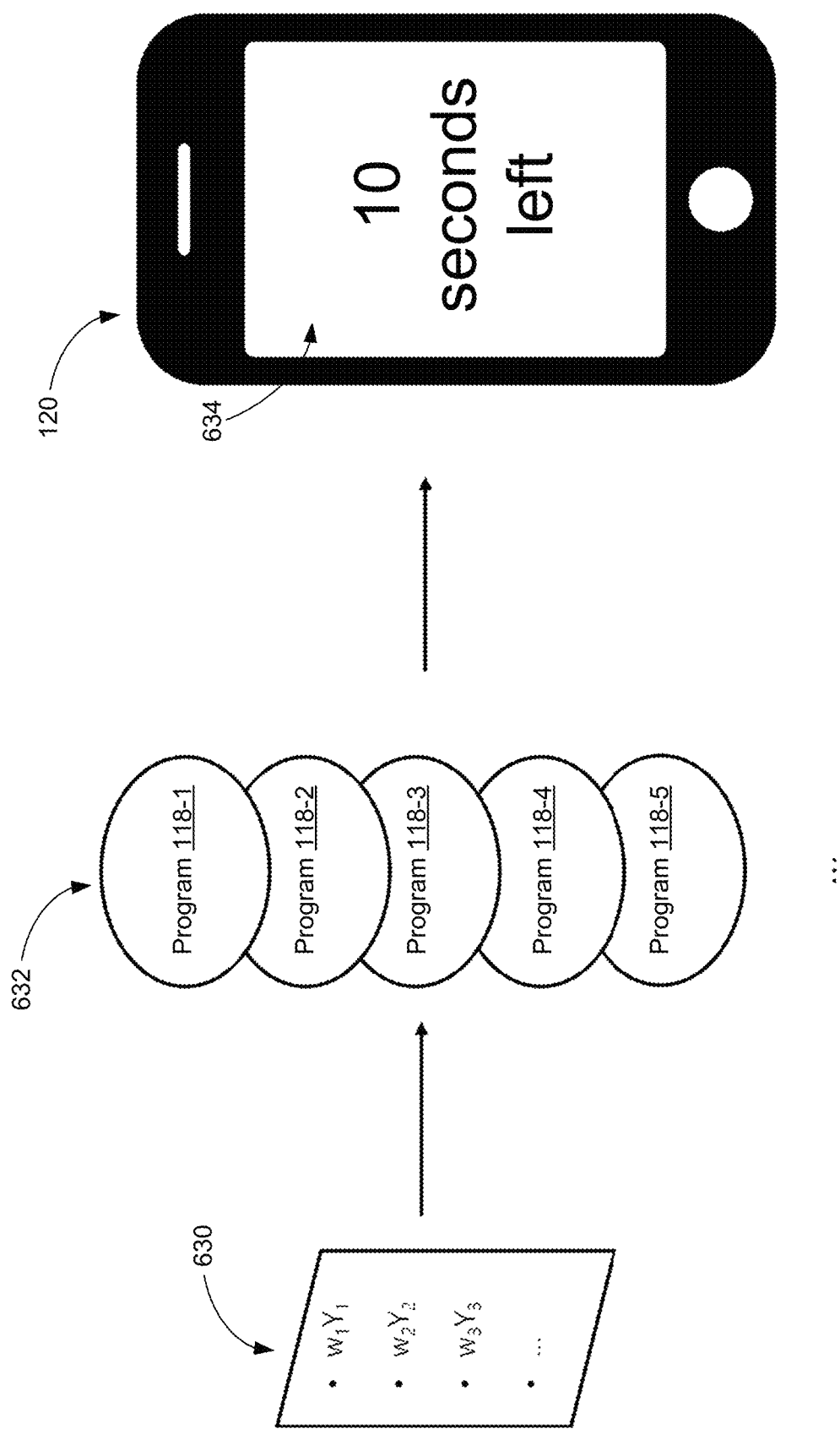
FIG. 6B illustrates providing a treatment regimen for a health condition to a patient according to some implementations.

FIG. 6B illustrates providing a treatment regimen for a health condition 112 to a patient according to some implementations. In some implementations, a user provides a patient's health condition 112 to the healthcare model 114 and the healthcare model 114 provides an output 630 that includes one or more behaviors 116 (represented in the FIG. 6B by the variable Y) that the healthcare model 114 has determined to correspond to the patient's health condition 112.

In some implementations, a user provides a patient's health condition 112 to the healthcare model 114 and the healthcare model 114 provides an output 630 that includes one or more treatment programs 118, Y, that the healthcare model 114 has determined to correspond to the patient's health condition 112.

In some implementations, a user provides a patient's health condition 112 and information regarding the patient (such as age, weight, height, race, other health conditions, etc.) to the healthcare model 114 and the healthcare model 114 provides an output 630 that includes one or more customized treatment programs 416, Y, that the healthcare model 114 has determined to correspond to the patient's health condition 112.

In some implementations, the patient's health condition 112 is provided as a user input via a client device 120 that is configured to provide treatment programs 118 for the patient. Alternatively, the patient's health condition 112 may be provided by a healthcare provider.

In some implementations, as shown in FIG. 6B, each feature (e.g., behavior 116, treatment program 118, or customized treatment program 416) that is output from the healthcare model 114 is associated with a weight (w). For example, FIG. 6B shows that feature $Y_1$ is associated with weight $w_1$, represented as $w_1Y_1$, and feature $Y_2$ is associated with weight $w_2$, represented as $w_2Y_2$. The output 630 from the healthcare model 114 is used to select (e.g., determine) treatment programs 118 (and/or customized treatment programs 416) to be included in a treatment regimen 632 for the patient. For example, each of the treatment programs 118-1 through 118-5 are included in the treatment regimen 632 for the patient since each of the selected treatment programs, 118-1 through 118-5, target one or more behaviors 116 that are output from healthcare model 114 (e.g., have been identified by healthcare model 114 as being relevant or important to treating the patient's health condition 112). In some implementations, the treatment programs 118 in the treatment regimen 632 address (e.g., target or aim to modify) a subset, less than all, of the behaviors 116 in the output 630 provided by healthcare model 114. For example, the treatment programs 118 in the treatment regimen 632 may target the top 3, top 5, or top 10 behaviors that the healthcare model 114 identified as having the greatest impact (e.g., having the highest weights) on the outcome or improvement of the patient's health condition 112.

In some implementations, the output 630 from the healthcare model 114 is used to select (e.g., determine) any combination of treatment programs 118 and customized treatment programs 416 to be included in a treatment regimen 632 for the patient, such that the treatment regimen 632 may include one or more treatment programs 118 and may include one or more the customized treatment programs 416 that have been customized (e.g., modified) based on at least one characteristic of the patient that is included in the patient's patient profile.

Once the treatment regimen 632 has been finalized, the treatment programs 118 that are included in the treatment regimen 632 are provided to a client device 120 that the patient can access. The treatment programs 118 are provided to the patient through the client device 120, and may include any combination of treatment programs, such as physical exercise, breathing exercises, stretching, coordination tasks, game-like motor function tasks, and relaxation treatments that may involve music or relaxation cues. Each of the treatment programs 118 in the treatment regimen 632 are deployed (e.g., presented to the patient) in response to a user request for initiating a treatment program 118. The user request can be a gesture, such as a mouse click or tap on a touch-sensitive display, or a voice command (e.g., "start breathing exercise program"). In response to the user request to initiate a treatment program, the client device 120 presents a treatment interface 634 that corresponds to the requested treatment program 118.

In some implementations, presenting the treatment program 118 includes any of: presenting an audio and/or a visual request for the patient to perform an action (e.g., "Breath in for a count of three"), presenting audio and/or visual content (e.g., playing music, playing instructions, displaying video content) corresponding to the request (e.g., displaying a countdown or a visual cue for breath movements), and activating one or more sensors on the client device 120 (or sensors that are in communication with the client device 120) to track the requested action (e.g., activate a heart rate sensor to monitor the patient's heart rate, activate a microphone to listen for breathing sounds). In some implementations, while presenting the information corresponding to the treatment program 118 to the user, the client device may also activate one or more sensors of the client device 120 or one or more sensors in communication with the client device 120 (e.g., a smart watch connected to a smart phone) to track or monitor the patient's activity and/or vitals during the provision of the treatment program 118. For example, in response to a user selection of a fast exercise treatment program 118-1, the client device 120 may present a treatment interface 634 that corresponds to the fast exercise treatment program 118-1. The treatment interface 634 may include anything from, for example, a list of exercises, a video or graphic showing how to correctly perform exercises, a countdown screen, or a combination of any of these examples.

In some implementations, the client device 120 may receive a user request to initiate presentation of a second treatment program 118-2 that is different from the first treatment program 118-1. For example, after completing the fast exercise treatment program 118-1, the user may select a meditation treatment program 118-2. In response to receiving the user request to initiate presentation of the meditation treatment program 118-2, the client device 120 presents a second user interface that corresponds to the meditation treatment program 118-2. In some implementations, the second treatment program 118-2 is different from (e.g., is a different treatment program) from the first treatment [program 118-1.

In some implementations, such as when the treatment program 118-2 is different from the first treatment program 118-1, the treatment interface corresponding to the second treatment program 118-2 is different from the treatment interface corresponding to the first treatment program 118-1. For example, the treatment interface corresponding to the fast exercise treatment program 118-1 may include audio and/or visual cues and/or content that is different from the audio and/or visual cues and/or content that are presented for the meditation treatment program 118-2. In some implementations, the one or more sensors that are activated during presentation of the first treatment program 118-1 are different from (e.g., include different sensors, include more or fewer sensors, include at least one sensor that is different from) one or more sensors that are activated during presentation of the second treatment program 118-2. For example, a heart rate monitor may be activated to track the patient's heart rate during provision of the fast exercise treatment program 118-1, and a microphone may be activated to track the user's breathing during the meditation treatment program 118-2. In some implementations, in response to receiving the user request to initiate presentation of the meditation treatment program 118-2, the client device 120 determines a stop time of the first treatment program 118-1 (e.g., a time when the treatment program 118-1 concluded), and determines if a lapsed time between the stop time of the first treatment program 118-1 and a current time exceed a predetermined time period (e.g., 30 minutes, 1 hour). In the case where the lapsed time exceeds the predetermined time period, the client device 120 initiates presentation of the treatment interface, corresponding to the second treatment program 118-2, to the patient. In the case where the lapsed time does not exceed the predetermined time period, the client device 120 does not present the treatment interface, corresponding to the second treatment program 118-2, to the patient until the lapsed time exceeds the predetermined time period. In some implementations, different combinations of treatment programs may have different predetermined time periods. For example, the client device 120 may allow the patient to start another treatment program 118-3 immediately or after 5 minutes of completing the first treatment program 118-1. However, the patient may have to wait at least 2 hours after completing the first treatment program 118-1 before starting the other treatment program 118-3. In some implementations, the predetermined time period between two respective treatment programs 118 is determined based at least in part on the activity associated with each of the respective treatment programs, NHFs associated with each of the respective treatment programs (e.g., via the respective behaviors each treatment program is targeting), and/or whether the respective treatment programs are intended to activate or suppress specific NHFs. For example, it may be desirable to wait at least one hour after completing a fast exercise treatment program 118 before starting a meditation treatment program 118 since it may be harder to meditate after feast exercise or it may be counter-productive to try and reduce cortisol levels so quickly after raising them (during the fast exercise treatment).

In some implementations, after presenting the treatment interface to the patient (e.g., once the treatment program 118 has concluded), the client device 120 stores the sensor information recorded during presentation of the treatment program 118 (e.g., presentation of the treatment interface corresponding to the treatment program 118) in a patient profile. In some implementations, the information stored in the patient profile can include any of sensor information, information regarding the patient that is input by a user (e.g., weight, height, age, gender), and treatment adherence information (e.g., how often does the user initiate treatment). In some implementations, the client device 120 updates the treatment interface according to the recoded sensor information. For example, if the sensor information corresponding to a first treatment program 118-1 shows that the patient was not able to complete all of the exercises due to fatigue, the first treatment program 118-1 may be updated to be less strenuous (e.g., more rest, shorter duration, fewer repetitions). In some implementations, the client device 120 transmits (e.g., sends) the sensor information (which may include adherence information) to a health care provider associated with the patient (e.g., family doctor, physician). In some implementations, the health care provider may send one or more instructions to modify the treatment regimen 632 based on the sensor information and/or adherence information, and the treatment regimen 632 is updated in accordance with the one or more instructions received from the health care provider. The one or more instructions received from the health care provider may include any of: instructions to remove a treatment program 118 from the treatment regimen 632, instructions to add a treatment program 118 to the treatment regimen 632, and instructions to modify a treatment program 118 that is included in the treatment regimen 632. For example, the health care provider may provide instructions to increase the pace of an exercise treatment program 118 after seeing that the patient's heart rate did not increase as much as the healthcare provider deems is necessary for the treatment to be effective. In another example, the health care provider may provide instructions to remove a treatment program 118 that requires kneeling, from the treatment regimen 632, in response to receiving information in the patient profile that the patient is experiencing discomfort in his/her knees (or has injured his/her knee). In some implementations, the healthcare provider may provide one or more instructions to customize the treatment regimen 632 (and treatment programs 118) to the patient (e.g., based on the patient's weight or age).

Figure 7B:
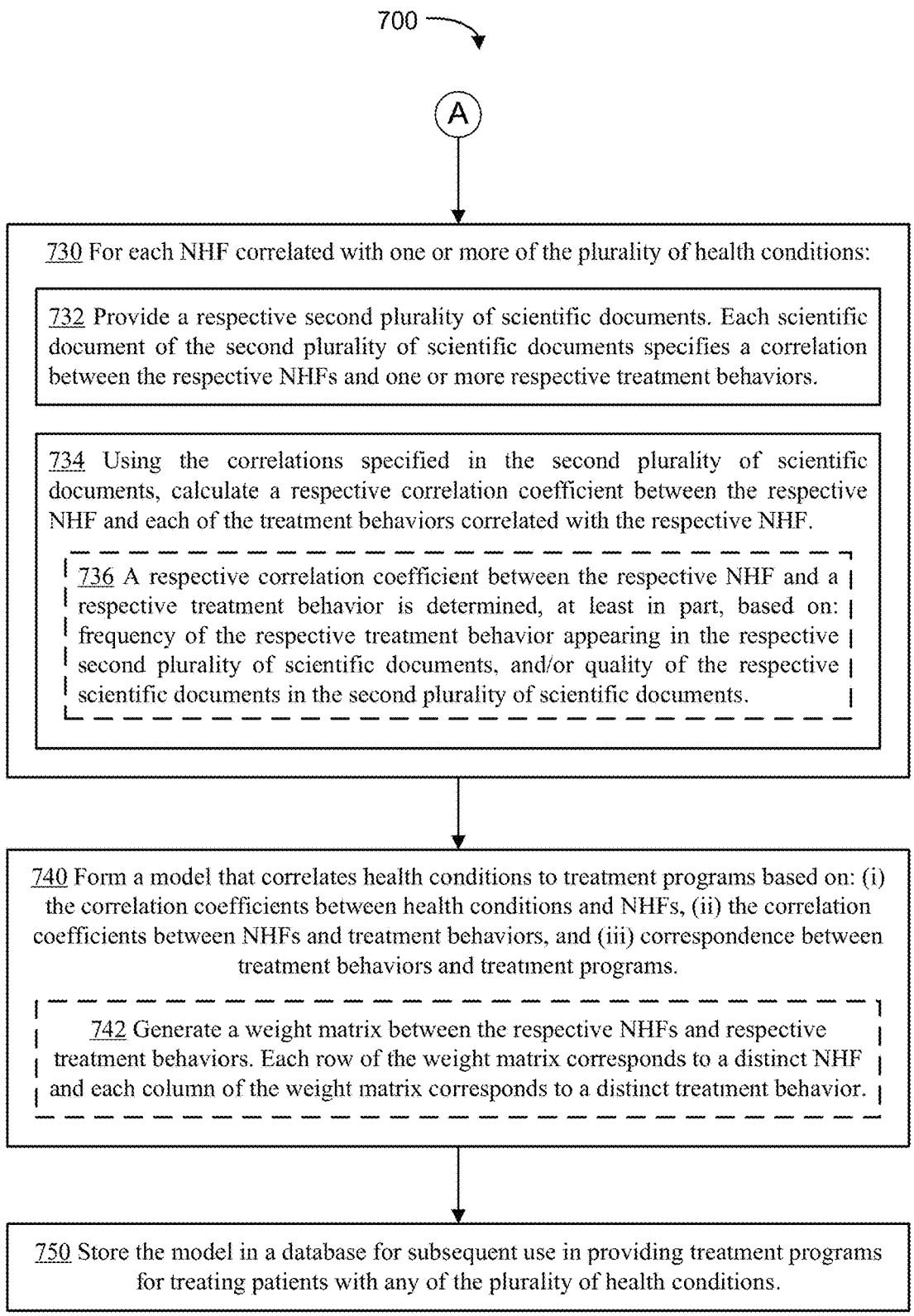
Figure 8C:
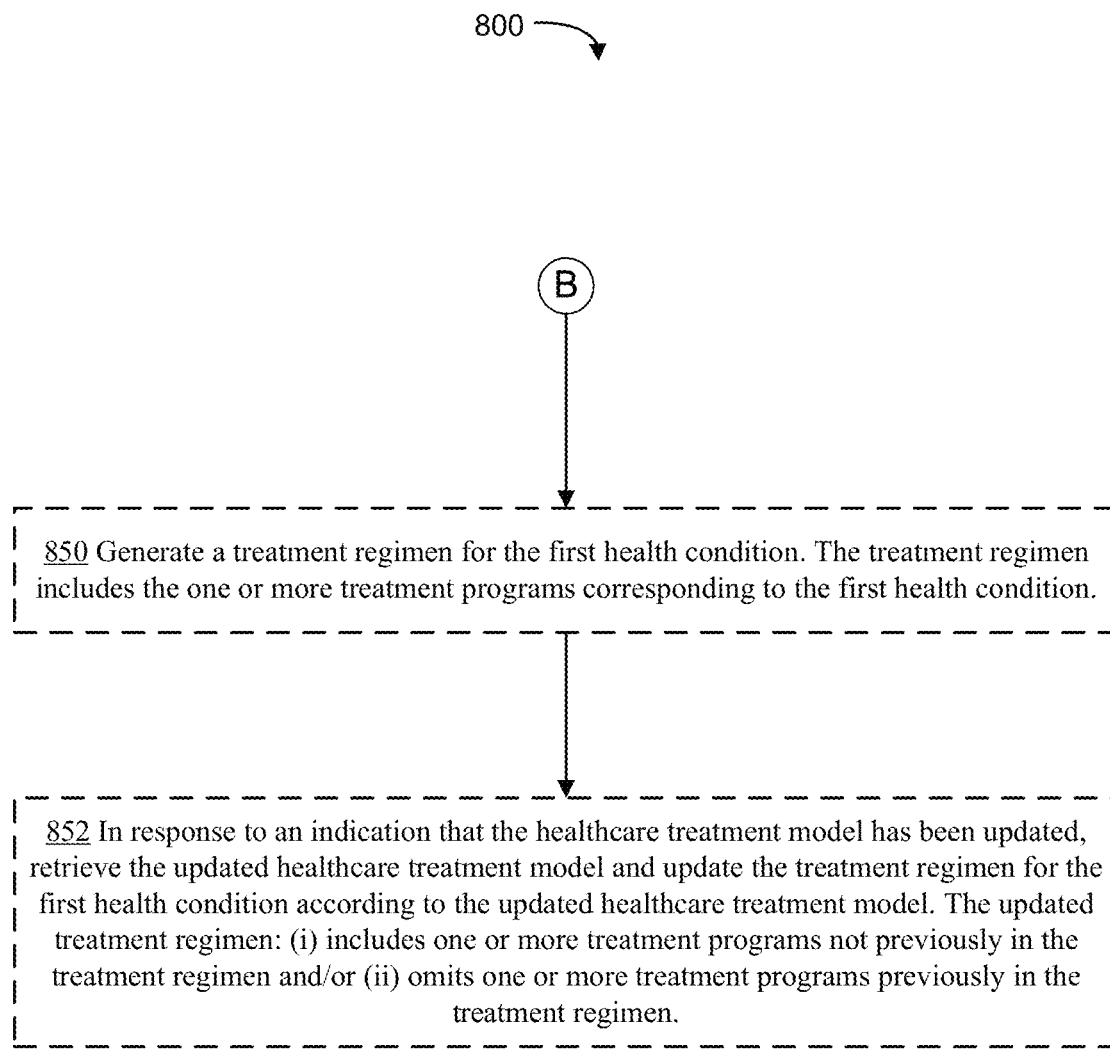
Figure 8D:
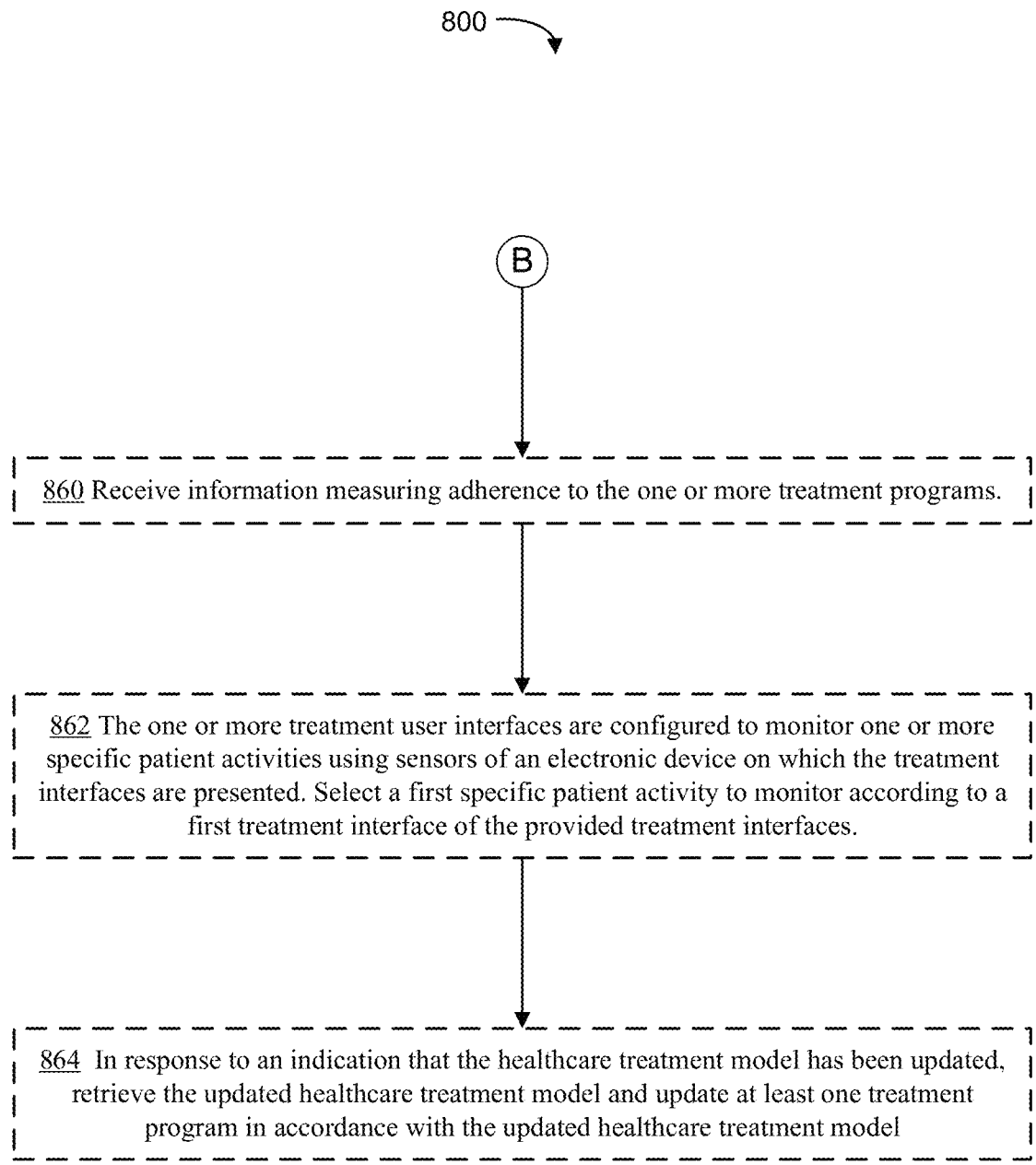
Figure 9A:
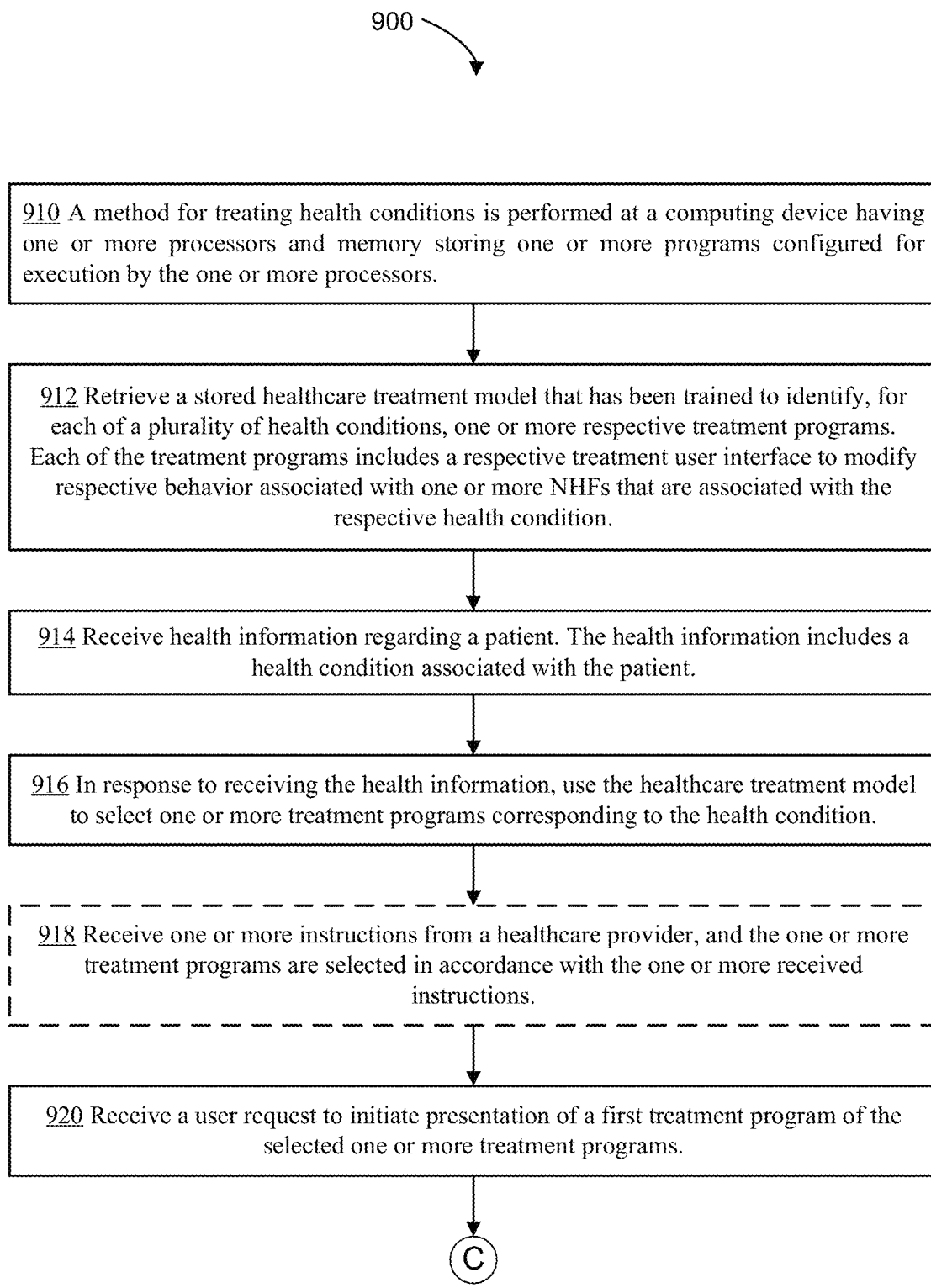
FIGS. 9A-9E provide a flow diagram of a method for treating health conditions according to some implementations.
Figure 9B:
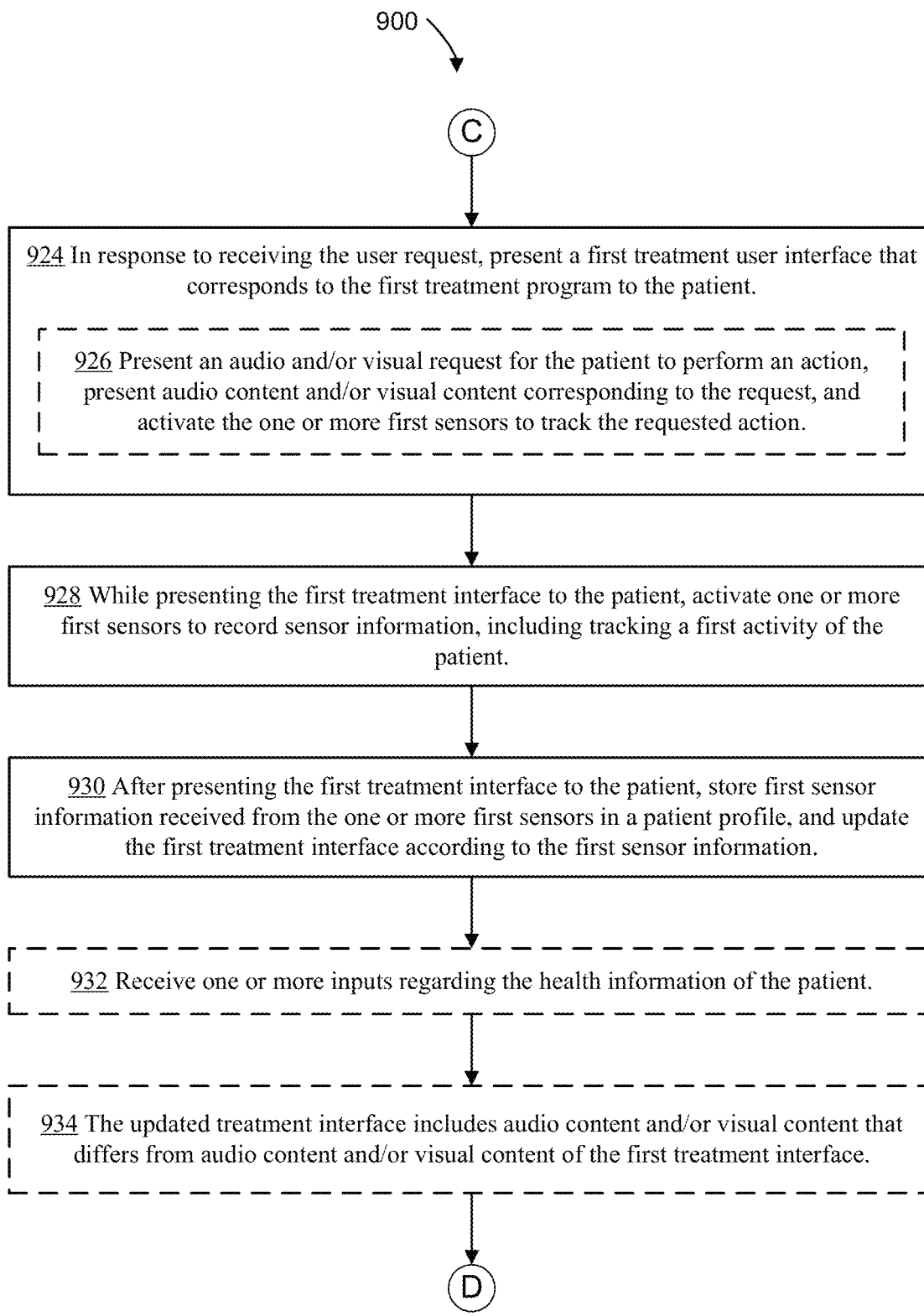
Figure 9C:
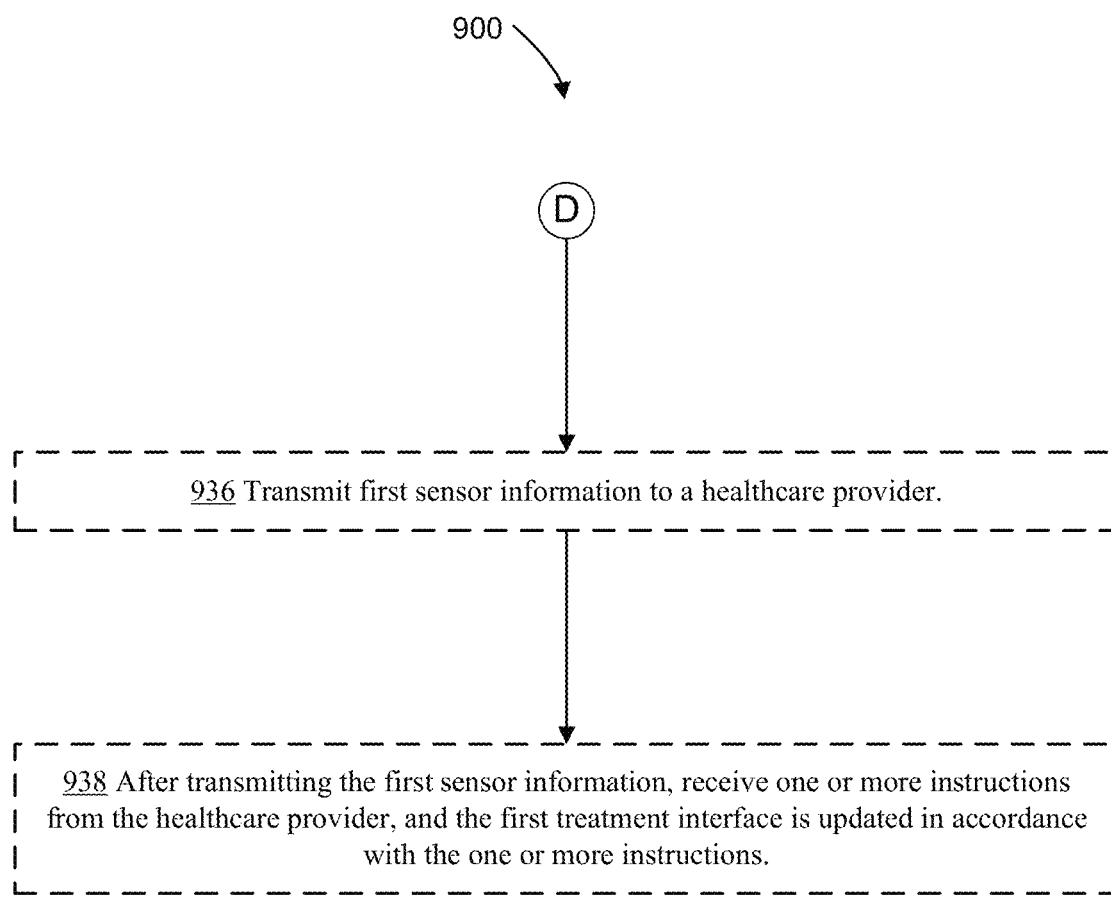
Figure 9D:
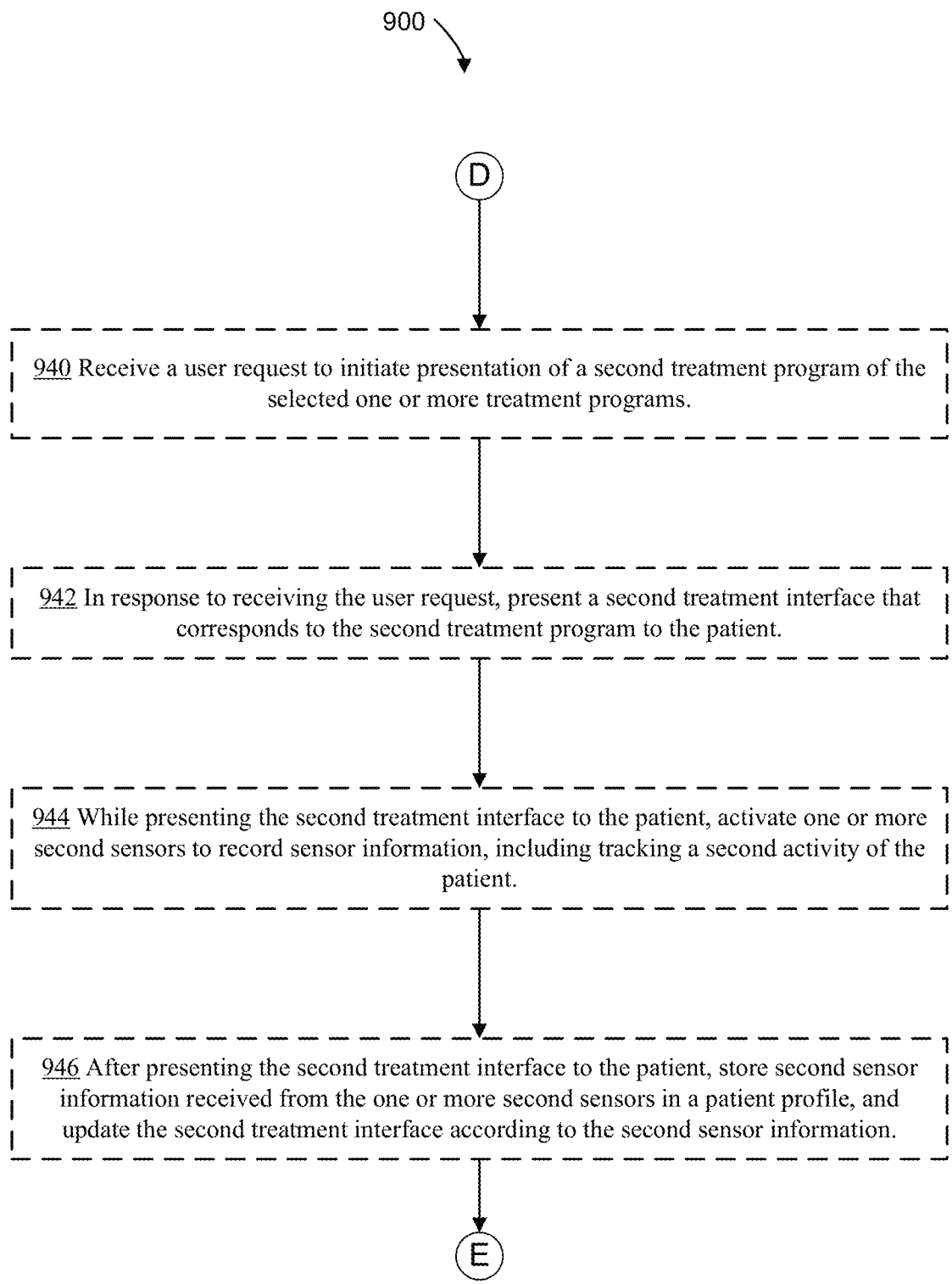
Figure 9E:
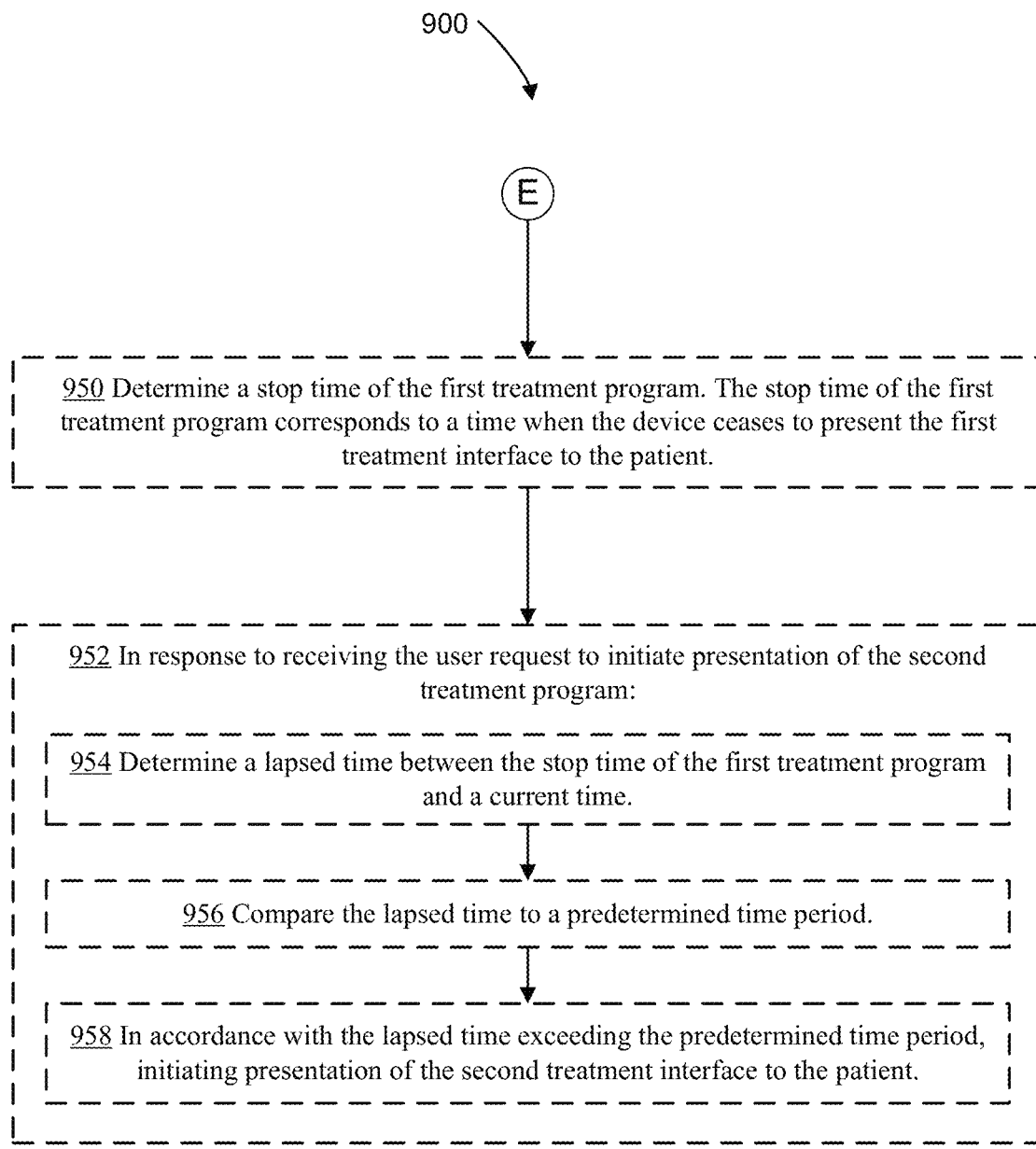

FIGS. 7A and 7B provide a flow diagram of a method 700 for building healthcare models 114 for selecting healthcare treatment programs 118 according to some implementations. The steps of the method 700 may be performed by a computer system, corresponding to a computer device 200 or a server 250. In some implementations, the computer includes one or more processors and memory. FIGS. 7A and 7B correspond to instructions stored in computer memory or a computer-readable storage medium (e.g., the memory 206 of the computing device 200). The memory stores (710) one or more programs configured for execution by the one or more processors. For example, the operations of the method 700 are performed, at least in part, by a machine learning engine 239.

In accordance with some implementations, a computer system, computing device 200, or a server 250 performs (720) a series of operations for a plurality of health conditions 102. The system 200 provides (722) a respective first plurality of scientific documents (e.g., scientific documents P). Each scientific document of the first plurality of scientific documents specifies a correlation between the respective health condition 102 (e.g., health conditions A) and one or more respective NHFs 104 (e.g., NHFs B). Using the correlations specified in the first plurality of scientific documents, the system 200 calculates (724) a respective correlation coefficient between the respective health condition 102 and each of the NHFs 104 correlated with the respective health condition 102. For each NHF 104 that is correlated with one or more of the plurality of health conditions 102 (734), the system 200 provides (732) a respective second plurality of scientific documents (e.g., scientific documents Q). Each scientific document of the second plurality of scientific documents specifies a correlation between the respective NHFs 104 and one or more respective treatment behaviors 106. Using the correlations specified in the second plurality of scientific documents, the system 200 calculates (734) a respective correlation coefficient, y(B,C), between the respective NHF 104 and each of the treatment behaviors 106 correlated with the respective NHF 104. The system 200 then forms a model 114 (e.g., healthcare model 114) that correlates health conditions 102 to treatment programs 118 based on: (i) the correlation coefficients, x(A,B), between health conditions 102 and NHFs 104, (ii) the correlation coefficients, y(B,C), between NHFs 104 and treatment behaviors 106, and (iii) correspondence between treatment behaviors 106 and treatment programs 118. The system 200 then stores the model 114 a database (e.g., database 240 and/or database 290) for subsequent use in providing treatment programs 118 for treating patients with any of the plurality of health conditions 102.

In some implementations, the system 200 also determines (726) a respective correlation coefficient, x(A,B), between the respective health condition 102 and a respective NHF 104 based at least in part on: (i) a frequency of the respective NHF 104 appearing in the respective first plurality of scientific documents, and/or (ii) a quality of the respective scientific document(s) in the first plurality of scientific documents.

In some implementations, the system 200 determines (736) a respective correlation coefficient between the respective NHF 104 and a respective treatment behavior 106 based at least in part on: (i) a frequency of the respective treatment behavior 106 appearing in the respective second plurality of scientific documents, and/or (ii) a quality of the respective scientific document(s) in the second plurality of scientific documents.

In some implementations, the system 200 generates (742), for each health condition 102 of the plurality of health conditions, a weight matrix between the respective NHFs 104 and respective treatment behaviors 118. Each row of the weight matrix corresponds to a distinct NHF 104 and each column of the weight matrix corresponds to a distinct treatment behavior 106.

FIGS. 8A-8D provide a flow diagram of a method 800 for generating treatment programs 118 for one or more health conditions 112 using a trained healthcare model 114 according to some implementations. The steps of the method 800 may be performed by a computer system, corresponding to a computer device 200 or a server 250. In some implementations, the computer includes one or more processors and memory. FIGS. 8A-8D correspond to instructions stored in computer memory or a computer-readable storage medium (e.g., the memory 206 of the computing device 200). The memory stores (810) one or more programs configured for execution by the one or more processors. For example, the operations of the method 800 are performed, at least in part, by a treatment module 237.

In accordance with some implementations, a computer system, computing device 200, or a server 250 retrieves (820) a stored healthcare treatment model 114 that has been trained to identify, for each of a plurality of health conditions 102, one or more respective treatment programs 118. Each of the treatment programs 118 includes a respective treatment user interface (e.g., treatment interface 634) to modify respective behavior 106 associated with one or more NHFs 104 that are associated with the respective health condition 102. 830 In response to receiving input that specifies a first health condition 112 of the one or more health conditions 102, the system 200 uses (830) the healthcare treatment model 114 to select one or more treatment programs 118 corresponding to the first health condition 112, and provides the treatment user interfaces for the one or more treatment programs 118.

In some implementations, in response to receiving input that specifies a second health condition of the one or more health conditions, the system 220 uses (840) the healthcare treatment model 114 to select one or more treatment programs 118 corresponding to the second health condition, and provide the treatment user interfaces for the one or more treatment programs 118 corresponding to the second health condition. The second health condition is different from the first health condition 112. The one or more treatment programs corresponding to the second health condition differ from the one or more treatment programs corresponding to the first health condition 112.

In some implementations, the system 200 generates (850) a treatment regimen (e.g., a treatment regimen 632 for the first health condition 112. The treatment regimen includes the one or more treatment programs 118 corresponding to the first health condition 112. In response to an indication that the healthcare treatment model 114 has been updated, the system 200 retrieves (852) the updated healthcare treatment model and updates the treatment regimen (e.g., treatment regimen 234, treatment regimen 632) for the first health condition 112 according to the updated healthcare treatment model. The updated treatment regimen: (i) includes one or more treatment programs not previously in the treatment regimen and/or (ii) omits one or more treatment programs previously in the treatment regimen.

In some implementations, the system 200 receives (860) information measuring adherence to the one or more treatment programs 118.

In some implementations, the one or more treatment user interfaces (e.g., treatment interfaces 634) are configured to monitor one or more specific patient activities using sensors of an electronic device (e.g., client device 120) on which the treatment interfaces are presented. The system 200 selects (862) a first specific patient activity to monitor according to a first treatment interface of the provided treatment interfaces.

In some implementations, in response to an indication that the healthcare treatment model 114 has been updated, the system 200 retrieves (864) the updated healthcare treatment model and updates at least one treatment program 118 in accordance with the updated healthcare treatment model.

FIGS. 9A-9E provide a flow diagram of a method for treating health conditions 112 according to some implementations. The steps of the method 900 may be performed by a computer system, corresponding to a client device (e.g., client device 120, client device 300). In some implementations, the client device includes one or more processors and memory. FIGS. 9A-9E correspond to instructions stored in computer memory or a computer-readable storage medium (e.g., the memory 306 of the client device 300). The memory stores (910) one or more programs configured for execution by the one or more processors.

In accordance with some implementations, a client device, such as client device 120 or client device 300, retrieves a stored healthcare treatment model 114 that has been trained to identify, for each of a plurality of health conditions 102, one or more respective treatment programs 118. Each of the treatment programs 118 includes a respective treatment user interface to modify respective behavior 106 associated with one or more NHFs 104 that are associated with the respective health condition 102. The client device receives (914) health information regarding a patient. The health information includes a health condition 112 associated with the patient. In response to receiving the health information, the client device uses (916) the healthcare treatment model 114 to select one or more treatment programs 118 corresponding to the health condition 112. The client device receives (920) a user request to initiate presentation of a first treatment program (e.g., treatment program 118-1) of the selected one or more treatment programs 118, and in response to receiving the user request, the client device presents (924) a first treatment user interface that corresponds to the first treatment program to the patient. While presenting the first treatment interface to the patient, the client device (928) activates one or more first sensors to record sensor information, including tracking a first activity of the patient. After presenting the first treatment interface to the patient, the client device stores (930) first sensor information received from the one or more first sensors in a patient profile, and updates the first treatment interface according to the first sensor information.

In some implementations, the client device receives (918) one or more instructions from a healthcare provider, and the one or more treatment programs 118 are selected in accordance with the one or more received instructions.

In some implementations, the client device presents (926) an audio and/or visual request for the patient to perform an action, present audio content and/or visual content corresponding to the request, and activate the one or more first sensors to track the requested action.

In some implementations, the client device receives (934) one or more inputs regarding the health information of the patient. For example, a user may input health information of the patient at client device.

In some implementations, the client device transmits (936) first sensor information to a healthcare provider, and after transmitting the first sensor information, the client device (938) receives one or more instructions from the healthcare provider, and the first treatment interface is updated in accordance with the one or more instructions.

In some implementations, the client device receives (940) a user request to initiate presentation of a second treatment program (e.g., second treatment program 118-2) of the selected one or more treatment programs 118, in response to receiving the user request, the client device presents (942) a second treatment interface that corresponds to the second treatment program to the patient. While presenting the second treatment interface to the patient, the client device activates one or more second sensors to record sensor information, including tracking a second activity of the patient. After presenting the second treatment interface to the patient, the client device stores (946) second sensor information received from the one or more second sensors in a patient profile, and updates the second treatment interface according to the second sensor information.

In some implementations, the client device determines (950) a stop time of the first treatment program (e.g., first treatment program 118-1). The stop time of the first treatment program corresponds to a time when the device ceases to present the first treatment interface to the patient.

In some implementations, in response to receiving the user request to initiate presentation of the second treatment program (e.g., second treatment program 118-2) (952), the client device determines (954) a lapsed time between the stop time of the first treatment program (e.g., first treatment program 118-1) and a current time, and compares (956) the lapsed time to a predetermined time period. In accordance with the lapsed time exceeding the predetermined time period, the client device (958) initiates presentation of the second treatment interface to the patient.

FIG. 10A is a diagram illustrating flow of information between a patient 1122, an integrated application 1100, and a doctor 1132 in a digital behavior-based treatment system 130 according to some implementations. In some implementations, a digital behavior-based treatment system 130 (see FIG. 1D) allows communication between a patient 1122 (e.g., a first user 1112) and a second user 1132 (e.g., a prescribing subject doctor or a healthcare professional) through an application 1100 (e.g., the integrated application 1100).

In some implementations, the digital behavior-based treatment system 130 includes one or more sensors 1124, a patient application 1120, a doctor application 1130, and a cloud server 1140. A digital behavior-based treatment integration application 1100 is formed by (e.g., is configured by) integrating the patient application 1120, the doctor application 1130, and the cloud server 1140.

In some implementations, the digital behavior-based treatment system 130 is created by a first party, and is provided for use by a second party distinct from the first party. For example, the digital behavior-based treatment system is a platform (e.g., the platform includes the set of applications supported by cloud server 1140) that can be licensed to, or otherwise used by, one or more other parties. In some implementations, the platform is populated with different sets of data for each party of the one or more other parties. For example, the cloud server 1140 is provided by a different entity than the entity that provides the data (e.g., an entity that conducts experiments), and a different entity than the users of the platform (e.g., a company that licenses the set of applications). For example, a first party trains the model (e.g., and/or provides the data for training the model) and a second party, distinct from the first party, uses the platform provided by a third party (e.g., the provider of cloud server 1140) that is distinct from the first and second parties. Alternatively, in some implementations, any of the first, second and third parties are a same entity. For example, the user of the platform is the same entity as the entity that provides the data (e.g., the first party and the second party are the same, while the third party (e.g., the provider of the platform) is distinct).

In some implementations, the doctor application 1130 (e.g., also described with reference to FIGS. 23A-23H) is provided to users other than doctors (e.g., the application is referred to as a "doctor application" by example only, and the "doctor application" may be provided to another non-doctor entity, such as to a company). Further, in some implementations, the data (e.g., the data used to train the healthcare model described with reference to FIG. 1A) is controlled by (e.g., updated by and/or provided by) a doctor, a third-party, the provider of the platform, or a combination of these entities. For example, a first entity accesses a first set of data to use the platform, and a second entity accesses a second set of data to use the platform, where the first set of data and the second set of data are independently controlled and/or modified. As such, within the platform (e.g., within the applications), the data used by each party that licenses the platform is tailored to (e.g., personalized for) the respective party.

The one or more sensors 1124 are configured to track one or more behaviors of the patient 1112, and may include any one or more of: sensors on a personal device (such as accelerometers and/or cameras on a smart phone or a smart accessory, such as a smart watch or a smart headset), a camera (such as a camera on a smart phone, a web-enabled camera, and/or a stand-alone camera for capturing images of video), and an activity monitoring sensor (such as a heartrate sensor or a step tracker).

The patient application 1120 may be accessible via a client device (e.g., a personal device) such as a laptop computer, a smart phone, tablet, or other computing device. The patient application 1120 may be a desktop application, a web-based user interface, and/or a device-specific application (e.g., a smartphone application).

The doctor application 1130 may be accessible via a client device (e.g., a personal device) such as a laptop computer, a smart phone, a tablet, or other computing device. The patient application 1120 may be a desktop application, a web-based user interface, and/or a device-specific application (e.g., an smartphone application).

The cloud server 1140 is configured to provide services related to the patient application 1120 and the doctor application 1130 (e.g., front end and/or back end services), and may be in communication with one or more databases for storing information related to the patient application 1120 and the doctor application 1130, such as patient profile information and/or patient behavior information obtained via the one or more sensors 1124.

For example, a patient 1122 may request, via the digital behavior-based treatment system 130 (e.g., via the patient application 1120), a personalized digital behavior and cognitive task that is based on a doctor's behavioral and cognitive prescription. The personalized digital behavior and cognitive task (e.g., a treatment 118) may be delivered to the patient 1122 via the patient application 1120, allowing the patient to complete the personalized digital behavior and cognitive task and realize the therapeutic effect of a digital therapeutic agent that is prescribed by the doctor 1132 for the patient's disease. In some implementations, the patient application 1120 allows the patient 1122 to directly input his or her task performance corresponding to the corresponding behavioral and cognitive task. Alternatively, the patient application 1122 may allow the one or more sensors 1124 to collect the patient's task performance in the form of passive data. Upon receiving the patient's task performance data through the network 1150, the doctor 1132 can, via the doctor application 1130, check the patient's compliance to the behavioral and cognitive prescription, including any one or more of: the patient's participation, persistence, intensity, and whether the task is being performed correctly.

In some implementations, the digital behavior-based treatment system 130 is implemented by a network 1150, which transmits the encrypted information to the terminals of the patient application 1120, the doctor application 1130, and the cloud server 1140. In some implementations, the cloud server 1140 is in charge of a backend service that includes a processing module that analyzes the task performance data of the patient 1122 and creates a report regarding the patient's task performance data.

In some implementations, the digital behavior-based treatment system 130 includes a database (e.g., a database 135 shown in FIG. 1D) that collects and manages the task and performance information of the patient 1122, and a security module (e.g., a security unit 136 shown in FIG. 1D) that encrypts and decodes related information before and after data corresponding to the patient 1122 is transmitted.

The sensor 100 may be a separate module that is variably plugged in according to the patient's disease, the doctor's behavior, and cognitive prescription, and according to the accuracy, reproducibility of the sensor, and cost-benefit analysis of sensor utilization.

The software configuration of the digital behavior-based treatment system according to some implementations of the present invention can be implemented as an integrated application 500 connecting the patient application 200, the doctor application 300, and the cloud server 400 through a network. This integrated application 500 provides compatibility for input/output with various external sensors 100 from a system perspective, an environment required for the operation of interfaces in various computers or mobiles of the patient 10 and the doctor 30, and security solutions for legal management of related information.

Figure 11:
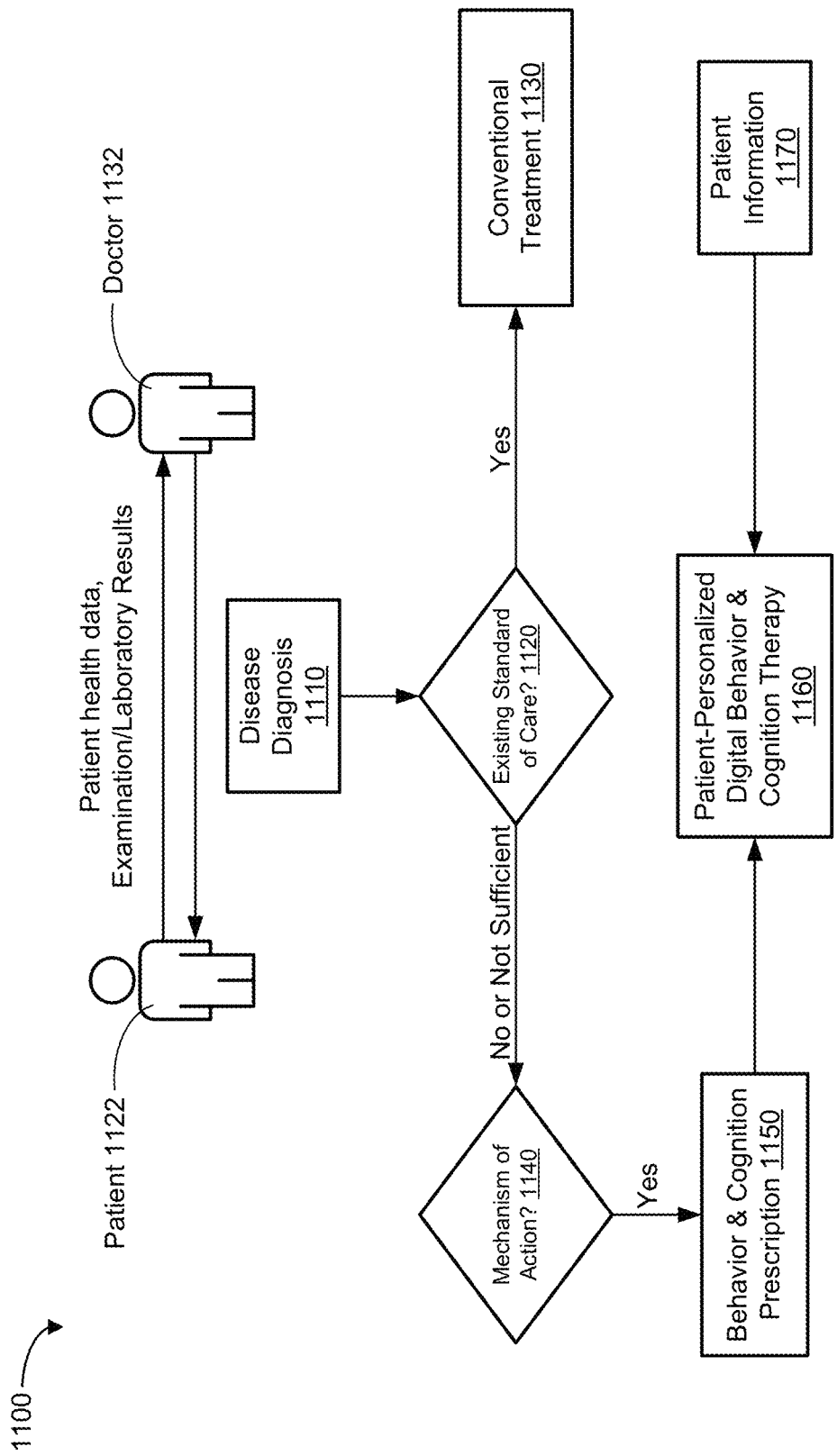
FIG. 11 is a flow chart illustrating a process of creating the patient-specific digital behavioral and cognitive prescription according to some implementations.

FIG. 11 provides a flow chart 1100 illustrating a process of creating the patient-specific digital behavioral and cognitive prescription according to some implementations. The prescription for patient-specific digital behavior and cognition can be said to be a behavioral command given to the patient in the form of a clear task for the purpose of treating diseases, in contrast to the range and intensity of conventional behavioral and cognitive prescriptions that were only vague and unspecified behavioral suggestions. The patient 1122 provides medical information, questionnaire, and test result data to the doctor 1132. Based on this, the doctor 1132 may prescribe personalized digital behavior and cognitive prescription to the patient 1122. The doctor 1132 diagnoses the current disease of the patient 1122 (step 1110), and determines whether treatment with an existing treatment is possible (1120). If it is possible to treat the disease of the patient 1122 with an existing treatment ("Yes"), the doctor 1132 may prescribe a conventional treatment (step 1130), such as a drug prescription. However, if the disease of the patient 1122 cannot be treated with an existing treatment or if existing treatment is insufficient ("No" or "Not Sufficient"), the pathogenesis of the disease is determined (step 1140), and a behavioral and cognitive prescription or a behavioral and cognitive prescription hypothesis for the disease is provided (step 1150). At this time, patient information, such as medical information, information regarding a digital environment, and the patient's participation degree may be received (step 1170). Based on the behavioral and cognitive hypothesis and patient information, a personalized digital behavioral and cognitive prescription may be generated and provided to the patient (step 1160). In some implementations, the patient information is received prior to generating and administering the personalized digital behavioral and cognitive prescription.

Figure 12:
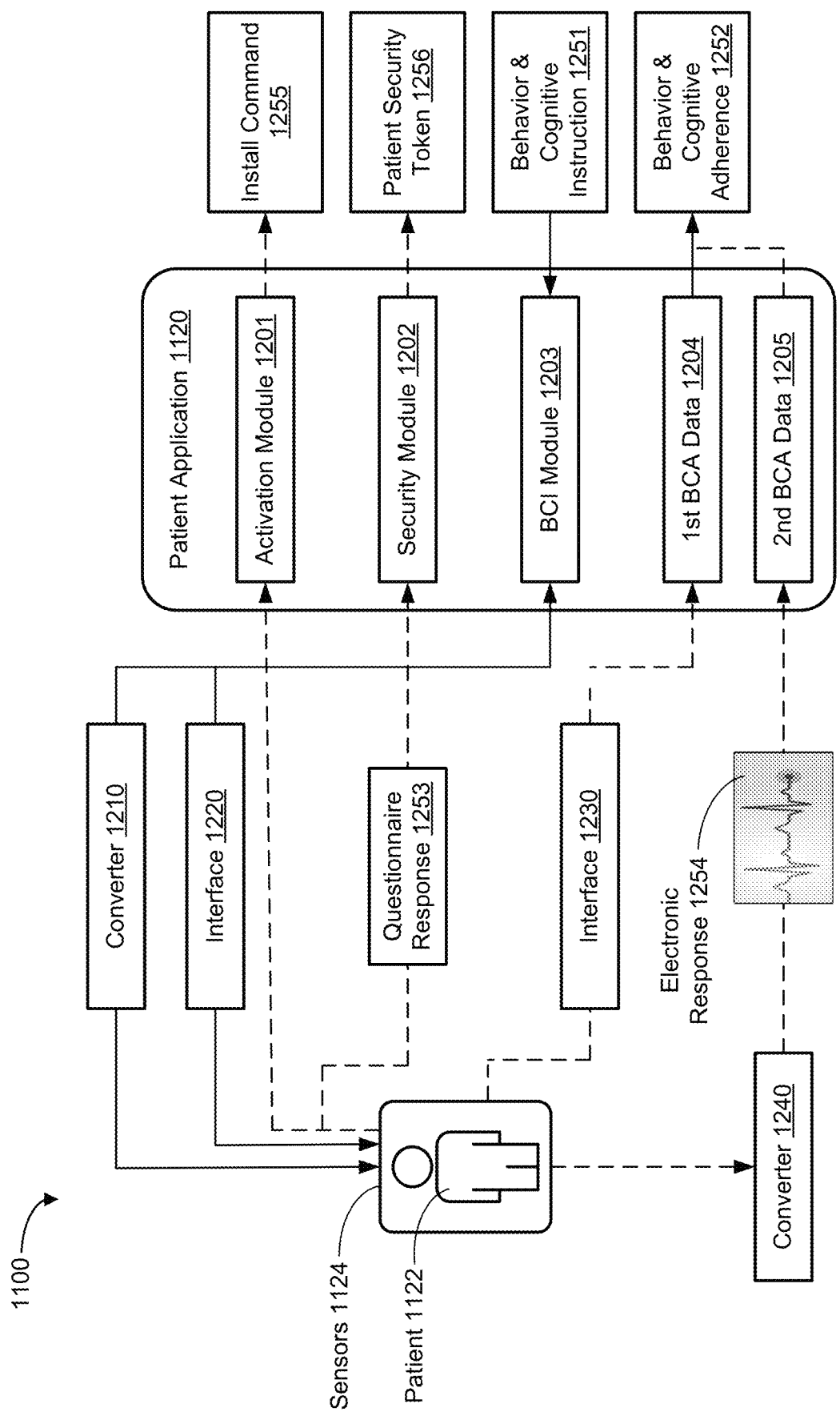
FIGS. 12-14 illustrate execution of the digital behavior-based treatment system according to some implementations.
Figure 13:
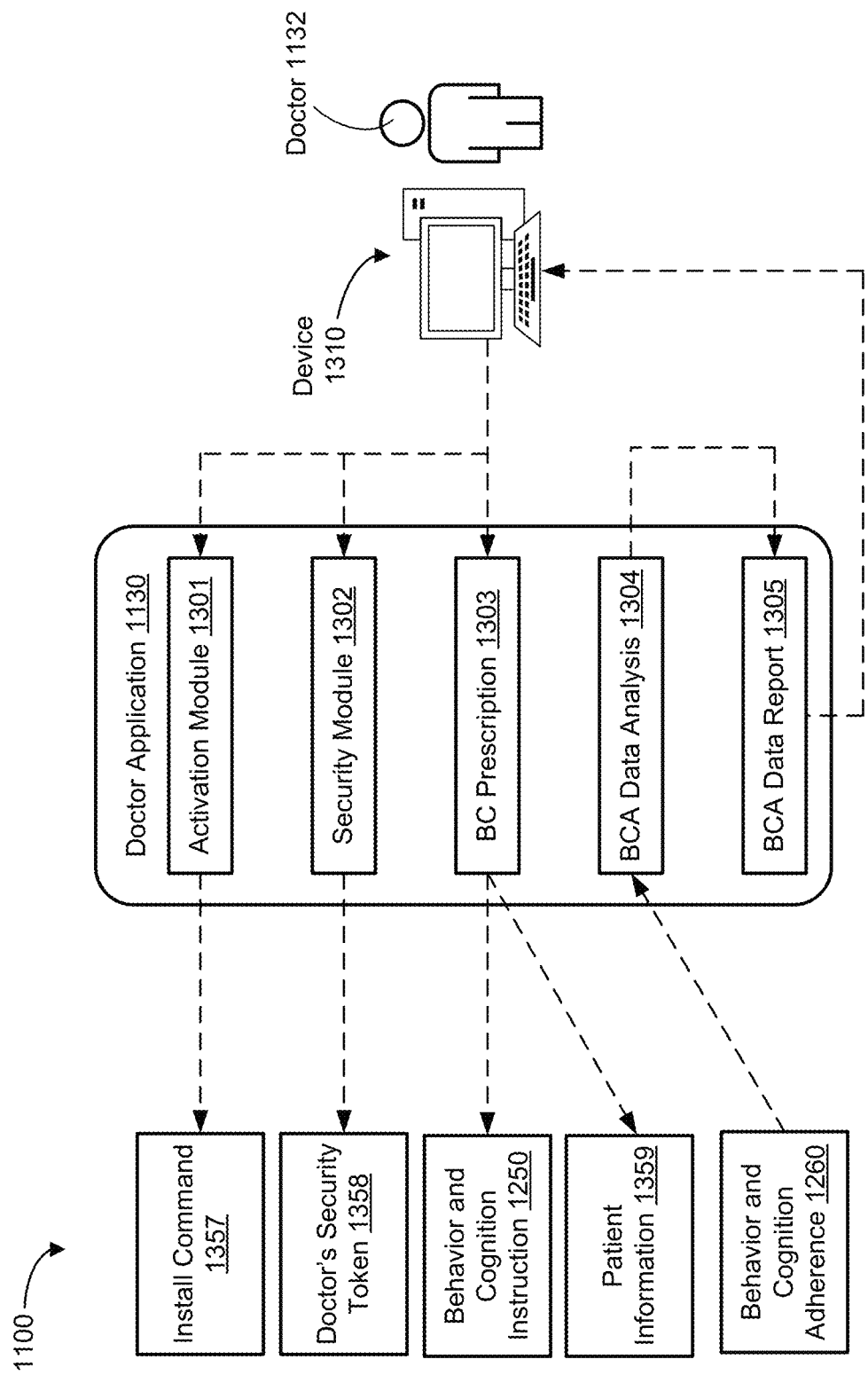
Figure 14:
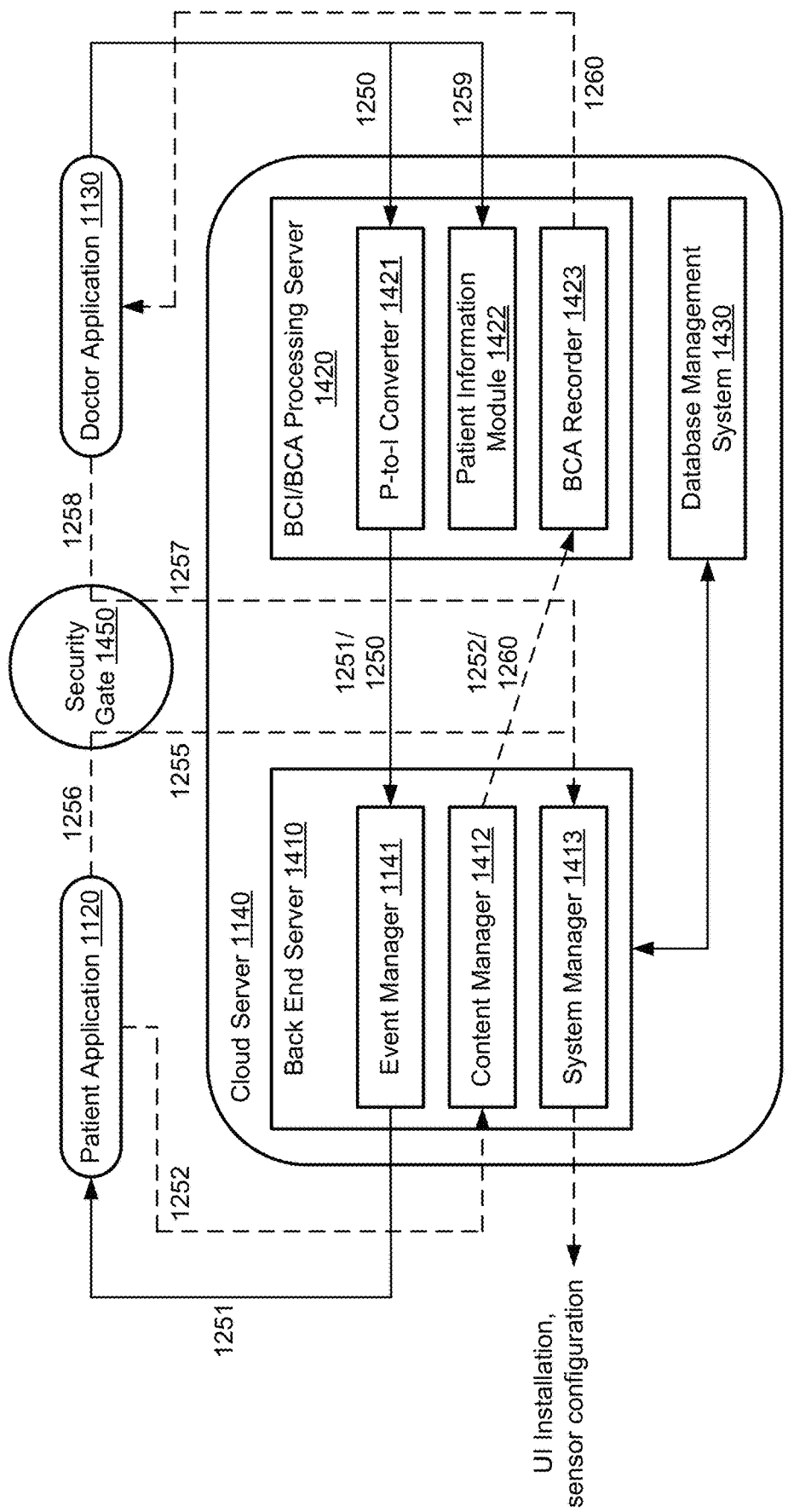

FIGS. 12-14 illustrate execution of the digital behavior-based treatment system according to some implementations. The solid lines shown in FIGS. 12-14 represent the flow of input information that is related to behavior and cognitive prescription and task (e.g., correspond to behavior and cognitive tasks that are prescribed by a doctor that are provided to a patient 1122 via the patient application 1120). The dashed lines shown in FIGS. 12-14 represent the flow of output information regarding the task performance result (e.g., correspond to patient data regarding patient behavior, performance, compliance, and adherence to the prescribed tasks).

FIG. 12 has a diagram illustrating a configuration of the input of digital behavioral/cognitive tasks (e.g., at the execution input unit 1130), a patient user interface (UI) (e.g., presented as part of the patient application 1120) for outputting behavioral and cognitive compliance for the input, sensing, and patient input data collection unit 1120. In some implementations, the patient application 1120 includes an activation module 1201 for a patient to initiate the system (e.g., via install command 1255), a security module 1202 for generating a patient security token 1256 for patient information and behavioral/cognitive prescription, a BCI presentation module 1203 (e.g., BCI Module 1203) for providing patient behavioral/cognitive tasks (e.g., via the patient application 1120), a first BCA data module 1204 for collecting patient behavioral/cognitive compliance data through direct patient input (e.g., via a patient interface 1220 of the patient application 1120), and a second BCA data module 1205 for collecting sensing data on the patient's behavioral/cognitive compliance from the one or more sensors 1124.

In some implementations, the patient application 1120 includes a converter 1210 that converts behavioral and cognitive tasks into sensing commands that are provided to the one or more sensors 1124, a patient interface 1220 that presents behavioral and cognitive tasks to the patient, a patient interface 230 that provides behavioral and cognitive compliance information (e.g., text-based qualitative data) input by the patient to the patient application 1120, and converter 1240 for converting signals generated by the one or more sensors 1124 into behavioral and cognitive compliance information (e.g., bio-signal-based quantitative data).

The digital behavioral and cognitive instructions 1251 provide the patient 1122 (e.g., via the BCI module 1203 and the patient application 1120) with one or more digital behavioral and cognitive tasks to be performed. The behavior and cognitive adherence information 1252 includes performance results (e.g., performance data) of behavioral and cognitive tasks (e.g., behavioral and cognitive compliance) that are received via the patient application 1120 as first BCA data 1204 The questionnaire response 1253 includes information that is directly input into the patient application 1122 on behavioral and cognitive task performance. The patient information input via the questionnaire response 1253 is included as part of the 1st BCA data 1204. The electronic response 1254 includes performance result data output from the one or more sensors 1124 and is related to behavioral and cognitive task performance. The install command 55 is an installation command for an interface. The patient security token 1256 is a security token for the patient that is used by the patient application 1120.

In some implementations, the one or more sensors 1124 include output units of one or more sensor devices. For example, the one or more sensors 1124 may include a heartrate monitor output from a fitness band and video captured by a camera on a smart phone. In some implementations, the patient application 1120 is configured to present specific behavioral and cognitive tasks related to the doctor's behavioral and cognitive prescription to the patient 1122, and instructions corresponding to the specific behavioral and cognitive tasks may include any of: a visual component (such as displaying a visual cue, displaying a video, displaying one or more images), au auditory component (such as audio to accompany a video, audio cues, audio instructions), a tactile stimulation, a motion (e.g., a requested motion, such as "sit down" or "track the red button with your left eye"), or a combination thereof.

In this case, the task presented through the patient application 1120 is not abstract, but refers to a specific action that the one or more sensors 1124 and the patient 1122 can objectively convert into data as a result of performing the task. For example, the one or more sensors 1124 can measure activity volume, heart rate, and electrocardiac data using a wearable device, and collect image data using video recording. In addition, the one or more sensors 1124 can collect information on the result of performing behavioral and cognitive tasks using various sensors. Each of the one or more sensors 1124 may be configured in different configurations (e.g., different settings) in accordance with the desired treatment method (e.g., in accordance with the prescribed tasks).

The patient application 1120 has a user interface for providing a doctor's behavioral and cognitive prescription to the patient 1122 as a behavioral and cognitive task. In some implementations, the patient application 1120 monitors and records one or more behaviors of the patient 1122, and quantifies the patient's results.

In some implementations, data generated by the patient application 1120 includes information that is objective, quantifiable, and trackable over time about the patient's performance on the presented task. In order to acquire such information, the patient application 1120 outputs the patient's direct recording information on the performance of behavioral and cognitive tasks, the patient's application 1120 login time, and sensing data collected using the one or more sensors 1124.

In some implementations, the one or more sensors 1124 and the patient application 1120 play a key role in generating compliance information for the patient's behavioral and cognitive prescription. The degree of behavioral and cognitive compliance refers to the patient's performance result of patient-specific digital behavior and cognitive prescription, which can be reported to the doctor, by being directly input by the patient or collected, stored and analyzed in the form of manual data that use sensors.

FIG. 13 is a diagram showing the configuration of a doctor user interface (e.g., provided via the doctor application 1130) for receiving a doctor's behavioral and cognitive prescription (e.g., input by a doctor 1132) and for receiving a report on the behavioral and cognitive compliance of a patient 1122. The doctor application 1132 includes a user interface that receives behavioral and cognitive prescription from a doctor 1132, provides the behavioral and cognitive prescription to a patient (e.g., via a patient application 1120), and receives a behavioral and cognitive compliance report on a patient's behavioral and cognitive task performance results for reporting to the doctor 1132.

In some implementations, the doctor application 1130 includes an activation module 1301 for a doctor 1132 to initiate a system, a security module 1302 for generating a doctor security token 1358, a BC prescription module 1303 for inputting a patient's medical record and behavioral and cognitive prescription, a BCA data analysis module 1304 that calls the patient's behavior and cognitive compliance and performs data processing, and a BCA data reporting module 1305 that generates a report on the patient's behavioral and cognitive compliance. Various information corresponding to each of the described modules may be visually provided (e.g., displayed) to a doctor 1132 through the a computing device 1310.

The behavior and cognitive instruction 1250 indicates a doctor's behavioral and cognitive prescription, the installation command 1357 is a command for installing components (e.g., modules or updates) required by the doctor application 1130. The doctor security token 1358 is a security token corresponding to the doctor 1132 that is used by the doctor application 1130. Patient information 1359 includes patients' medical records. Behavior and cognition adherence 1260 includes a patient's behavioral and cognitive compliance data.

FIG. 14 has a diagram showing the configuration of a cloud server 1140 and a security gate 1450. In some implementations, the cloud server 1140 includes a backend server 1410 and a BCI/BCA processing server 1420. The In some implementations, the backend server 1410 includes an event management module 411, which presents behavioral and cognitive tasks to the patient application 1120 (e.g., via a user interface provided by the patient application 1120), a content manager 1412 (e.g., a content management module 1412) that transmits and receives the patient's behavior and cognitive compliance, and a system manager 1413 (e.g., system management module 1413) that installs user interface(s) for the patient application 1120 and configures one or more sensors 1124 of a client device that executes the patient application 1120. In some implementations, the BCI/BCA processing server 1420 may include a P-to-I (prescription to instruction) conversion module 1421 that converts behavioral and cognitive prescriptions into behavioral and cognitive tasks, and a patient information module 1422 that provides patient information, and a BCA recording module 1423 that records the patient's behavioral and cognitive compliance. In some implementations, the BCI/BCA processing server 1420 includes a database management system (DBMS) 1430 that stores information on the behavioral and cognitive tasks of the patient, and behavioral and cognitive compliance (e.g., adherence) information for the patient.

In some implementations, the security gate 1450 is configured to encrypt and manage various types of patient information that are provided or transferred between the patient application 1120, the doctor application 1130, and the cloud server 1140.

Figure 10:
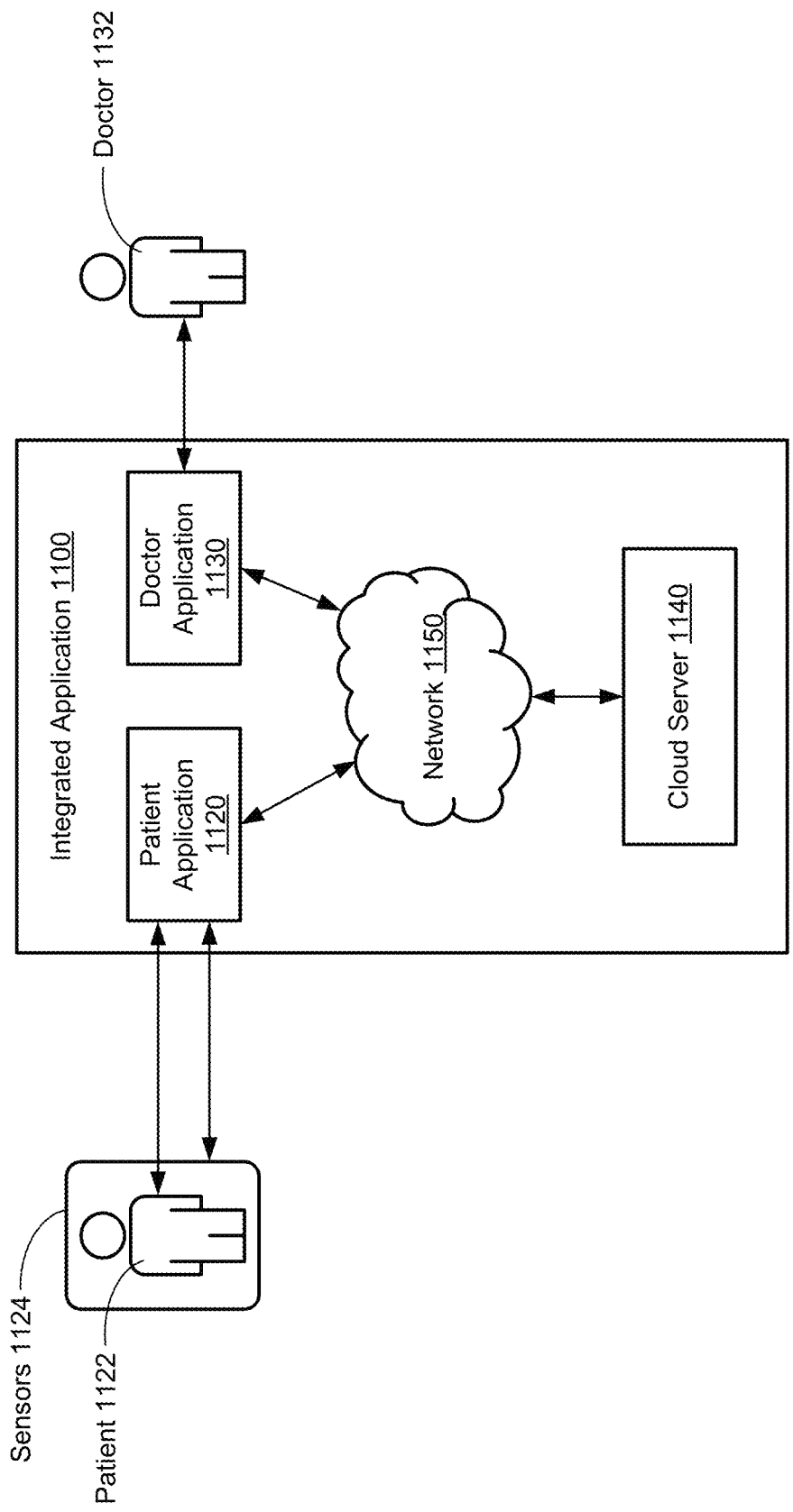
FIG. 10 is a diagram illustrating flow of information between a patient, and integrated application, and a doctor in a digital behavior-based treatment system according to some implementations.

In some implementations, the cloud server 1140 connects (e.g., allows for communication between) the patient application 1120 and the doctor application 1130 through a network (such as the network 1150 shown in FIG. 10). In some implementations, the cloud server 1140 also manages a back-end service that oversees data management, storage, and security of patient-specific behavioral and cognitive tasks and behavioral and cognitive compliance in response to behavioral and cognitive prescriptions. In some implementations, the database management system 1430 is a database that stores information about behavioral and cognitive tasks and performance (input/output) that are repeatedly performed.

In some implementations, the security gate 1450 includes a security module (such as security module is a module 1202 shown in FIG. 12 and/or security module 1302 shown in FIG. 13, each of which may be included as part of security unit 136 shown in FIG. 1D) that encrypts and securely manages behavioral and cognitive tasks and performance data to block a third party's access to patient medical information (e.g., block access from a party other than the specific doctor 1132 who is prescribing the behavioral and cognitive tasks and the specific patient 1122 who is receiving the prescribed behavioral and cognitive tasks). In some implementations, personal information generated according to behavioral and cognitive prescriptions for the purpose of digital therapy is not legally permitted to be accessed and used by third parties, so the information must be transmitted through an encryption process to satisfy a sufficient level of security before being transmitted to a doctor 1132.

Figure 15:
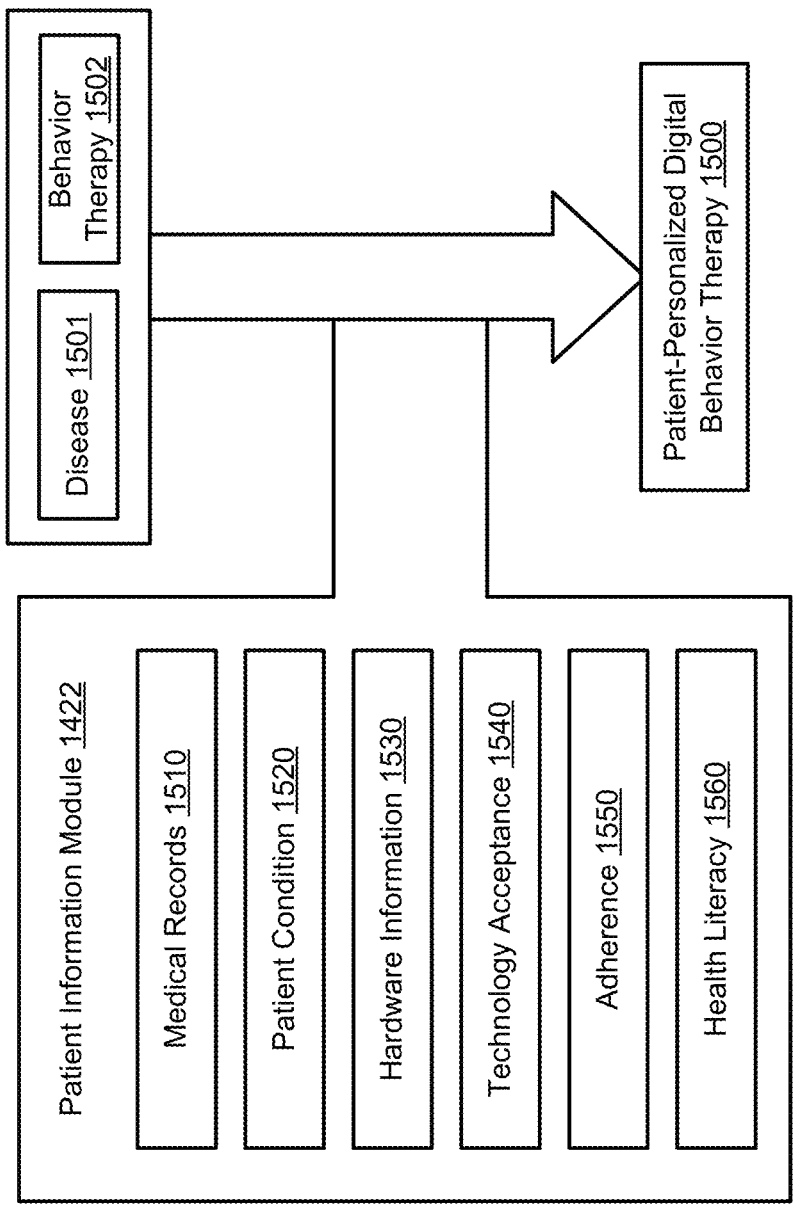
FIG. 15 is a block diagram showing an information module for generation of patient-specific digital behavior and cognitive prescriptions according to some implementations.
Figure 16:
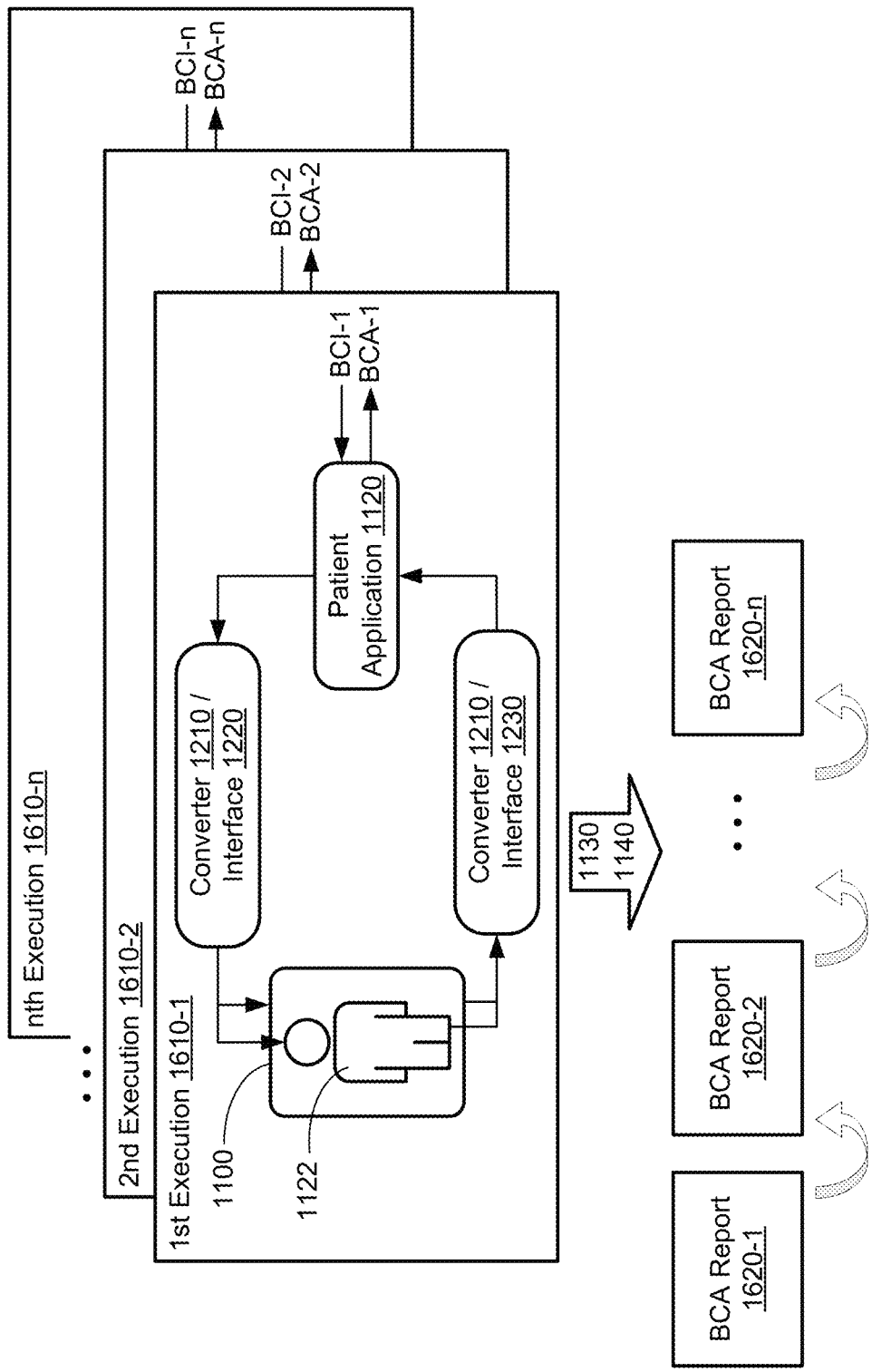
FIG. 16 is a diagram illustrating generating patient-specific digital behavioral and cognitive tasks using a digital behavioral and cognitive task 130 and feedback of the behavioral and cognitive compliance for prescribed task according to some implementations.

FIGS. 15 and 16 illustrate the use of patient information and the use of feedback for each time of task-performing in order to extend the digital behavior-based treatment system of the present invention to a patient-customized digital behavior-based treatment system.

FIG. 15 is a block diagram showing a patient information module 1422 for generation of patient-specific digital behavior and cognitive prescriptions. In some implementations, a method of generating and providing personalized digital behavior and cognitive prescriptions for patients 1122 include collecting patient medical information, generating and providing patient a digital environment information, collection of patient participation information, and creation of customized digital behavioral and cognitive prescriptions for each patient based on the collected patient information.

In some implementations, the patient information module 1422 includes medical records 1510 (e.g., health record information, medical record information, such as diagnosis, gender, age, medical history, family history), patient condition information 1520 (e.g., patient state information, such as physical/physiological/psychological diagnosis data), digital hardware information 1530 (e.g., information regarding hardware configuration(s) such as communication or sensor modules), technology acceptance information 1540 (such as patient acceptance attitudes toward digital treatment), adherence information 1550 about patient participation in treatment or confidence in doctors, and health literacy 1560 (e.g., health knowledge information, such as feedback on treatment or participation in education.

In some implementations, the digital behavior-based treatment system 130 provides a general behavioral prescription (e.g., exercise, diet, lifestyle) as a personalized digital behavioral and cognitive prescription for each patient using information (e.g., data) regarding the patient. In some implementations, the patient information module 1422 provides auxiliary data for behavioral and cognitive prescriptions specifically suggested by doctor(s) 1232. In some implementations, the patient information module 1422 also provides exponentially increasing patient-related medical information, rapidly changing digital technology and environment, and patient digital attitude information that can voluntarily induce patient compliance to the P-to-I Converter 1421 (e.g., P-to-I conversion module 1421). Thus, the digital behavior-based treatment system 130 is able to create patient-specific digital behavioral and cognitive prescriptions and corresponding patient-specific digital behavioral and cognitive tasks.

FIG. 16 is a diagram illustrating generating patient-specific digital behavioral and cognitive tasks using a digital behavioral and cognitive task 130 and feedback of the behavioral and cognitive compliance for prescribed task. In some implementations, a first behavioral and cognitive task (BCI-1) a the first behavioral and cognitive compliance (BCA-1) are given as input values and output values, respectively, in a single loop for a single execution (e.g., a single round of provided behavioral and cognitive task(s) from a doctor 1132 to a patient 1122 and the corresponding behavioral and cognitive compliance information regarding the patient's behavior and/or response to the prescribed tasks). When the process is repeated (e.g., executed n times, a plurality of rounds that each include prescribed task(s) and patient response information or patient behavior information), a second behavioral and cognitive task BCI-2 (e.g., a behavioral and cognitive task of a second loop or a second execution) is generated and input from the BCI-1/BCA-1 value, which is generated in through a loop feedback process to provide second behavioral and cognitive task BCI-2 as an output. This feedback loop can be repeated n−1 times to derive patient-specific digital behavioral and cognitive tasks.

The digital behavior-based treatment system 130 uses data regarding the patient's digital behavioral and cognitive tasks and behavioral and cognitive compliance provided in previous rounds (e.g., round n−1) to calculate the patient's digital behavioral and cognitive tasks and behavioral and cognitive adherence to the current execution (e.g., the nth execution). Based on the patient's behavioral and cognitive task and compliance level calculated in the previous loop, the behavioral and cognitive task in the next loop (e.g., succeeding loop, subsequent loop) may be generated. In some implementations, the feedback process utilizes one or more algorithms and statistical models. In some implementations, the digital behavior-based treatment system 130 can optimize patient-specific behavioral and cognitive tasks suitable for a patient through a rapid feedback loop.

Figure 17:
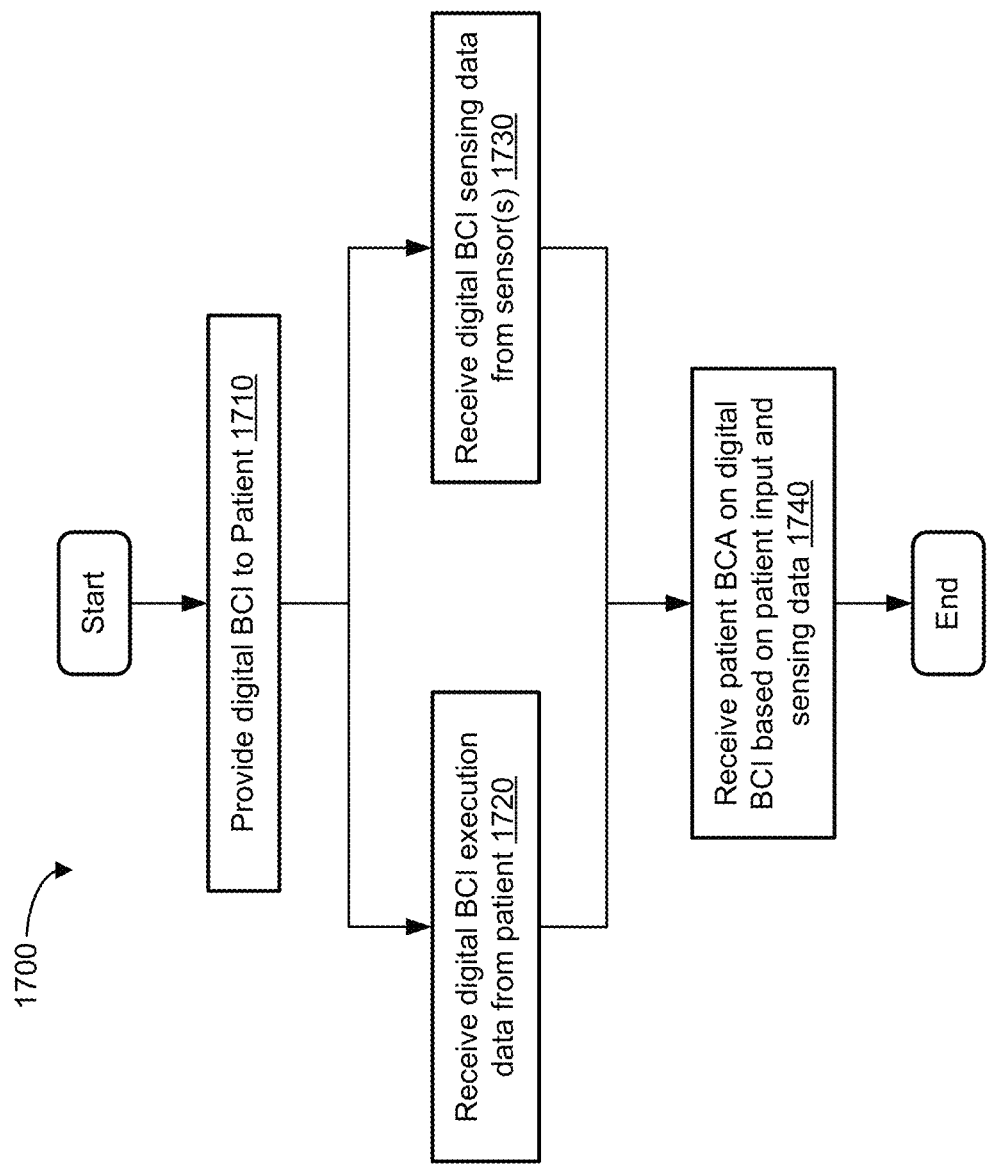
FIG. 17 is a flowchart illustrating operation of a digital behavior-based treatment application 130 according to some implementations.

FIG. 17 has a flowchart illustrating operation of a digital behavior-based treatment application 130 according to some implementations. The digital behavior-based treatment application 130 provides (1710) a digital behavioral and cognitive task to a patient 1122 (e.g., a first user 1122). The digital behavioral and cognitive task may be generated by converting the behavioral and cognitive prescription received from the doctor 1132 (e.g., a second user 1132). The digital behavior-based treatment application 130 also receives patient information (e.g., patient medical information, digital environment and patient engagement information) through the patient application 1120, which may include patient-specific digital behavioral and cognitive task(s) that are created based on the patient's information. The digital behavior-based treatment application 130 also receives (1720) an input regarding a result of performing a digital action and a cognitive task presented from a patient 1122. In some implementations, a patient 1122 may directly input results of digital behavioral and cognitive tasks through the patient application 1120. The digital behavior-based treatment application 130 also receives (1730) sensing data (e.g., from the one or more sensors 1124 via sensing data collection unit 132, shown in FIGS. 10 and 1D, respectively), regarding the patient's performance with regards to (e.g., behavior in response to) the prescribed digital behavioral and cognitive task(s). For example, the sensing data collection unit 132 may collect information on a result of performing a behavioral and cognitive task, using an activity amount with the use of wearable devices, ECG measurement, a data collection using video shooting and other various sensors. Based on the patient's input and sensing data received in steps 1720 and 1730, respectively, the digital behavior-based treatment application 130 determines (1740) (e.g., calculates) the patient's behavioral and cognitive compliance to the digital behavior and cognitive task may be calculate. Step 1740 is repeatedly performed (e.g., performed multiple times) using data on the patient's digital behavioral and cognitive tasks and behavioral and cognitive compliance provided in the previous executions 1610 (e.g., previous rounds 1610 as shown in FIG. 16) and to generate the patient's digital behavioral and cognitive tasks and behavioral and cognitive compliance for the current round can be calculated.

In some implementations, the digital behavior-based treatment application 130 also encrypts and manages data regarding a patient's digital behavior and cognitive tasks and behavior and cognitive compliance. In some implementations, the digital behavior-based treatment application 130 also collects the calculated behavior and cognitive compliance of the patient at a preset period and reports it externally (e.g., to an external server, to an external system, to an external database).

In some implementations, the digital behavior-based treatment application 130 tacks (e.g., observes and/or records) the patient's performance and compliance with the doctor's behavioral and cognitive prescription in real time. Since long-term tracking and database storage are possible, data for clinical validation of doctors' behavioral and cognitive prescriptions can be obtained through quantification.

Figure 18:
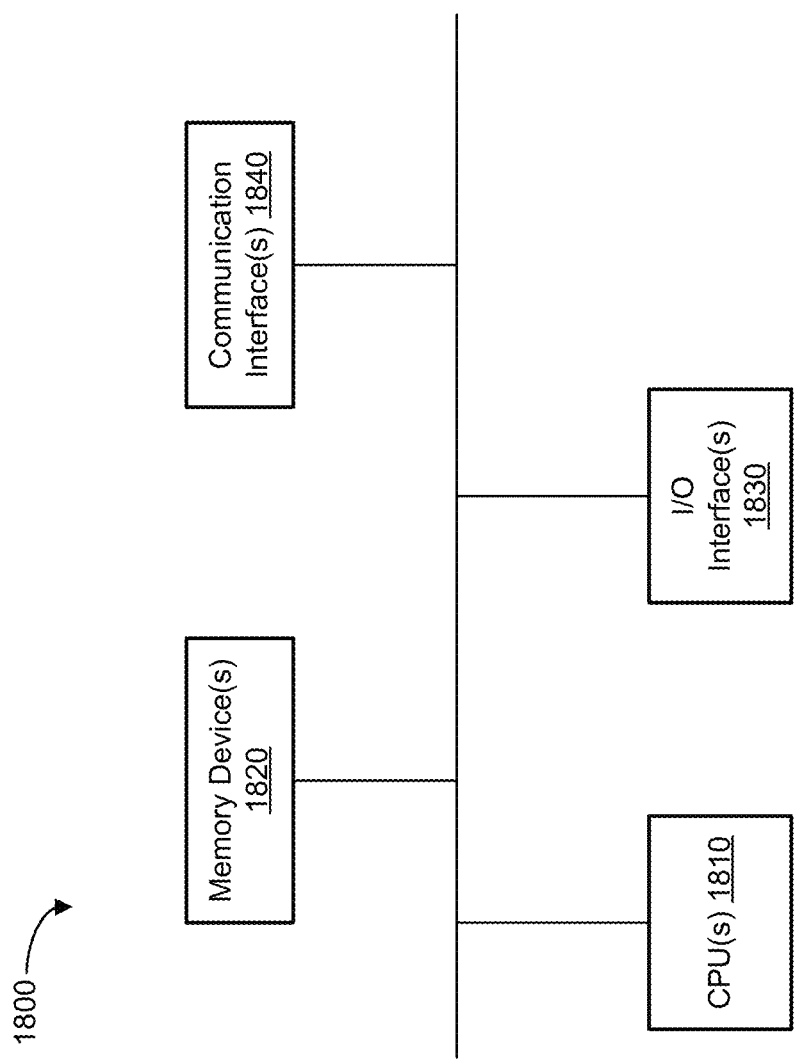
FIG. 18 is a diagram showing a hardware configuration of a digital behavior-based treatment system 130 according to some implementations.
Figure 19A:
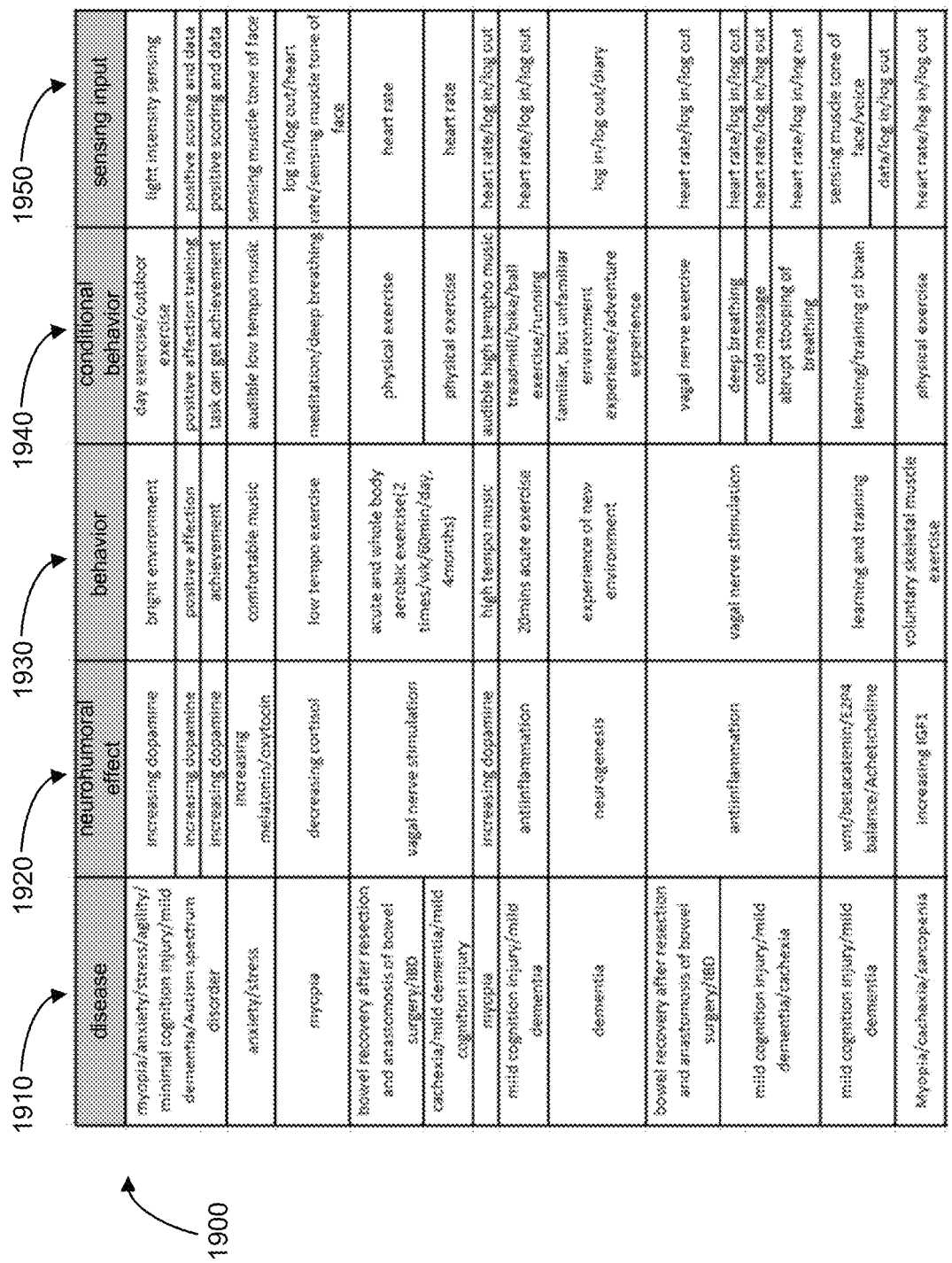

FIG. 18 has a diagram showing a hardware configuration of a digital behavior-based treatment system 130 according to some implementations. A server system 1800 (e.g., hardware of a server system 1800) of the digital behavior-based treatment system 130 includes one or more computer processing units (CPUs) 1810, one or more memory devices 1820 (e.g., non-transitory memory devices, non-volatile memory devices, volatile memory devices, and transitory memory devices), one or more input/output (I/O) interface(s) 1830, and one or more communication interfaces 1840.

The one or more CPU(s) 1810 may include a processor that executes the digital behavior-based treatment program 130 that is stored in the one or more memory devices 1820, process various data for digital behavior-based treatment, and perform functions related to digital behavior-based treatment. The CPU(s) 1810 may execute the digital behavior-based treatment program 130 stored in the memory devices 1820 to perform the functions of each components shown in FIG. 10.

In some implementations, the one or more memory devices 1820 stores the digital behavior-based treatment program 130. In some implementations, the memory devices 1820 include data used for digital behavior-based treatment, which is included in a database (e.g., the database 135 shown in FIG. 1D), such as a patient's digital behavioral and cognitive tasks, behavioral and cognitive compliance, and a patient's medical information.

The one or more memory devices 1820 may include volatile memory and/or nonvolatile memory. For example, any of the one or more memory devices 1820 may include RAM, DRAM, SRAM, or the like. In addition, any of the one or more memory devices 1820 may include ROM, PROM, EAROM, EPROM, EEPROM, or flash memory.

In some implementations, the input/output (I/O) interface 1830 includes input devices (such as keyboard, mouse, and touch panel) and/or output devices (such as a display) that connect with the CPU(s) 1810 to transmit and receive data (e.g., user input).

The communication interface(s) 1840 are configured to transmit and receive various types of data to and from a server, and may include a verity of various devices that are capable of supporting wired and/or wireless communication. For example, through the communication interface(s) 1840, various data related to the aforementioned digital behavior-based treatment may be received from an external server that is provided separately.

In some implementations, a computer program stored in the memory device(s) 1820 and processed by the CPU(s) 1810 may be implemented as a module that performs each functional block shown in FIG. 1D.

In the above, even though all the components constituting some implementations of the present invention are described as being combined into one or operating in combination, the present invention is not necessarily limited to these specific implementations. That is, within the scope of the object of the present invention, all of the constituent elements may be selectively combined and operated in one or more.

In addition, in the digital behavior-based treatment application in the present invention, the performance data on the patient's behavioral and cognitive prescription can be used as important primary data for the clinical decision of the doctor at a later visit, and further, accumulated behavioral and cognitive task-performance data can be combined with big data analysis and artificial intelligence analysis to be used to develop and improve patient-specific behavioral and cognitive prescriptions.

As described above, according to the digital behavior-based treatment application according to the present invention, it is possible to observe the patient's performance and compliance with the doctor's behavioral and cognitive prescription in real time, and, since long-term tracking and storage in a database are possible, data for clinical validation of doctors' behavioral and cognitive prescriptions can be obtained through quantification.

In addition, in the digital behavior-based treatment application in the present invention, the performance data on the patient's behavioral and cognitive prescription can be used as important primary data for the clinical decision of the doctor at a later visit, and further, accumulated behavioral and cognitive task-performance data can be combined with big data analysis and artificial intelligence analysis to be used to develop and improve patient-specific behavioral and cognitive prescriptions.

FIGS. 19A-19D show a table 1900 of different diseases 1910 and their corresponding neurohumoral effects 1920, behavior(s) 1930, behavioral treatment options 1940, and treatment sensing inputs 1950 according to some implementations. Table 1900 includes examples of different diseases 1900 that may be treated using neurohumoral behavioral therapy. Each disease 1900 is associated with at least one neurohumoral effect 1920, and the neurohumoral effect 1920 is also associated with at least one behavior 1930. A conditional behavior 1940 (e.g., behavioral treatment 1940) can be prescribed to address the behavior 1930, and providing the conditional behavior 1940 as part of neurohumoral behavioral therapy may include receiving and/or tracking treatment sensing inputs 1950.

For example, table 1900 shows that a patient who is diagnosed with autism spectrum disorder may have a neurohumoral effect of increasing Adrenocorticotropic hormone (ACTH) in the patient's system (e.g., the patient's body). A physician may want to address the patient's behavior 1930 regarding social exercise (e.g., regarding the patient's social abilities). Thus, a physician may prescribe, as part of neurohumoral behavioral therapy, treatment (such as treatment(s) in a treatment program 118) that includes exercise(s) for improving social communication. In order to track the patient's behavior (e.g., activity) and adherence to the neurohumoral behavioral therapy, the treatment may require the patient to provide data regarding his or her exercises as sensing inputs 1950. For example, the patient may provide one or more diary entries reflecting on his or her social exercise. In another example, the patient may log into a session that provides one or more exercises for social communication in order to receive the treatment and complete the prescribed exercise.

In some implementations, a disease 1910 may be associated with a plurality of neurohumoral effects 1920. For example, disc herniation is shown to be associated with a reduction in Tumour Necrosis Factor alpha (TNF alpha), inflammation, reduction in Interleukin 6 (IL-6), and a reduction in locally produced Insulin-like growth factor 1 (IGF1). Thus, in some implementations, neurohumoral behavioral therapy may include prescribing one or more conditional behaviors 1940 (e.g., treatments) as part of a treatment program in order to address one or more behaviors 1930 associated with the disease. Additionally, the patient's progress or activity with regards to each prescribed conditional behavior 1940 is tracked via one or more sensing inputs 1950.

In some implementations, a neurohumoral effect 1920 and its corresponding behavior 1930 may be associated with a plurality of diseases 1910. In such cases, a specific conditional behavior 1940 (e.g., treatment) prescribed to address the behavior 1930 may be provided (e.g., prescribed) as part of a treatment program (e.g., treatment program 118) to treat a variety of different diseases 1910.

Figure 20:
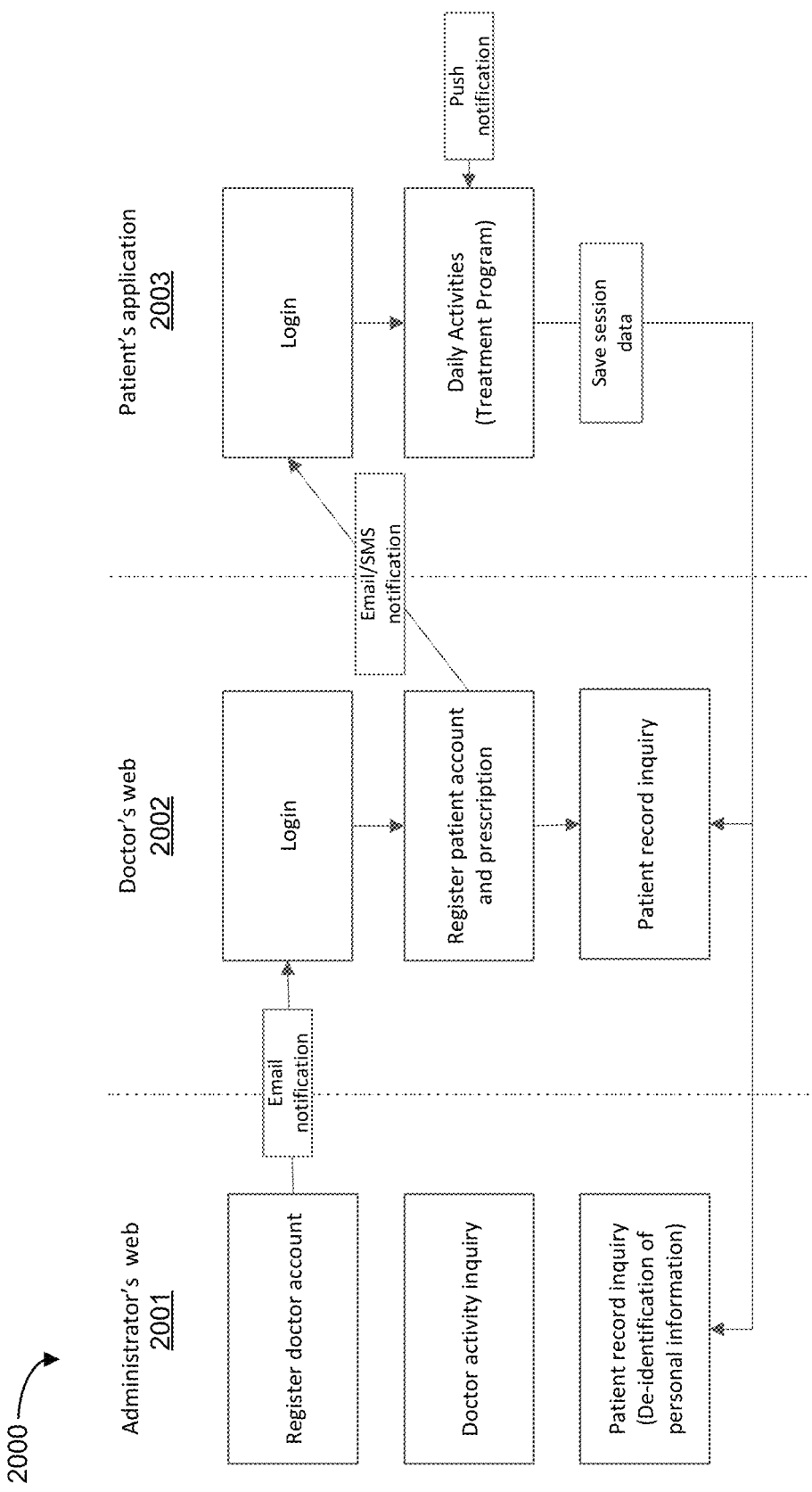
FIG. 20 is a diagram illustrating interactions between applications provided to an administrator, a doctor, and a patient for the digital behavior-based treatment system according to some implementations.

FIG. 20 is a diagram illustrating a registration process 2000 for the mobile and/or web applications for the digital behavior-based treatment system provided to an administrator, a doctor, or a patient. FIG. 20 illustrates that an administrator, using a web application 2001, instructs the system to initiate registration for a doctor account on behalf of a doctor, including specifying an email address for the doctor (e.g., as described with reference to FIGS. 22X-22Y below). Examples of the administrator's application are described with reference to FIGS. 22A-22CC.

In some implementations, in response to the administrator initiating the registration for the doctor's account, the doctor receives (e.g., via email) a notification that optionally includes login information for the doctor (e.g., a login ID and/or a password). In some implementations, after the doctor receives the email notification, the doctor is enabled to login to the doctor's web application 2002 (e.g., a web portal) to access the digital behavior-based treatment system with the doctor's credentials. Examples of the doctor's application are described with reference to FIGS. 23A-23H.

In some implementations, after the doctor has logged into the web application 2002, the doctor is enabled to register a new patient account with a new prescription (e.g., as described with reference to FIG. 23H, the doctor can select "Add a new patient if not already registered"). In some implementations, in response to the doctor registering the new patient, the patient is provided (e.g., via email and/or a text message (e.g., SMS)) with a notification that the patient's account has been registered and/or updated with a new prescription.

In some implementations, in response to the email notification, the patient logs into the patient's application 2003 (e.g., a web and/or a mobile application), where the patient is enabled to view the treatment program provided by the doctor. In some implementations, push notifications are also provided to the patient to remind the patient of daily activities for the patient to perform in accordance with the treatment program. For example, sessions are guided by duration and frequency prescribed by the doctor. In some implementations, a notification (e.g., a push alarm) is provided on the mobile device of the patient (e.g., that runs the patient's application). In some implementations, an activity history is logged to show the progress of whether the patient is using the application on the schedule (e.g., according to the duration and frequency prescribed by the doctor). Examples of the patient's application are described with reference to FIGS. 21A-21I.

In some implementations, during a patient's session in the patient application, a patient logs various activities in the patient application. In some implementations, session data is collected (e.g., using one or more sensors of the patient's device) for the activities, and the session data is reported to the applications for the doctor and the administrator. In some implementations, the doctor is enabled to view all of the information about the patient's records, while an administrator is only enabled to view a subset of the information (e.g., the information is anonymized before the administrator can view). As such, patient records and personal information (e.g., identification of the patient) are not accessible to the administrator.

Figure 21A:
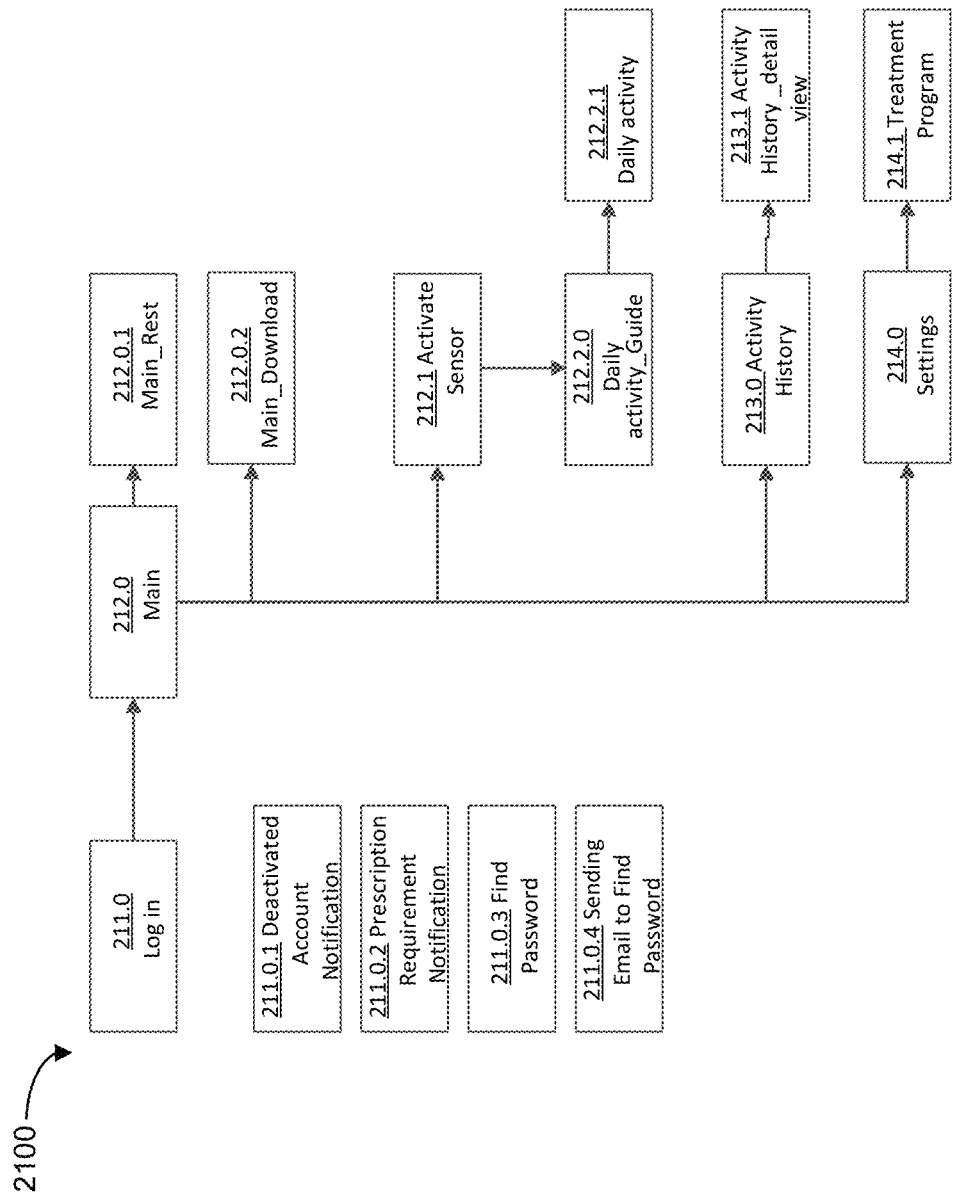
FIGS. 21A-21I illustrate examples of an application provided to a patient for interacting with the digital behavior-based treatment system according to some implementations.

FIGS. 21A-21I illustrate examples of interactions with a patient's application for the digital behavior-based treatment system. FIG. 21A illustrates an overview of the patient's application structure 2100. For example, the patient is enabled to login (211.0) to the application, and from the main menu (212.0) displayed in the application, the patient is enabled to indicate whether the patient would like a rest (212.0.1) day or to download (212.0.2) the treatment program for the patient (if it is not downloaded to the patient's device already).

In some implementations, if the treatment program requires one or more sensors for performing and/or tracking the patient's participation, the application activates the one or more sensors (212.1). In some implementations, after the one or more sensors are optionally activated, the application presents the patient with a daily activity guide (212.2.0) that displays, for the patient, an overview of activities the patient will perform as part of the treatment program for the day (e.g., in the current session), and after presenting the guide, the application prompts the user to perform the daily activity (212.2.1) (e.g., while recording the patient's activities using the one or more sensors).

In some implementations, the patient is also enabled to access, from the main menu (212.0), an activity history (213.0) of the patient. For example, the patient selects to view a detailed view (213.1) of the patient's activity (e.g., a frequency and duration of the treatment program that the patient has been active in and/or results and data gathered (e.g., from the sensors) tracking the patient's activities).

In some implementations, the main menu (212.0) also provides the patient with access to one or more settings (214.0) that the patient can view and update, including settings for a particular treatment program (214.1), such as alert settings (e.g., reminders for the treatment program) and/or other settings (e.g., login credentials, etc.).

In some implementations, the patient's application also provides the patient with a notification if the patient's account has been deactivated (211.0.1). For example, in accordance with the administrator deactivating the patient account, an alert is provided to the patient. In some implementations, a notification is provided to the patient stating that a prescription is required (211.0.2) if the patient attempts to access the application without an active prescription from a doctor. In some implementations, the patient's application also provides the patient with an option to find the patient's password (211.0.3) or request to send an email to find the patient's password (211.0.4) if the patient is unable to login to the application (e.g., the patient forgot the patient's password for the application).

Figure 21B:
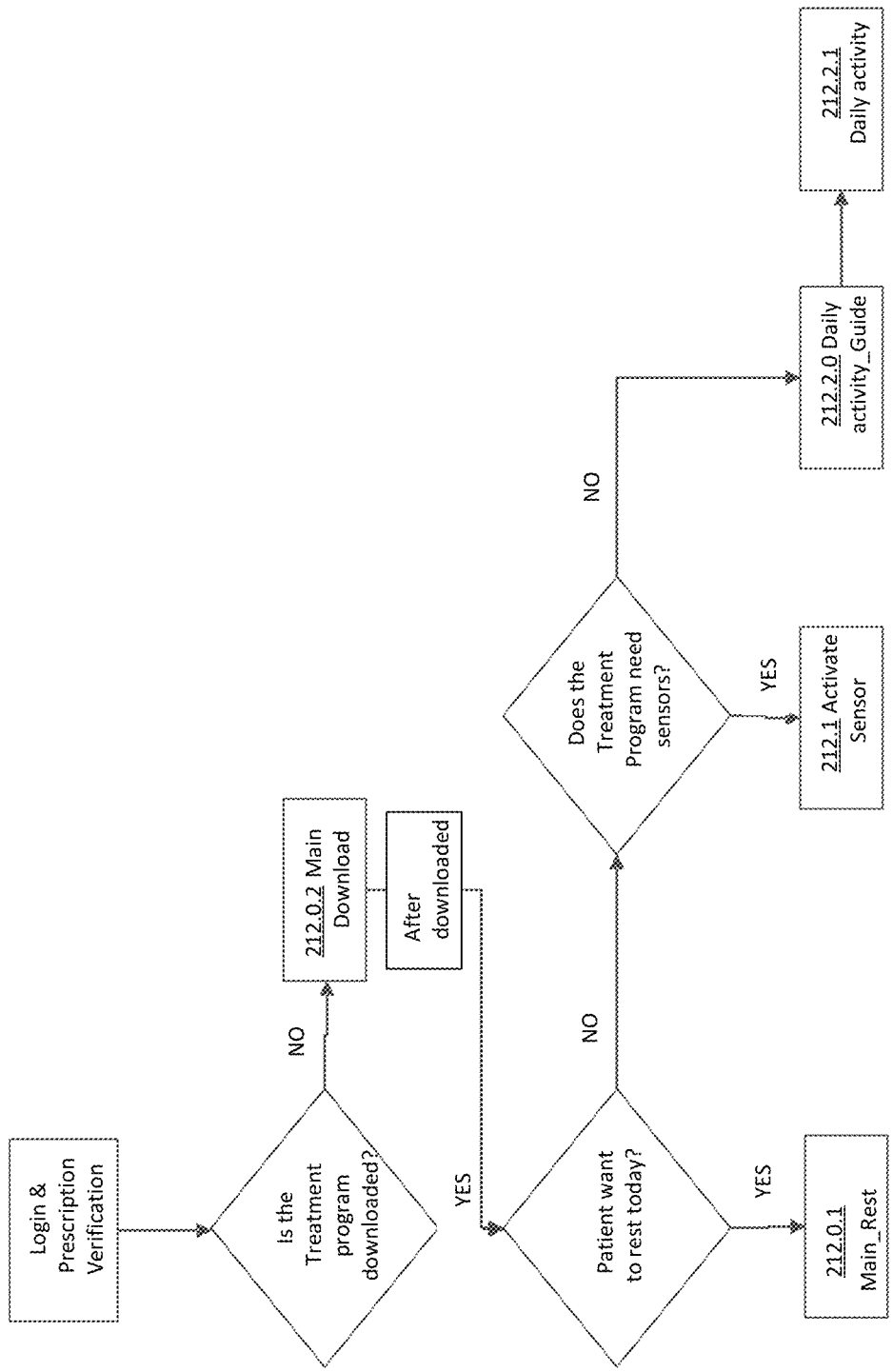
Figure 21C:
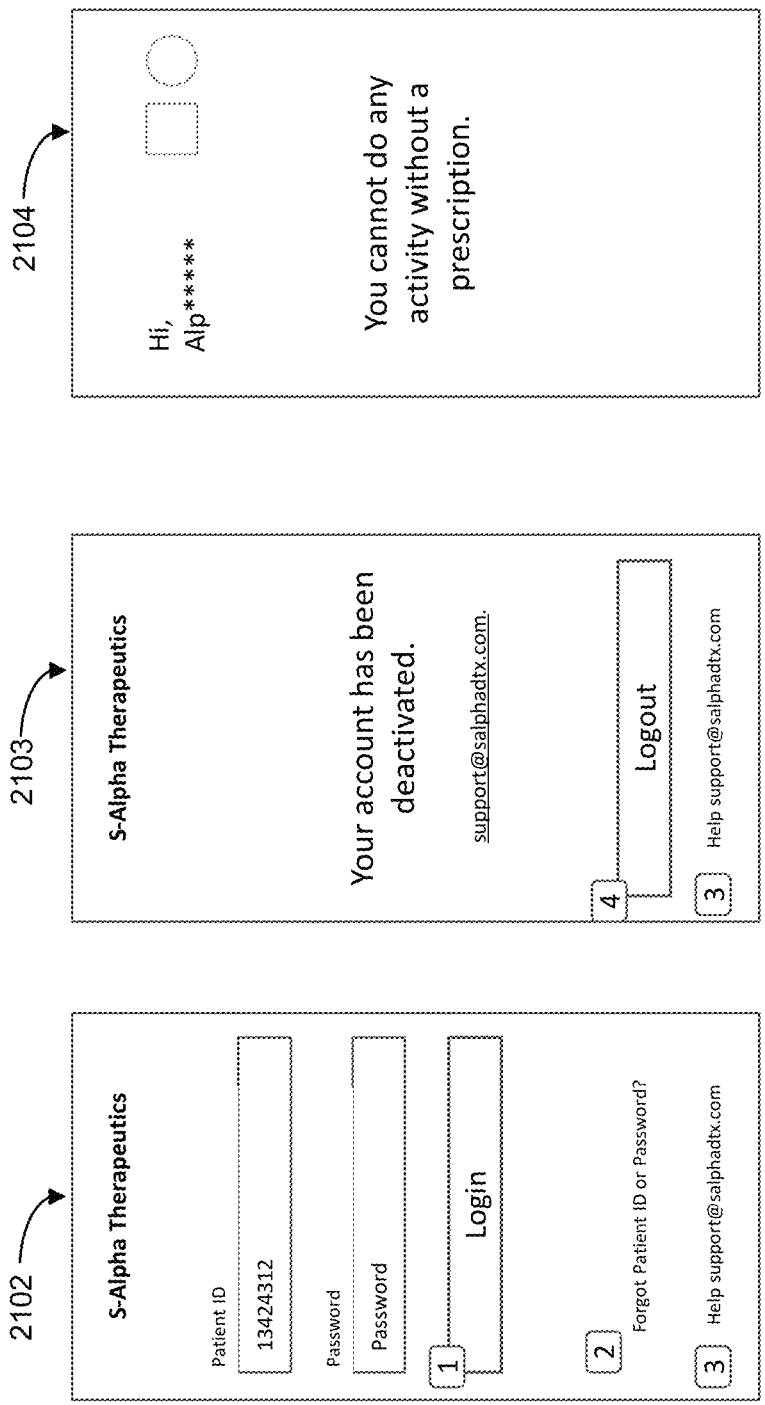

FIG. 21B illustrates a service flow available to the patient in the patient's application. For example, the service flow begins with the patient logging into the application, where the application verifies that the prescription(s) for the patient are prescribed by a doctor. The application determines whether the treatment program, for the prescription(s), is downloaded (e.g., locally to the device of the patient that is executing the application). If the treatment program has not been downloaded (e.g., from a server system of the digital behavior-based treatment system), the application requests (e.g., from the server system) to download the treatment program.

In some implementations, after downloading the treatment program (e.g., or if the treatment program is already downloaded to the patient's device), the application prompts the patient to input whether the patient would like to rest today (e.g., not participate in the treatment program using the application). For example, the application provides a user-selectable option to the patient that the patient uses to select whether to continue with the treatment program, or to rest for today's session. In accordance with a determination that the patient would like to rest (212.0.1) today (e.g., the patient selects the option corresponding to rest), the application reports back (e.g., to the server system) that the patient is resting, and, optionally, returns the patient to a main menu of the application (e.g., without initiating user interfaces that correspond to the treatment program).

In some implementations, in accordance with a determination that the patient does not want to rest today, the application continues with the treatment program. For example, the application determines whether the treatment program for the patient requires one or more sensors (e.g., sensors of the patient's device that is executing the application), and if so, activates the one or more sensors (212.1). In some implementations, the application displays a guide (212.2.0) for the patient that describes, for example, the activities that the patient will perform in the current session to participate in the treatment program. The patient's activity for the session (e.g., daily activity (212.2.1)) is logged, and, e.g., stored at the server system (e.g., to be accessible to the doctor and/or administrator via applications for the doctor and/or administrator, as described below).

FIGS. 21C-21I illustrate example user interfaces displayed to the patient (e.g., also referred to herein as the user) during the service flow described in FIG. 21B. For example, the device of the patient initially displays a login user interface 2102 for the patient application. In some implementations, in response to the patient inputting the patient's login credentials (e.g., login ID and password), the device (e.g., or a server system in communication with the device) checks the login credentials. In accordance with a determination that the patient ID does not exist or match the password, a pop up (or other user interface element) is displayed on the user interface of the device. For example, a notification is displayed indicating that the patient's account has been deactivated in the user interface 2103. In accordance with a determination that the patient ID and password is valid, the device displays determines whether the patient has an active (e.g., ongoing) prescription.

In some implementations, the patient does not have an ongoing prescription and the user interface 2104 is displayed to inform the patient that a prescription is required to use the application.

Figure 21D:
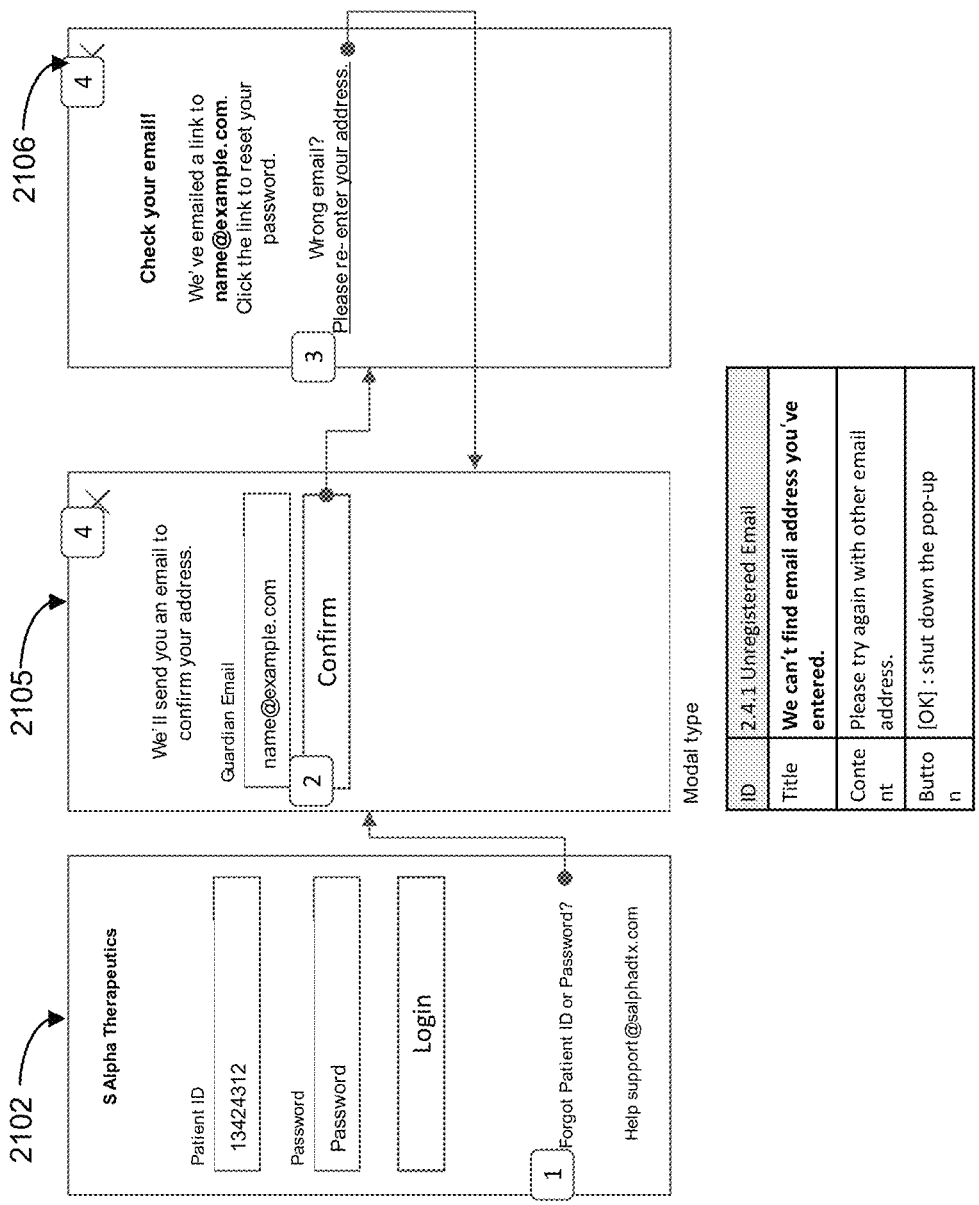

FIG. 21D illustrates the patient requesting a password reset. In some implementations, in accordance with a determination that the patient selects "Forgot Patient ID or Password" from the login user interface 2102, the application displays the user interface 2105 to allow the patient to input the patient's email address and request their user login and/or a password reset, as confirmed in the user interface 2106.

Figure 21E:
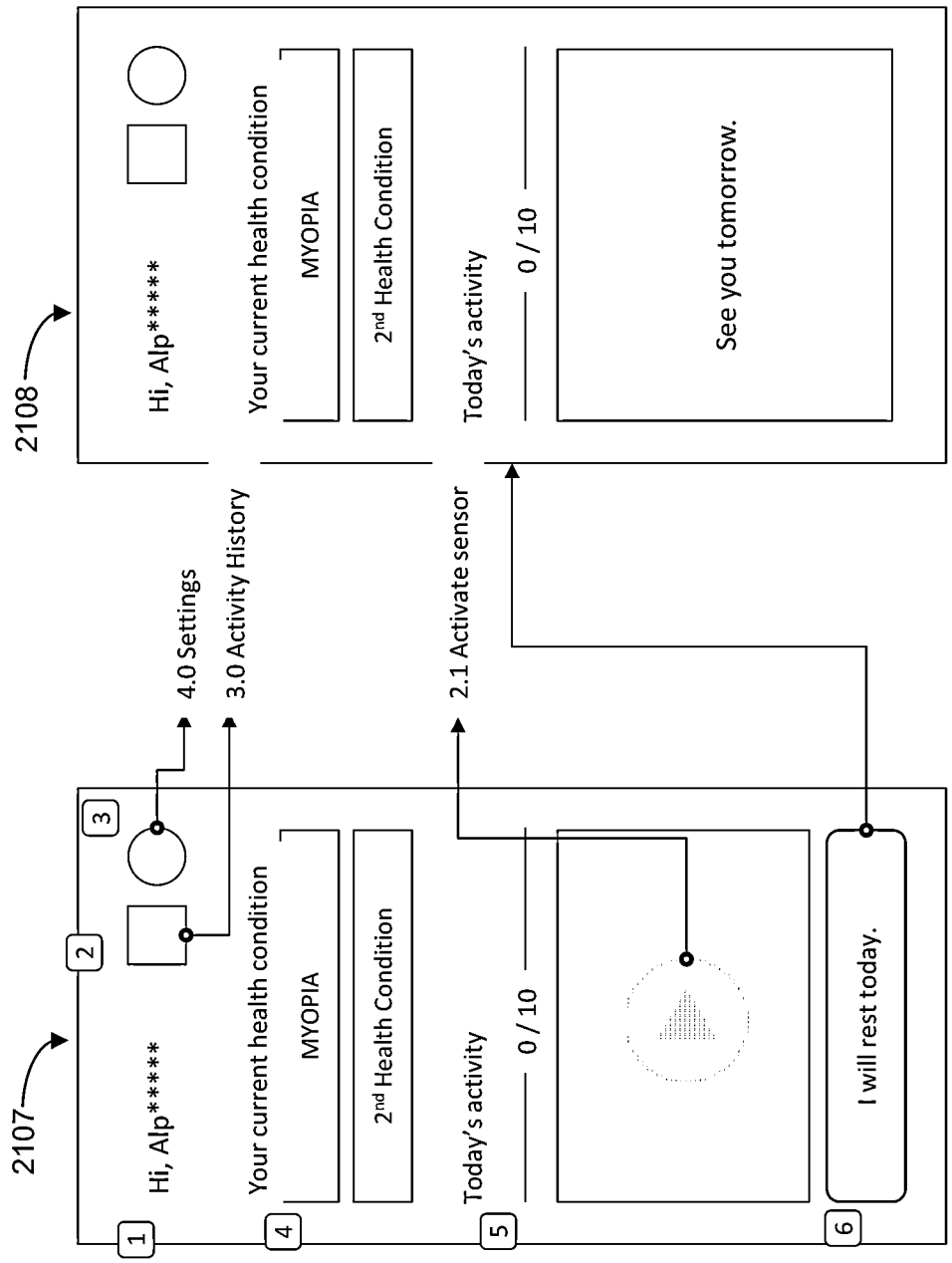

FIG. 21E illustrates a home (e.g., main menu) user interface 2107. In some implementations, the home user interface 2107 includes the patient's name (or username, or other identifier), and a plurality of user-selectable options for accessing the settings (214.0) and the activity history (213.0), as described with reference to the flow of application 2100 in FIG. 21A.

In some implementations, the home user interface 2107 further includes a list of the patient's health conditions (e.g., that have been input by a doctor and associated with the user's digital treatment account). In some implementations, a guide for "Today's activity" is also shown to the patient. In some implementations, as described above, a user-selectable option for resting today is provided. In some implementations, in response to the user selecting to rest today (e.g., the button 6 in the user interface 2107), the application updates the home user interface 2108 to remove the activity guide for today's activity and display "See you tomorrow."

Figure 21F:
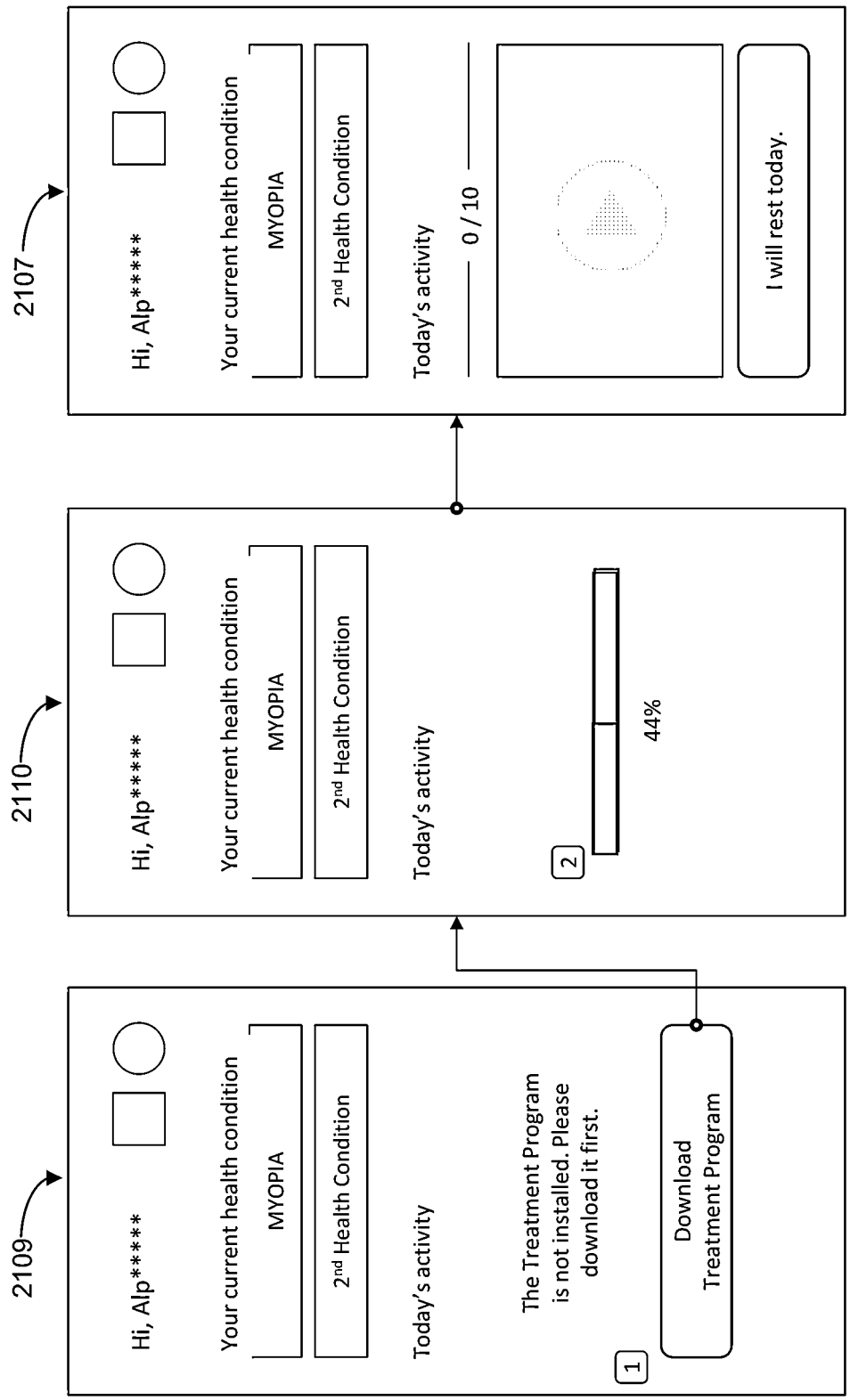

FIG. 21F illustrates downloading a treatment program that has not been installed on the patient's device. For example, the first time the patient accesses the application and/or the patient's first interaction with the application after the patient's prescription(s) have been updated by a doctor, the application displays the home user interface 2109 with a button to "Download Treatment Program." After the patient selects the Download Treatment Program button, the application updates the user interface to illustrate progress of the download (as shown in the progress screen 2110), before displaying the home user interface 2107 (described above).

Figure 21G:
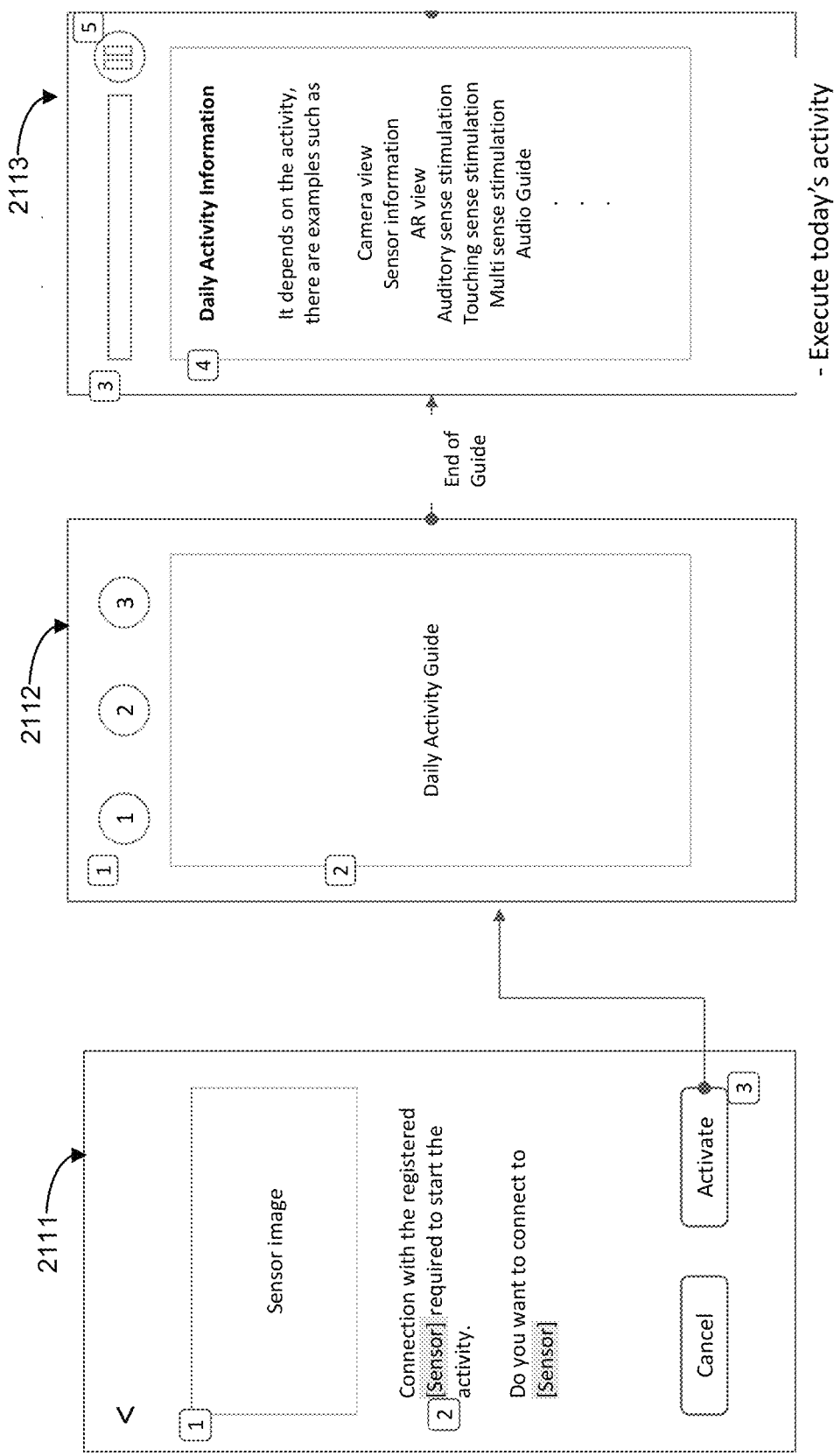

FIG. 21G illustrates a user interface that is displayed in response to the user selecting the "play" icon to begin today's activity. In some implementations, the user interface 2111 is displayed in accordance with a determination that an activity scheduled for today requires observation of the patient by one or more sensors. After the patient confirms to activate the one or more sensors (e.g., by selecting the Activate button 3), a daily activity guide (e.g., including a list and/or overview of the activities that the patient is to perform during the current session (e.g., day)) is displayed in the user interface 2112. In some implementations, the patient begins performing the activities, as prompted by the daily activity guide, and while the patient is executing the activities, a user interface 2113 is displayed, including a progress bar, a pause button, and information related to the current activity (e.g., a camera view, sensor information, an augmented reality (AR) view, auditory sense stimulation, multi-sense stimulation, and/or an audio guide). In some implementations, after the patient has completed the activity (e.g., for the duration, as prescribed by the doctor), the application stores the data obtained while the user performed the activity (e.g., and updates the patient's activity record with the data, including sending the data to the server system) and returns to the home user interface 2107.

Figure 21H:
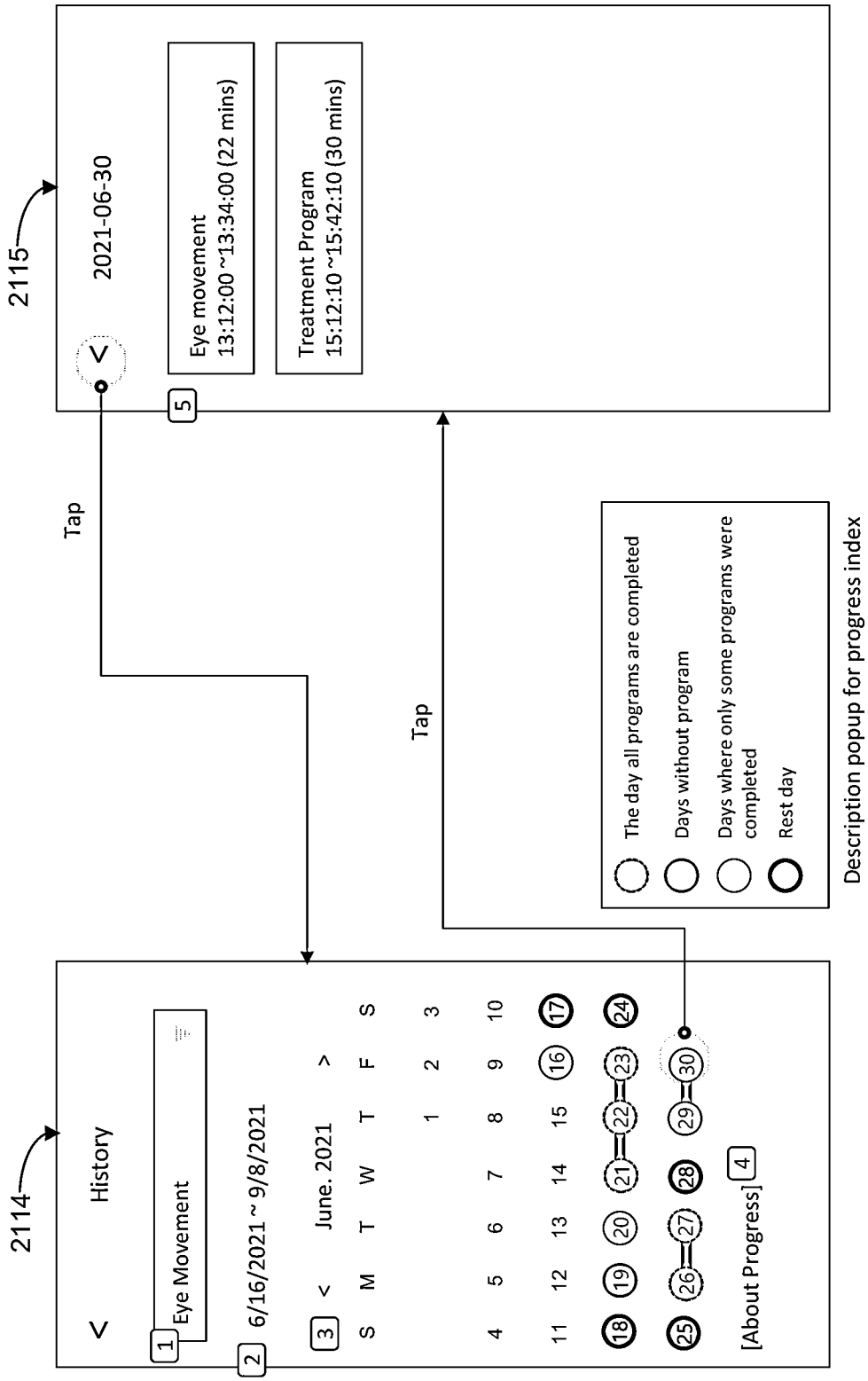

FIG. 21H illustrates a user interface for the activity history of the patient. In some implementations, the user interface 2114 is displayed in response to the user selecting, from the home user interface 2107, a control (e.g., the button 3 in FIG. 21E) for "Activity History." For example, a patient is enabled to select, from a dropdown, a treatment program (e.g., eye movement). In some implementations, the date range for which the prescription for the selected treatment program is displayed (e.g., 6/16/2021-9/8/2021). In some implementations, the user interface 2114 includes a calendar view with indications of the activity for each day in the calendar view. In some implementations, only the month(s) during which the prescription (e.g., for the selected treatment program) is active is displayed or accessible in the calendar view. In some implementations, navigating forward or backward in the calendar view (e.g., to a next or a previous month) does not display the calendar if the prescription was not active during the selected month. In some implementations, the calendar view is automatically populated to display today's date in the current view (e.g., or to display a first date of a prescription of the selected treatment).

In some implementations, each date during the prescription period is displayed with an indicator (e.g., a color) corresponding to an amount of activity logged for the date. For example, a first indicator (e.g., a first color, such as green) is displayed on the dates in which the patient completed all of the programs on that date, a second indication (e.g., a second color, such as red) is displayed on the dates in which no program was available that day, a third indication (e.g., a third color, such as orange) is displayed on the dates in which only a portion, less than all, of the prescribed programs (e.g., activities) were completed, and a fourth indication (e.g., a fourth color, such as grey) is displayed on the dates in which the user selected to rest.

In some implementations, the patient is enabled to select any date (e.g., from the calendar view) to view additional information about the logged activity for the day. For example, the user selects Jun. 30, 2021, and the application displays the user interface 2115 with detailed information about the user's eye movement (e.g., which lasted 22 minutes) and another treatment program (e.g., which lasted 30 minutes).

Figure 21I:
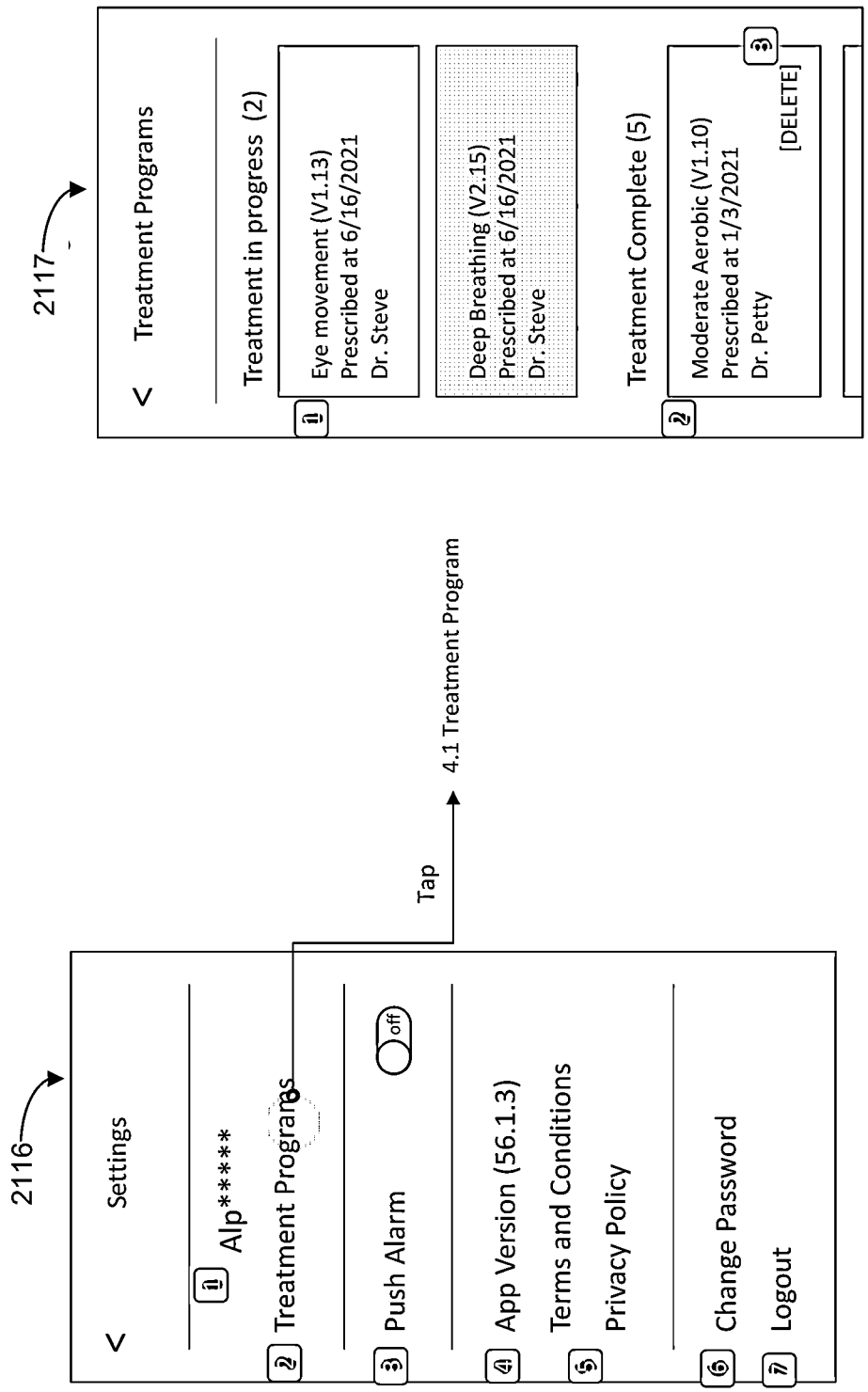

FIG. 21I illustrates a settings user interface 2116, which, in some implementations, is displayed in response to the patient selecting settings button 3 illustrated in FIG. 21E. In some implementations, the settings user interface includes user-selectable options for modifying completed treatments (e.g., the patient is enabled to delete a completed treatment, as illustrated in the user interface 2117). In some implementations, the patient selects to view additional details about the treatment programs, and in response to the patient selecting "Treatment Programs," details of the activities prescribed to the user are displayed (e.g., "Eye movement, prescribed at 6/16/2021, Dr. Steve").

In some implementations, the settings user interface 2116 includes an option to toggle push notifications (e.g., a push alarm reminding the user of the daily treatment), and includes additional information, such as the currently installed version of the application, terms and conditions, and privacy policy. In some implementations, the patient is further enabled to change the patient's password and logout of the patient's account from the application.

Figure 22A:
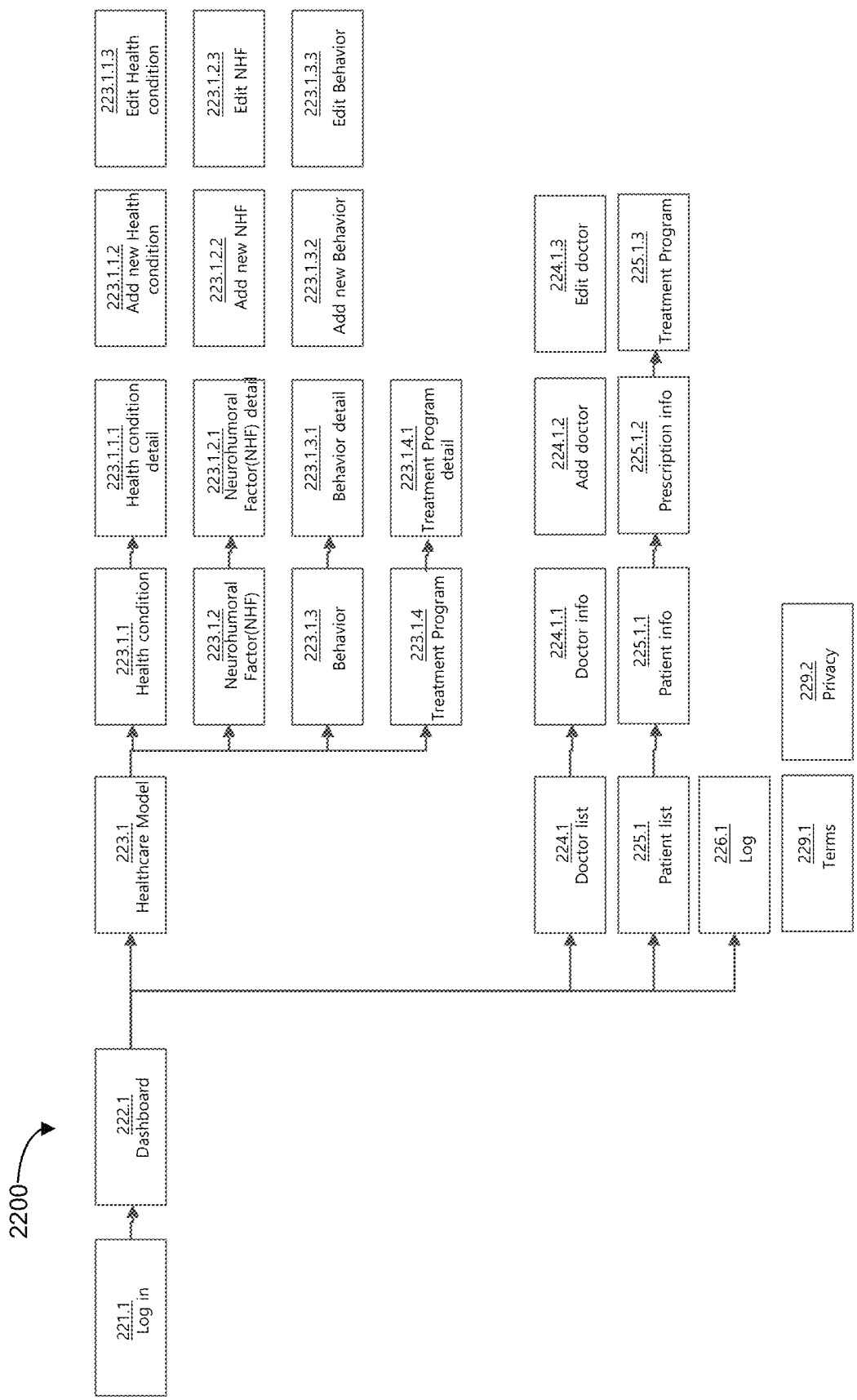
FIGS. 22A-22CC illustrate examples of a web application provided to an administrator for interacting with the digital behavior-based treatment system according to some implementations.

FIG. 22A illustrates an overview of an administrator's application structure 2200. In some implementations, the administrator's application is provided as a web application (e.g., and/or a mobile application). For example, the administrator is enabled to login (221.1) to the application, and from the administrator dashboard (222.1) displayed in the application, the administrator is enabled to view the healthcare model (223.1) day, in which the administrator can view health conditions (223.1.1) and the health condition details (223.1.1.1), as well as add new health conditions (223.1.1.2) and edit health conditions (223.1.1.3), to be stored, for example, by a server system for the digital behavior-based treatment system. The administrator is also enabled to view the neurohumoral factor (NHF) (223.1.2), and details for the NHF (223.1.2.1), as well as add new NHFs (223.1.2.2) and edit the NHFs (223.1.2.3).

The administrator is further enabled to view behaviors (223.1.3) and detail about the behaviors (223.1.3.1), as well as add new behaviors (223.1.3.2) and edit behaviors (223.1.3.3). The administrator is further enabled to view treatment program (223.1.4) and details about the treatment programs (223.1.4.1).

In some implementations, the administrator can also access a doctor list (224.1) for which the administrator has been assigned (e.g., or all doctors that are registered with the digital behavior-based treatment system). In some implementations, the administrator is able to view information (224.1.1) about the doctors, and is further enabled to add new doctors (224.1.2) and edit information about doctors (224.1.3) that are saved in the system.

In some implementations, the administrator can also access a patient list (225.1) (e.g., a list of patients that are registered with the digital behavior-based treatment system). In some implementations, the patient list is anonymized, with no identifying information about the patient (e.g., the patient's name is removed or replaced with asterisks). In some implementations, the administrator is able to view information (225.1.1) about the patients, and is further enabled to view prescription information about the patient (225.1.2) and information about the patient's treatment program (225.1.3), as stored by the system.

In some implementations, the administrator's application is enabled in accordance with terms (229.1) and a privacy policy (229.2) to ensure privacy for the patients (e.g., providing the administrator certain privileges to view patient information without the identity of the patient).

Figure 22B:
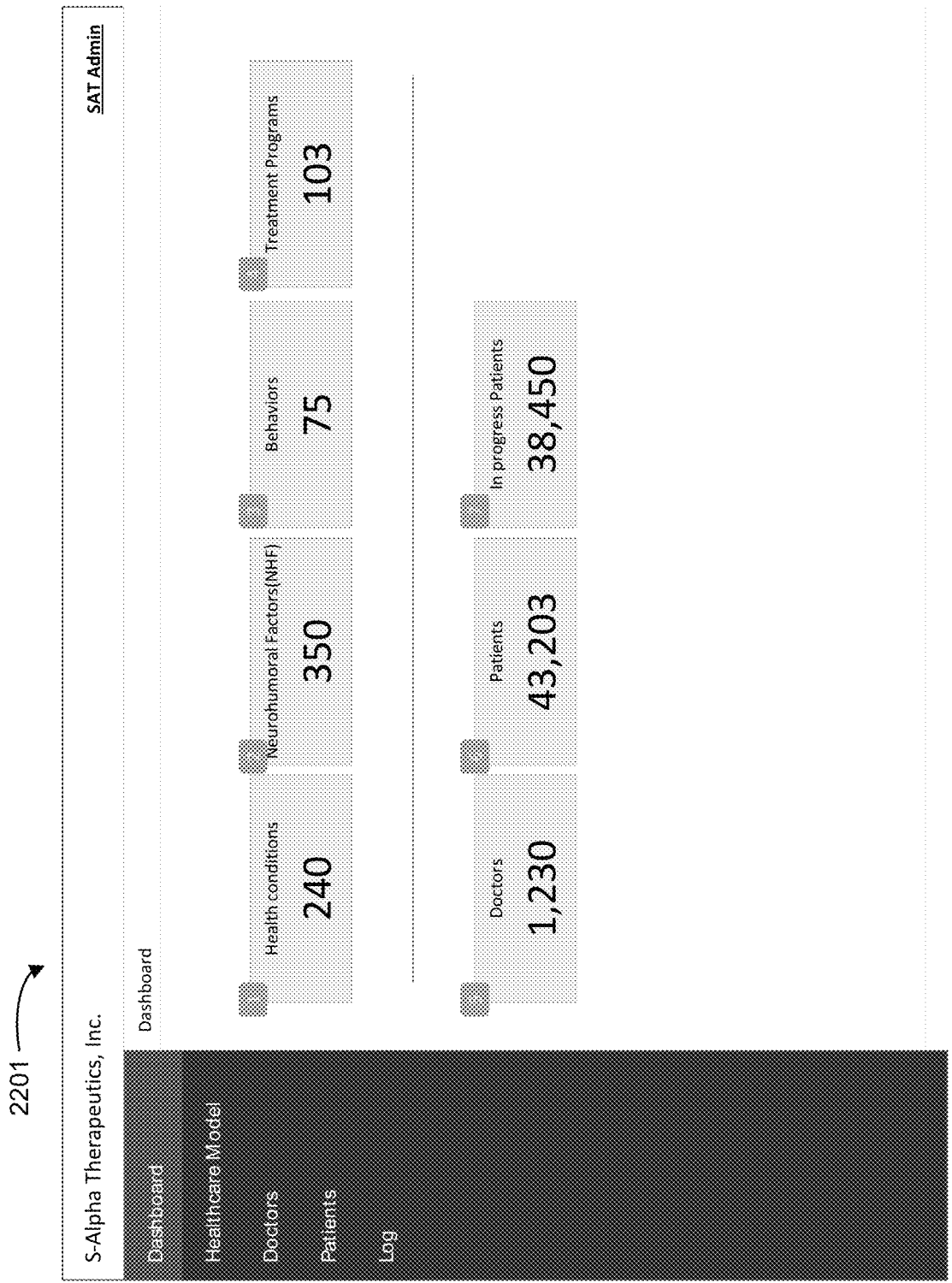

FIG. 22B illustrates a dashboard user interface 2201 for the administrator's web application. For example, the dashboard user interface includes a numeric indicator for the number of health conditions stored by the system, the number of NHFs stored by the system, the number of behaviors stored by the system, and the number of treatment programs stored by the system. In some implementations, the administrator is enabled to select (e.g., click) on any of these numeric indicators to view more detailed information about the selected set. In some implementations, the dashboard user interface 2201 further includes a numeric indicator for the number of doctors registered with the system, the number of patients registered with the system, and the number of in-progress patients (e.g., that are currently participating in a treatment program). The administrator can also select any of these sets to view more detailed information about the doctors, patients, and in-progress patients.

Figure 22C:
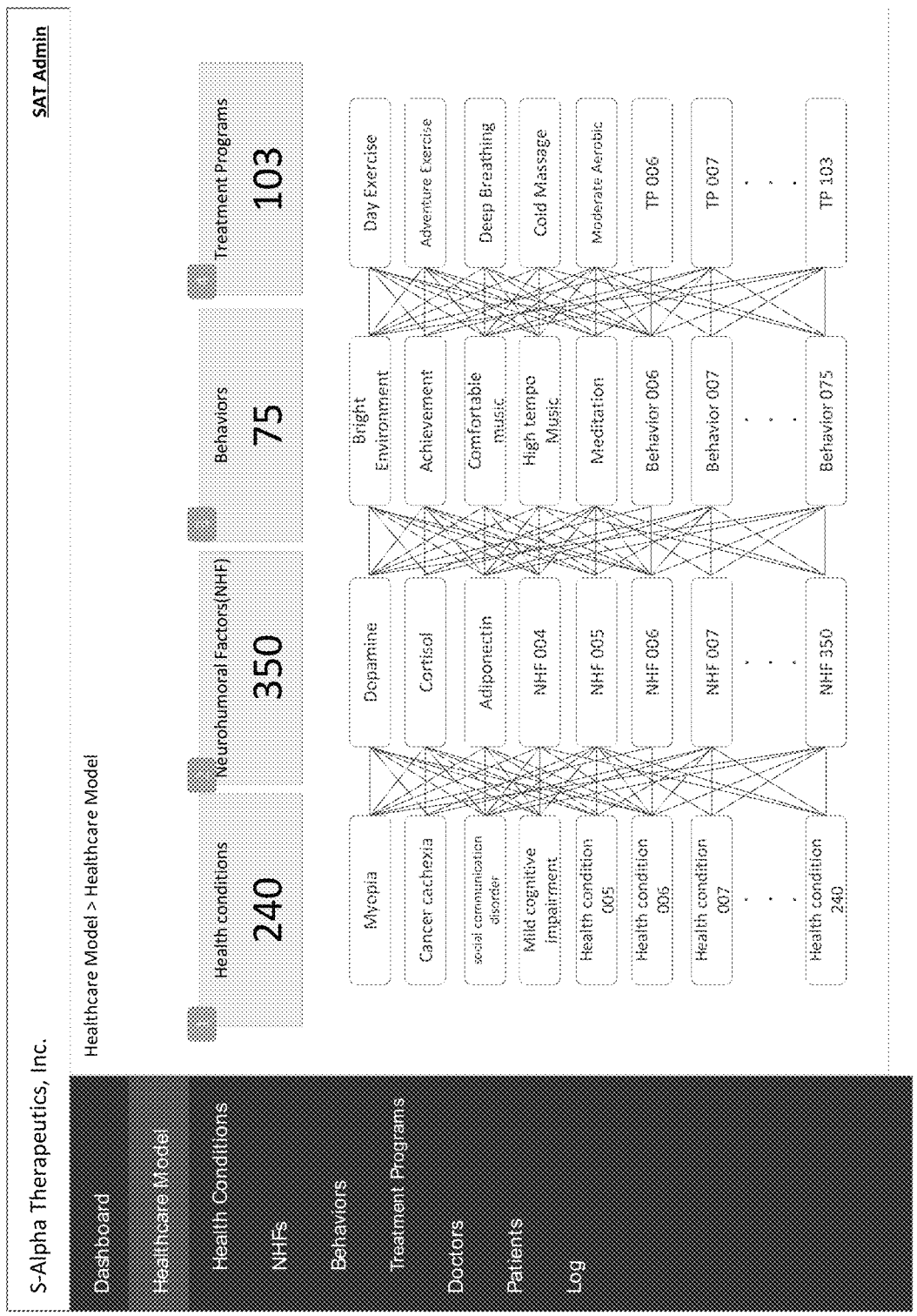

FIG. 22C illustrates the administrator selecting "Healthcare Model" on the left menu in the user interface 2202. In some implementations, the healthcare model user interface displays relationships (e.g., in a Healthcare Model network view) between health conditions, NHFs, behaviors, and treatment programs (e.g., as described with reference to FIG. 1A). For example, the administrator is enabled to zoom in and zoom out of the network view to see the full view, or sub portions of the view.

Figure 22D:
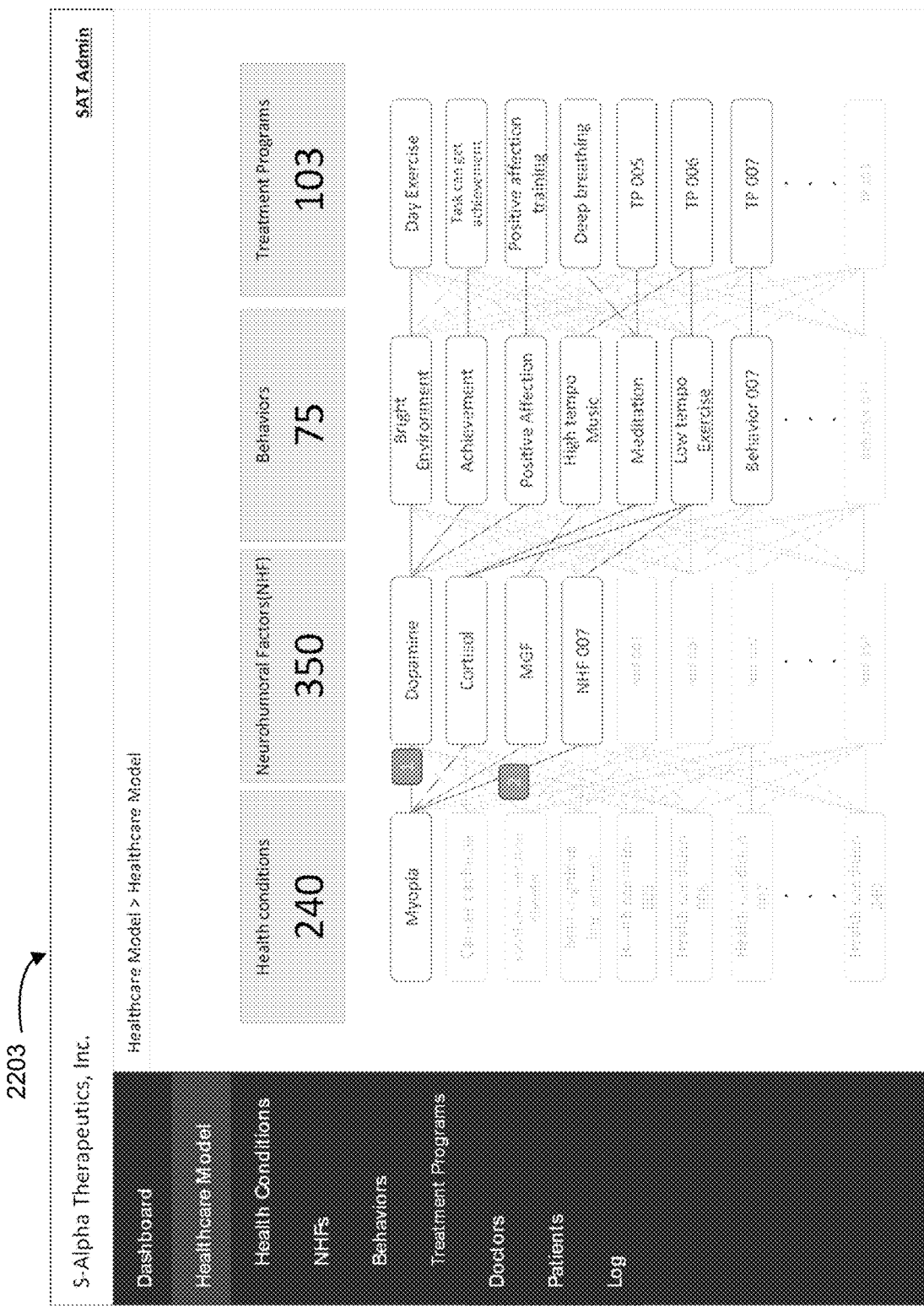

FIG. 22D illustrates a user interface 2203 displayed in response to the administrator selecting a health condition (e.g., Myopia) in the Healthcare Model. In some implementations, in response to the administrator selecting a health condition, related NHFs, behaviors, and treatment programs are visually emphasized in the user interface (e.g., the unrelated NHFs, behaviors, and treatment programs are faded). In some implementations, a positive correlation line between the health condition and related NHFs and behaviors is displayed with a first color (e.g., green), and a negative correlation between the health condition and related NHFs and behaviors is displayed with a second color (e.g., red), such that the administrator can easily and efficiently view the positive and negative correlations related to the selected health condition.

FIG. 22E illustrates a user interface 2204 displayed by selecting "Health Conditions" from the menu (e.g., nested within the Healthcare Model option). For example, the health condition list is displayed in the user interface 2204. In some implementations, in the displayed list, only a first related NHF is displayed, and the administrator navigates (e.g., using a cursor) to, for example, hover (e.g., or otherwise select) the "related NHF," which causes the application to display an overlay listing the additional related NHFs. For example, by navigating (e.g., hovering) over "Dopamine and 3 more" for the first listed health condition, "Myopia," an overlay (e.g., a popup) window is displayed that lists the additional NHFs related to the health condition, as well as their numeric correlation coefficient to the health condition (e.g., "Dopamine [1.0], Cortisol [−1.0], MGF [+0.7], NHF007 [−0.6]). The user interface 2204 also provides the administrator with an option to search health conditions (e.g., using search bar 6 in FIG. 22E) and an option to add a new health condition (e.g., by selecting button 5 "Add New Health condition").

Figure 22F:
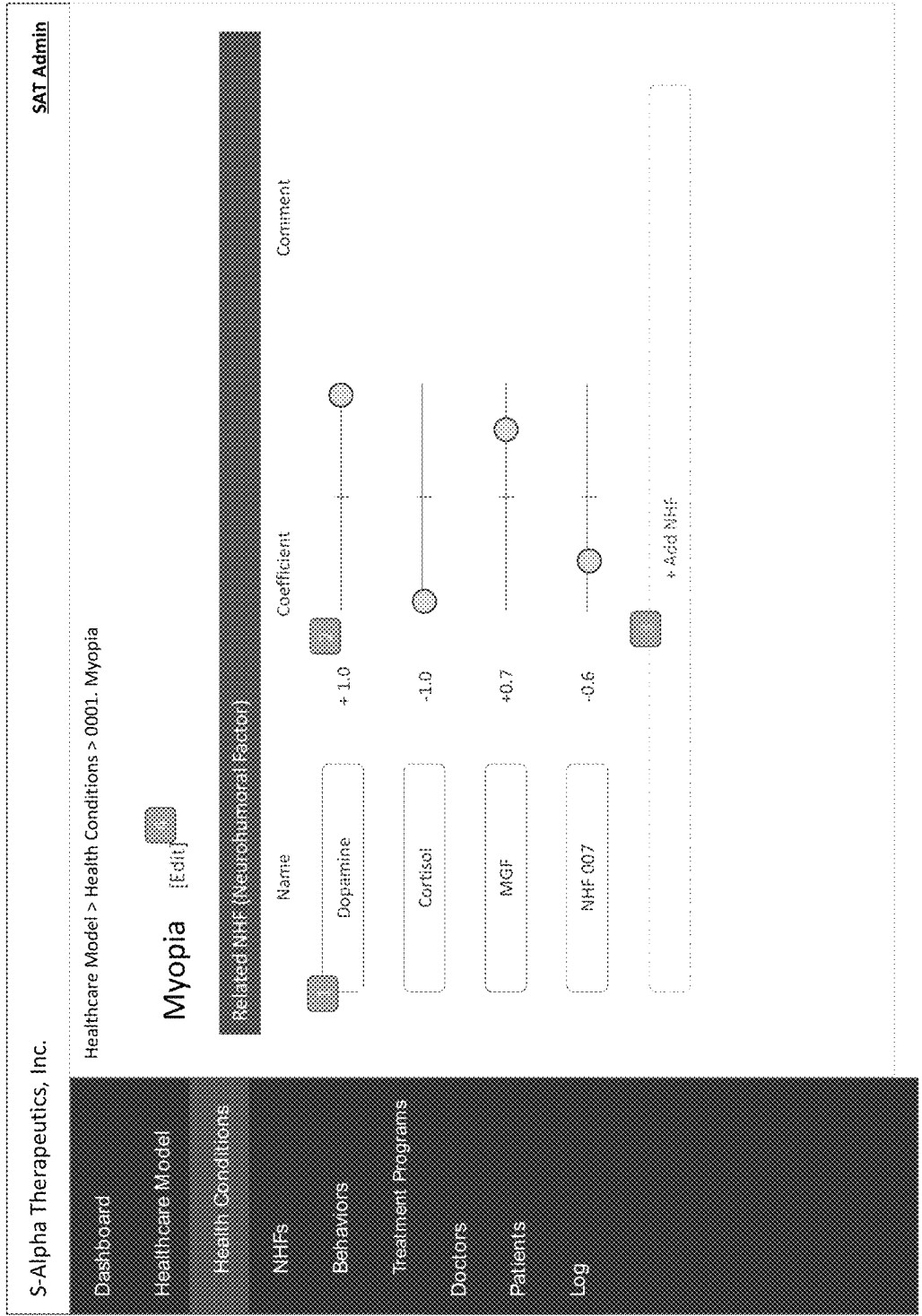

FIG. 22F illustrates a user interface 2205 that is displayed in response to the administrator selecting a health condition. In this example, "Myopia" has been selected from the list displayed in the user interface 2204. In some implementations, the administrator is enabled to modify the related NHFs (e.g., by changing the correlation coefficients, adding a new NHF as related to a particular health condition, or adding a comment related to any of the NHFs).

In some implementations, correlation coefficients and/or related NHFs are identified by a third-party. For example, a third-party (e.g., at a server system of the third-party) stores and/or updates data for correlation coefficients and NHFs. In some implementations, the third-party (e.g., or another party) conducts experiments or research in order to determine correlation coefficients and to identify related NHFs. In some implementations, a server system of the third-party (e.g., that stores the data (e.g., results) collected by the third-party) is in communication with the digital behavior-based treatment system (e.g., a server of the digital behavior-based treatment system). In some implementations, as the third-party collects additional data (e.g., and stores the new data at the server system of the third-party), the correlation coefficients and/or related NHFs are automatically updated in the digital behavior-based treatment system. For example, the patient's application, the administrator's application, and the doctor's application of the digital behavior-based treatment system are automatically (e.g., without user input) updated in accordance with an update to the correlation coefficients and/or related NHFs by the third-party. As such, the digital behavior-based treatment system continues to remain up-to-date with the latest treatment programs based on experimental data from the third-party. In some implementations, the digital behavior-based treatment system is in communication with a plurality of third-parties (e.g., a plurality of external data sources). For example, different third-parties provide data for different correlation coefficients and NHFs (e.g., or collectively provide data that is combined to determine the correlation coefficients). In some implementations, an administrator manually updates the correlation coefficients and/or related NHFs in the digital behavior-based treatment system (e.g., in accordance with data collected from experiments and research, which may or may not be provided by a third-party), as described with reference to FIGS. 22F and 22G. In some implementations, the digital behavior-based treatment system is updated by a combination of data from the third-party server (e.g., performed automatically) and the administrator (e.g., performed manually) of the digital behavior-based treatment system.

Figure 22G:
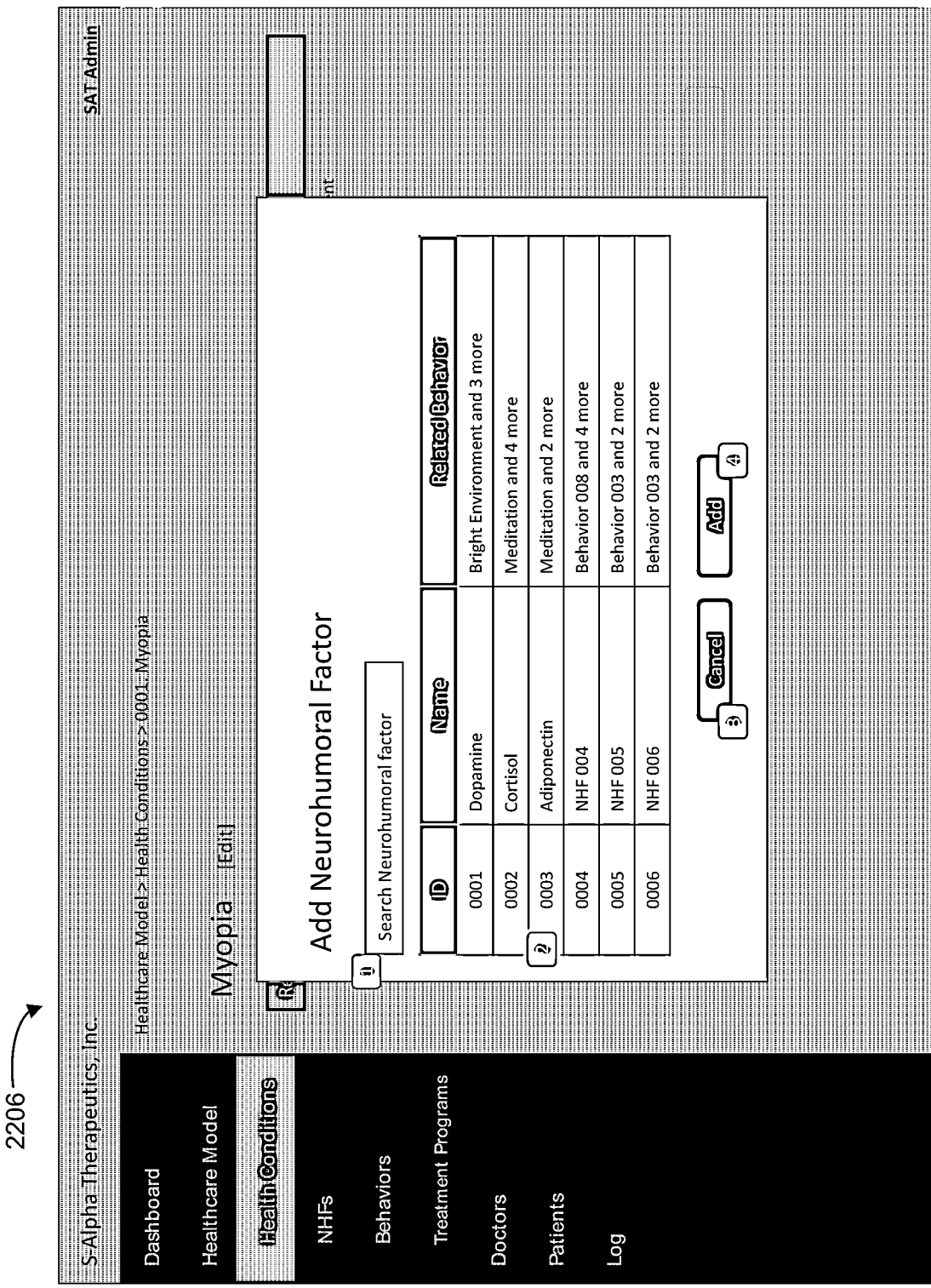

FIG. 22G illustrates a user interface 2206 that includes a popup to add an NHF for the selected health condition, Myopia. For example, the administrator is enabled to search for NHFs and add a related NHF to the health condition from the popup illustrated in user interface 2206.

Figure 22H:
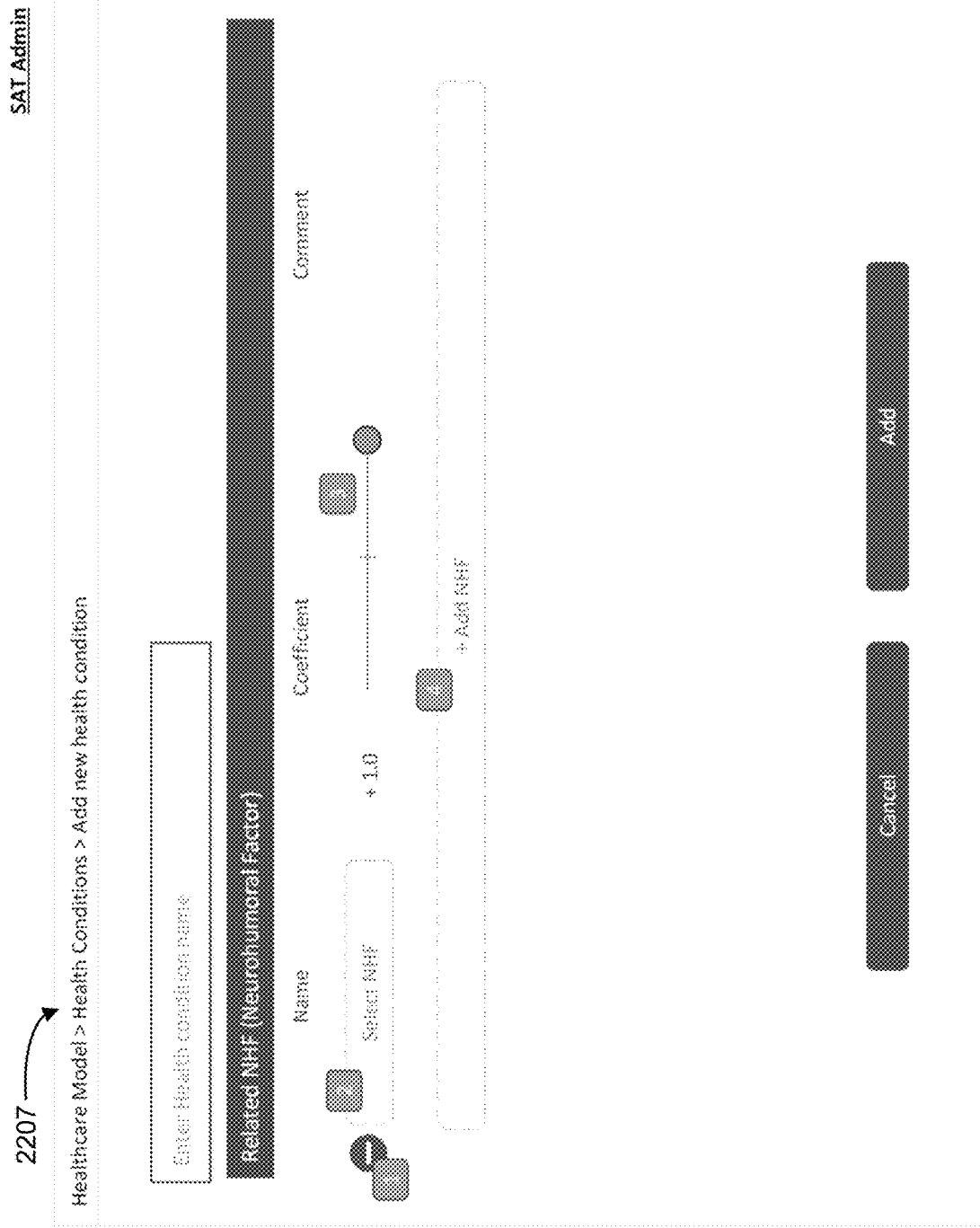

FIG. 22H illustrates a user interface 2207 for adding a new health condition. For example, to add a new health condition, the administrator is provided with the option to "Enter Health condition name," and add one or more NHFs that are related to the new health condition. The administrator is further enabled to set a correlation coefficient for each related NHF for the new health condition. As such, the administrator is provided with access to update the system by adding and editing health conditions, NHFs, and related behaviors.

Figure 22I:
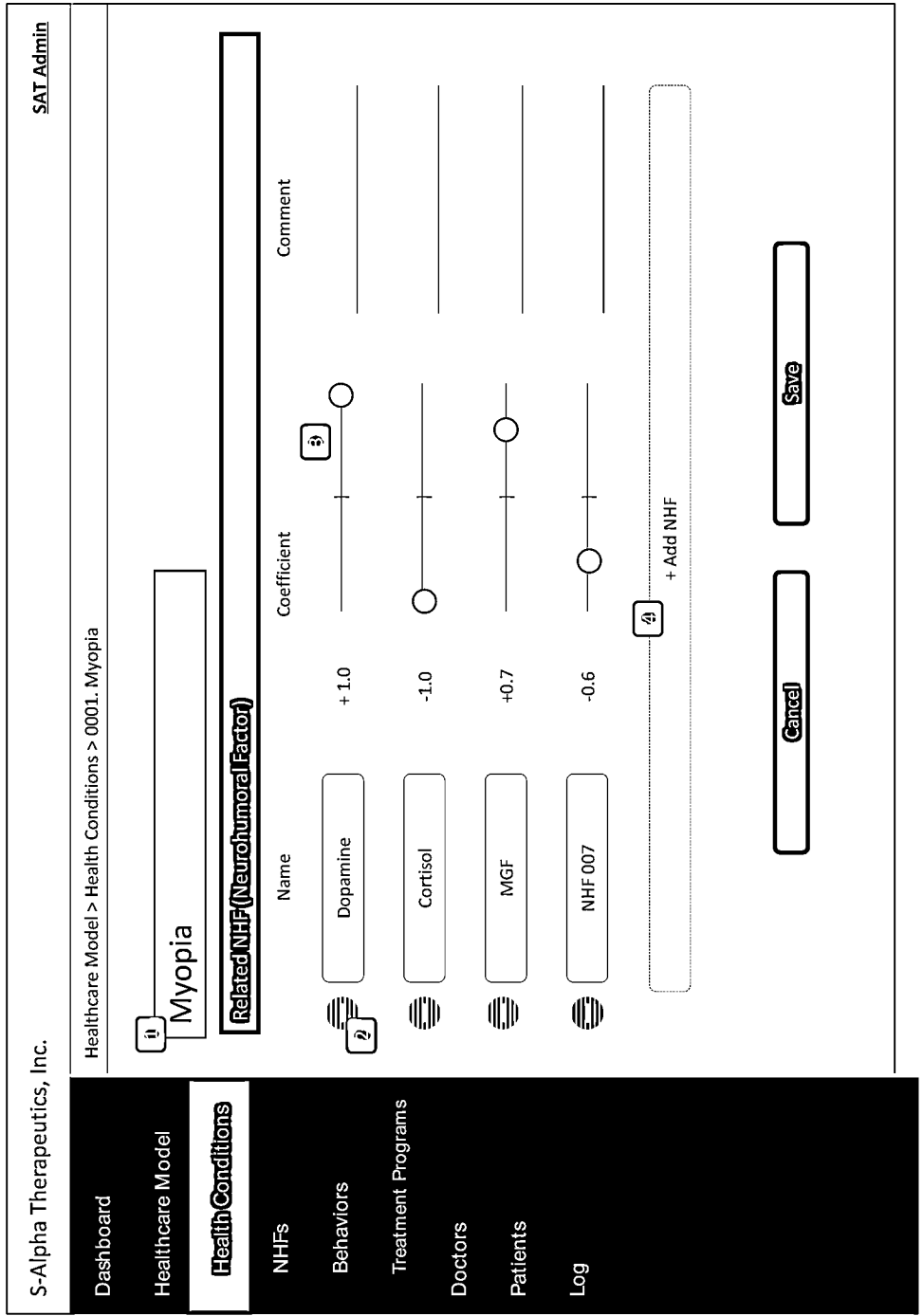

FIG. 22I illustrates a user interface 2208 for editing an existing health condition (e.g., myopia). For example, in response to the administrator selecting the "edit" option in user interface 2204 (FIG. 22F), the user interface 2208 is displayed, which includes options to remove NHFs, modify the correlation coefficient, and add additional NHFs to the existing health condition, Myopia.

FIG. 22J illustrates a user interface 2209 for viewing a list of NHFs (e.g., in response to selecting the NHFs option in the menu on the left of the user interface). In some implementations, the NHF list includes, for each NHF, the NHF ID, the NHF name, related behaviors, and optionally a memo about the NHF. In some implementations, the entire list of "related behaviors" is displayed as a popup for the administrator in response to the administrator navigating (e.g., with a cursor) over the related behavior for a respective NHF. In some implementations, the user interface 2209 further includes a search bar 6 for using a text search to search through the NHFs, and a button to "Add new NHF."

Figure 22K:
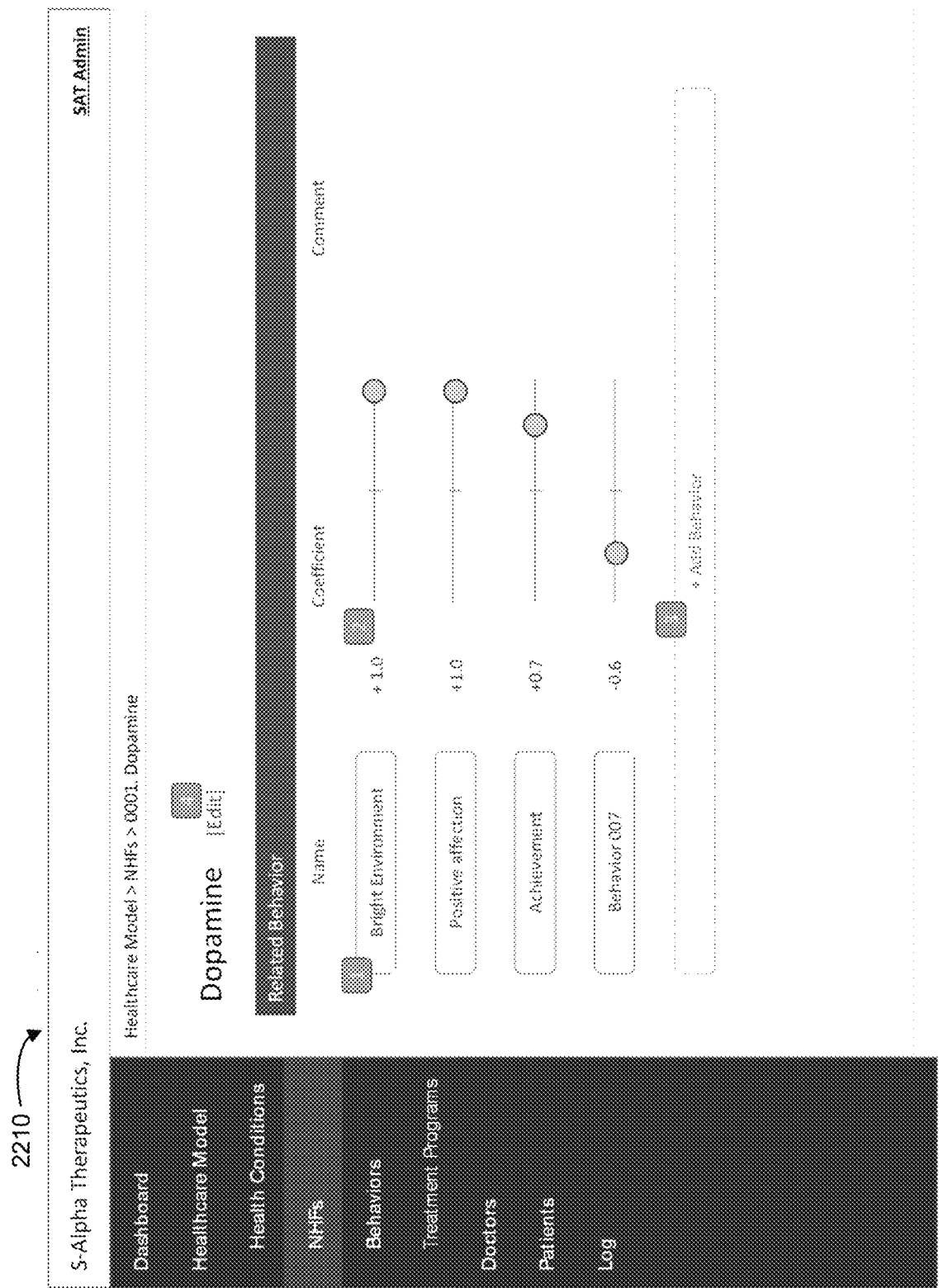

FIG. 22K illustrates a user interface 2210 that is displayed in response to the administrator selecting an NHF, such as Dopamine. In some implementations, the user interface 2210 is the detailed view for the NHF Dopamine. For example, each of the related behaviors, and its coefficient of correlation, is displayed. The user interface further includes an option to add new behaviors to the selected NHF, or to edit the NHF (e.g., by selecting the edit option 4).

Figure 22L:
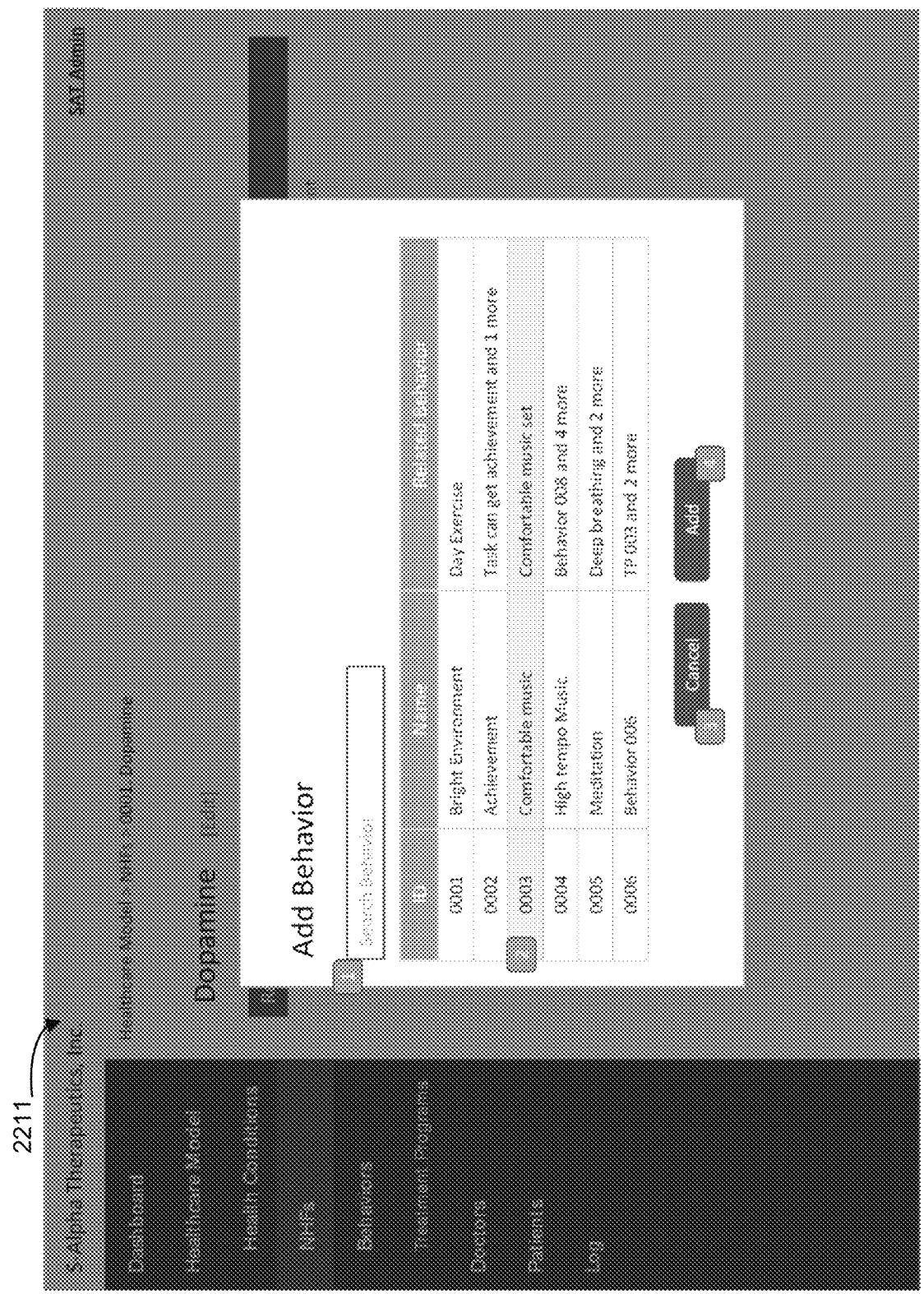

FIG. 22L illustrates a user interface 2211 for adding a behavior to the NHF. For example, in response to the administrator selecting "Add new behavior" in user interface 2210, the popup window to add new behaviors is displayed.

Figure 22M:
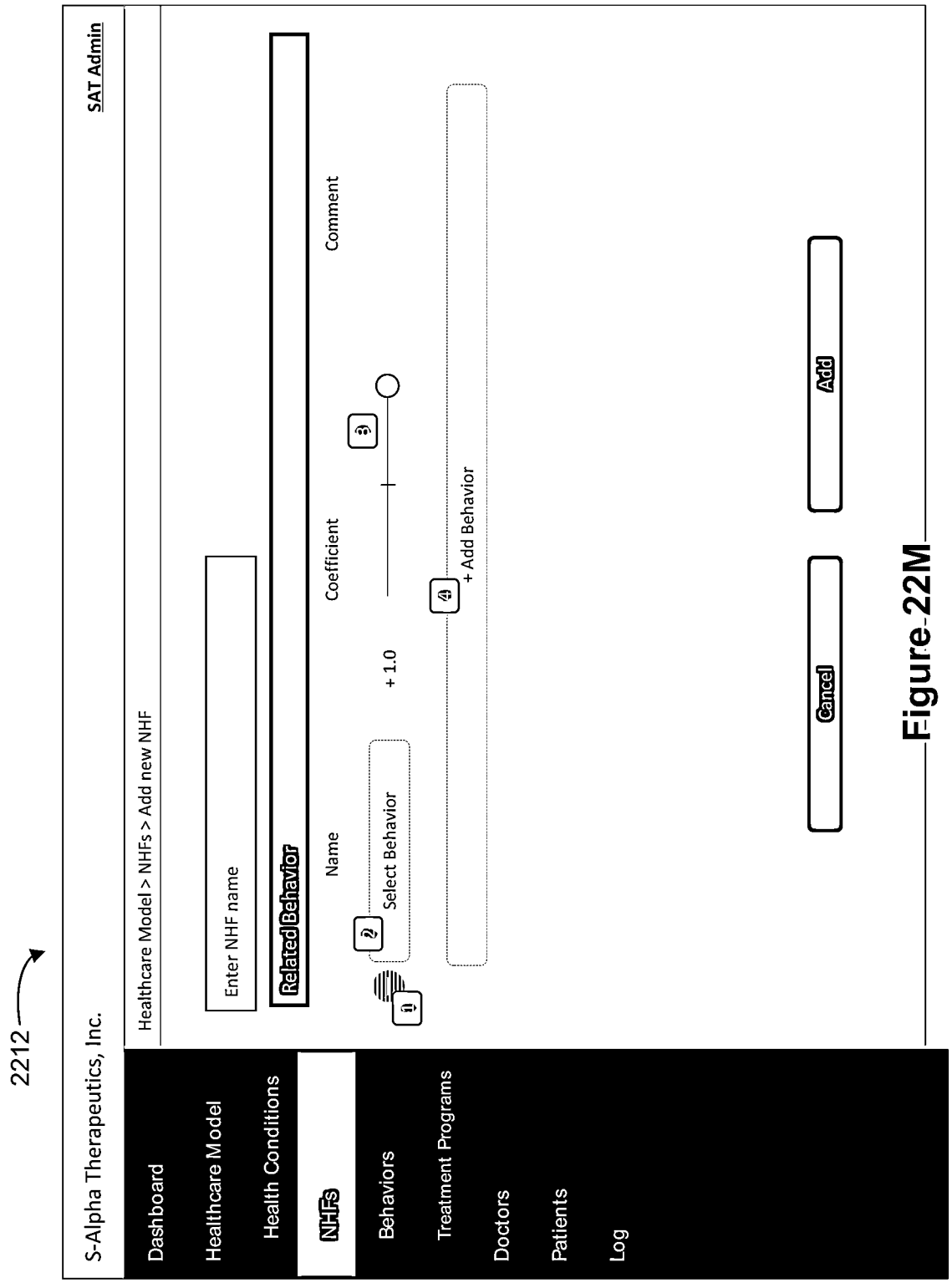

FIG. 22M illustrates a user interface 2212 for adding a new NHF. For example, the administrator is enabled to enter the NHF name, edit related behaviors (e.g., delete, add, or change the coefficient, and/or comment for each behavior). In some implementations, after the administrator adds the new NHF, the new NHF is stored (e.g., at the server), and other administrators (e.g., and doctors) are enabled to view the new NHF (e.g., the new NHF is saved to the system).

Figure 22N:
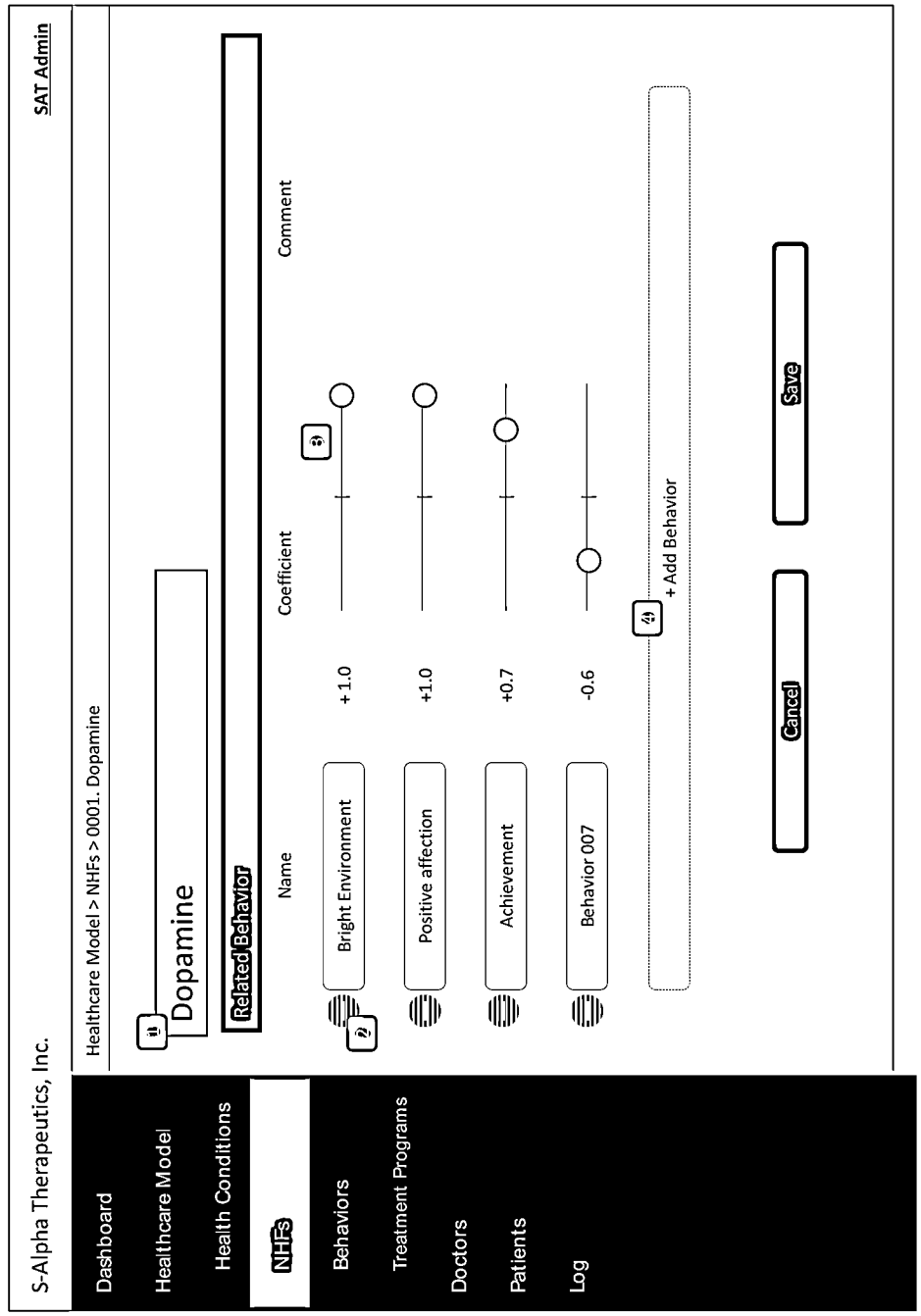

FIG. 22N illustrates a user interface 2213 for editing an existing NHF, such as Dopamine. In some implementations, the administrator is enabled to delete behaviors, change the coefficient for the behaviors, and add new behaviors for the selected NHF.

FIG. 22O illustrates a user interface 2214 having a list view of the behaviors (e.g., in response to the Behaviors option selected in the menu on the left of the user interface). Similar to the list of NHFs (described with reference to FIG. 22J) and the list of health conditions (described with reference to FIG. 22E), the administrator is enabled to view additional related treatment programs by hovering over the treatment program column for a particular behavior.

Figure 22P:
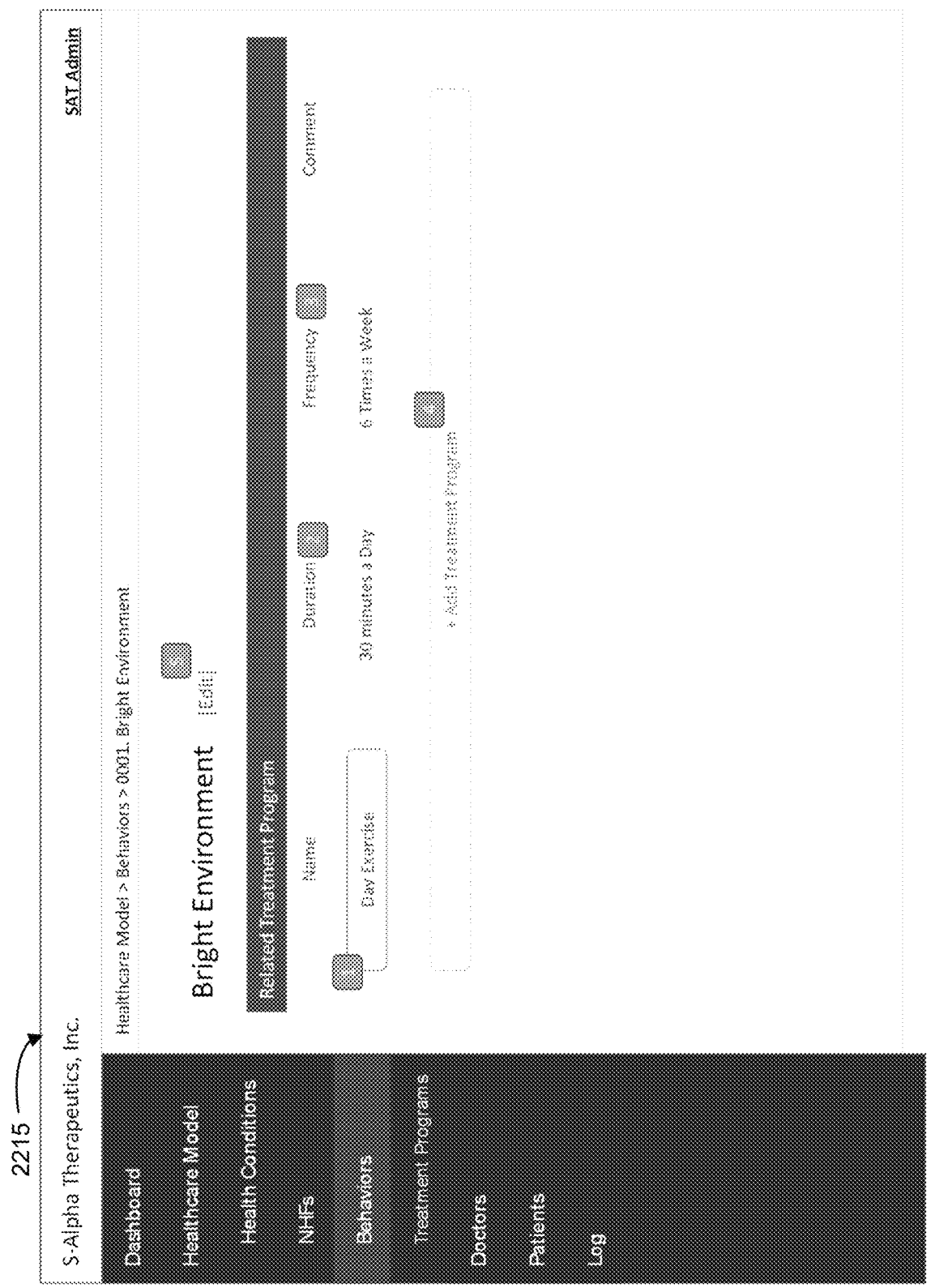

FIG. 22P illustrates a user interface 2215 for viewing details about a selected behavior, such as Bright Environment. In some implementations, the related treatment program for the selected behavior is displayed (e.g., Day Exercise). In some implementations, the duration and frequency of each related treatment program is also displayed (e.g., 30 minutes a day, 6 times a week). The administrator is further enabled to add a treatment program to the selected behavior, as well as edit (e.g., by selecting the edit option 5) the behavior.

Figure 22Q:
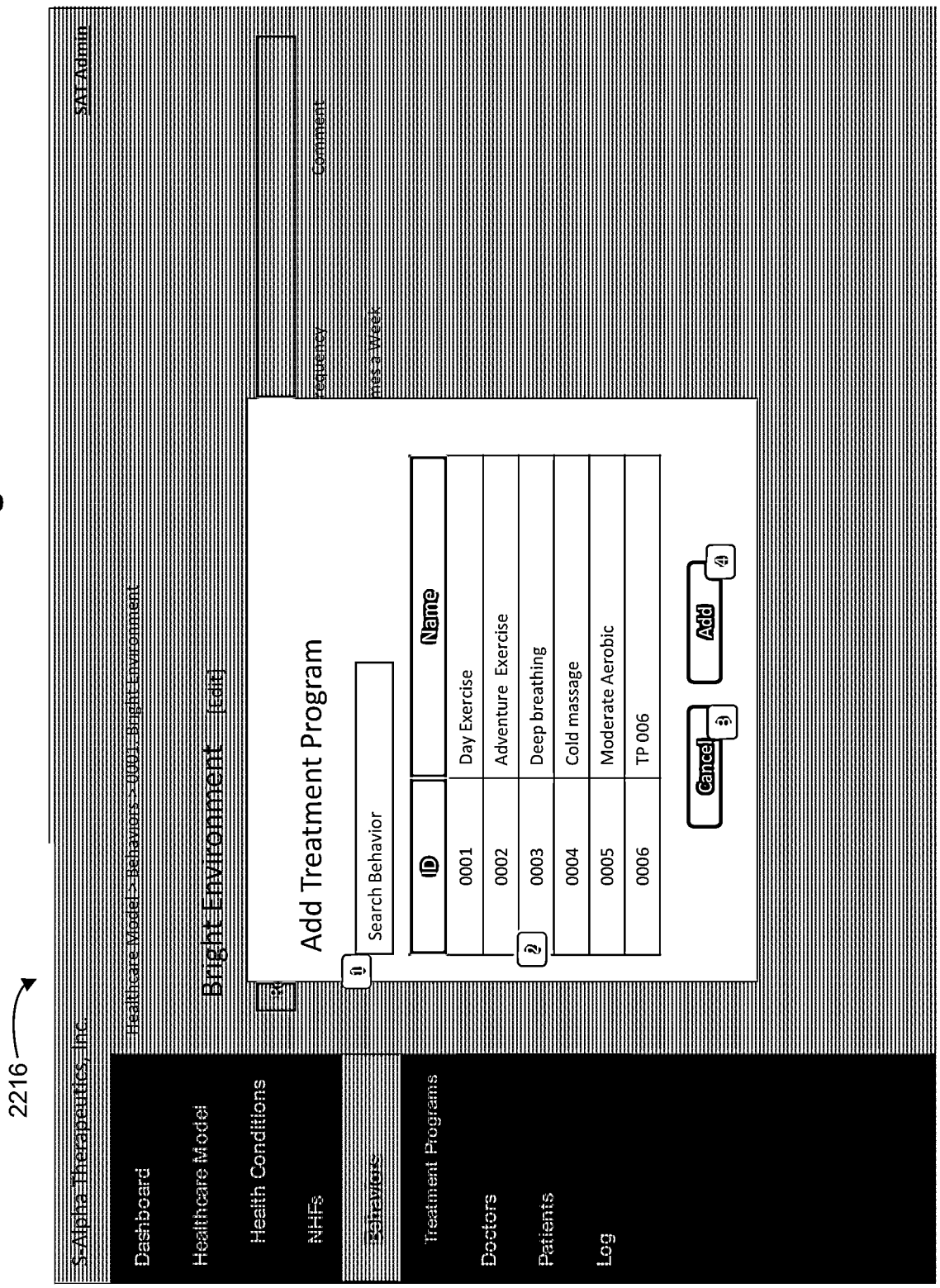

FIG. 22Q illustrates a user interface 2216 that includes a popup user interface element for adding a treatment program for the selected behavior. For example, the administrator can select to add "Deep breathing" as a treatment program for Bright environment behavior.

Figure 22R:
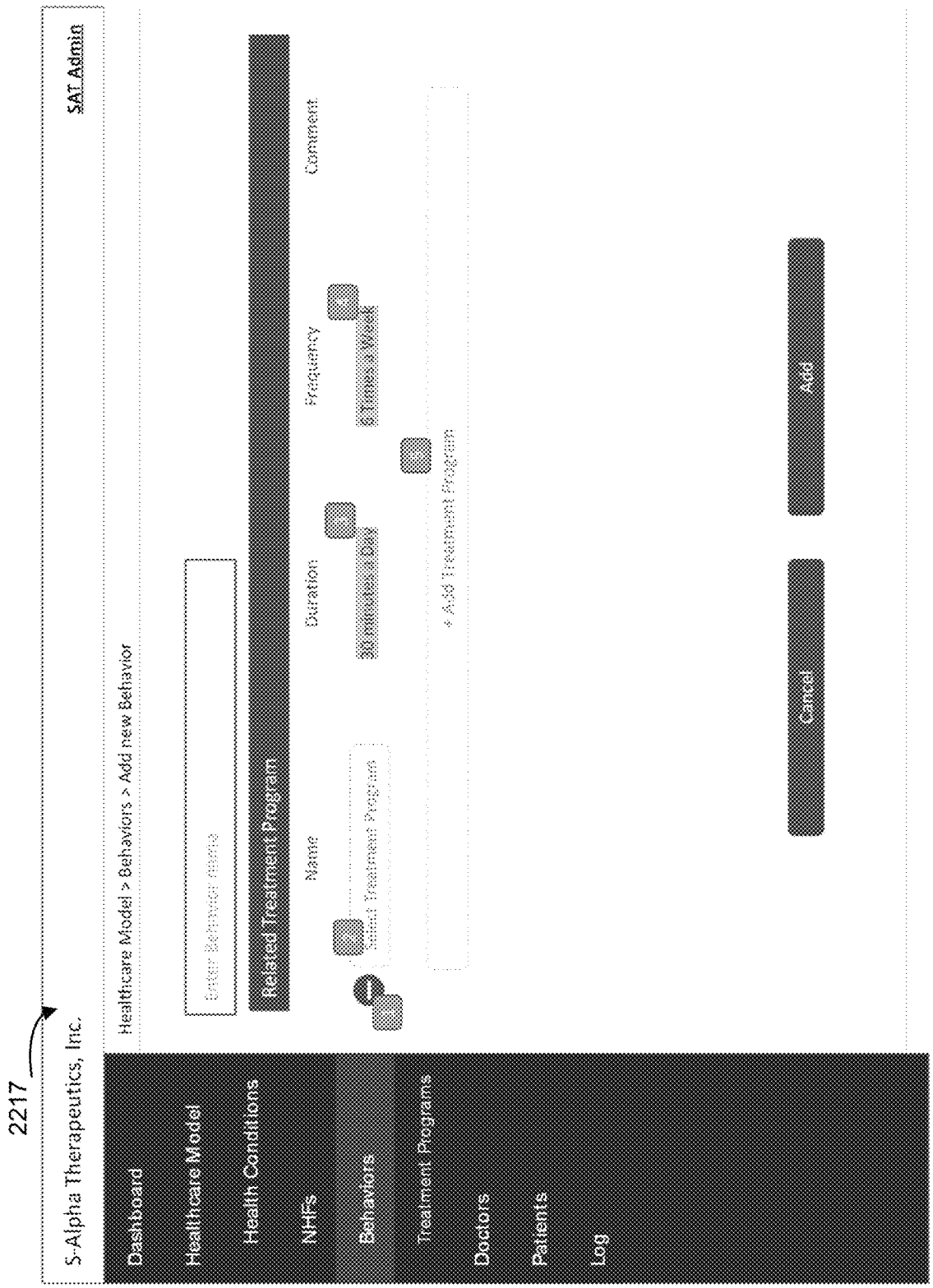

FIG. 22R illustrates a user interface 2217 for editing information about a newly added treatment program for a selected behavior. For example, the administrator is enabled to delete the newly added treatment programs, change the duration and/or frequency of the program, and add additional new treatment programs.

Figure 22S:
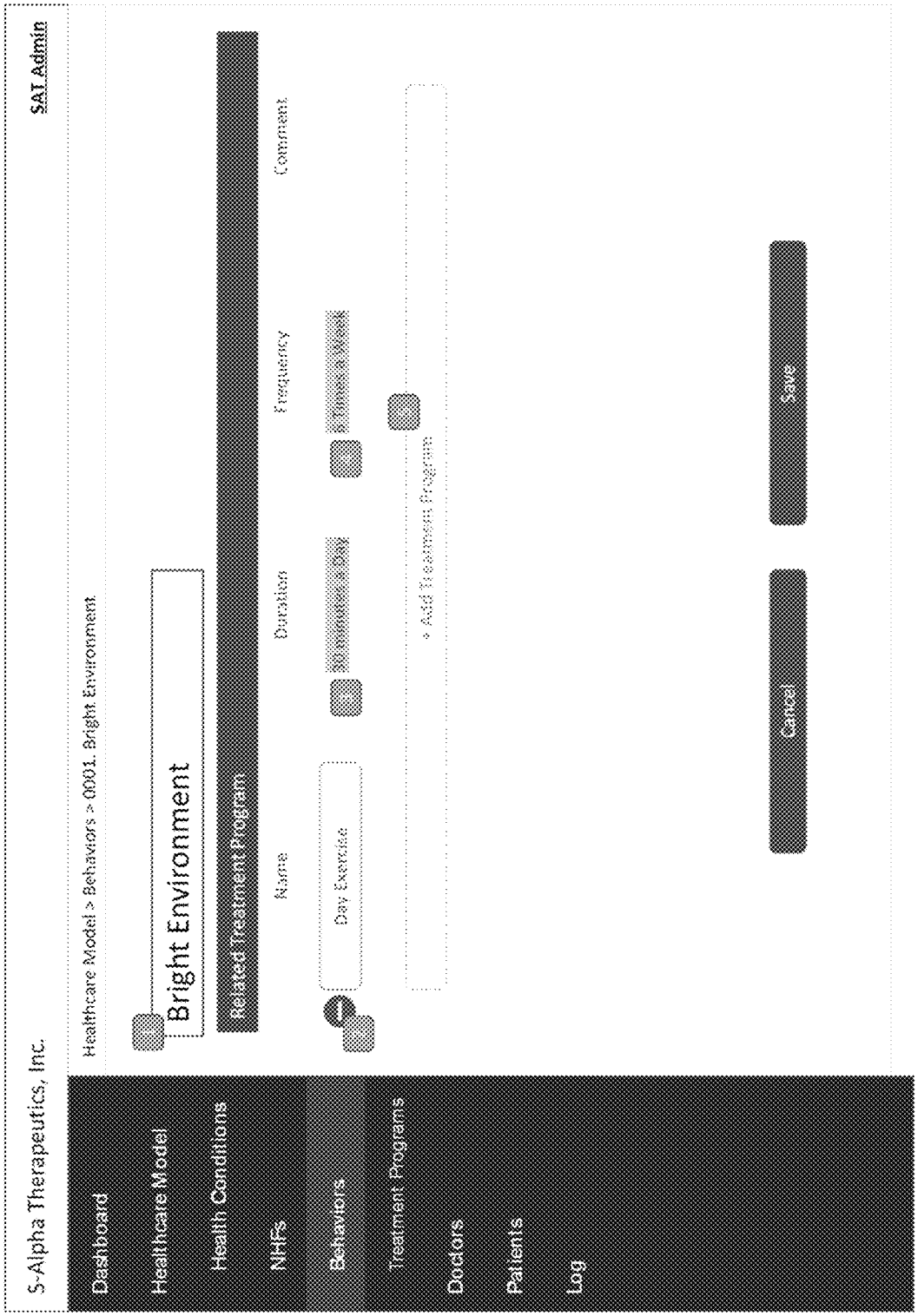

FIG. 22S illustrates editing the treatment programs for a selected behavior. For example, the administrator is enabled to delete treatment programs, change the duration and/or frequency of the program, and add new treatment programs.

Figure 22T:
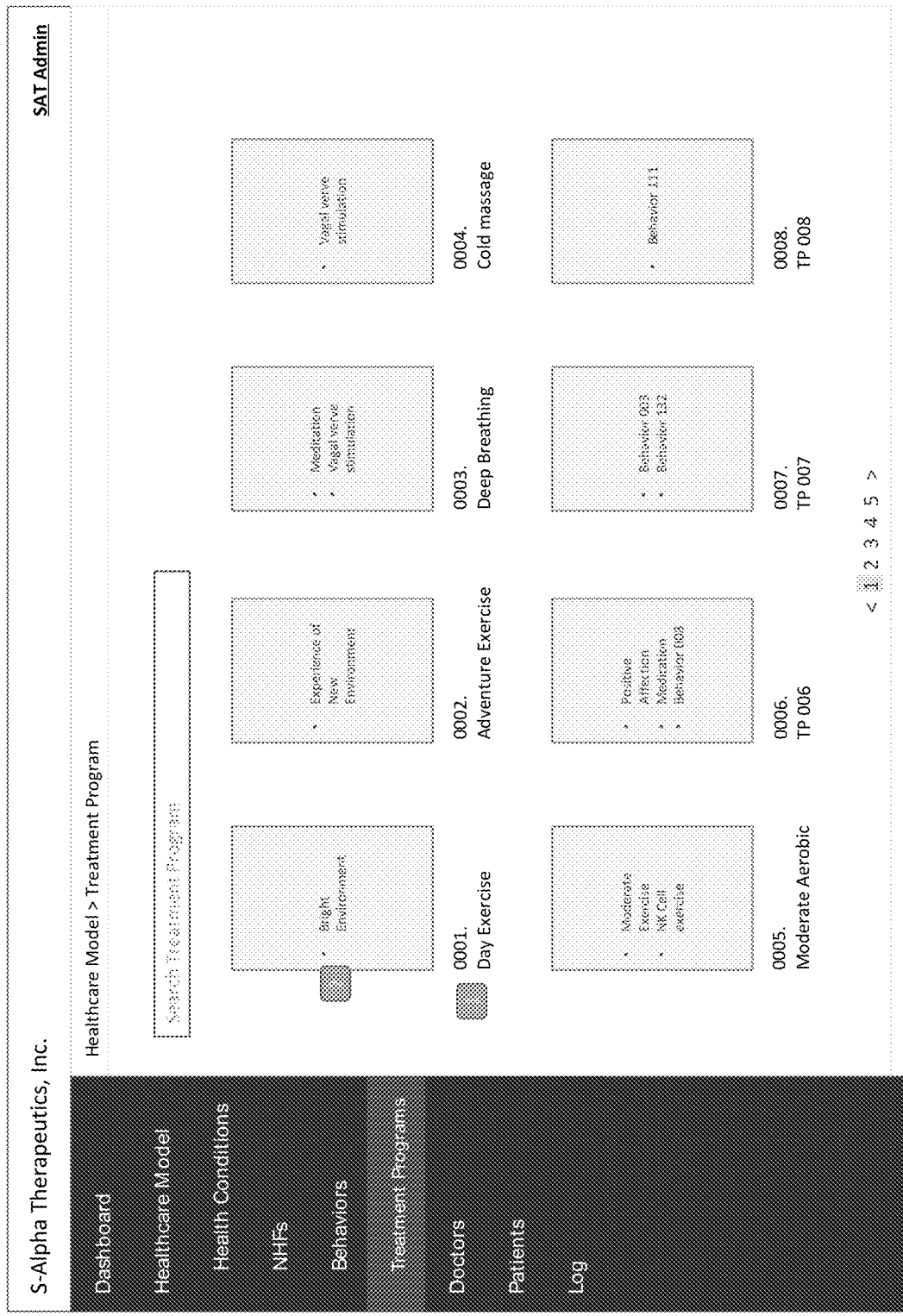

FIG. 22T illustrates a user interface 2219 for viewing treatment programs (e.g., in response to the administrator selecting the treatment programs option in the menu on the left of the user interface). In some implementations, the user interface 2219 includes a list of treatment programs that are available in the system (e.g., stored at the server). In some implementations, the treatment programs are downloaded and executed by the patient on a mobile device after a doctor prescribes the treatment program (as described above with reference to FIGS. 21A-21I). In some implementations, the list of treatment programs includes, for each treatment program, a treatment program identifier (e.g., a number, "0001"), a name of the treatment program (e.g., "Day Exercise"), and a list of behaviors related to the treatment program.

Figure 22U:
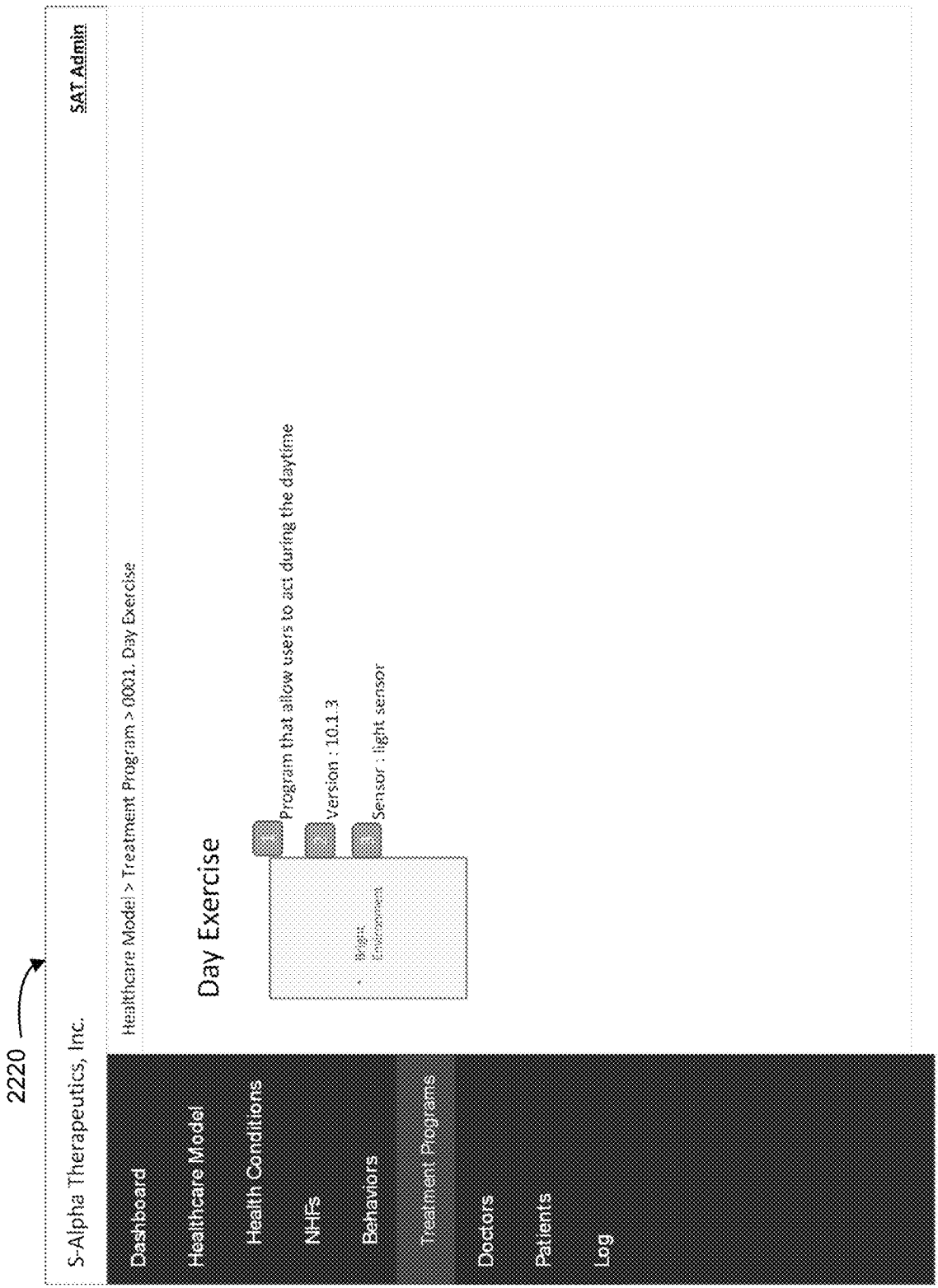

FIG. 22U illustrates the administrator selecting a treatment program, "Day Exercise," and displaying a detailed user interface 2220 for the selected treatment program. For example, the detailed view of the treatment program includes a description of the treatment program "Program that allow users to act during the daytime", a version of the treatment program, and sensor information (e.g., one or more sensors to be used to collect data while the patient is using the treatment program).

Figure 22V:
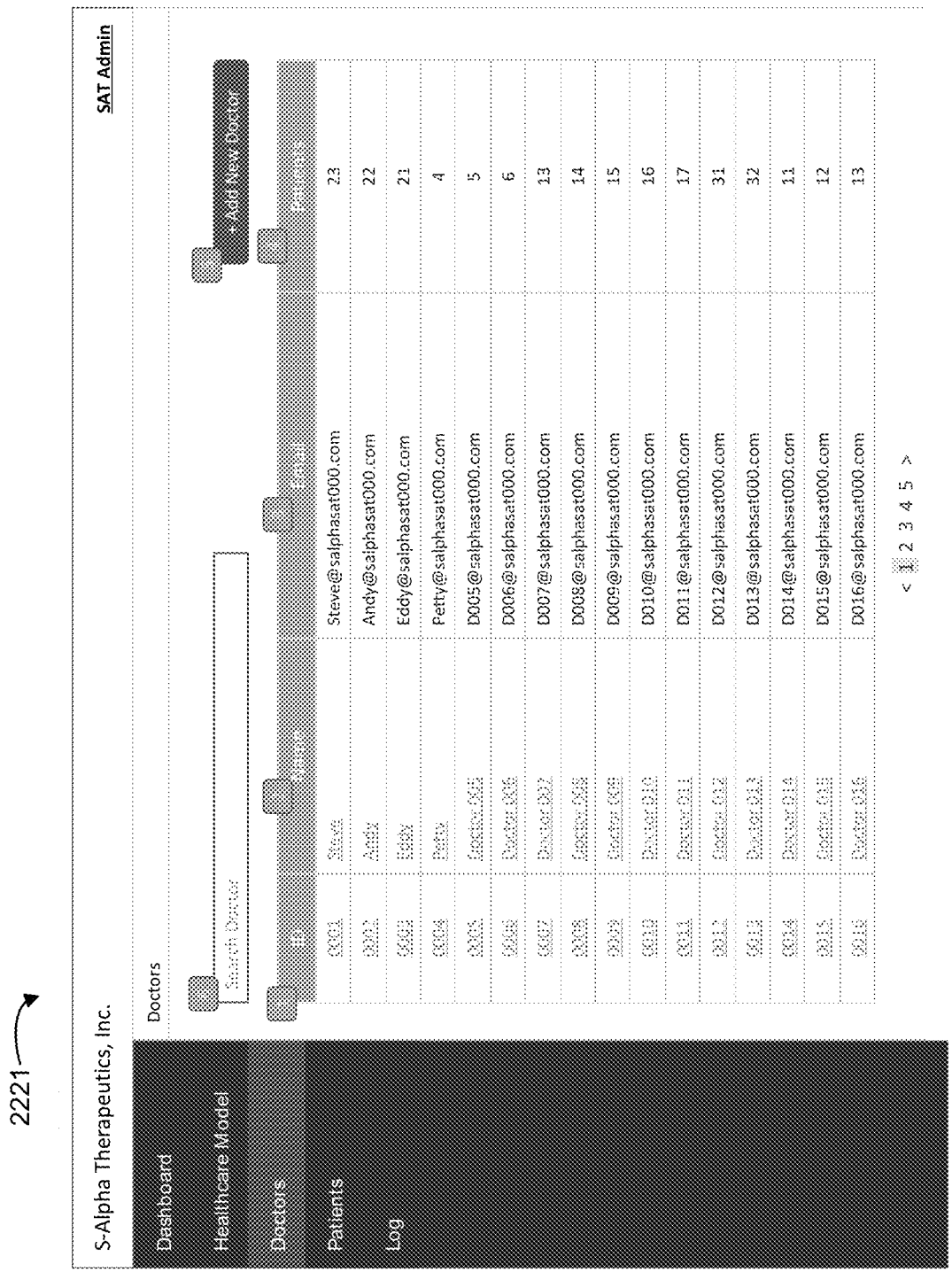

FIG. 22V illustrates a user interface 2221 that displays a list of doctors that have registered with the system. In some implementations, the administrator is enabled to check doctors' accounts (e.g., view the number of patients being treated using the system), and is enabled to create a new account for a doctor. For example, the administrator is enabled to select a doctor, and view detailed information about the doctor, as illustrated in FIG. 22W.

Figure 22W:
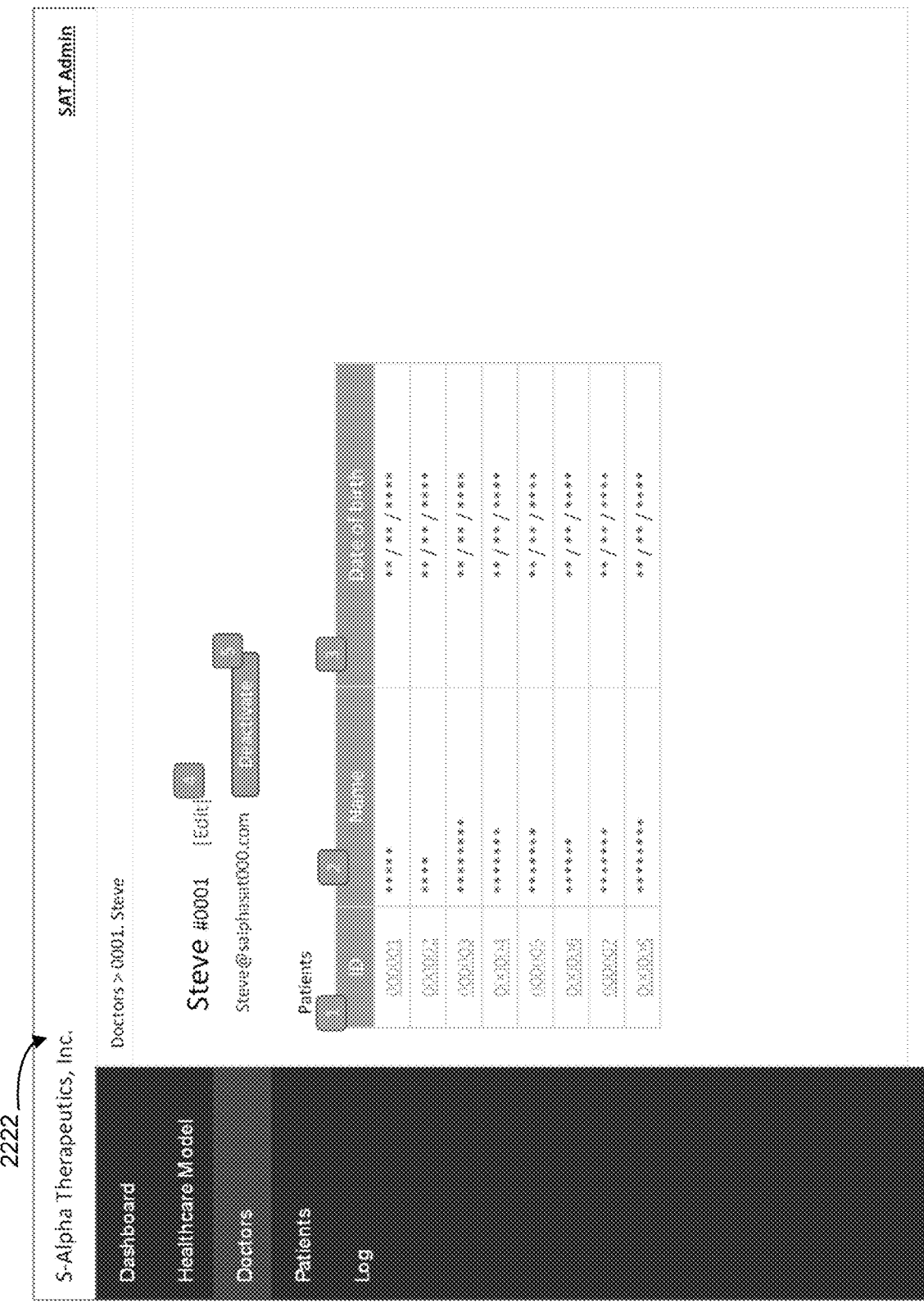

FIG. 22W illustrates a user interface 2222 that includes detailed information about a selected doctor. For example, an email address of the doctor, and a list of patient identifiers representing people who are treated by the doctor using the system. In some implementations, the administrator is also enabled to edit the doctor's profile and deactivate the doctor's account.

Figure 22X:
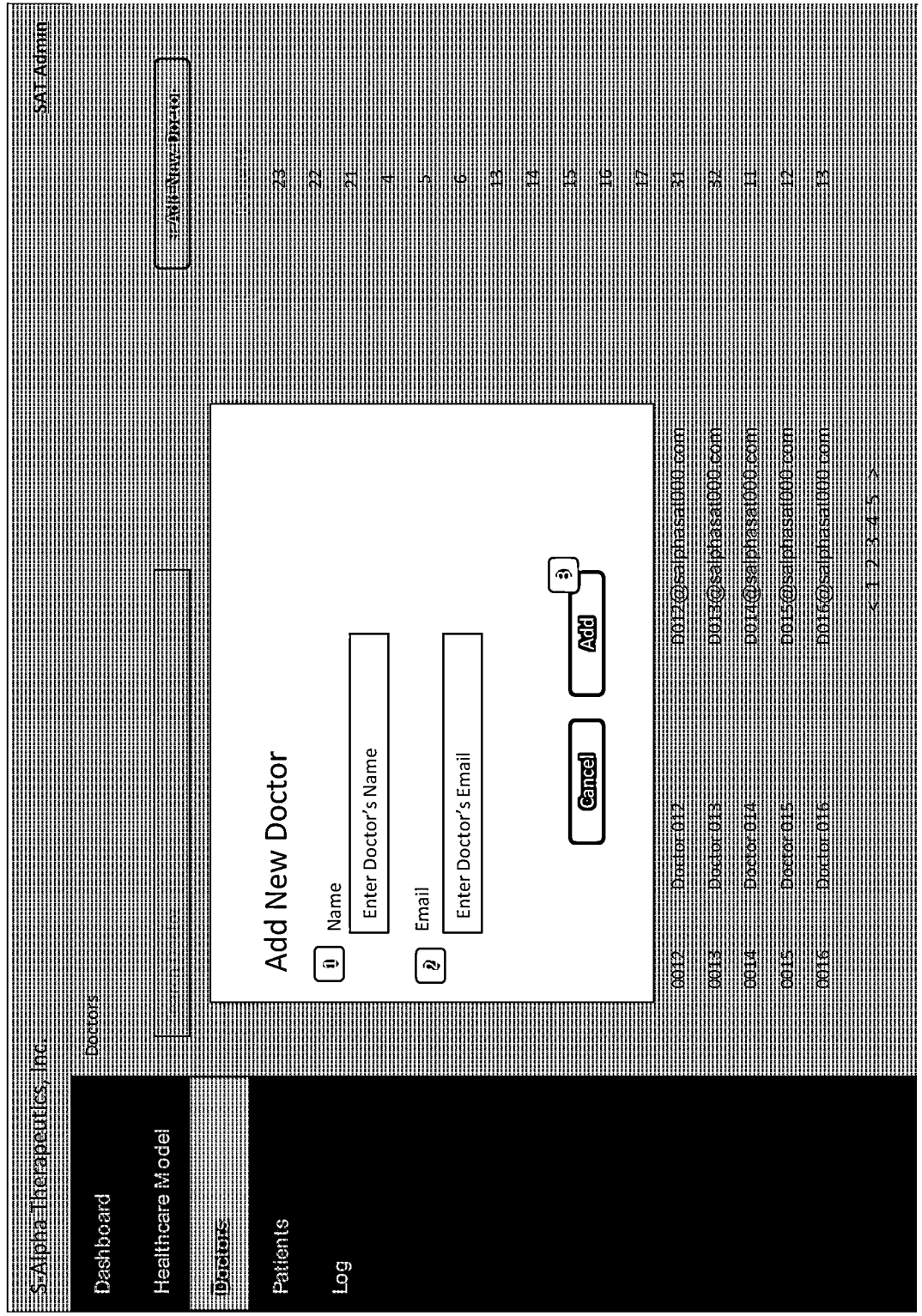

FIG. 22X illustrates adding a new doctor to the system (e.g., creating a new doctor account) using the user interface 2223. For example, the administrator inputs the doctor's name and email address (e.g., and registration instructions are sent to the doctor's email address). In some implementations, if the administrator fails to enter a name and/or email, an error message is displayed (e.g., as a popup window). For example, the system requires the administrator to enter a name and email address (e.g., in a valid email format) before allowing the administrator to add the new doctor to the system.

Figure 22Y:
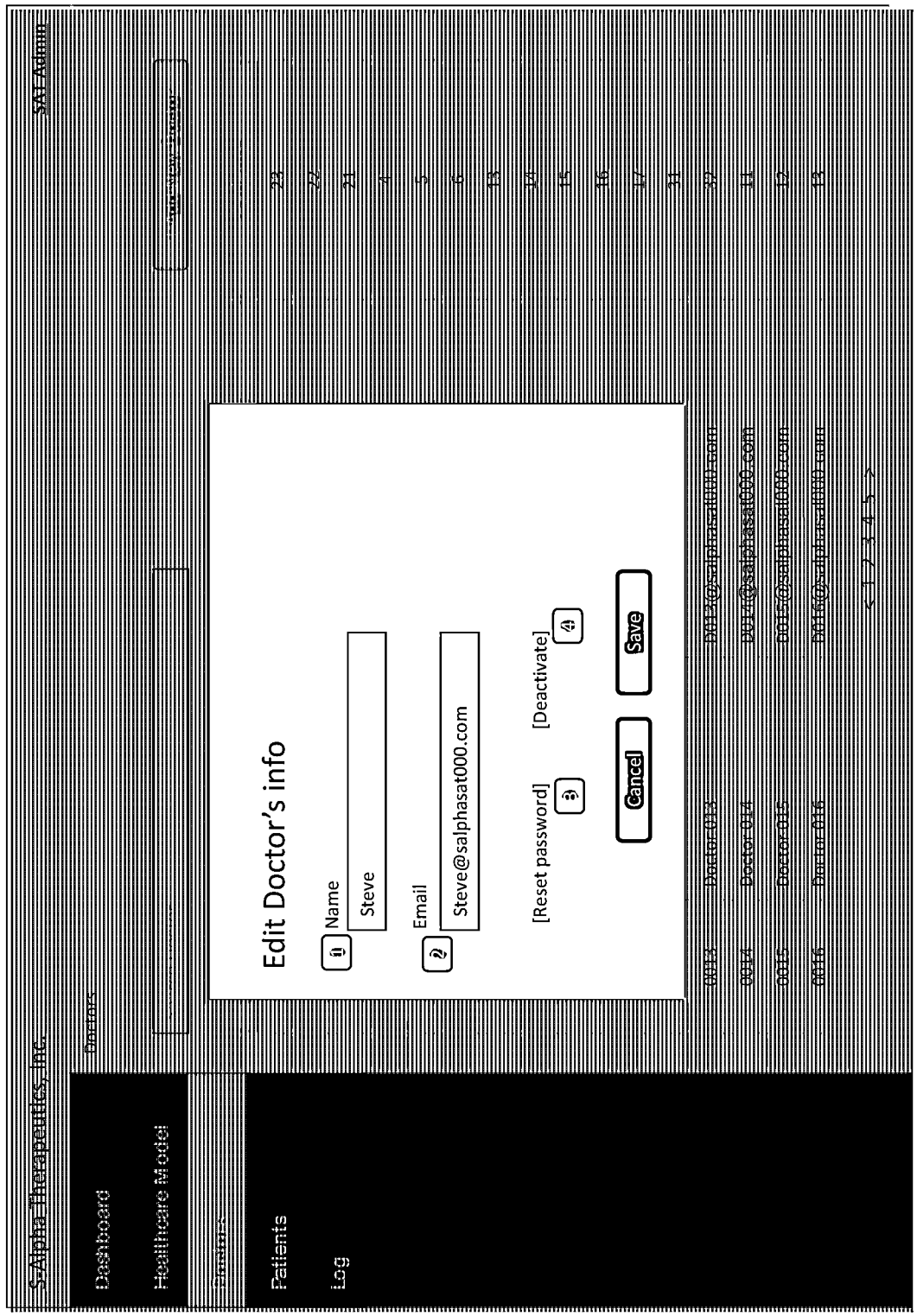
Figure 22A:
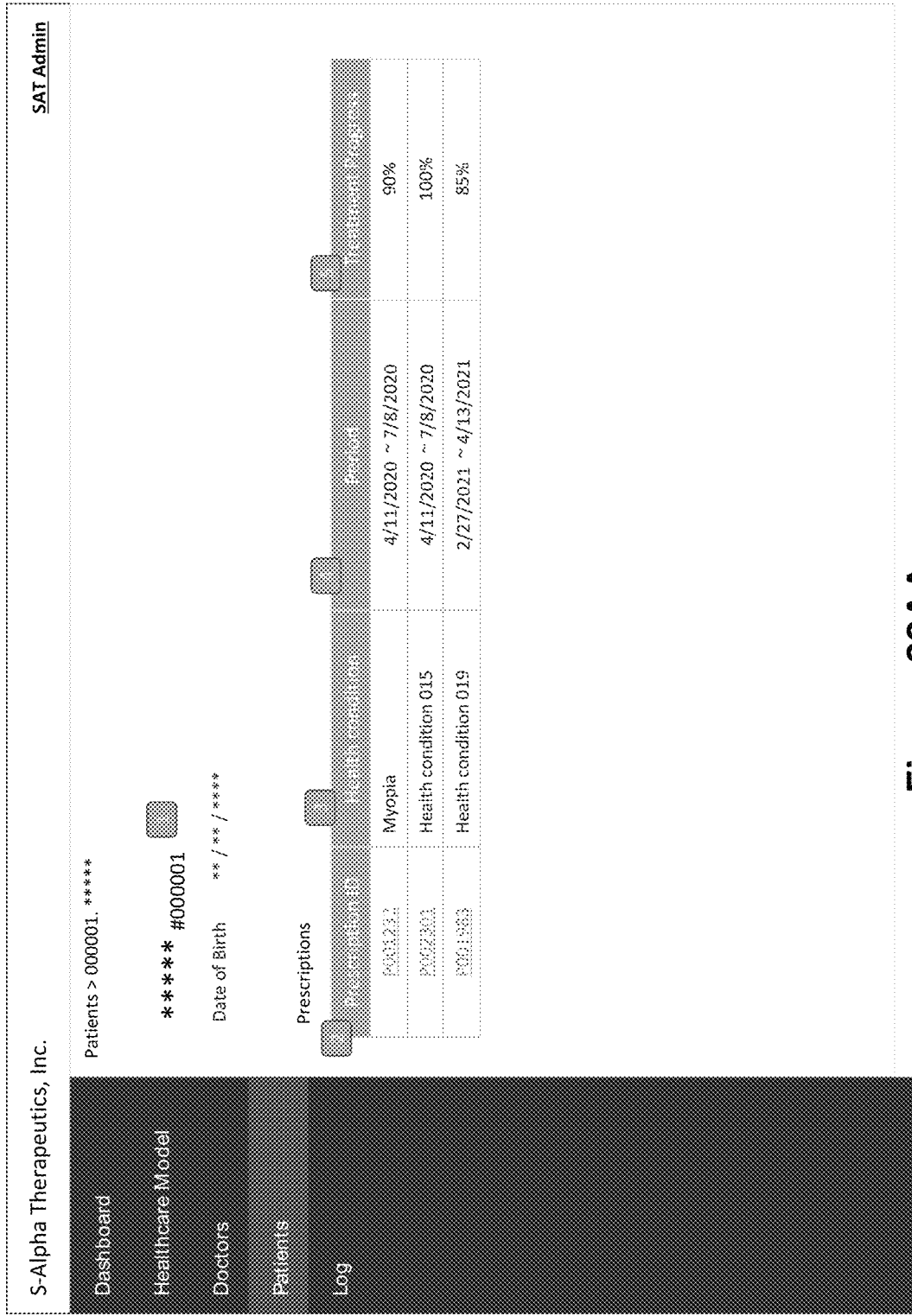
Figure 22B:
Figure 22Z:
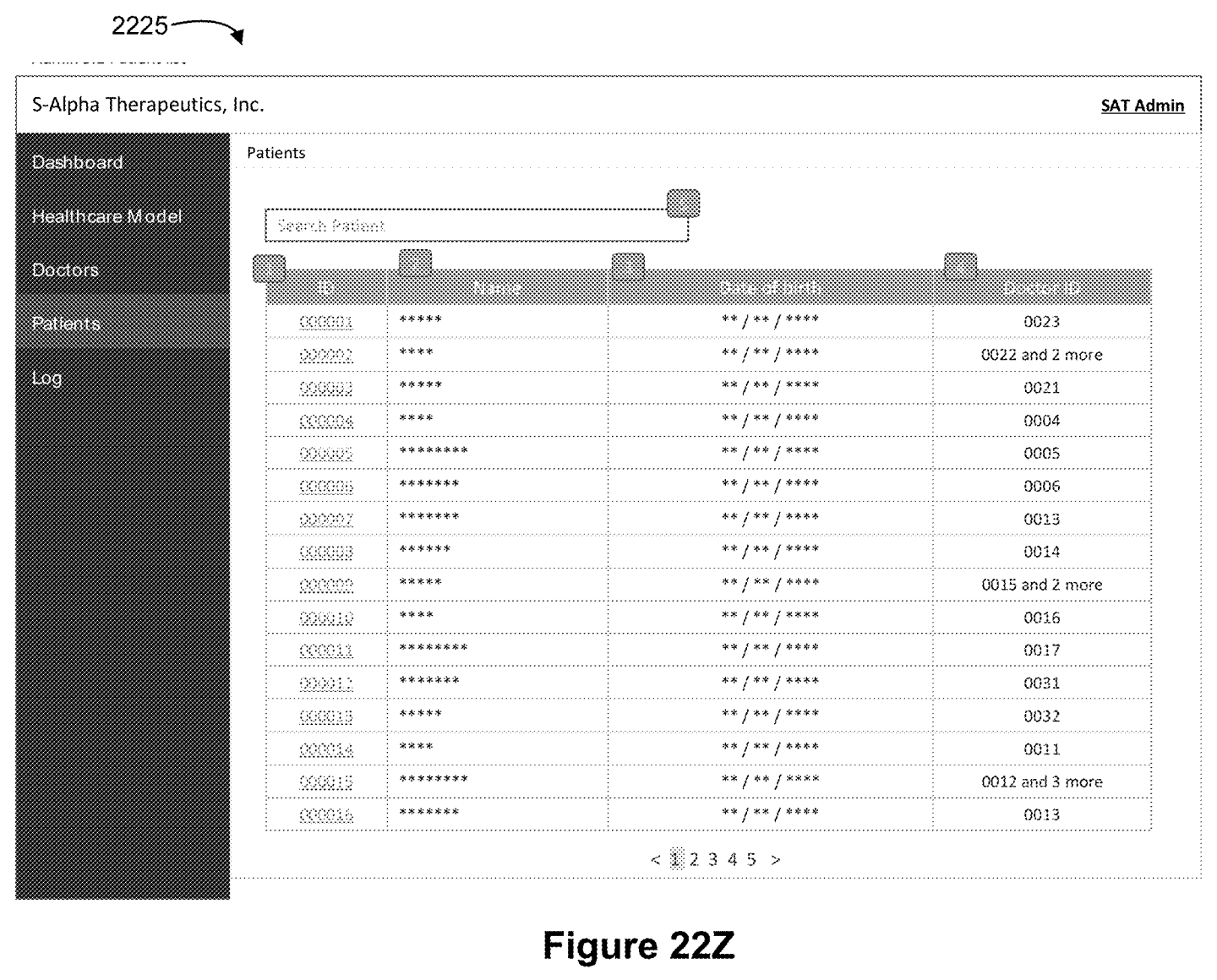
Figure 22C:
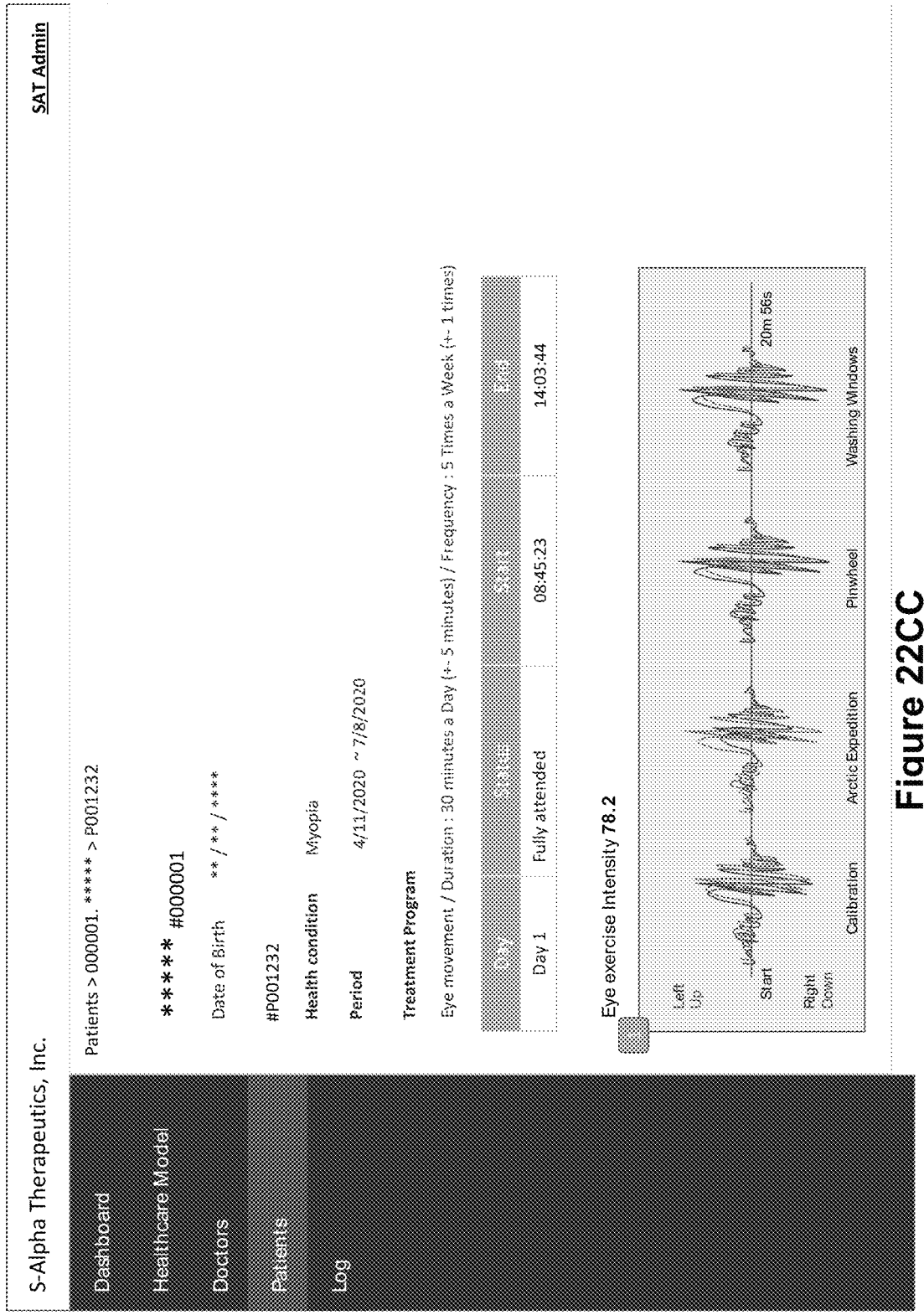

FIG. 22Y illustrates the administrator editing a doctor's information in the user interface 2224. For example the administrator is enabled to edit the doctor's name and email address associated with the account. In some implementations, the administrator is further enabled to reset the doctor's password, and deactivate the doctor's account. In some implementations, deactivation of the doctor's account causes a current session of the doctor to be exhausted, and the doctor can no longer login to the doctor's account, and patients that are associated with the doctor account (e.g., who are not associated with any other activated doctor account) are unable to start a new session (e.g., the patient accounts that have prescriptions from the deactivated doctor account are also deactivated). In some implementations, even after the doctor account is deactivated, the data (e.g., from the doctor's patients) remains stored on the system (e.g., at the server). In some implementations, the doctor's account information is stored such that the administrator can reactivate the doctor account (e.g., and reactivate the doctor's patients).

FIG. 22Z illustrates a user interface 2225 with a list of patients registered with the system. In some implementations, the name and date of birth of the patients are anonymized in the administrator's view. In some implementations, each patient is assigned an anonymized identifier (e.g., a number). For each patient, one or more doctors that are associated with the patient are further listed.

FIG. 22AA illustrates a user interface 2226 that displays a detailed view of a selected patient from the patient list illustrated in FIG. 22Z. In some implementations, the patient identifier is displayed, as well as prescriptions for the patient. For example, each prescription is displayed with a prescription ID, an indication of the health condition, a period of the prescription (e.g., the treatment period), and an indication of the treatment progress (e.g., 90% complete or 100% complete).

FIG. 22BB illustrates a user interface 2227 that displays a detailed view for a selected prescription of the patient. In some implementations, the detailed view includes patient information (e.g., anonymized in the administrator's view), the health condition related to the prescription, the prescription period (e.g., dates that the prescription is active), and detailed information about the treatment program. For example, the treatment program name, duration, and frequency, as well as a table showing the daily progress of the patient (e.g., as recorded by the patient's application).

FIG. 22CC illustrates a user interface 2228 that shows a detailed treatment program by day. For example, the administrator is enabled to select a day from the table showing details about the daily progress of the patient displayed in user interface 2227. In some implementations, in response to the administrator selecting a day, detailed information for the day is displayed. For example, the system stores information collected by the sensors of the patient's device that is executing the application to check the patient's activity and track the user's compliance with the treatment program. In some implementations, the system generates a graphical visualization of the patient's activity (e.g., a graph) and/or bio-signal-based quantitative data (e.g., as collected by the sensors of the patient's device). In some implementations, the visualization illustrates the variation in the collected data from the sensors based on the treatment plan.

Figure 23A:
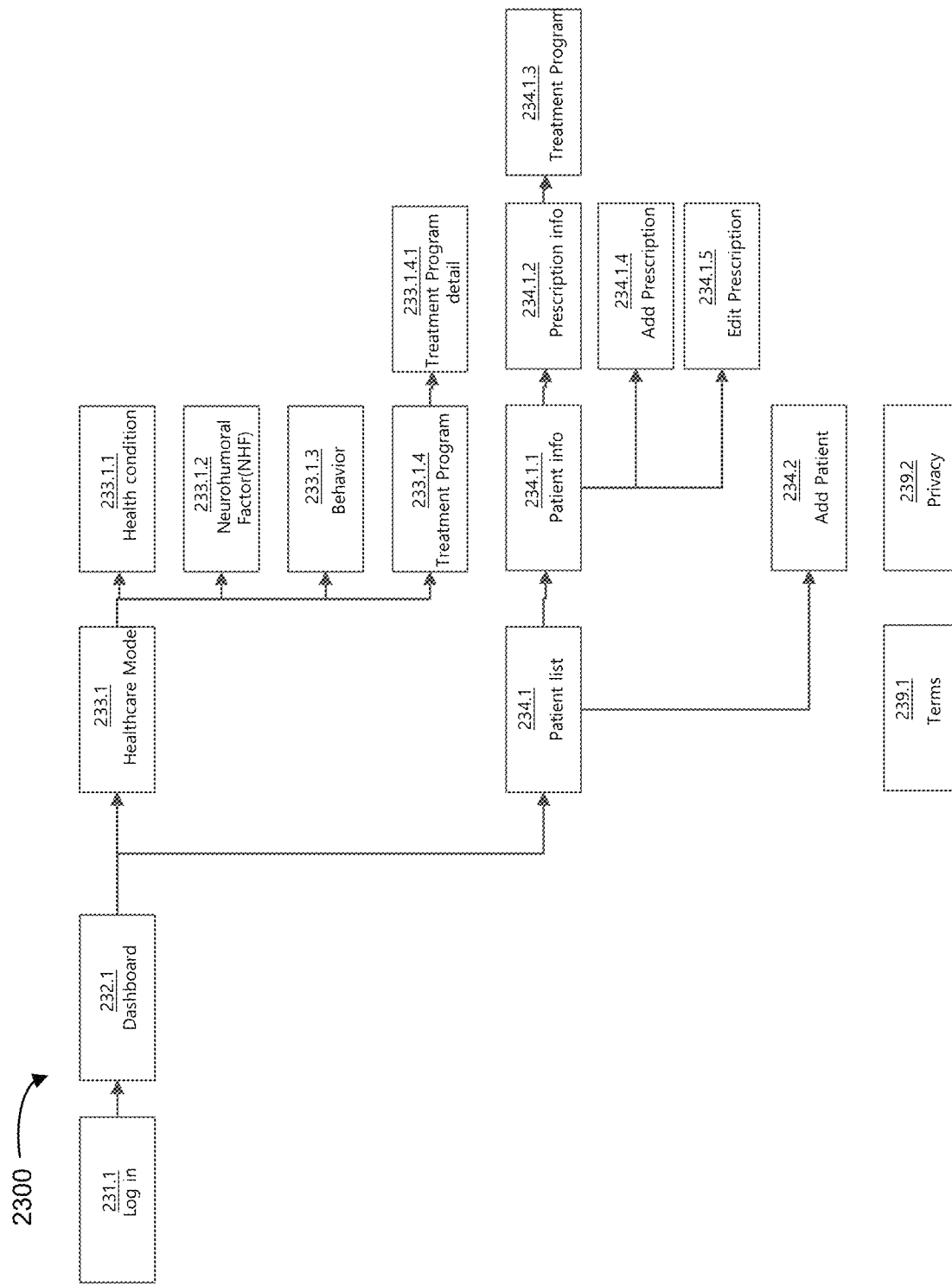

FIG. 23A illustrates an overview of a doctor's application structure 2300. In some implementations, the doctor's application is provided as a web application and/or a mobile application. For example, the doctor is enabled to login (231.1) to the application, and from the doctor's dashboard (232.1) displayed in the application, the doctor is enabled to view the healthcare model (233.1), from which the doctor can view health conditions (233.1.1). The doctor is also enabled to view the neurohumoral factors (NHFs) (233.1.2) and behaviors (233.1.3). In some implementations, unlike the administrator, the doctor is not enabled to view detailed information about the health conditions, NHFs, and behaviors, and the doctor is also unable to edit or add new health conditions, NHFs, or behaviors.

In some implementations, the doctor is further enabled to view treatment programs (233.1.4) and details about the treatment programs (233.1.4.1).

In some implementations, the doctor can also access a patient list (234.1) that includes patients the doctor has been assigned (e.g., or all patients that are registered with the digital behavior-based treatment system). In some implementations, the patient list is not anonymized (e.g., unlike in the administrator's view of the patient list). For example, the doctor has access to identifying information, such as the patient's name. In some implementations, the doctor is able to view information (234.1.1) about the patients, and is further enabled to view prescription information about a patient (234.1.2) and information about the patient's treatment program (234.1.3), as stored by the system. In some implementations, the doctor is also enabled to add a new prescription (234.1.4) and edit the existing prescriptions (234.1.5), for example, the frequency and/or duration of the prescription.

In some implementations, the doctor's application is enabled in accordance with terms (239.1) and/or a privacy policy (239.2).

Figure 23B:
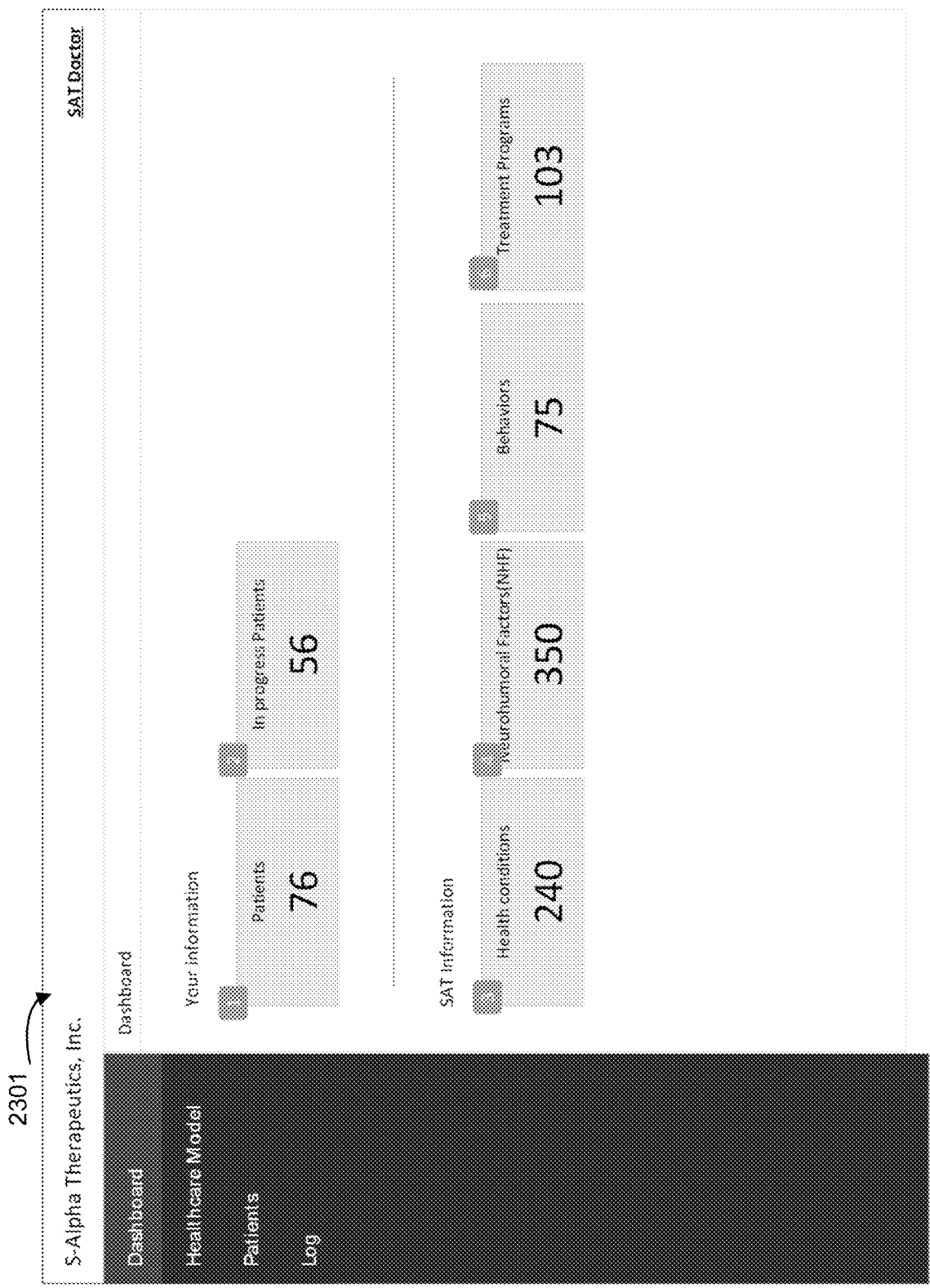

FIG. 23B illustrates a user interface 2301 that includes a dashboard view of the doctor's application (e.g., a web application). For example, the dashboard user interface includes a numeric indicator for the number of patients registered with the system that are assigned to the doctor, and the number of in-progress patients (e.g., that are currently participating in a treatment program) that are assigned to the doctor. In some implementations, the dashboard user interface 2301 also includes a numeric indicator for the number of health conditions stored by the system, the number of NHFs stored by the system, the number of behaviors stored by the system, and the number of treatment programs stored by the system. In some implementations, the doctor is enabled to select (e.g., click) on any of these numeric indicators to view more detailed information about the selected set. For example, the doctor can also select any of these sets to view more detailed information about the patients, and in-progress patients.

For brevity, the doctor's view of the healthcare model, including viewing lists of the health conditions, NHFs, behaviors, and treatment programs, is not included in the Figures. It will be understood that in some implementations, the doctor's view of the healthcare model includes the same list view that is provided to the administrator in the administrator's view of the healthcare model (e.g., without providing the doctor with the option to add or edit the healthcare model), as described with reference to FIGS. 22C-22E, 22J, 22O, and 22T-22U. For example, the doctor is provided with a view of health conditions (e.g., in a relationship format as shown in FIGS. 22C-22D, and in a list format as illustrated in FIG. 22E, without being provided with the option to add a new health condition (e.g., without the button 5 illustrated in FIG. 22E)). Similarly, the doctor is provided with a list view of the NHFs, as illustrated in FIG. 22J for the administrator's view, without the option to add a new NHF, and the doctor is provided with a list of behaviors, as illustrated in FIG. 22O for the administrator's view, without the option to add a new behavior. In some implementations, the doctor is further provided with the treatment programs views illustrated in FIG. 22T-22U.

Figure 23C:
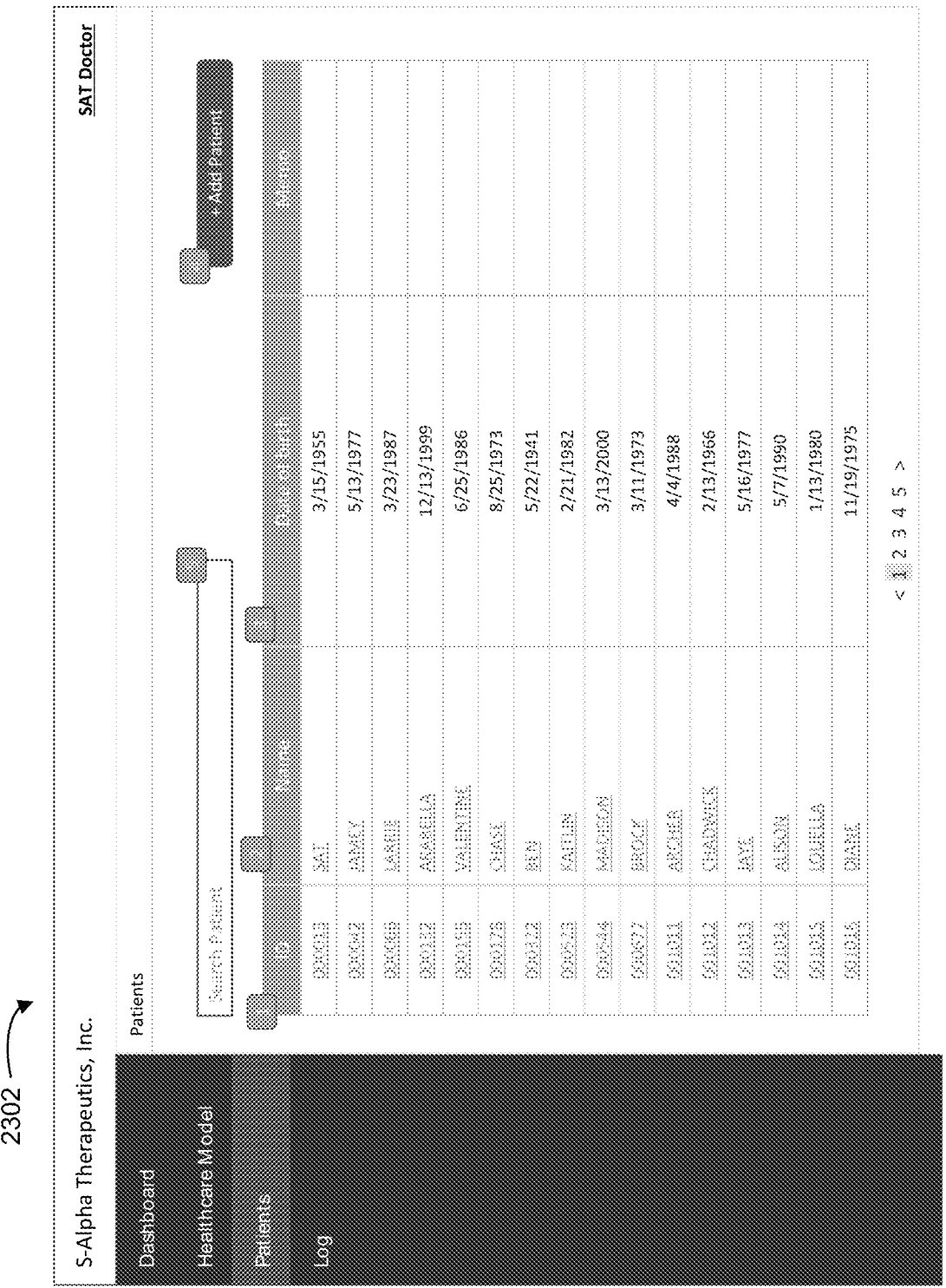
Figure 23E:
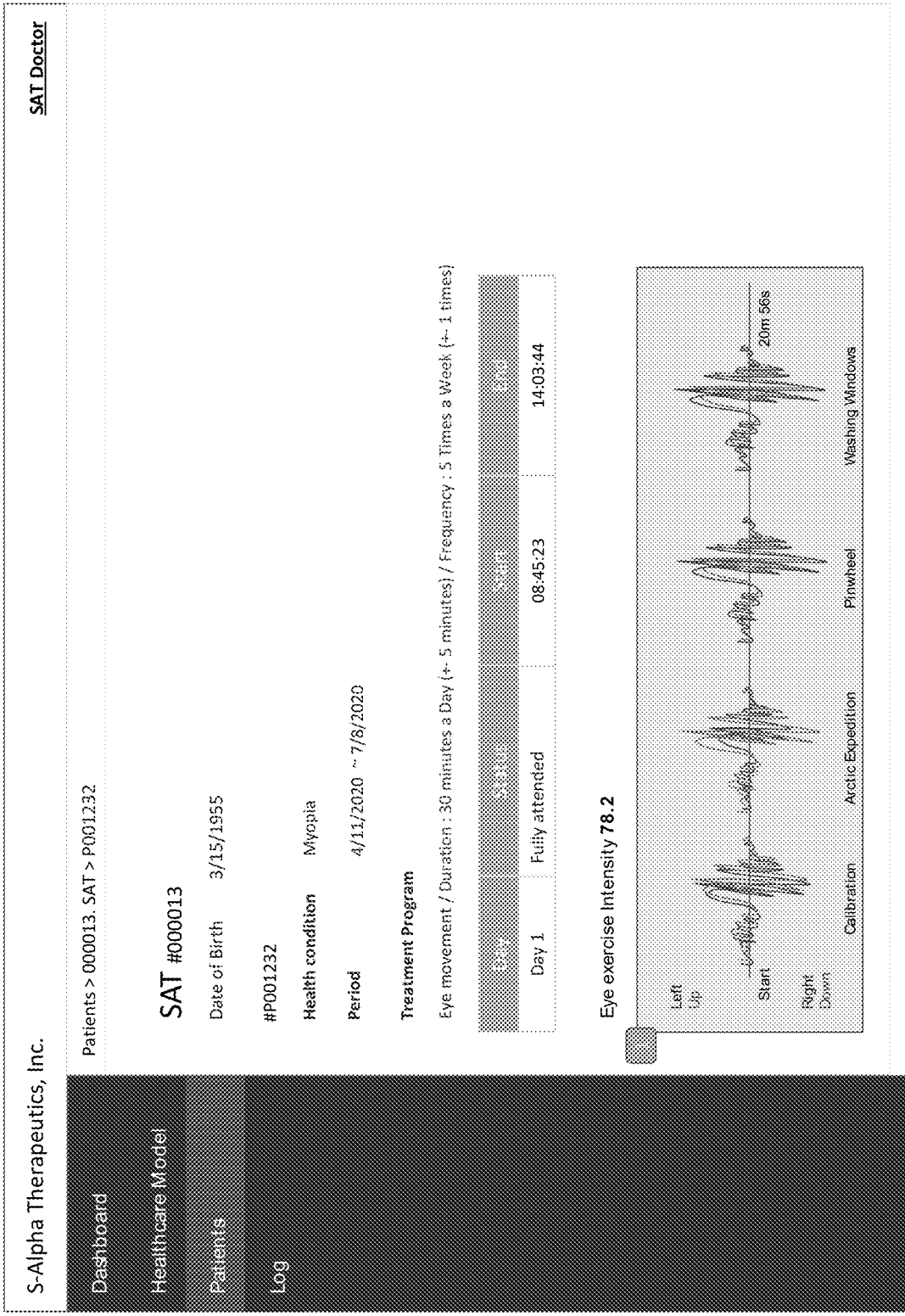

FIG. 23C illustrates a user interface 2302 that includes a patient list. In some implementations, unlike in the administrator's view of the patient list, the patient identifiers are not anonymized for the doctor's view of the patient list.

FIG. 23D illustrates a user interface 2303 for viewing details of a selected patient, including viewing the prescriptions of the patient, the health condition(s) of the patient, the period for treatment, and detailed information about the patient's progress in the treatment program (e.g., whether the patient fully attended, partially attended, or rested on each day of the treatment program). In some implementations, the doctor is enabled to select a particular day to view additional details about the patient's performance in the treatment program for that day, as illustrated in the user interface 2304 shown in FIG. 23E.

Figure 23F:
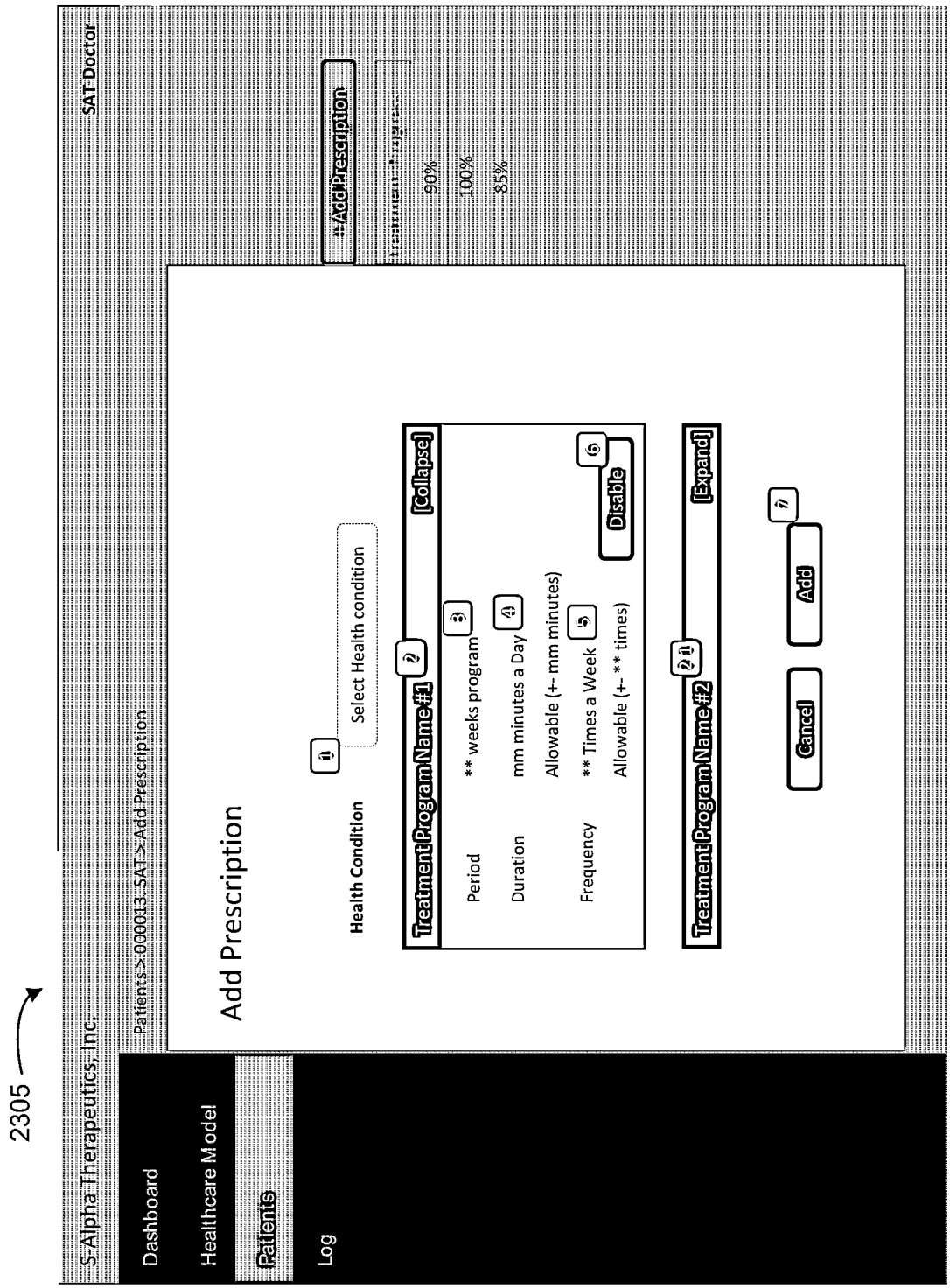

FIG. 23F illustrates a user interface 2305 for adding a prescription for a selected patient. For example, a doctor is enabled to customize a treatment program according to the patient's condition. In some implementations, the doctor selects a health condition (e.g., using the "Select Health condition" button in the popup window) for the patient. In some implementations, the doctor is enabled to search and view treatment programs according to the patient's health status through the Healthcare model that is stored at the server. In some implementations, all treatment programs related to the selected health condition are shown. In some implementations, default values for period (e.g., the length, in weeks, of the prescribed treatment program), duration (e.g., the number of minutes per day), and frequency (e.g., the number of times per week) are provided, and the doctor is enabled to modify the default values for the patient (e.g., after diagnosing the patient and determining a best period, the duration and frequency for the treatment program). In some implementations, the doctor is further enabled to disable a treatment program (e.g., using the Disable button 6), and add new prescriptions for treatment programs.

Figure 23G:
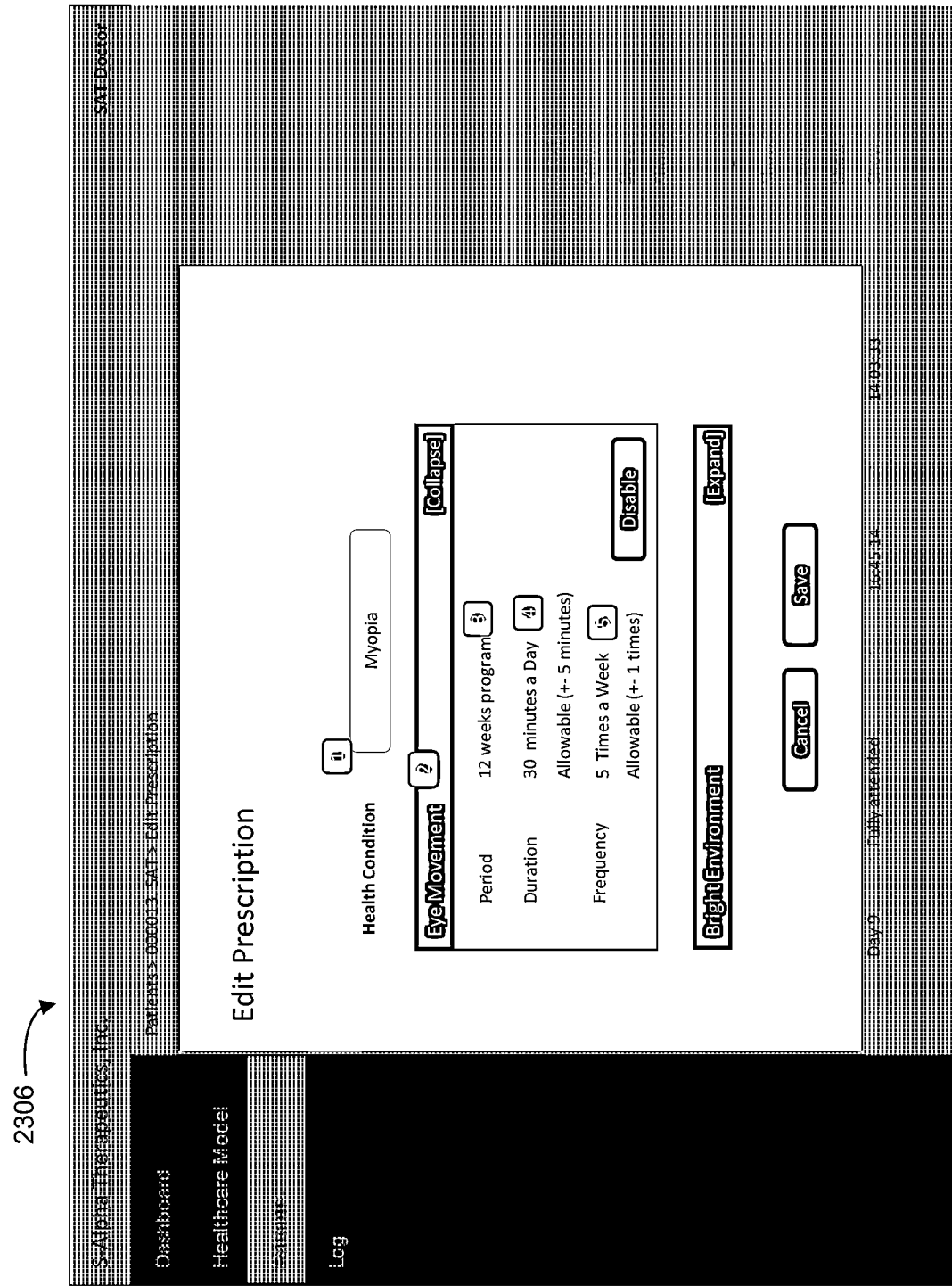

FIG. 23G illustrates a user interface 2306 for editing an existing prescription for a selected patient. For example, in FIG. 23G, the patient has already been prescribed a treatment program for the patient's health condition, Myopia. In some implementations, the doctor is enabled to modify the values for the treatment program, including modifying the period, duration, and/or frequency of the treatment program (e.g., based on the patient's needs). The doctor can also disable the existing treatment program (e.g., which causes the treatment program to disappear from the patient's application in the patient's next activities session). In some implementations, the Disable button, when activated, removes the program from the patient's daily activities and the Disable button is replaced with an "Allow" button (e.g., such that the doctor can toggle the treatment program back on after disabling the program). In some implementations, the doctor is enabled to view more detail about other treatment programs (e.g., Bright Environment) by selecting "[Expand]" for the other listed programs. For example, a plurality of (e.g., two or more) treatment programs may be prescribed to the patient for the same health condition.

Figure 23H:
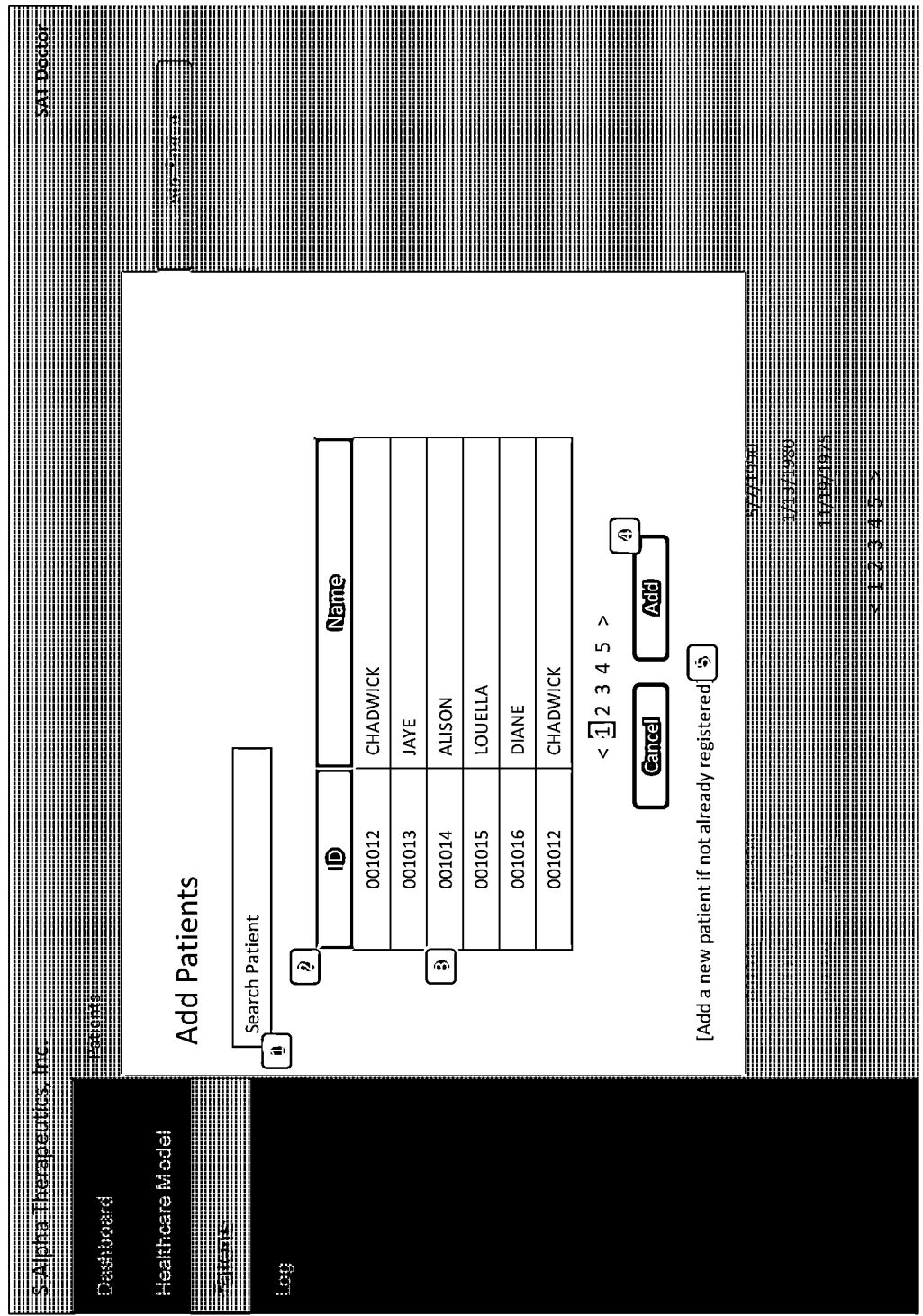

FIG. 23H illustrates the doctor adding a new patient using the user interface 2307. In some implementations, the doctor searches, from the list of registered patients with the system, for a respective patient before prescribing a treatment program to the patient (e.g., the patient is registered with the system but the doctor has not yet prescribed a treatment program for this patient). In some implementations, the doctor is further provided with an option to request to add a new patient if the patient is not already registered with the system.

FIGS. 24A-24D provide block diagrams that outline examples of mechanisms of action (MOAs) for a plurality of health conditions. In some embodiments, the MOA for a respective health condition is stored as a healthcare treatment model. For example, in response to receiving an input that specifies a first health condition for a patient, a computing device accesses and retrieves the stored MOAs to determine a particular treatment program for the first health condition for the patient. In some embodiments, the MOAs illustrated in FIGS. 24A-24D are built by a computing device (e.g., by calculating correlation coefficients between health conditions and neurohumoral factors using correlations specified in provided scientific documents). In some embodiments, the MOAs in FIGS. 24A-24D are manually derived, and stored as models for the system described herein to access to generate a treatment program for a patient.

Figure 24A:
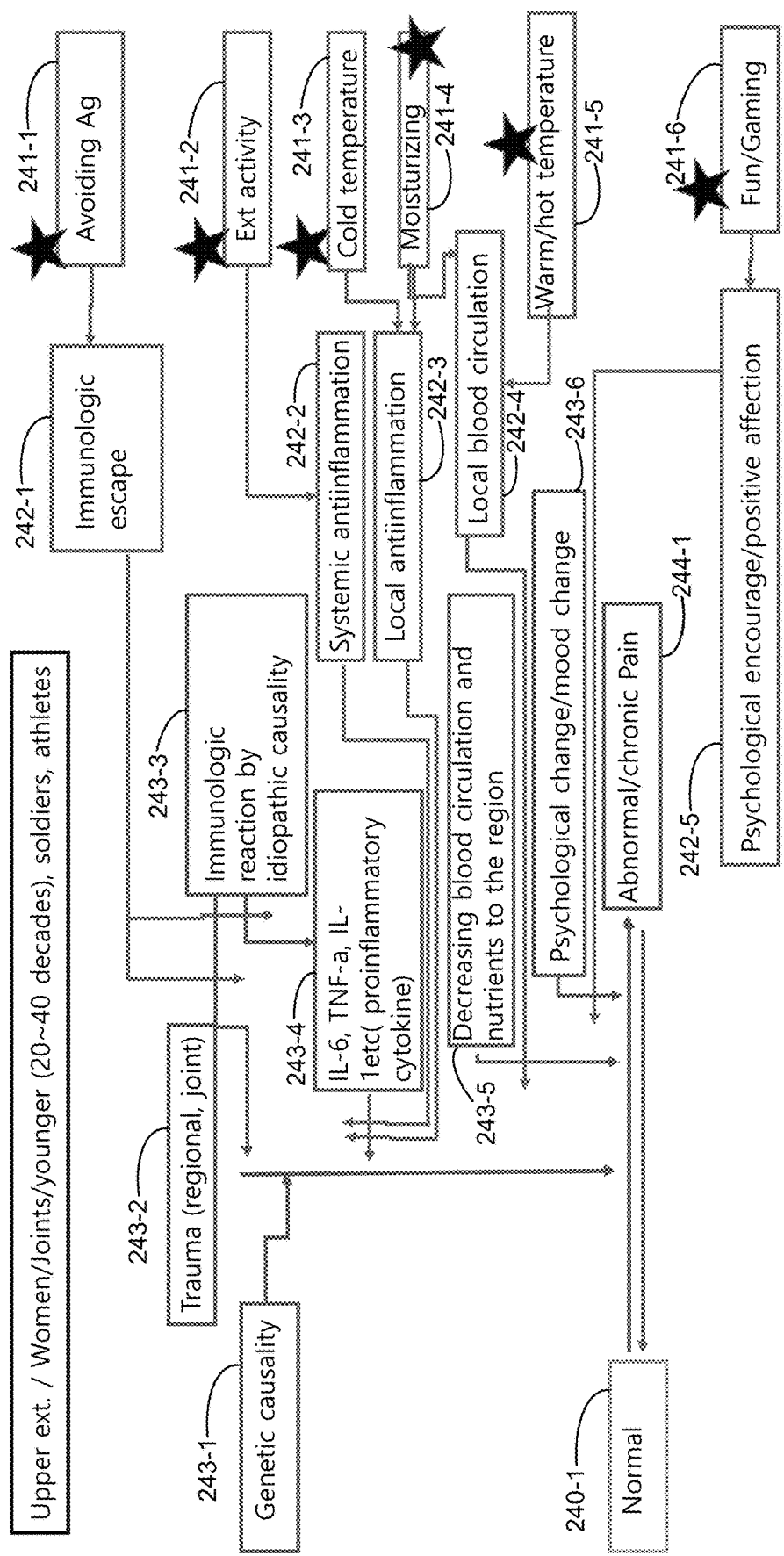
FIGS. 24A-24D illustrate block diagrams of examples of healthcare treatment models for a plurality of health conditions that may be stored by a computing device according to some implementations.

FIG. 24A shows an MOA for pain management. In some embodiments, the MOA is designed to be particularly effective for patients that have chronic joint pain 244-1 and meet one or more of the following criteria: women, between 20-40 years old or have a history as a soldier and/or a history as an athlete. FIG. 24A illustrates a plurality of treatment options that target blocking particular symptoms and/or physical responses in the patient to treat the patient with a goal of reaching normalcy 240-1. The boxes 241 (i.e., boxes, 241-1 through 241-6) are examples of the treatment options (e.g., actions) a patient should take as part of a treament plan to treat various pathways of chronic pain. The boxes 242 (i.e., boxes 242-1 through 242-5) represent the mechanisms (e.g., biological responses) that the treatment options target. The boxes 243 (i.e., boxes, 243-1 through 243-6) represent possible triggers (or symptoms) for abnormal/chronic pain 244. As illustrated in FIG. 24A, in some embodiments, the treatment options target one or more triggers of the condition (as indicated by the intercepting arrows from boxes 241 and 242 that cut off respective triggers along the pathway).

For example, avoiding silver (Ag) 241-1 can help a patient's immunologic escape 242-1, which can help decrease the symptoms of an immunologic reaction that is linked to regional and/or joint trauma 243-2. In some embodiments, avoiding Ag can also aid in decreasing the immunologic reaction by idiopathic causality 243-3, which can further progress the patient and lead to IL-6, TNF-α, IL-1 proinflammatory cytokine trigger 243-4. Another treatment option includes performing external activity (e.g., exercises) 241-2 to help with systemic antiinflammation 242-2, which can also help block the IL-6, TNF-α, IL-1 proinflammatory cytokine trigger 243-4. In some embodiments, the treatment options of using cold temperature 241-3 and moisturizing 241-4 (e.g., on the region of the pain) apply local antiinflammation 242-3, which can also block the IL-6, TNF-α, IL-1 proinflammatory cytokine trigger 243-4.

In some embodiments, moisturizing 241-4 and applying warm or hot temperature 241-5 to the affected area can improve local blood circulation 242-4, which can decrease the blood circulation and nutrients to the region 243-5, which is another trigger that leads to abnormal/chronic pain 244-1 in the region.

In some embodiments, the treatment options includes participating in fun activities or gaming 241-6, which provides psychological encouragement and positive affection 242-5, and can help prevent a negative psychological and/or mood change 243-6 that tends to occur in patients with chronic pain 244-1. By performing one, or a combination of the treatment options, a patient is likely better able to handle the abnormal and chronic pain 244.

Figure 24B:
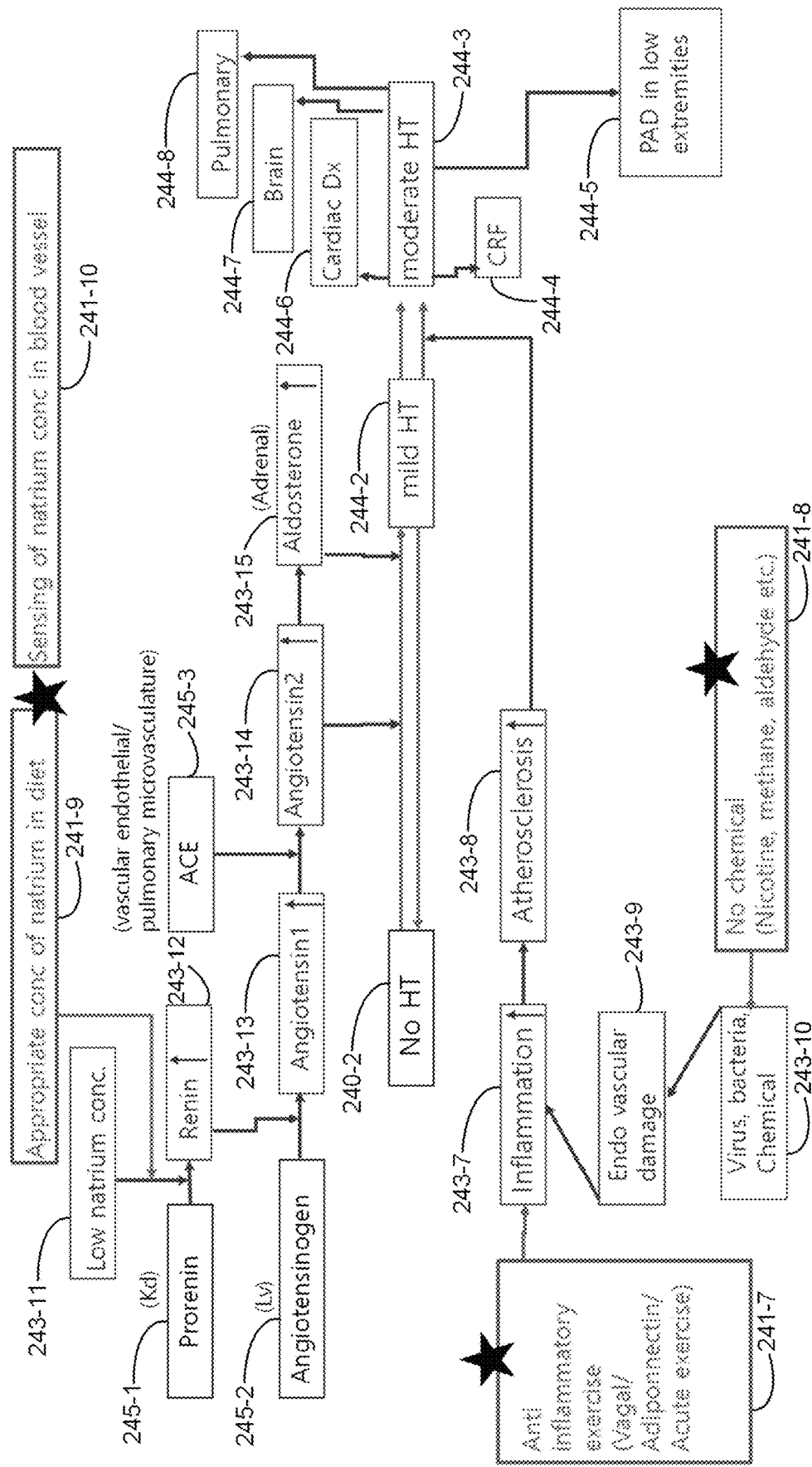

FIG. 24B shows an MOA for treating hypertension (HT), where "no HT" 240-2 represents normalcy (e.g., without hypertension). In some embodiments, the MOA identifies different stages of hypertension, which can have progressively worse symptoms, including mild HT 244-2 and moderate HT 244-3. Moderate HT can also lead to congestive renal failure (CRF) 244-4, peripheral arterial disease (PAD) in low extremities 244-5, cardiac disease 244-6, as well as brain (244-7) and pulmonary hypertension 244-8. Accordingly, the MOA illustrated in FIG. 24B includes treatment options that can also be directed toward treating any of these other health conditions.

In some embodiments, the treatment options 241 include performing anti-inflammatory exercises 241-7, including vagal and/or acute exercise to increase adiponectin, which helps to reduce inflammation 243-7, helps to reduce atherosclerosis 243-8, and also helps prevent (e.g., or slows down the progression of) mild HT 244-2 from further developing into moderate HT 244-3. In some embodiments, the treatment option includes taking a negative action, including avoiding (e.g., not ingesting) chemicals, such as nicotine, methane, and/or aldehyde, 241-8. Avoiding these chemicals helps prevent moderate HT 244-3 by removing the patient's exposure to viruses, bacteria and chemicals 243-10 and prevents endovascular damage 243-9 that can then lead to inflammation 243-7.

In some embodiments, a treatment option (e.g., an action that can be taken to help prevent HT) includes having an appropriate concentration of natrium in the patient's diet 421-9 (e.g., which also requires taking the action of sensing the natrium concentration in blood vessels 241-10 to determine the natrium concentration) because a low natrium concentration 243-11 can cause an increase in renin 243-12, which then increases angiotensin 1 (243-13) and angiotensin 2 (243-14) levels. All of these factors further contribute to mild HT 244-2 and/or can increase aldosterone levels 243-15, which also contributes to mild HT 244-2. In some embodiments, the treatment options include increasing an intake of prorenin 245-1 to improve renin levels, increasing an intake of angiotensinogen 245-2 to improve angiotensin 1 levels, and taking angiotensin-converting enzyme (ACE) 245-3 to improve angiotensin 2 levels (e.g., and lower blood pressure).

Figure 24C:
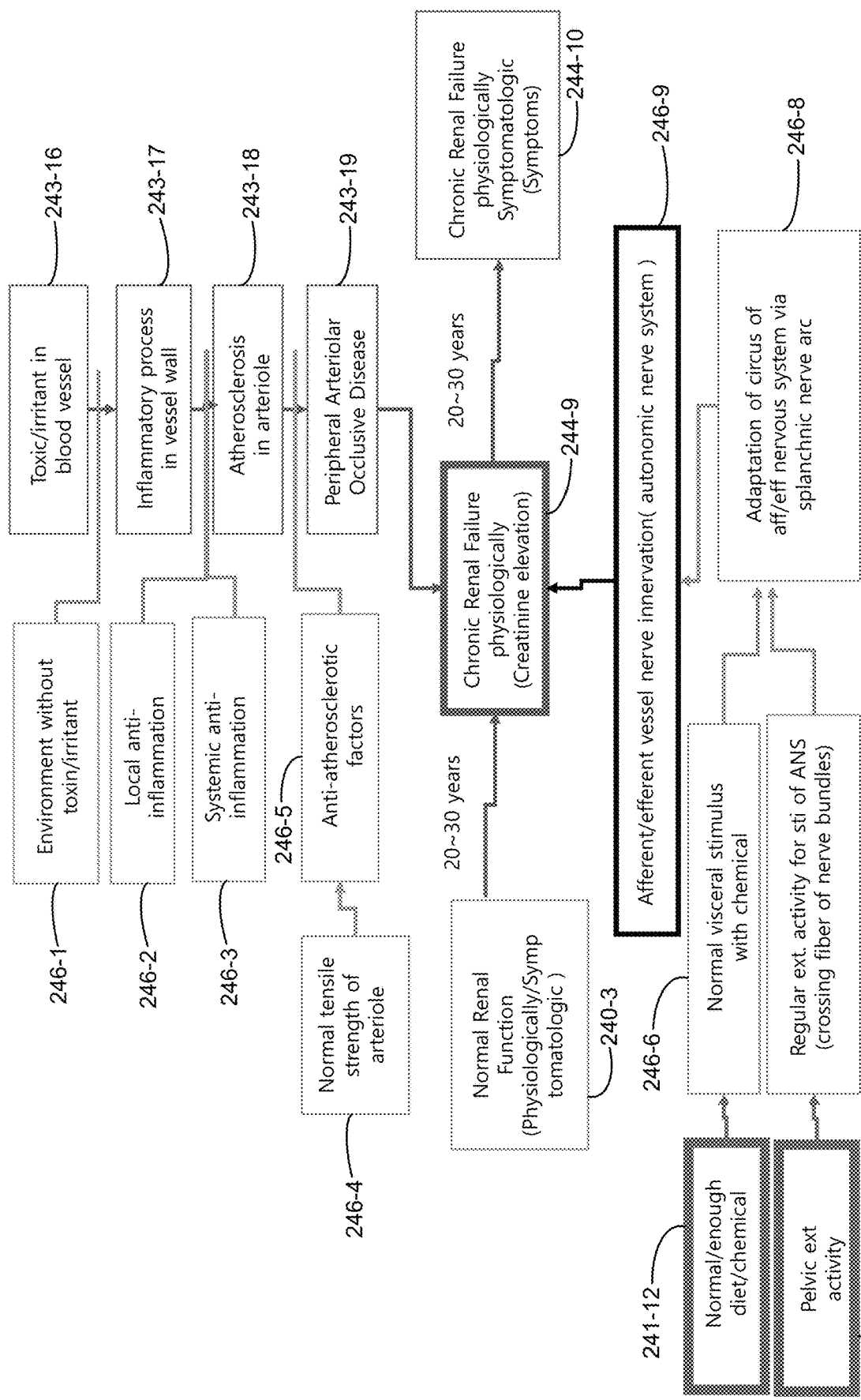

FIG. 24C shows recommended treatment options 241-11 and 241-12 for addressing chronic renal failure (CRF), including physiological CRF 244-9 in which creatinine is elevated, and symptomatologic CRF 244-10, which can develop over time after normal renal function 240-3. In some embodiments, boxes 246 represent activities and/or goals of the treatment (e.g., how a treatment option can stop the triggers/symptoms represented in boxes 243). In some embodiments, treatment options can be traced to early events in the patient's lifetime (before having the health condition) in order to help prevent CRF from occurring in the patient. For example, some of the activities are preventative measures, such as providing an environment that does not have toxins/irritants 246-1, which would prevent the toxins/irritants 243-16 from entering the blood vessel (e.g., which can then lead to CRF). Another activity includes local anti-inflammation 246-2 and systemic anti-inflammation 246-3 to reduce the inflammatory process 243-17 that occurs in the vessel wall. In some embodiments, maintaining a normal tensile strength of arteriole 246-4 can also improve the patient's anti-atherosclerotic factors 246-5, which can reduce atherosclerosis in arteriole 243-18. Reducing each of these responses 243-16 through 243-19 in the body can help prevent peripheral arteriolar occlusive disease 243-19, which can further reduce the patient's risk for developing CRF 244-9 or CRF 244-10 (e.g., which can occur ~20-30 years after CRF 244-9). In some embodiments, it takes ~20-30 years for a patient to develop CRF from normal renal function 240-3. Accordingly, early treatment and preventative treatment options are important in addressing CRF 244-9.

In some embodiments, the treatment options include performing pelvic external activities 241-11 (e.g., pelvic exercises), regularly checking for sexually transmitted infections (STIs) of the autonomic nervous system (ANS) 246-7, as well as maintaining a normal diet 241-12 to maintain chemical balance can help maintain normal visceral stimulus 246-6, all of which improve adaptation of circus of the afferent/efferent nervous system via the splanchnic nerve arc 246-8, which can keep the ANS healthy 246-9 to help reduce the risk of CRF 244-9.

Figure 24D:
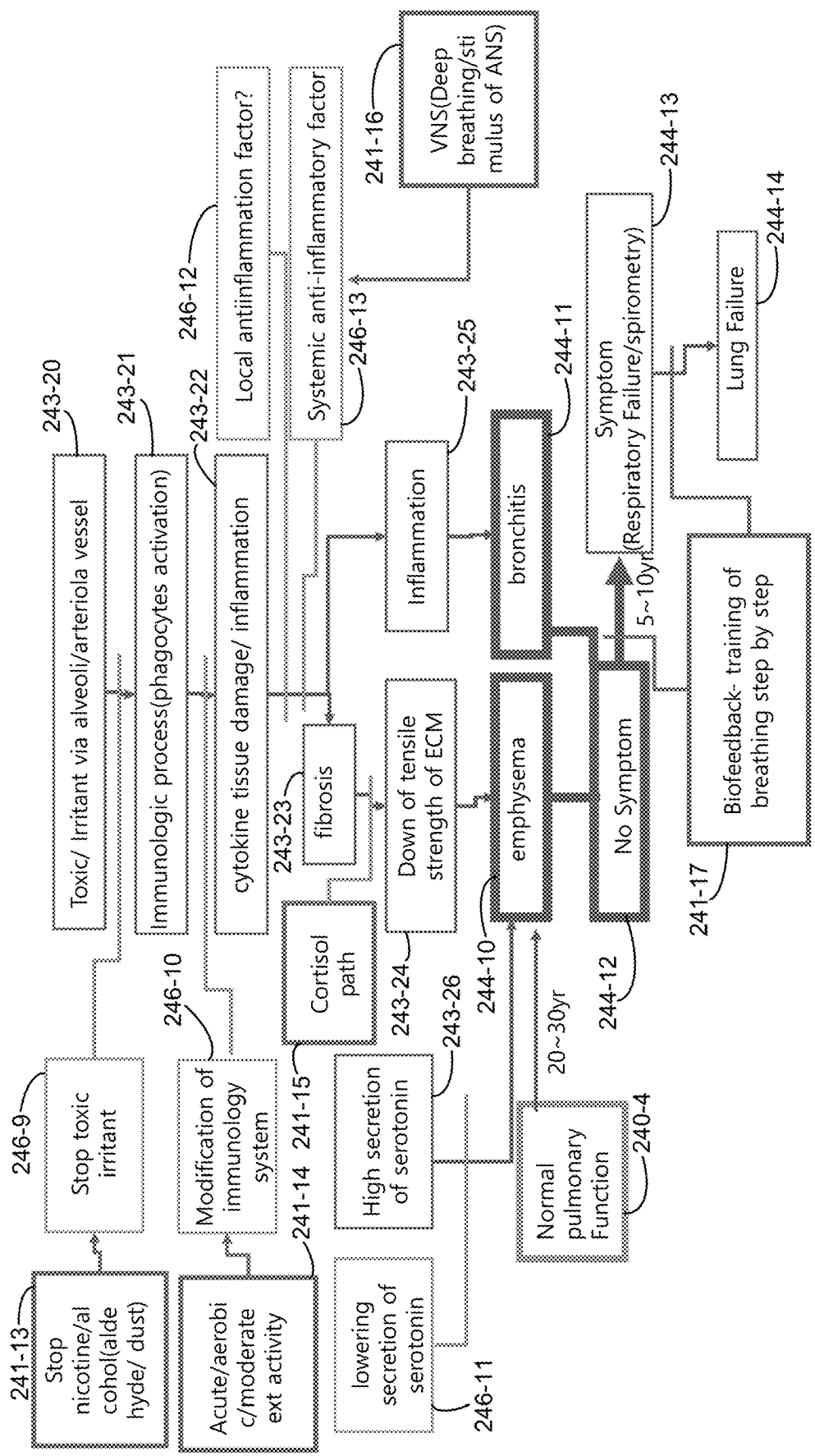

FIG. 24D shows a model for treating Chronic Obstructive Pulmonary Disease (COPD), which can manifest as emphysema 244-10, bronchitis 244-11, no symptom COPD 244-12, respiratory failure/spirometry 244-13, and/or lung failure 244-14, each of which are modeled in FIG. 24D relative to normal pulmonary function 240-4. In some embodiments, a first preventative measure is to stop nicotine, alcohol, aldehyde and/or dust 241-13 from being in the patient's environment (e.g., including consumption of these chemicals), which would stop the patient's exposure to a toxic irritant 246-9 in the first place, thus reducing the patient's risk for suffering from a toxic irritant via the alveoli/arteriola vessel 243-20. In some embodiments, another preventative measure is to have the patient do acute, aerobic and/or moderate activity (e.g., exercises) 241-14, which can modify the immunology system 246-10 of the patient, and can help keep the immunologic process of phagocytes activation 243-21 at a normal level.

In some embodiments, the model recommends the patient perform vagus nerve stimulation (VNS), and/or perform deep breathing to stimulate the ANS 241-16, which can improve the patient's systemic anti-inflammatory factor 246-13 (and potentially another activity to improve the patient's local antiinflammation factor 246-12), which can help prevent cytokine tissue damage and/or inflammation 243-22 from developing into fibrosis 243-23 or other inflammation 243-25 (which can lead to bronchitis 244-11).

In some embodiments, the model recommends improving the cortisol path 241-15 of the patient to limit the development of fibrosis 243-23, which causes a decrease in tensile strength of the extra cellular matrix (ECM) in the lung 243-24, and could then lead to emphysema 244-10.

In some embodiments, a high secretion of serotonin 243-26 can also contribute to development of emphysema, so taking actions to lower secretion of serotonin 246-11 is another treatment option to reduce the risk of developing emphysema.

In some embodiments, COPD (without symptoms) 244-12 develops in a normal, healthy individual after ~20-30 years. In some embodiments, having the patient participate in biofeedback training of breathing 241-17 can help the patient from developing symptoms of respiratory failure 244-13 and/or from experiencing lung failure 244-14 (or can delay the onset of symptoms).

Accordingly, FIGS. 24A-24D provide examples of models for treating a plurality of different health conditions by identifying the mechanisms that lead to the health condition, and assigning treatment options for various steps in the mechanism to help the patient manage symptoms or prevent the symptoms from developing into a more serious health condition. In some embodiments, the user interfaces described herein allow a user to input a health condition, and the computer system identifies one or more treatment plans based on models stored for the respective health condition. As such, the models described in FIGS. 24A-24D are examples of models. Other models can be stored by the system to create a database for recommending treatments for various health conditions, at different stages of the health conditions.

The terminology used in the description of the invention herein is for the purpose of describing particular implementations only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The foregoing description, for purpose of explanation, has been described with reference to specific implementations. However, the illustrative discussions above are not intended to be exhaustive or to limit the invention to the precise forms disclosed. Many modifications and variations are possible in view of the above teachings. The implementations were chosen and described in order to best explain the principles of the invention and its practical applications, to thereby enable others skilled in the art to best utilize the invention and various implementations with various modifications as are suited to the particular use contemplated.

What is claimed is:

1. A method of treating myopia, performed at a device having one or more processors and memory storing one or more programs configured for execution by the one or more processors:

retrieving a stored healthcare treatment model that has been trained to identify, for each of a plurality of health conditions, one or more respective treatment programs based on respective behavior associated with one or more neurohumoral factors that are associated with a respective health condition, wherein each of the treatment programs includes a respective treatment user interface to provide one or more tasks for a user to follow, thereby treating the myopia, wherein the stored healthcare treatment model includes a healthcare model for treating the myopia; and in response to receiving input that specifies a first health condition of the one or more health conditions as the myopia:

using the healthcare treatment model to select one or more treatment programs corresponding to the first health condition;

providing the treatment user interfaces for the one or more treatment programs;

obtaining treatment adherence information related to the one or more treatment programs from one or more sensors;

encrypting the treatment adherence information and transmitting the encrypted treatment adherence information to a server;

receiving encrypted data related to a new treatment program for the first health condition based on the treatment adherence information from the server, the new treatment program including at least one selected from the group consisting of performing day exercise/outdoor exercise, positive affection training, meditation/deep breathing, audible high tempo music, and physical exercise;

decoding the encrypted data;

using the healthcare treatment model to generate the new treatment program for the first health condition based on the decoded data; and providing a new treatment user interface for the new treatment programs for the first health condition.

2. The method of claim 1, further comprising:
in response to receiving input that specifies a second health condition of the one or more health conditions, wherein the second health condition is different from the first health condition:
using the healthcare treatment model to select one or more treatment programs corresponding to the second health condition, wherein the one or more treatment programs corresponding to the second health condition differ from the one or more treatment programs corresponding to the first health condition; and
providing the treatment user interfaces for the one or more treatment programs corresponding to the second health condition.

3. The method of claim 1, further comprising:
generating a treatment regimen for the first health condition, wherein the treatment regimen includes the one or more treatment programs corresponding to the first health condition.

4. The method of claim 3, further comprising:
in response to an indication that the healthcare treatment model has been updated, retrieving the updated healthcare treatment model and updating the treatment regimen for the first health condition according to the updated healthcare treatment model, wherein the updated treatment regimen (i) includes one or more treatment programs not previously in the treatment regimen and/or (ii) omits one or more treatment programs previously in the treatment regimen.

5. The method of claim 1, further comprising:
determining a time to stop the one or more treatment user interfaces and a time to provide the new treatment user interface.

6. The method of claim 1, wherein one or more of the treatment interfaces are configured to monitor one or more specific patient activities using sensors of an electronic device on which the treatment interfaces are presented, the method further comprising selecting a first specific patient activity to monitor according to a first treatment interface of the provided treatment interfaces.

7. The method of claim 1, further comprising:
in response to an indication that the healthcare treatment model has been updated, retrieving the updated healthcare treatment model and updating at least one treatment program in accordance with the updated healthcare treatment model.

8. The method of claim 1, wherein the method further treats one or more additional health conditions other than: cancer cachexia, social communication disorder, mild cognitive impairment, and ophthalmologic rehabilitation.

9. The method of claim 1, wherein the one or more treatment programs include at least one treatment regimen other than: improving antiviral immunology and strengthening a pelvic floor muscle.

10. The method of claim 1, wherein:
the first health condition is chronic pain,
the stored healthcare treatment model includes a model for treating chronic pain, and
the one or more treatment programs are selected from the group consisting of avoiding silver, performing external activity, applying cold temperature, moisturizing, applying warm temperatures, and providing games or other fun activities.

11. The method of claim 1, wherein:
the first health condition is hypertension,
the stored healthcare treatment model includes a model for treating hypertension, and
the one or more treatment programs are selected from the group consisting of performing anti-inflammatory exercises, avoiding nicotine, avoiding methane, avoiding aldehyde, and having an appropriate concentration of natrium in diet.

12. The method of claim 1, wherein:
the first health condition is peripheral arterial disease (PAD) in low extremities,
the stored healthcare treatment model includes a model for treating PAD, and
the one or more treatment programs are selected from the group consisting of performing anti-inflammatory exercises, avoiding nicotine, avoiding methane, avoiding aldehyde, and having an appropriate concentration of natrium in diet.

13. The method of claim 1, wherein:
the first health condition is chronic renal failure (CRF),
the stored healthcare treatment model includes a model for treating CRF, and
the one or more treatment programs are selected from the group consisting of performing pelvic exercises, following a specialized dietary plan, and removing chemical stimuli.

14. The method of claim 1, wherein:
the first health condition is chronic obstructive pulmonary disease (COPD),
the stored healthcare treatment model includes a model for treating COPD, and
the one or more treatment programs are selected from the group consisting of avoiding nicotine, avoiding alcohol, performing acute, aerobic and moderate exercise, implementing biofeedback-training of breathing, and performing Vagus Nerve Stimulation (VNS).

15. A device of treating myopia, comprising:
one or more processors;
memory; and
one or more programs stored in the memory and configured for execution by the one or more processors, the one or more programs comprising instructions for:
retrieving a stored healthcare treatment model that has been trained to identify, for each of a plurality of health conditions, one or more respective treatment programs based on respective behavior associated with one or more neurohumoral factors that are associated a respective health condition, wherein each of the treatment programs includes a respective treatment user interface to provide one or more tasks for a user to follow, thereby treating the myopia, wherein the stored healthcare treatment model includes a healthcare model for treating the myopia; and
in response to receiving input that specifies a first health condition of the one or more health conditions as the myopia:
using the healthcare treatment model to select one or more treatment programs corresponding to the first health condition; and
providing the treatment user interfaces for the one or more treatment programs;
obtaining treatment adherence information related to the one or more treatment programs from one or more sensors;
encrypting the treatment adherence information and transmitting the encrypted treatment adherence information to a server;
receiving encrypted data related to a new treatment program for the first health condition based on the treatment adherence information from the server, the new treatment program including at least one selected from the group consisting of performing day exercise/outdoor exercise, positive affection training, meditation/deep breathing, audible high tempo music, and physical exercise;
decoding the encrypted data;
using the healthcare treatment model to generate the new treatment program for the first health condition based on the decoded data; and
providing a new treatment user interface for the new treatment programs for the first health condition.

16. The device of claim 15, wherein the one or more programs further include instructions for:
in response to receiving input that specifies a second health condition of the one or more health conditions, wherein the second health condition is different from the first health condition:
using the healthcare treatment model to select one or more treatment programs corresponding to the second health condition, wherein the one or more treatment programs corresponding to the second health condition differ from the one or more treatment programs corresponding to the first health condition; and
providing the treatment user interfaces for the one or more treatment programs corresponding to the second health condition.

17. The device of claim 15, wherein the one or more programs further include instructions for:
generating a treatment regimen for the first health condition, wherein the treatment regimen includes the one or more treatment programs corresponding to the first health condition.

18. The device of claim 17, wherein the one or more programs further include instructions for:
in response to an indication that the healthcare treatment model has been updated, retrieving the updated healthcare treatment model and updating the treatment regimen for the first health condition according to the updated healthcare treatment model, wherein the updated treatment regimen (i) includes one or more treatment programs not previously in the treatment regimen and/or (ii) omits one or more treatment programs previously in the treatment regimen.

19. The device of claim 15, wherein the one or more of the treatment interfaces are configured to monitor one or more specific patient activities using the one or more sensors while the treatment interfaces are presented, the one or more programs further include instructions for: selecting a first specific patient activity to monitor according to a first treatment interface of the provided treatment interfaces.

20. A non-transitory computer readable storage medium storing one or more programs configured for execution by a computer system having one or more processors, memory, and a display, the one or more programs comprising instructions for treating myopia including:
retrieving a stored healthcare treatment model that has been trained to identify, for each of a plurality of health conditions, one or more respective treatment programs based on respective behavior associated with one or more neurohumoral factors that are associated with a respective health condition, wherein each of the treatment programs includes a respective treatment user interface to provide one or more tasks for a user to follow, thereby treating the myopia, wherein the stored healthcare treatment model includes a healthcare model for treating the myopia; and
in response to receiving input that specifies a first health condition of the one or more health conditions as the myopia:
using the healthcare treatment model to select one or more treatment programs corresponding to the first health condition;
providing the treatment user interfaces for the one or more treatment programs;
obtaining treatment adherence information related to the one or more treatment programs from one or more sensors;
encrypting the treatment adherence information and transmitting the encrypted treatment adherence information to a server;
receiving encrypted data related to a new treatment program for the first health condition based on the treatment adherence information from the server, the new treatment program including at least one selected from the group consisting of performing day exercise/outdoor exercise, positive affection training, meditation/deep breathing, audible high tempo music, and physical exercise;
decoding the encrypted data;
using the healthcare treatment model to generate the new treatment program for the first health condition based on the decoded data; and
providing a new treatment user interface for the new treatment programs for the first health condition.

* * * * *